US008283518B2

(12) United States Patent
Cooper et al.

(10) Patent No.: US 8,283,518 B2
(45) Date of Patent: *Oct. 9, 2012

(54) ADMINISTRATION OF TRANSPOSON-BASED VECTORS TO REPRODUCTIVE ORGANS

(75) Inventors: Richard K. Cooper, Baton Rouge, LA (US); William C. Fioretti, Grapevine, TX (US); Gary G. Cadd, Grapevine, TX (US)

(73) Assignees: TransGenRx, Inc., Baton Rouge, LA (US); The Board of Supervisors of Louisiana State University and Agricultural and Mechanical College, Baton Rouge, LA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/981,629

(22) Filed: Oct. 31, 2007

(65) Prior Publication Data
US 2008/0235815 A1    Sep. 25, 2008

Related U.S. Application Data

(63) Continuation of application No. 10/746,149, filed on Dec. 24, 2003, now abandoned, and a continuation-in-part of application No. 10/609,019, filed on Jun. 26, 2003, now Pat. No. 7,527,966.

(60) Provisional application No. 60/441,392, filed on Jan. 21, 2003, provisional application No. 60/441,377, filed on Jan. 21, 2003, provisional application No. 60/441,502, filed on Jan. 21, 2003, provisional application No. 60/441,405, filed on Jan. 21, 2003, provisional application No. 60/441,447, filed on Jan. 21, 2003, provisional application No. 60/441,381, filed on Jan. 21, 2003, provisional application No. 60/392,415, filed on Jun. 26, 2002.

(51) Int. Cl.
C12N 15/00 (2006.01)
C12P 21/00 (2006.01)
A01K 67/027 (2006.01)

(52) U.S. Cl. .................... 800/21; 800/4; 800/19
(58) Field of Classification Search ................... 800/21, 800/4, 19, 25, 8
See application file for complete search history.

(56) References Cited

U.S. PATENT DOCUMENTS

| 4,670,388 | A | 6/1987 | Rubin et al. |
|---|---|---|---|
| 4,870,009 | A | 9/1989 | Evans et al. |
| 4,914,025 | A | 4/1990 | Manoil et al. |
| 5,102,797 | A | 4/1992 | Tucker et al. |
| 5,162,215 | A | 11/1992 | Bosselman et al. |
| 5,212,080 | A | 5/1993 | Nag et al. |
| 5,512,483 | A | 4/1996 | Mader et al. |
| 5,556,782 | A | 9/1996 | Cooper et al. |
| 5,565,362 | A | 10/1996 | Rosen |
| 5,645,991 | A | 7/1997 | Berg et al. |
| 5,648,244 | A | 7/1997 | Kuliopulos et al. |
| 5,703,055 | A | 12/1997 | Felgner et al. |
| 5,719,055 | A | 2/1998 | Cooper |
| 5,733,779 | A | 3/1998 | Reff |
| 5,753,502 | A | 5/1998 | Kilgannon et al. |
| 5,861,478 | A | 1/1999 | Jaynes |
| 5,869,296 | A | 2/1999 | Nag et al. |
| 5,925,545 | A | 7/1999 | Reznikoff et al. |
| 5,948,622 | A | 9/1999 | Reznikoff et al. |
| 5,958,775 | A | 9/1999 | Wickstrom et al. |
| 5,962,410 | A | 10/1999 | Jaynes et al. |
| 5,965,443 | A | 10/1999 | Reznikoff et al. |
| 5,998,698 | A | 12/1999 | Cooper et al. |
| 6,080,912 | A | 6/2000 | Bremel et al. |
| 6,107,477 | A | 8/2000 | Whitney et al. |
| 6,140,129 | A | 10/2000 | Cox et al. |
| 6,156,568 | A | 12/2000 | Cooper et al. |
| 6,159,730 | A | 12/2000 | Reff |
| 6,159,736 | A | 12/2000 | Reznikoff et al. |
| 6,171,861 | B1 | 1/2001 | Hartley et al. |
| 6,218,185 | B1 | 4/2001 | Shirk et al. |
| 6,255,282 | B1 | 7/2001 | Jaynes |
| 6,258,571 | B1 | 7/2001 | Chumakov et al. |
| 6,261,554 | B1 | 7/2001 | Valerio et al. |
| 6,291,214 | B1 | 9/2001 | Richards et al. |
| 6,291,243 | B1 | 9/2001 | Fogarty et al. |
| 6,291,740 | B1 | 9/2001 | Bremel et al. |
| 6,303,568 | B1 | 10/2001 | Jaynes et al. |
| 6,316,692 | B1 | 11/2001 | Readhead et al. |
| 6,358,710 | B1 | 3/2002 | Graves et al. |
| 6,376,218 | B1 | 4/2002 | Hsu et al. |
| 6,376,743 | B1 | 4/2002 | Yanagimachi |
| 6,475,798 | B2 | 11/2002 | Fogarty et al. |

(Continued)

FOREIGN PATENT DOCUMENTS

AU        2003261096        1/2004

(Continued)

OTHER PUBLICATIONS

Ivarie R. Trends in Biotechnology, 2003, 21(1): 14-19.*
Mozdziak et al Developmental Dynamics, 2004, 229: 414-421.*
Lillico et al Drug Discovery Today, 2005, 10(3): 191-196.*
Ochiai H Poult Sci 1998 77(2): 299-302.*
Jeltsch et al Eur J Biochem. Feb. 1982;122(2):291-5.*
Sang et al Mech Dev. 2004, 121(9): 1179-86.*
Von Specht Dissertation, 2002, pp. 49-68.*
Abdel-Salam et al., "Expression of Mouse Anticreatine Kinase (MAK33) Monoclonal Antibody in the Yeast," *Appl. Microbiol. Biotechnol.*, 2001, vol. 56, 157-164.
Afanassieff et al., "Intratesticular Inoculation of Avian Leukosis Virus (ALV) in Chickens—Production of," *Avian Diseases*, 1996, 841-852.

(Continued)

*Primary Examiner* — Anoop Singh
(74) *Attorney, Agent, or Firm* — Kilpatrick Townsend & Stockton LLP

(57) ABSTRACT

Methods and compositions for the administration of transposon-based vectors to the reproductive organs of animals and the creation of transgenic animals. Preferred methods involve administration of the transposon-based vectors to the lumen of the oviduct of an avian, expression of a vector derived transgene in the avian, and deposition of the resultant polypeptide in an egg. This invention allows for large amounts of protein to be deposited in the egg.

17 Claims, 5 Drawing Sheets

U.S. PATENT DOCUMENTS

| | | | |
|---|---|---|---|
| 6,489,458 B2 * | 12/2002 | Hackett et al. | 536/23.2 |
| 6,492,510 B2 | 12/2002 | Hasebe et al. | |
| 6,503,729 B1 | 1/2003 | Bult et al. | |
| 6,514,728 B1 | 2/2003 | Kai et al. | |
| 6,515,199 B1 | 2/2003 | Petitte et al. | |
| 6,528,699 B1 | 3/2003 | Meade et al. | |
| 6,563,017 B2 | 5/2003 | Muramatsu et al. | |
| 6,602,686 B1 | 8/2003 | Harrington et al. | |
| 6,670,185 B1 | 12/2003 | Harrington et al. | |
| 6,716,823 B1 | 4/2004 | Tang et al. | |
| 6,730,822 B1 | 5/2004 | Ivarie et al. | |
| 6,759,573 B2 | 7/2004 | Olhoft et al. | |
| 6,825,396 B2 * | 11/2004 | MacArthur | 800/19 |
| 6,852,510 B2 | 2/2005 | Bremel et al. | |
| 6,939,959 B2 | 9/2005 | Hu | |
| 7,005,296 B1 | 2/2006 | Handler | |
| 7,019,193 B2 | 3/2006 | Ditullio et al. | |
| 7,034,115 B1 | 4/2006 | Kawakami | |
| 7,083,980 B2 | 8/2006 | Reznikoff et al. | |
| 7,105,343 B1 | 9/2006 | Fraser, Jr. et al. | |
| 7,129,390 B2 | 10/2006 | Ivarie et al. | |
| 7,160,682 B2 | 1/2007 | Hackett et al. | |
| 7,199,279 B2 | 4/2007 | Rapp | |
| 7,294,507 B2 | 11/2007 | Harvey et al. | |
| 7,335,761 B2 | 2/2008 | Harvey et al. | |
| 7,375,258 B2 | 5/2008 | Harvey et al. | |
| 7,381,712 B2 * | 6/2008 | Christmann et al. | 514/44 R |
| 7,527,966 B2 | 5/2009 | Cooper et al. | |
| 7,608,451 B2 | 10/2009 | Cooper | |
| 2001/0044937 A1 | 11/2001 | Schatten et al. | |
| 2002/0007051 A1 | 1/2002 | Cheo et al. | |
| 2002/0013955 A1 | 1/2002 | Ogden et al. | |
| 2002/0016975 A1 | 2/2002 | Hackett et al. | |
| 2002/0028488 A1 | 3/2002 | Singh et al. | |
| 2002/0028513 A1 | 3/2002 | Fogarty et al. | |
| 2002/0042137 A1 | 4/2002 | Richards et al. | |
| 2002/0052047 A1 | 5/2002 | Hasebe et al. | |
| 2002/0053092 A1 | 5/2002 | Readhead et al. | |
| 2002/0055172 A1 | 5/2002 | Harrington | |
| 2002/0056148 A1 | 5/2002 | Readhead et al. | |
| 2002/0072097 A1 | 6/2002 | deCardayre et al. | |
| 2002/0076797 A1 | 6/2002 | Lin | |
| 2002/0083479 A1 | 6/2002 | Winston et al. | |
| 2002/0099015 A1 | 7/2002 | Barber | |
| 2002/0104109 A1 | 8/2002 | Bremel et al. | |
| 2002/0108132 A1 | 8/2002 | Rapp | |
| 2002/0119573 A1 | 8/2002 | Shaw et al. | |
| 2002/0129398 A1 | 9/2002 | Winston et al. | |
| 2002/0132349 A1 | 9/2002 | Goryshin et al. | |
| 2002/0133835 A1 | 9/2002 | Winston et al. | |
| 2002/0138865 A1 | 9/2002 | Readhead et al. | |
| 2002/0148000 A1 | 10/2002 | Shen | |
| 2002/0150577 A1 | 10/2002 | Lee et al. | |
| 2002/0151034 A1 | 10/2002 | Zhang et al. | |
| 2002/0157125 A1 | 10/2002 | Lee et al. | |
| 2002/0160507 A1 | 10/2002 | Novy et al. | |
| 2002/0188105 A1 | 12/2002 | Craig | |
| 2002/0199214 A1 | 12/2002 | Rapp | |
| 2003/0009026 A1 | 1/2003 | Hasebe et al. | |
| 2003/0017534 A1 | 1/2003 | Buelow et al. | |
| 2003/0055017 A1 | 3/2003 | Schwarz et al. | |
| 2003/0056241 A1 | 3/2003 | Matsuda et al. | |
| 2003/0061629 A1 | 3/2003 | Sutrave | |
| 2003/0074680 A1 | 4/2003 | Lee et al. | |
| 2003/0074681 A1 | 4/2003 | Macarthur | |
| 2003/0101472 A1 | 5/2003 | Baltimore et al. | |
| 2003/0115622 A1 | 6/2003 | Ponce de Leon et al. | |
| 2003/0121062 A1 | 6/2003 | Radcliffe et al. | |
| 2003/0126628 A1 | 7/2003 | Harvey et al. | |
| 2003/0126629 A1 * | 7/2003 | Rapp et al. | 800/19 |
| 2003/0140363 A1 | 7/2003 | Rapp | |
| 2003/0143740 A1 | 7/2003 | Wooddell et al. | |
| 2003/0150006 A1 | 8/2003 | Petitte et al. | |
| 2003/0150007 A1 | 8/2003 | Savakis et al. | |
| 2003/0154502 A1 | 8/2003 | Wimmer et al. | |
| 2003/0167492 A1 | 9/2003 | Lee et al. | |
| 2003/0170888 A1 | 9/2003 | Van de Lavoir et al. | |
| 2003/0172387 A1 | 9/2003 | Zhu et al. | |
| 2003/0177516 A1 | 9/2003 | Horseman et al. | |
| 2003/0182672 A1 | 9/2003 | Graham et al. | |
| 2003/0182675 A1 | 9/2003 | Etches et al. | |
| 2003/0217375 A1 | 11/2003 | Zcharia et al. | |
| 2003/0221206 A1 | 11/2003 | Schatten et al. | |
| 2003/0224519 A1 | 12/2003 | Harrington et al. | |
| 2004/0006776 A1 | 1/2004 | Meade et al. | |
| 2004/0018624 A1 | 1/2004 | Harrington et al. | |
| 2004/0019922 A1 | 1/2004 | Ivarie et al. | |
| 2004/0040052 A1 | 2/2004 | Radcliffe et al. | |
| 2004/0142475 A1 | 7/2004 | Barman et al. | |
| 2004/0158882 A1 | 8/2004 | Ivarie et al. | |
| 2004/0172667 A1 | 9/2004 | Cooper et al. | |
| 2004/0197910 A1 | 10/2004 | Cooper et al. | |
| 2004/0203158 A1 | 10/2004 | Hackett et al. | |
| 2004/0210954 A1 | 10/2004 | Harvey et al. | |
| 2004/0226057 A1 | 11/2004 | Christmann et al. | |
| 2004/0235011 A1 | 11/2004 | Cooper et al. | |
| 2004/0255345 A1 | 12/2004 | Rapp et al. | |
| 2005/0003414 A1 | 1/2005 | Harvey et al. | |
| 2005/0004030 A1 | 1/2005 | Fishetti et al. | |
| 2005/0034186 A1 | 2/2005 | Harvey et al. | |
| 2005/0050581 A1 | 3/2005 | Harvey et al. | |
| 2005/0066383 A1 | 3/2005 | Harvey | |
| 2005/0176047 A1 | 8/2005 | Harvey et al. | |
| 2005/0198700 A1 | 9/2005 | Christmann et al. | |
| 2005/0208038 A1 | 9/2005 | Fischetti et al. | |
| 2005/0273872 A1 | 12/2005 | Sang et al. | |
| 2005/0273873 A1 | 12/2005 | Christmann et al. | |
| 2006/0046248 A1 | 3/2006 | Rapp et al. | |
| 2006/0121509 A1 | 6/2006 | Hermiston et al. | |
| 2006/0123488 A1 | 6/2006 | Ivarie et al. | |
| 2006/0123504 A1 | 6/2006 | Leavitt et al. | |
| 2006/0171921 A1 | 8/2006 | Ivarie et al. | |
| 2006/0185024 A1 | 8/2006 | Ivarie et al. | |
| 2006/0185029 A1 | 8/2006 | Ivarie et al. | |
| 2006/0188478 A1 | 8/2006 | Ivarie et al. | |
| 2006/0210977 A1 | 9/2006 | Kaminski | |
| 2006/0218652 A1 | 9/2006 | Horn et al. | |
| 2006/0236413 A1 | 10/2006 | Ivics et al. | |
| 2006/0258603 A1 | 11/2006 | Ivics et al. | |
| 2007/0009991 A1 | 1/2007 | Horseman et al. | |
| 2007/0022485 A1 | 1/2007 | Tadeda et al. | |
| 2007/0113299 A1 | 5/2007 | Harvey et al. | |
| 2007/0243165 A1 | 10/2007 | Ivarie | |
| 2008/0235813 A1 | 9/2008 | Cooper et al. | |
| 2010/0081789 A1 | 4/2010 | Cooper | |
| 2010/0093036 A1 | 4/2010 | Cooper | |
| 2010/0099148 A1 | 4/2010 | Cooper et al. | |
| 2010/0261227 A1 | 10/2010 | Cooper | |

FOREIGN PATENT DOCUMENTS

| | | |
|---|---|---|
| EP | 1375654 | 1/2004 |
| EP | 1364205 B1 | 5/2007 |
| EP | 1700914 A1 | 9/2008 |
| EP | 1539785 | 5/2009 |
| JP | 2000512149 | 9/2000 |
| JP | 2001513336 | 9/2001 |
| WO | WO-92/20316 | 11/1992 |
| WO | WO-93/24626 | 12/1993 |
| WO | WO-94/20608 | 9/1994 |
| WO | WO-95/31566 | 11/1995 |
| WO | WO-97/47739 | 12/1997 |
| WO | WO-99/09817 | 3/1999 |
| WO | WO-99/19472 | 4/1999 |
| WO | WO-99/40213 | 8/1999 |
| WO | WO-99/42569 | 8/1999 |
| WO | WO-00/11151 | 3/2000 |
| WO | WO-00/23579 | 4/2000 |
| WO | WO-00/30437 | 6/2000 |
| WO | WO-00/23579 A9 | 9/2000 |
| WO | WO-00/56932 | 9/2000 |
| WO | WO-01/14537 | 3/2001 |
| WO | WO-01/17344 | 3/2001 |
| WO | WO-01/19846 | 3/2001 |
| WO | WO-01/23525 | 4/2001 |
| WO | WO-01/26455 | 4/2001 |
| WO | WO-01/43540 | 6/2001 |
| WO | WO-01/71019 | 9/2001 |

| | | |
|---|---|---|
| WO | WO-01/73094 | 10/2001 |
| WO | WO-01/83786 | 11/2001 |
| WO | WO-01/85965 | 11/2001 |
| WO | WO-0202738 | 1/2002 |
| WO | WO-02/46430 | 6/2002 |
| WO | WO-02/47475 | 6/2002 |
| WO | WO-02/063293 | 8/2002 |
| WO | WO-03/014344 | 2/2003 |
| WO | WO-03/024199 | 3/2003 |
| WO | WO-03/025146 | 3/2003 |
| WO | WO-03/048364 A2 | 6/2003 |
| WO | WO-03/064627 | 8/2003 |
| WO | WO-2004/009792 A2 | 1/2004 |
| WO | WO-2004/047531 | 6/2004 |
| WO | WO-2004/065581 A2 | 8/2004 |
| WO | WO-2004/067707 A3 | 8/2004 |
| WO | WO-2004/067743 | 8/2004 |
| WO | WO-2004/080162 A2 | 9/2004 |
| WO | WO-2004/092351 | 10/2004 |
| WO | WO-2004/110143 | 12/2004 |
| WO | WO-2005/040215 A2 | 5/2005 |
| WO | WO-2005/062881 | 7/2005 |
| WO | WO-2005/084430 A1 | 9/2005 |
| WO | WO-2006/024867 A2 | 3/2006 |
| WO | WO-2006/026238 A2 | 3/2006 |
| WO | WO-2006/053245 A2 | 5/2006 |
| WO | WO-2006/055040 A2 | 5/2006 |
| WO | WO-2006/055931 A2 | 5/2006 |
| WO | WO-2006/065821 A2 | 6/2006 |
| WO | WO-2006/093847 | 9/2006 |
| WO | WO-2010118360 A1 | 10/2010 |

OTHER PUBLICATIONS

Alexeyev et al., "Mini-TN10 Transposon Derivatives for Insertion Mutagenesis and Gene Delivery into the Chromosome of Gram-negative Bacteria," *Gene*, 1995, vol. 160, 59-62.
Andra et al., "Generation and Characterization of Transgenic Mice Expressing Cobra Venom," *Molecular Immunology*, 2002, vol. 39, 357-365.
Araki et al., "Site-Specific Recombination of a Transgene in Fertilized Eggs by Transient," *Proc. Natl. Acad. Sci. USA*, 1995, vol. 92, 160-164.
Argaud et al., "Regulation of Rat Liver Glucose-6-Phosphatase Gene Expression in Different," *Diabetes*, Nov. 1996, 1563-1571.
AU 2003261096 Examiner's First Report dated Jun. 7, 2007.
AU 2003261096 Response to Examiner's First Report dated May 12, 2008.
AU 2003261096 Examiner's Second Report dated Jun. 6, 2008.
AU 2003261096 Response to Examiner's Second Report dated Sep. 8, 2008.
Awade et al., "Comparison of Three Liquid Chromatographic Methods for Egg-White Protein," *Journal of Chromatography B.*, 1999, vol. 723, 69-74.
Awade, "On Hen Egg Fractionation: Applications of Liquid Chromatography to the Isolation and," *Z Lebensm Unters Forsch*, 1996, vol. 202, 1-14.
Beardsley, "Gene Therapy Setback: A Tragic Death Clouds the Future of an Innovative Treatment," *Scientific American*, Jun. 11, 2001, No. 2.
Bell et al., "Nucleotide Sequence of a cDNA Clone Encoding Human Preproinsulin," *Nature*, Nov. 29, 1979, vol. 282, 525-527.
Bolli et al., "Insulin Analogues and Their Potential in the Management of Diabetes Mellitus," *Diabetologia*, 1999, vol. 42, 1151-1167.
Brinster, "Germline Stem Cell Transplantation and Transgenesis," *Science* Jun. 21, 2002, vol. 296, 2174-2176.
Chatterjee et al., "Retrofitting High Molecular Weight DNA Cloned in P1: Introduction of Reporter," *Genetic Analysis: Biomolecular*, 1994, vol. 13, 33-42.
Ciampi et al., "Transposon Tn10 Provides a Promoter for Transcription of Adjacent Sequences," *Proc Natl Acad Sci USA*, Aug. 1982, vol. 79, No. 16, 5016-5020.
Ciftci et al., "Applications of Genetic Engineering in Veterinary Medicine," *Advanced Drug Delivery Reviews*, 2000, vol. 43, 57-64.
Davis, C. G., "The Many Faces of Epidermal Growth Factor Repeats," *New Biologist*, May 1990, 2(5), 410-419.
Davis, M. A. et al., "Tn10 Protects Itself at Two Levels from Fortuitous Activation by External Promoters," *Cell*, Nov. 11, 1985, vol. 43, No. 1, 379-387.
DeMatteo et al., "Engineering Tissue-Specific Expression of a Recombinant Adenovirus: Selective," *Journal of Surgical Research*, 1997, vol. 72, 155-161.
Desert et al., "Comparisons of Different Electrophoretic Separations of Hen Egg White Proteins," *J. Agric. Food Chem.*, 2001, vol. 49, 4553-4561.
Dierich et al., "Cell-Specificity of the Chicken Ovalbumin and Conalbumin Promoters," *EMBO. Journal*, 1987, 6(8), 2305-2312.
Dobeli et al., "Recombinant Fusion Proteins for the Industrial Production of Disulfide Bridge Containing Peptides: Purification, Oxidation without Concatamer Formation, and Selective Cleavage," *Protein Expression and Purification*, 1998, 12, 404-414.
Dong et al., "Hepatic Insulin Production Type-1 Diabetes," *Trends in Endocrinology*, Dec. 2001, vol. 12, 441-446.
Dunham et al., "Enhanced Bacterial Disease Resistance of Transgenic Channel Catfish *Ictalurus punctatus* Possessing Cecropin Genes," *Marine Biotechnology*, Jun. 2002, Springer Verlag, New York, NY, US, vol. 4, No. 3, 38-344.
Dupuy et al., "Mammalian Germ-like Transgenesis by Transposition," *PNAS*, Apr. 2, 2002, vol. 99, 4495-4499.
Ebara et al., "In Vivo Gene Transfer into Chicken Embryos via Primordial Germ Cells Using Green," *Journal of Reproduction*, 2000, vol. 46, 79-83.
Ebara et al., "Possible Abnormalities of Chimeric Chicken Caused by the Introduction of," *Asian-Aus. J. Anim. Sci.*, 2000, vol. 13, 1514-1517.
Eggleston et al., "A Sensitive and Rapid Assay for Homologous Recombination in Mosquito Cells," *BMC Genetics*, Dec. 17, 2001, vol. 2, No. 21, 1-9.
EP 037621729 Supplementary Search Report dated Feb. 15, 2006.
EP 037621729 First Office Action dated Jun. 9, 2006.
EP 037621729 Response to First Office Action dated Oct. 18, 2006.
EP 037621729 Second Office Action dated Nov. 23, 2006.
EP 037621729 Response to Second Office Action dated Apr. 2, 2007.
EP 037621729 Third Office Action dated Apr. 24, 2007.
EP 037621729 Response to Third Office Action dated Aug. 31, 2007.
EP 037621729 Fourth Office Action dated Oct. 10, 2007.
EP 037621729 Response to Fourth Office Action dated Feb. 11, 2008.
EP 037621729 Fifth Office Action dated Feb. 26, 2008.
EP 037621729 Response to Fifth Office Action dated Jul. 4, 2008.
EP 037621729 Communication Under Rule 71(3) EPC dated Nov. 11, 2008.
EP 038002259 Supplementary Partial Search Report dated May 26, 2006.
EP 038002259 Office Action dated Aug. 30, 2006.
EP 038002259 Response to Office Action dated Oct. 17, 2006.
EP 038002259 Second Office Action dated Jun. 14, 2007.
EP 038002259 Response to Second Office Action dated Oct. 23, 2007.
EP 038002259 Third Office Action dated Nov. 7, 2007.
EP 038002259 Response to Third Office Action dated Mar. 17, 2008.
EP 038002259 Fourth Office Action dated Mar. 31, 2008.
EP 038002259 Response to Fourth Office Action dated May 30, 2008.
EP 038002259 Communication Under Rule 71(3) EPC dated Aug. 19, 2008.
EP 038085635 Communication Pursuant to Rules 109 and 110 EPC dated Oct. 5, 2005.
EP 038085635 Response to Communication dated Oct. 18, 2005.
EP 038085635 Supplementary Partial Search Report dated Jan. 23, 2007.
EP 038085635 Supplementary Search Report dated Apr. 12, 2007.
EP 038085635 Office Action dated May 2, 2007.
Etches et al., "Gene Transfer: Overcoming the Avian Problems (Abstract Provided)," *Proceedings, 5th World Congress*, Aug. 1994, vol. 20, 97-101.
Etches et al., "Manipulation of the Avian Genome," 1993, pp. 15-28, 81-101, 103-119, 121-133, 165-184, 205-222, 223-230.
Etches et al., "Strategies for the Production of Transgenic Chicken," *Methods in Molecular Biology*, 1997, vol. 62, 433-450.

Falqui et al., "Reversal of Diabetes in Mice by Implantation of Human Fibroblasts Genetically Engineered to Release Mature Human Insulin," *Human Gene Therapy*, Jul. 20, 1999, vol. 10, 1753-1762.

Fischer, R. et al., "Antibody Production by Molecular Farming in Plants," *Journal of Biological Regulators and Hoeostatic Agents*, Apr. 2000, vol. 14, No. 2, 83-92, Wichtig Editore, Milan, IT.

Fischer, S. et al., "Regulated Transposition of a Fish Transposon in the Mouse Germ Line," *Proc. Natl. Acad. Sci. USA*, 2001, vol. 98, No. 12, 6759-6764.

Fisher et al., "Induction of Terminal Differentiation in Cancer Cells as a Therapeutic Modality for Suppressing Tumor Growth: Studies Employing Human Melanoma," *Anticancer Research*, 1988, vol. 8 (5B), 1057.

Fong et al., "The Genes for Benzene Catabolism in *Pseudomonas putida* ML2 are Flanked by Two," *Plasmid*, Mar. 2000, vol. 43, No. 2, 103-110.

Gaub et al., "The Chicken Ovalbumin Promoter is Under Negative Control which is Relieved by Steroid Hormones," *EMBO. Journal*, 1987, 6(8), 2313-2320.

"Gene Therapy a Suspect in Leukemia-Like Disease," *Science*, News of the Week Oct. 4, 2002.

Ghosh et al., "Liver-Directed Gene Therapy: Promises, Problems and Prospects at the Turn of the," *Journal of Hepatology*, 2000, vol. 32, 238-252.

Gibbins, "Chickens as Bioreactors—Harvesting Commercially-Valuable Proteins from the Egg," *Agri-Food Research in Ontario*, 1996, 39-41.

Gibbins et al., "Exploring the Product Possibilities Arising from Transgenic Poultry Technology," *Kungl. Skogs-och*, 1997, vol. 136, 57-68.

Gibbins et al., "Genetically-Engineered Poultry," *Lohmann Information*, 1997, No. 21, 3-6.

Gibbins, "The Chicken, the Egg, and the Ancient Mariner," *Nat. Biotechnol.*, 1998, vol. 16, 1013-1014.

Gibbins, "Transgenic Poultry Technology and Food Production," *Animal Biotechnology*, 1998, vol. 9, No. 3, 173-179.

Giddings, "Transgenic Plants as Protein Factories," *Current Opinion in Biotechnology*, Oct. 2001, vol. 12, No. 5, 450-454, London, GB.

Ginsberg et al., "The Road Ahead for Biologics Manufacturing," *Equity Research*, 2002, 1-23.

Hackett et al., "Development of Genetic Tools for Transgenic Animals," *Transgenic Animals in Agriculture*, 1999, 19-35.

Han et al., "Gene Transfer by Manipulation of Primordial Germ Cells in the Chicken," *AJAS*, 1994, vol. 7, No. 3, 427-434.

Harvey et al., "Expression of Exogenous Protein in the White Egg of Transgenic Chickens," *Nature Biotechnology*, Apr. 2002, vol. 19, 396-399.

Heilig et al., "NCBI Accession No. V00437-Gallus Gallus Fragment of Ovalbumin Gene Coding for the First Leader Exon.," 1997.

Heilig et al., "The Ovalbumin Gene Family, The 5' End Region of the X and Y Genes," *J. Mol. Bio.*, 1982, vol. 156, No. 1, 1-19.

Hermann et al., "Lipoprotein Receptors in Extraembryonic Tissues of the Chicken," *J. Biol. Chem.*, Jun. 2000, vol. 275, 16837-16844.

Herrero et al., "Transposon Vectors containing Non-Antibiotic Resistance Selection Markers for Cloning and Stable Chromosomal Insertion of Foreign Genes in Gram-Negative Bacteria," *Journal of Bacteriology*, 1990, vol. 172, No. 11, 6557-6567.

Hillel et al., "Strategies for the Rapid Introgression of a Specific Gene Modification into a," *Poultry Science*, 1993, vol. 72, 1197-1211.

Hong et al., "Improved Transfection Efficiency of Chicken Gonadal Primordial Germ Cells for the," *Transgenic Research*, 1998, vol. 7, 247-252.

Horn et al., "A Versatile Vector Set for Animal Transgenesis," *Development Genes and Evolution*, 2000, vol. 210, No. 12, 630-637.

Houdebine, "The Methods to Generate Transgenic Animals and to Control Transgene Expression," *J. Biotechnol.*, Sep. 25, 2002, vol. 98, 145-160.

Houdebine, "Transgenic Animal Bioreactors," *Transgenic Research*, Oct. 2000, vol. 9, No. 4-5, 305-320.

IN 99/KOL NP/2005 Official Action dated Jun. 17, 2006.

Ivarie et al., "Avian Transgenesis: Progress Towards the Promise," *Trends in Biotech*, 2003, vol. 21, No. 1, 14-19.

Izsvak et al., "Sleeping Beauty, A Wide Host-Range Transposon Vector for Genetic Transformation," *J. Mol. Biol.*, 2000, vol. 302, 93-102.

Jarvis et al., "Influence of Different Signal Peptides and Prosequences on Expression and," *The Journal of Biological Chemistry*, Aug. 5, 1993, vol. 268, No. 22, 16754-16762.

Jeltsch et al., "The Complete Nucleotide Sequence of the Chicken Ovotransferrin mRNA," *Eur.J. Biochem*, 1982, 122, 291-295.

Kaminski et al., "Design of a Nonviral Vector for Site-Selective, Efficient Intregration into the Human," *The FASEB Journal*, Aug. 2002, vol. 16, 1242-1247.

Kanda et al., "Genetic Fusion of an a-Subunit Gene to the Follicle-Stimulating Hormone and," *Molecular Endocrinology*, Nov. 1999, vol. 13, No. 11, 1873-1881.

Kay et al., "Viral Vectors for Gene Therapy: the Art of Turning Infectious Agents into Vehicles of Therapeutics," *Nature Medicine*, Jan. 2001, vol. 7 No. 1, 33-40.

Kleckner et al., "Transposon Tn10: Genetic Organization, Regulation and Insertion Specificity," *Fed Proc*, Aug. 1982, vol. 41, No. 10, 2649-2652.

Kluin et al., "Proliferation of Spermatogonia and Sertoli Cells in Maturing Mice," *Anat. Embryol.*, 1984, vol. 169, 73-78.

Koga et al., "The Medaka Fish Tol2 Transposable Element can Undergo Excision in Human and," *J Hum Genet*, Mar. 28, 2003, vol. 48, No. 5, 231-235.

Kousteni et al., "Reversal of Bone Loss in Mice by Nongenotropic Signaling of Sex Steroids," *Science*, Oct. 25, 2002, vol. 298, 843-846.

Kozak, "At Least Six Nucleotides Preceding the AUG Initiator Codon Enhance Translation in," *J. Mol. Biol.*, 1987, vol. 196, 947-950.

Kozak, "Initiation of Translation in Prokaryotes and Eukaryotes," *Gene*, 1999, vol. 234, 187-208.

Kumaran et al., "The Normal Development of the Testes in the White Plymouth Rock," *Testis Development in White*, 1948, 511-519.

Lampe et al., "Hyperactive Transposase Mutants of the Himar1 Mariner Transposon," *Proc. Natl. Acad. Sci. USA*, Sep. 1999, vol. 96, 11428-11433.

Marshak et al., "Purification of the Beta-Cell Glucose-Sentitive Factor that Transactivates the Insulin," *Proc. Natl. Acad. Sci. USA*, Dec. 1996, vol. 93, 15057-15062.

Massoud et al., "The Deleterious Effects of Human Erythropoietin Gene Driven by the Rabbit Whey Acidic Protein Gene Promoter in Transgenic Rabbits," *Reprod Nutr Dev*, 1996, 36(5), 555-563.

Mather et al., "The Mariner Transposable Element: A Potential Vector for Improved Integration of," *British Poulty Science*, Sep. 2000, vol. 41, S27-S28.

Meiss et al., "Vectors for Dual Expression of Target Genes in Bacterial and Mammalian Cells," *BioTechniques*, 2000, vol. 29, No. 3, 476, 478, 480.

Mohammed et al., "Deposition of Genetically Engineered Human Antibodies into the Egg Yolk of Hens," *Immunotechnology*, 1998, vol. 4, 115-125.

Monroe et al., "The COUP-Adjacent Repressor (CAR) Element Participates in the Tissue-Specific," *Biochemica et Biophysica Acta*, 2000, vol. 1517, 27-32.

Muramatsu et al., "Regulation of Ovalbumin Gene Expression," *Poultry and Avian Biology*, 1995, vol. 6, No. 2, 107-123.

Muzzin et al., "Hepatic Insulin Gene Expressions as Treatment for aType 1 Diabetes Mellitus in Rats," *Mol Endo*, 1997, vol. 11, 833-837.

Nicklin et al., "Analysis of Cell-Specific Promoters for Viral Gene Therapy Targeted at the Vascular," *Hypertension*, 2001, vol. 38, 65-70.

Oakberg, "Duration of Spermatogenesis in the Mouse and Timing of Stages of the Cycle of the," *Duration of Spermatogenesis*, 507-516.

Ochiai et al., "Synthesis of Human Erythropoietin in Vivo in the Oviduct of Laying Hens by," *Poultry Science*, 1998, vol. 77, No. 2, 299-302.

Ono et al., "Gene Transfer into Circulating Primorial Germ Cells of Quail Embryos," *Exp. Anim.*, 1995, vol. 4, No. 4, 275-278.

Osborne et al., "A System for Insertional Mutagenesis and Chromosomal Rearrangement Using the," *Plant J.*, Apr. 1995, vol. 7, No. 4, 687-701.

Pain et al., "Chicken Embryonic Stem Cells and Transgenic Strategies," *Cell Tissues Organs*, 1999, vol. 165, 212-219.
Park, "COUP-TF Plays a Dual Role in the Regulation of the Ovalbumin Gene," *Biochemistry*, 2000, vol. 39, 8537-8545.
PCT/US03/20389 Written Opinion dated Jun. 17, 2004.
PCT/US03/41261 International Search Report dated Nov. 3, 2004.
PCT/US03/41269 International Search Report dated May 18, 2004.
PCT/US03/41335 International Search Report dated Nov. 3, 2004.
PCT/US04/43092 International Search Report and Written Opinion dated May 11, 2006.
Phan et al., "Structural Basis for the Substrate Specificity of Tobacco Etch Virus Protease," *Journal of Biological Chemistry*, Dec. 27, 2002, vol. 277, 50564-50572.
Pieper, et al., "Restoration of Vascular Endothelial Function in Diabetes," *Diabetes Res. Clin. Pract. Suppl.*, 1996, S157-S162.
Platon et al., "A Shortage of Monoclonal Antibody Manufacturing Capacity," *Pharmaceutical Fine Chemicals and BioMolecule Manufacturing Report*, 2002, Pharma Ventures Ltd.
Prudhomme et al., "Diversity of Tn4001 Transposition Products: the Flanking IS256 Elements can form," *J Bacteriol*, 2002, vol. 184, No. 2, 433-443.
Qiu, "Spatiotemporal Expression Patterns of Chicken Ovalbumin Upstream Promoter," *Proc. Natl. Acad. Sci.*, 1994, vol. 91, 4451-4455.
Richardson, "Gene Repair and Transposon-Mediated Gene Therapy," *Stem Cells*, 2002, vol. 20, 112-115.
Sakai et al., "Two Classes of Tn10 Transposase Mutants that Suppress Mutations in the Tn10," *Genetics*, Nov. 1996, vol. 144, No. 3, 861-870.
Sang et al., "Prospects for Transgenesis in the Chick," *Mech. Dev.*, 2004, 121(9):1179-86.
Sarmasik et al., "Transgenic Live-Bearing Fish and Crustaceans Produced by Transforming Immature," *Marine Biotechnology*, 2001, vol. 3, No. 5, 470-477.
Sasakawa et al., "Control of Transposon Tn5 Transposition in *Escherichia coli*," *Prod Natl Acad Sci USA*, Dec. 1982, vol. 79, No. 23, 7450-7454.
Schillberg et al., "Apoplastic and Cytosolic Expression of Full-Size Antibodies and Antibody Fragments in *Nicotiana tabacum*," *Transgenic Research*, Aug. 1999, vol. 8, No. 4, 255-263.
Schillberg et al., "Molecular Farming of Recombinant Antibodies in Plants," *CMLS Cellular and Molecular Life Sciences*, Mar. 2003, Birkhauser Verlag, Heidelberg, DE, vol. 60, No. 3, 433-445.
Schlenstedt et al., "Structural Requirements for Transport of PreprocecropinA and Related Presecretory," *The Journal of Biological Chemistry*, Dec. 5, 1992, vol. 236, No. 34, 24328-24332.
Schneider et al., "An Epitope Tagged Mammalian / Prokaryotic Expression Vector with Positive," *Gene: An International Journal on*, 1997, vol. 197, 337-341.
Schultz et al., "Translation Initiation of IS50R Read-through Transcripts," *J. Mol. Biol*, 1991, vol. 221, 65-80.
Seal et al., "Mutational Studies Reveal a Complex Set of Positive and Negative Control Elements," *Mol. Cell Biol.*, May 1991, vol. 11, 2704-2717.
Sekine et al., "DNA Sequences Required for Translational Frameshifting in Production of the," *Mol Gen Genet*, Nov. 1992, vol. 235, No. 2-3, 325-332.
Sekine et al., "Identification of the Site of Translational Frameshifting Required for Production of the," *Mol Gen Genet*, Nov. 1992 , vol. 235, No. 2-3, 317-324.
Sharma et al., "Pancreatic Islet Expression of the Homeobox Factor STF-1 Relies on and E-box," *Journal of Biological Chemistry*, Jan. 26, 1996, vol. 271, 2294-2299.
Sherman et al., "Transposition of the *Drosophila* Element Mariner into the Chicken Germ Line," *Nature Biotechnology*, Nov. 1, 1998, vol. 16, 1050-1053.
Sherratt, "Tn3 and Related Transposable Elements: Site-Specific Recombination and," *Mobile DNA*, 1989, 163-184.
Simons et al., "Translational Control of IS10 Transposition," *Cell*, Sep. 1, 1983, vol. 34, No. 2, 683-691.
Skolnik et al., "From Genes to Protein Structure and Function: Novel Applications of Computational Approaches in the Genomic Era," *Trends in Biotech.*, 2000, 18:34-39.

Slowinski et al., "Pattern of Prepo-Endothelin-1 Expression Revealed by Reporter-Gene Activity in," *Clinical Science*, 2002, vol. 103, Supp. No. 48, 445-475.
Vilen et al., "Construction of Gene-Targeting Vectors: a Rapid Mu in Vitro DNA Transposition," *Transgenic Research*, 2001, vol. 10, 69-80.
Von Specht, English Translation of Dissertation entitled "Expression of a Recombinant Human Protein in Vitro and in Vivo in Oviduct Cells of Chickens, with Human Erythroprotein (hrEPO) as an Example," 2002, 49-68.
Von Specht, Dissertation entitled "Expression Eines Rekombinanten Humanen Proteins in Vitro and in Vivo in," 2002, 49-68.
Wallace et al., *Biology the Science of Life*, 1986, vol. 2, 235.
Wang et al., "Activation of Silent Genes by Transposons Tn5 and Tn10," *Genetics*, Dec. 1988, vol. 120, No. 4, 875-885.
Williamson et al., "Expression of the Lysostaphin Gene of *Staphylococcus* Simulans in a Eukaryotic System," *Appl. Environ. Microbil.*, Mar. 1994, 60(3), 771-776.
Xanthopoulos et al., "The Structure of the Gene for Cecropin B, an Antibacterial Immune Protein from," *European Journal of Biochemistry*, 1988, vol. 172, 371-376.
Zagoraiou, "In Vivo Transposition of Minos, a *Drosophila* Mobile Element, in Mammalian Tissues," *Proc. Natl. Acad. Sci. USA*, 2001, vol. 98, No. 20, 11474-11478.
Zhukova et al., "Expression of the Human Insulin Gene in the Gastric G Cells of Transgenic Mice," *Transgenic Research*, 2001, vol. 10, 329-338.
JP2004-518011 First Office Action mailed Sep. 8, 2009.
JP 2004-518011 Final Decision of Rejection dated Mar. 2, 2010.
Canadian Application No. 2,490,693, Response to Office Action filed Nov. 4, 2010.
Canadian Application No. 2,490,693, Office Action dated Dec. 30, 2010.
Canadian Application No. 2,490,693, Response to Office Action filed Mar. 7, 2011.
Canadian Application No. 2,490,693, Notice of Allowance dated Mar. 24, 2011.
Sarkar, et al., "Insulated piggyBac vectors for insect transgenesis" BMC Biotechnology, 2006, 6(27):1-9.
Blatt, LM et al., "Human variant interferon-alpha 2b protein SEQ ID No. 1440.", Database Geneseq [Online] Derwent;XP002601423 Dec. 13, 2007.
Canadian Patent Application No. 2,490,693, Office Action issued May 4, 2010, 3 pages.
Kwaks, T. H. et al., ""Employing epigenetics to augment the expression of therapeutic proteins in mammalian cells"", Trends in Biotechnology, Elsevier Publications, Cambridge, GB LNKDD0I: 10.1016/J.Tibtech Mar. 1, 2006 , pp. 137-142.
International Application No. PCT/US2009/058498, International Search Report and Written Opinion mailed on Oct. 6, 2010, 16 Pages.
International Application No. PCT/US2010/030589, International Search Report and Written Opinion, mailed on Sep. 24, 2010, 26 Pages.
U.S. Appl. No. 12/757,591, Office Action mailed Apr. 6, 2012 (12 pages).
U.S. Appl. No. 12/941,448, Notice of Allowance mailed Apr. 17, 2012 (13 pages).
Australian Patent Application No. 2003261096, Notice of Acceptance, dated Sep. 25, 2008.
Canadian Patent Application No. 2490693, Office Action, mailed Oct. 5, 2009.
Canadian Patent Application No. 2490693, Response to Office Action, filed Apr. 1, 2010.
U.S. Appl. No. 10/609,019, Office Action, mailed Dec. 27, 2005 (15 pages).
U.S. Appl. No. 10/609,019, Office Action, mailed Jun. 26, 2006 (13 pages).
U.S. Appl. No. 10/609,019, Office Action, mailed Nov. 7, 2006 (11 pages).
U.S. Appl. No. 10/609,019, Office Action, mailed May 4, 2007 (12 pages).
U.S. Appl. No. 10/609,019, Office Action, mailed Oct. 17, 2007 (18 pages).

U.S. Appl. No. 10/609,019, Office Action, mailed Feb. 12, 2008 (26 pages).
U.S. Appl. No. 10/609,019, Notice of Allowance, mailed Jan. 9, 2009 (9 pages).
U.S. Appl. No. 10/746,149, Office Action, mailed Aug. 9, 2006 (38 pages).
U.S. Appl. No. 10/746,149, Office Action, mailed Feb. 28, 2007 (29 pages).
U.S. Appl. No. 10/746,149, Office Action, mailed Oct. 18, 2007 (21 pages).
U.S. Appl. No. 10/746,149, Office Action, mailed Feb. 8, 2008 (25 pages).
U.S. Appl. No. 10/746,149, Office Action, mailed Aug. 20, 2008 (31 pages).
U.S. Appl. No. 10/746,149, Office Action, mailed Feb. 3, 2009 (22 pages).
U.S. Appl. No. 11/981,574, Office Action, mailed Jan. 7, 2009 (19 pages).
U.S. Appl. No. 11/981,574, Office Action, mailed Jun. 24, 2009 (8 pages).
U.S. Appl. No. 11/981,574, Notice of Allowance, mailed Aug. 10, 2009 (7 pages).
U.S. Appl. No. 12/567,214, Office Action mailed Apr. 2, 2012 (4 pages).
U.S. Appl. No. 12/567,334, Request for Continued Examination and Response to Office Action filed Apr. 3, 2012 (16 pages).
U.S. Appl. No. 12/567,334, Response to Office Action filed Feb. 6, 2012 (13 pages).
U.S. Appl. No. 12/567,334, Response to Office Action filed Jul. 13, 2011 (9 pages).
U.S. Appl. No. 12/567,513, Request for Continued Examination and Response to Office Action filed Apr. 3, 2012 (16 pages).
U.S. Appl. No. 12/567,513, Response to Office Action mailed Feb. 6, 2012 (12 pages).
U.S. Appl. No. 12/567,513, Response to Office Action mailed Jul. 13, 2011 (9 pages).
U.S. Appl. No. 12/941,448, Response to Office Action filed Feb. 23, 2012 (10 pages).
U.S. Appl. No. 12/941,448, Supplemental Response to Office Action filed Apr. 4, 2012 (16 pages).
European Patent Application No. 09815462.8, Response to Office Action, filed Nov. 16, 2011 (10 pages).
Gasser, et al., "A glimpse at chromosomal order", TIG, 1987, (3) 16-22.
Schubeler, et al., "Scaffold/Matrix-Attached Regions Act upon Transcription in a Context-Dependent Manner", Biochemistry, 1996, 35: 11160-11169.

* cited by examiner

FIGURE 4

| IS | Tet; Pro | Ovgen | Pro | Ovotrans | Pro | Ovomucin | IS |

ADMINISTRATION OF TRANSPOSON-BASED VECTORS TO REPRODUCTIVE ORGANS

This application is a continuation application of U.S. patent application Ser. No. 10/746,149 filed Dec. 24, 2003, now abandoned, and is a continuation-in-part application of 10/609,019 filed Jun. 26, 2003, now U.S. Pat. No. 7,527,966, dated May 5, 2009, which claims benefit to Provisional Patent Application No. 60/441,392 filed Jan. 21, 2003, Provisional Patent Application No. 60/441,377 filed Jan. 21, 2003, Provisional Patent Application No. 60/441,502 filed Jan. 21, 2003, Provisional Patent Application No. 60/441,405 filed Jan. 21, 2003, Provisional Patent Application No. 60/441,447 filed Jan. 21, 2003, Provisional Patent Application No. 60/441,381 filed Jan. 21, 2003, and Provisional Patent Application No. 60/392,415 filed Jun. 26, 2002.

The U.S. Government has certain rights in this invention. The development of this invention was partially funded by the United States Government under a HATCH grant from the United States Department of Agriculture, partially funded by the United States Government with Formula 1433 funds from the United States Department of Agriculture and partially funded by the United States Government under contract DAAD 19-02016 awarded by the Army.

FIELD OF THE INVENTION

The present invention relates generally to administration of a transposon-based vector to the reproductive tract in an animal. The reproductive tract includes an ovary, ova within an ovary, and an oviduct. Such administration results in incorporation of a gene of interest contained in the vector in the ovary, the oviduct or an ovum of the animal. In some embodiments, the present invention further includes production of a protein encoded by the gene in an egg produced by the animal.

BACKGROUND OF THE INVENTION

Transgenic animals are desirable for a variety of reasons, including their potential as biological factories to produce desired molecules for pharmaceutical, diagnostic and industrial uses. This potential is attractive to the industry due to the inadequate capacity in facilities used for recombinant production of desired molecules and the increasing demand by the pharmaceutical industry for use of these facilities. Numerous attempts to produce transgenic animals have met several problems, including low rates of gene incorporation and unstable gene incorporation. Accordingly, improved gene technologies are needed for the development of transgenic animals for the production of desired molecules.

Improved gene delivery technologies are also needed for the treatment of disease in animals and humans. Many diseases and conditions can be treated with gene-delivery technologies, which provide a gene of interest to a patient suffering from the disease or the condition. An example of such disease is Type 1 diabetes. Type 1 diabetes is an autoimmune disease that ultimately results in destruction of the insulin producing β-cells in the pancreas. Although patients with Type 1 diabetes may be treated adequately with insulin injections or insulin pumps, these therapies are only partially effective. Insulin replacement, such as via insulin injection or pump administration, cannot fully reverse the defect in the vascular endothelium found in the hyperglycemic state (Pieper et al., 1996. Diabetes Res. Clin. Pract. Suppl. S157-S162). In addition, hyper- and hypoglycemia occurs frequently despite intensive home blood glucose monitoring. Finally, careful dietary constraints are needed to maintain an adequate ratio of calories consumed. This often causes major psychosocial stress for many diabetic patients. Development of gene therapies providing delivery of the insulin gene into the pancreas of diabetic patients could overcome many of these problems and result in improved life expectancy and quality of life.

Several of the prior art gene delivery technologies employed viruses that are associated with potentially undesirable side effects and safety concerns. The majority of current gene-delivery technologies useful for gene therapy rely on virus-based delivery vectors, such as adeno and adeno-associated viruses, retroviruses, and other viruses, which have been attenuated to no longer replicate. (Kay, M. A., et al. 2001. Nature Medicine 7:33-40).

There are multiple problems associated with the use of viral vectors. Firstly, they are not tissue-specific. In fact, a gene therapy trial using adenovirus was recently halted because the vector was present in the patient's sperm (Gene trial to proceed despite fears that therapy could change child's genetic makeup. The New York Times, Dec. 23, 2001). Secondly, viral vectors are likely to be transiently incorporated, which necessitates re-treating a patient at specified time intervals. (Kay, M. A., et al. 2001. Nature Medicine 7:33-40). Thirdly, there is a concern that a viral-based vector could revert to its virulent form and cause disease. Fourthly, viral-based vectors require a dividing cell for stable integration. Fifthly, viral-based vectors indiscriminately integrate into various cells, which can result in undesirable germline integration. Sixthly, the required high titers needed to achieve the desired effect have resulted in the death of one patient and they are believed to be responsible for induction of cancer in a separate study. (Science, News of the Week, Oct. 4, 2002).

Accordingly, what is needed is a new method to produce transgenic animals and humans with stably incorporated genes, in which the vector containing those genes does not cause disease or other unwanted side effects. There is also a need for DNA constructs that would be stably incorporated into the tissues and cells of animals and humans, including cells in the resting state that are not replicating. There is a further recognized need in the art for DNA constructs capable of delivering genes to specific tissues and cells of animals and humans.

When incorporating a gene of interest into an animal for the production of a desired protein or when incorporating a gene of interest in an animal or human for the treatment of a disease, it is often desirable to selectively activate incorporated genes using inducible promoters. These inducible promoters are regulated by substances either produced or recognized by the transcription control elements within the cell in which the gene is incorporated. In many instances, control of gene expression is desired in transgenic animals or humans so that incorporated genes are selectively activated at desired times and/or under the influence of specific substances. Accordingly, what is needed is a means to selectively activate genes introduced into the genome of cells of a transgenic animal or human. This can be taken a step further to cause incorporation to be tissue-specific, which prevents widespread gene incorporation throughout a patient's body (animal or human). This decreases the amount of DNA needed for a treatment, decreases the chance of incorporation in gametes, and targets gene delivery, incorporation, and expression to the desired tissue where the gene is needed to function. What is also needed is a rapid expression method for rapidly producing a protein or peptide of interest in eggs and milk of transgenic animals.

SUMMARY OF THE INVENTION

The present invention addresses the problems described above by providing new, effective and efficient compositions for producing transgenic animals and for treating disease in animals or humans. Transgenic animals include all egg-laying animals and milk-producing animals. Transgenic animals further include but are not limited to avians, fish, amphibians, reptiles, insects, mammals and humans. In another preferred embodiment, the animal is a milk-producing animal, including but not limited to bovine, porcine, ovine and equine animals. In a preferred embodiment, the animal is an avian animal. In another preferred embodiment, the animal is a mammal. Animals are made transgenic through administration of a composition comprising a transposon-based vector designed for incorporation of a gene of interest for production of a desired protein, together with an acceptable carrier. The compositions of the present invention are introduced into the reproductive system of an animal. The compositions of the present invention are administered to a reproductive organ including, but not limited to, an oviduct, an ovary, or into the duct system of the mammary gland. The compositions of the present invention are may be administered to a reproductive organ of an animal through the cloaca. The compositions of the present invention may be directly administered to a reproductive organ or can be administered to an artery leading to the reproductive organ. In a preferred embodiment, the compositions of the present invention are introduced into the reproductive system of an avian animal. In another preferred embodiment, the compositions of the present invention are introduced into the intramammary duct system of a mammal. A transfection reagent is optionally added to the composition before administration.

The transposon-based vectors of the present invention include a transposase, operably-linked to a first promoter, and a coding sequence for a protein or peptide of interest operably-linked to a second promoter, wherein the coding sequence for the protein or peptide of interest and its operably-linked promoter are flanked by transposase insertion sequences recognized by the transposase. The transposon-based vector also includes the following characteristics: a) one or more modified Kozak sequences at the 3' end of the first promoter to enhance expression of the transposase; b) modifications of the codons for the first several N-terminal amino acids of the transposase, wherein the nucleotide at the third base position of each codon is changed to an A or a T without changing the corresponding amino acid; c) addition of one or more stop codons to enhance the termination of transposase synthesis; and/or, d) addition of an effective polyA sequence operably-linked to the transposase to further enhance expression of the transposase gene. In some embodiments, the effective polyA sequence is an avian optimized polyA sequence.

The present invention also provides for tissue-specific incorporation and/or expression of a gene of interest. Tissue-specific incorporation of a gene of interest may be achieved by placing the transposase gene under the control of a tissue-specific promoter, whereas tissue-specific expression of a gene of interest may be achieved by placing the gene of interest under the control of a tissue-specific promoter. In some embodiments, the gene of interest is transcribed under the influence of an ovalbumin, or other oviduct specific, promoter. Linking the gene of interest to an oviduct specific promoter in an egg-laying animal results in synthesis of a desired molecule and deposition of the desired molecule in a developing egg.

The present invention advantageously produces a high number of transgenic animals having a gene of interest stably incorporated. In some embodiments wherein the transposon-based vector is administered to the ovary, these transgenic animals successfully pass the desired gene to their progeny. Accordingly, the present invention can be used to obtain transgenic animals having the gene of interest incorporated into the germline through transfection of the ovary or the present invention can be used to obtain transgenic animals having the gene of interest incorporated into the oviduct in a tissue-specific manner. Both types of transgenic animals of the present invention produce large amounts of a desired molecule encoded by the transgene. Transgenic egg-laying animals, particularly avians, produce large amounts of a desired protein that is deposited in the egg for rapid harvest and purification.

Any desired gene may be incorporated into the novel transposon-based vectors of the present invention in order to synthesize a desired molecule in the transgenic animals. Proteins, peptides and nucleic acids are preferred desired molecules to be produced by the transgenic animals of the present invention. Particularly preferred proteins are antibody proteins and other immunopharmecuetical proteins.

This invention provides a composition useful for the production of transgenic hens capable of producing substantially high amounts of a desired protein or peptide. Entire flocks of transgenic birds may be developed very quickly in order to produce industrial amounts of desired molecules. The present invention solves the problems inherent in the inadequate capacity of fermentation facilities used for bacterial production of molecules and provides a more efficient and economical way to produce desired molecules. Accordingly, the present invention provides a means to produce large amounts of therapeutic, diagnostic and reagent molecules.

Transgenic chickens are excellent in terms of convenience and efficiency of manufacturing molecules such as proteins and peptides. Starting with a single transgenic rooster, thousands of transgenic offspring can be produced within a year. (In principle, up to forty million offspring could be produced in just three generations). Each transgenic female is expected to lay at least 250 eggs/year, each potentially containing hundreds of milligrams of the selected protein. Flocks of chickens numbering in the hundreds of thousands are readily handled through established commercial systems. The technologies for obtaining eggs and fractionating them are also well known and widely accepted. Thus, for each therapeutic, diagnostic, or other protein of interest, large amounts of a substantially pure material can be produced at relatively low incremental cost.

A wide range of recombinant peptides and proteins can be produced in transgenic egg-laying animals. Enzymes, hormones, antibodies, growth factors, serum proteins, commodity proteins, biological response modifiers, peptides and designed proteins may all be made through practice of the present invention. For example, rough estimates suggest that it is possible to produce in bulk growth hormone, insulin, or Factor VIII, and deposit them in egg whites, for an incremental cost in the order of one dollar per gram. At such prices it is feasible to consider administering such medical agents by inhalation or even orally, instead of through injection. Even if bioavailability rates through these avenues were low, the cost of a much higher effective-dose would not be prohibitive.

In one embodiment, the egg-laying transgenic animal is an avian. The method of the present invention may be used in avians including Ratites, Psittaciformes, Falconiformes, Piciformes, Strigiformes, Passeriformes, Coraciformes, Ralliformes, Cuculiformes, Columbiformes, Galliformes, Anseriformes, and Herodiones. Preferably, the egg-laying transgenic animal is a poultry bird. More preferably, the bird is a chicken, turkey, duck, goose or quail. Another preferred bird is a ratite, such as, an emu, an ostrich, a rhea, or a cassowary. Other preferred birds are partridge, pheasant, kiwi, parrot, parakeet, macaw, falcon, eagle, hawk, pigeon, cockatoo, song birds, jay bird, blackbird, finch, warbler, canary, toucan, mynah, or sparrow.

Accordingly, it is an object of the present invention to provide novel transposon-based vectors.

It is another object of the present invention to provide novel transposon-based vectors that encode for the production of desired proteins or peptides in cells.

It is an object of the present invention to produce transgenic animals through intraoviduct or intraovarian administration of a transposon-based vector.

Another object of the present invention is to produce transgenic animals through intraoviduct or intraovarian administration of a transposon-based vector, wherein the transgenic animals produce desired proteins or peptides.

It is further an object of the present invention to provide a method to produce transgenic animals through intraovarian administration of a transposon-based vector that are capable of producing transgenic progeny.

Yet another object of the present invention is to provide a method to produce transgenic animals through intraoviduct or intraovarian administration of a transposon-based vector that are capable of producing a desired molecule, such as a protein, peptide or nucleic acid.

Another object of the present invention is to provide a method to produce transgenic animals through intraoviduct or intraovarian administration of a transposon-based vector, wherein such administration results in modulation of endogenous gene expression.

It is yet another object of the present invention to provide a method to produce transgenic avians through intraoviduct or intraovarian administration of a transposon-based vector that are capable of producing proteins, peptides or nucleic acids.

It is another object of the present invention to produce transgenic animals through intraoviduct or intraovarian administration of a transposon-based vector encoding an antibody or a fragment thereof.

Still another object of the present invention is to provide a method to produce transgenic avians through intraoviduct or intraovarian administration of a transposon-based vector that are capable of producing proteins or peptides and depositing these proteins or peptides in the egg.

Another object of the present invention is to provide transgenic avians that contain a stably incorporated transgene.

Still another object of the present invention is to provide eggs containing desired proteins or peptides encoded by a transgene incorporated into the transgenic avian that produces the egg.

It is further an object of the present invention to provide a method to produce transgenic milk-producing animals through administration of a transposon-based vector that are capable of producing proteins, peptides or nucleic acids.

Still another object of the present invention is to provide a method to produce transgenic milk-producing animals through administration of a transposon-based vector that are capable of producing proteins or peptides and depositing these proteins or peptides in their milk.

Another object of the present invention is to provide transgenic milk-producing animals that contain a stably incorporated transgene.

Another object of the present invention is to provide transgenic milk-producing animals that are capable of producing proteins or peptides and depositing these proteins or peptides in their milk.

Yet another object of the present invention is to provide milk containing desired molecules encoded by a transgene incorporated into the transgenic milk-producing animals that produce the milk.

Still another object of the present invention is to provide milk containing desired proteins or peptides encoded by a transgene incorporated into the transgenic milk-producing animals that produce the milk.

An advantage of the present invention is that transgenic animals are produced with higher efficiencies than observed in the prior art.

Another advantage of the present invention is that these transgenic animals possess high copy numbers of the transgene.

Another advantage of the present invention is that the transgenic animals produce large amounts of desired molecules encoded by the transgene.

Still another advantage of the present invention is that desired molecules are produced by the transgenic animals much more efficiently and economically than prior art methods, thereby providing a means for large scale production of desired molecules, particularly proteins and peptides.

Yet another advantage of the present invention is that the desired proteins and peptides are produced rapidly after making animals transgenic through introduction of the vectors of the present invention.

These and other objects, features and advantages of the present invention will become apparent after a review of the following detailed description of the disclosed embodiments and claims.

BRIEF DESCRIPTION OF THE FIGURES

FIG. 4 depicts schematically a transposon based-vector for expression of an RNAi molecule. "$Tet_i$ pro" indicates a tetracycline inducible promoter whereas "pro" indicates the pro portion of a prepro sequence as described herein. "Ovgen" indicates approximately 60 base pairs of an ovalbumin gene, "Ovotrans" indicates approximately 60 base pairs of an ovotransferrin gene and "Ovomucin" indicates approximately 60 base pairs of an ovomucin gene.

DETAILED DESCRIPTION OF THE INVENTION

Figure 1:
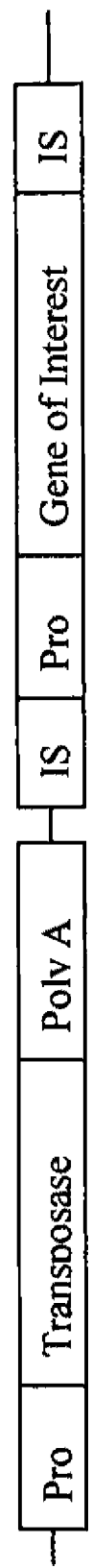
FIG. 1 depicts schematically a transposon-based vector containing a transposase operably linked to a first promoter and a gene of interest operably-linked to a second promoter, wherein the gene of interest and its operably-linked promoter are flanked by insertion sequences (IS) recognized by the transposase. "Pro" designates a promoter. In this and subsequent figures, the size of the actual nucleotide sequence is not necessarily proportionate to the box representing that sequence.

The present invention provides a new, effective and efficient method of producing transgenic animals, particularly egg-laying animals and milk-producing animals, through administration of a composition comprising a transposon-based vector designed for incorporation of a gene of interest and production of a desired molecule. The transposon-based vectors are administered to a reproductive organ including, but not limited to, an oviduct, an ovary, or into the duct system of the mammary gland. The vectors may be directly administered to a reproductive organ or can be administered to an artery leading to the reproductive organ or to a lymph system proximate to the cells to be genetically altered. The vectors may be administered to a reproductive organ of an animal through the cloaca. One method of direct administration is by injection, and in one embodiment, the lumen of the magnum of the oviduct is injected with a transposon-based vector. Another method of direct administration is by injection, and in one embodiment, the lumen of the infundibulum of the oviduct is injected with a transposon-based vector. A preferred intrarterial administration is an administration into an artery that supplies the oviduct or the ovary. In some embodiments, administration of the transposon-based vector to an oviduct or an artery that leads to the oviduct results in incorporation of the vector into the epithelial and/or secretory cells of the oviduct. In other embodiments, administration of the transposon-based vector to an ovary or an artery that leads to the ovary or a lymphatic system proximal to the ovary results in incorporation of the vector into an oocyte or a germinal disk inside the ovary.

Definitions

It is to be understood that as used in the specification and in the claims, "a" or "an" can mean one or more, depending upon the context in which it is used. Thus, for example, reference to "a cell" can mean that at least one cell can be utilized.

The term "antibody" is used interchangeably with the term "immunoglobulin" and is defined herein as a protein synthesized by an animal or a cell of the immune system in response to the presence of a foreign substance commonly referred to as an "antigen" or an "immunogen". The term antibody includes fragments of antibodies. Antibodies are characterized by specific affinity to a site on the antigen, wherein the site is referred to an "antigenic determinant" or an "epitope". Antigens can be naturally occurring or artificially engineered. Artificially engineered antigens include, but are not limited to, small molecules, such as small peptides, attached to haptens such as macromolecules, for example proteins, nucleic acids, or polysaccharides. Artificially designed or engineered variants of naturally occurring antibodies and artificially designed or engineered antibodies not occurring in nature are all included in the current definition. Such variants include conservatively substituted amino acids and other forms of substitution as described in the section concerning proteins and polypeptides.

As used herein, the term "egg-laying animal" includes all amniotes such as birds, turtles, lizards and monotremes. Monotremes are egg-laying mammals and include the platypus and echidna. The term "bird" or "fowl," as used herein, is defined as a member of the Aves class of animals which are characterized as warm-blooded, egg-laying vertebrates primarily adapted for flying. Avians include, without limitation, Ratites, Psittaciformes, Falconiformes, Piciformes, Strigiformes, Passeriformes, Coraciformes, Ralliformes, Cuculiformes, Columbiformes, Galliformes, Anseriformes, and Herodiones. The term "Ratite," as used herein, is defined as a group of flightless, mostly large, running birds comprising several orders and including the emus, ostriches, kiwis, and cassowaries. The term "Psittaciformes", as used herein, includes parrots and refers to a monofamilial order of birds that exhibit zygodactylism and have a strong hooked bill. A "parrot" is defined as any member of the avian family Psittacidae (the single family of the Psittaciformes), distinguished by the short, stout, strongly hooked beak. Avians include all poultry birds, especially chickens, geese, turkeys, ducks and quail. The term "chicken" as used herein denotes chickens used for table egg production, such as egg-type chickens, chickens reared for public meat consumption, or broilers, and chickens reared for both egg and meat production ("dual-purpose" chickens). The term "chicken" also denotes chickens produced by primary breeder companies, or chickens that are the parents, grandparents, great-grandparents, etc. of those chickens reared for public table egg, meat, or table egg and meat consumption.

The term "egg" is defined herein as including a large female sex cell enclosed in a porous, calcarous or leathery shell, produced by birds and reptiles. The term "ovum" is defined as a female gamete, and is also known as an egg. Therefore, egg production in all animals other than birds and reptiles, as used herein, is defined as the production and discharge of an ovum from an ovary, or "ovulation". Accordingly, it is to be understood that the term "egg" as used herein is defined as a large female sex cell enclosed in a porous, calcarous or leathery shell, when a bird or reptile produces it, or it is an ovum when it is produced by all other animals.

The term "milk-producing animal" refers herein to mammals including, but not limited to, bovine, ovine, porcine, equine, and primate animals. Milk-producing animals include but are not limited to cows, llamas, camels, goats, reindeer, zebu, water buffalo, yak, horses, pigs, rabbits, non-human primates, and humans.

The term "gene" is defined herein to include a coding region for a protein, peptide or polypeptide.

The term "transgenic animal" refers to an animal having at least a portion of the transposon-based vector DNA incorporated into its DNA. While a transgenic animal includes an animal wherein the transposon-based vector DNA is incorporated into the germline DNA, a transgenic animal also includes an animal having DNA in one or more cells that contain a portion of the transposon-based vector DNA for any period of time. In a preferred embodiment, a portion of the transposon-based vector comprises a gene of interest. More preferably, the gene of interest is incorporated into the animal's DNA for a period of at least five days, more preferably the reproductive life of the animal, and most preferably the life of the animal. In a further preferred embodiment, the animal is an avian.

The term "vector" is used interchangeably with the terms "construct", "DNA construct" and "genetic construct" to denote synthetic nucleotide sequences used for manipulation of genetic material, including but not limited to cloning, subcloning, sequencing, or introduction of exogenous genetic material into cells, tissues or organisms, such as birds. It is understood by one skilled in the art that vectors may contain synthetic DNA sequences, naturally occurring DNA sequences, or both. The vectors of the present invention are transposon-based vectors as described herein.

When referring to two nucleotide sequences, one being a regulatory sequence, the term "operably-linked" is defined herein to mean that the two sequences are associated in a manner that allows the regulatory sequence to affect expression of the other nucleotide sequence. It is not required that the operably-linked sequences be directly adjacent to one another with no intervening sequence(s).

The term "regulatory sequence" is defined herein as including promoters, enhancers and other expression control elements such as polyadenylation sequences, matrix attachment sites, insulator regions for expression of multiple genes on a single construct, ribosome entry/attachment sites, introns that are able to enhance expression, and silencers.

Transposon-Based Vectors

While not wanting to be bound by the following statement, it is believed that the nature of the DNA construct is an important factor in successfully producing transgenic animals. The "standard" types of plasmid and viral vectors that have previously been almost universally used for transgenic work in all species, especially avians, have low efficiencies and may constitute a major reason for the low rates of transformation previously observed. The DNA (or RNA) constructs previously used often do not integrate into the host DNA, or integrate only at low frequencies. Other factors may have also played a part, such as poor entry of the vector into target cells. The present invention provides transposon-based vectors that can be administered to an animal that overcome the prior art problems relating to low transgene integration frequencies. Two preferred transposon-based vectors of the present invention in which a tranposase, gene of interest and other polynucleotide sequences may be introduced are termed pTnMCS (SEQ ID NO:2) and pTnMod (SEQ ID NO:3).

The transposon-based vectors of the present invention produce integration frequencies an order of magnitude greater than has been achieved with previous vectors. More specifically, intratesticular injections performed with a prior art transposon-based vector (described in U.S. Pat. No. 5,719,055) resulted in 41% sperm positive roosters whereas intratesticular injections performed with the novel transposon-based vectors of the present invention resulted in 77% sperm positive roosters. Actual frequencies of integration were estimated by either or both comparative strength of the PCR signal from the sperm and histological evaluation of the testes and sperm by quantitative PCR.

The transposon-based vectors of the present invention include a transposase gene operably-linked to a first promoter, and a coding sequence for a desired protein or peptide operably-linked to a second promoter, wherein the coding sequence for the desired protein or peptide and its operably-linked promoter are flanked by transposase insertion sequences recognized by the transposase. The transposon-based vector also includes one or more of the following characteristics: a) one or more modified Kozak sequences comprising ACCATG (SEQ ID NO:1) at the 3' end of the first promoter to enhance expression of the transposase; b) modifications of the codons for the first several N-terminal amino acids of the transposase, wherein the third base of each codon was changed to an A or a T without changing the corresponding amino acid; c) addition of one or more stop codons to enhance the termination of transposase synthesis; and/or, d) addition of an effective polyA sequence operably-linked to the transposase to further enhance expression of the transposase gene. The transposon-based vector may additionally or alternatively include one or more of the following Kozak sequences at the 3' end of any promoter, including the promoter operably-linked to the transposase: ACCATGG (SEQ ID NO:4), AAGATGT (SEQ ID NO:5), ACGATGA (SEQ ID NO:6), AAGATGG (SEQ ID NO:7), GACATGA (SEQ ID NO:8), ACCATGA (SEQ ID NO:9), and ACCATGT (SEQ ID NO:52).

FIG. 1 shows a schematic representation of several components of the transposon-based vector. The present invention further includes vectors containing more than one gene of interest, wherein a second or subsequent gene of interest is operably-linked to the second promoter or to a different promoter. It is also to be understood that the transposon-based vectors shown in the Figures are representative of the present invention and that the order of the vector elements may be different than that shown in the Figures, that the elements may be present in various orientations, and that the vectors may contain additional elements not shown in the Figures.

Transposases and Insertion Sequences

In a further embodiment of the present invention, the transposase found in the transposase-based vector is an altered target site (ATS) transposase and the insertion sequences are those recognized by the ATS transposase. However, the transposase located in the transposase-based vectors is not limited to a modified ATS transposase and can be derived from any transposase. Transposases known in the prior art include those found in AC7, Tn5SEQ1, Tn916, Tn951, Tn1721, Tn2410, Tn1681, Tn1, Tn2, Tn3, Tn4, Tn5, Tn6, Tn9, Tn10, Tn30, Tn101, Tn903, Tn501, Tn1000 (γδ), Tn1681, Tn2901, AC transposons, Mp transposons, Spm transposons, En transposons, Dotted transposons, Mu transposons, Ds transposons, dSpm transposons and I transposons. According to the present invention, these transposases and their regulatory sequences are modified for improved functioning as follows: a) the addition one or more modified Kozak sequences comprising ACCATG (SEQ ID NO: 1) at the 3' end of the promoter operably-linked to the transposase; b) a change of the codons for the first several amino acids of the transposase, wherein the third base of each codon was changed to an A or a T without changing the corresponding amino acid; c) the addition of one or more stop codons to enhance the termination of transposase synthesis; and/or, d) the addition of an effective polyA sequence operably-linked to the transposase to further enhance expression of the transposase gene.

Although not wanting to be bound by the following statement, it is believed that the modifications of the first several N-terminal codons of the transposase gene increase transcription of the transposase gene, in part, by increasing strand dissociation. It is preferable that between approximately 1 and 20, more preferably 3 and 15, and most preferably between 4 and 12 of the first N-terminal codons of the transposase are modified such that the third base of each codon is changed to an A or a T without changing the encoded amino acid. In one embodiment, the first ten N-terminal codons of the transposase gene are modified in this manner. It is also preferred that the transposase contain mutations that make it less specific for preferred insertion sites and thus increases the rate of transgene insertion as discussed in U.S. Pat. No. 5,719,055.

In some embodiments, the transposon-based vectors are optimized for expression in a particular host by changing the methylation patterns of the vector DNA. For example, prokaryotic methylation may be reduced by using a methylation deficient organism for production of the transposon-based vector. The transposon-based vectors may also be methylated to resemble eukaryotic DNA for expression in a eukaryotic host.

Transposases and insertion sequences from other analogous eukaryotic transposon-based vectors that can also be modified and used are, for example, the *Drosophila* P element derived vectors disclosed in U.S. Pat. No. 6,291,243; the Drosophila mariner element described in Sherman et al. (1998); or the sleeping beauty transposon. See also Hackett et al. (1999); D. Lampe et al., 1999. Proc. Natl. Acad. Sci. USA, 96:11428-11433; S. Fischer et al., 2001. Proc. Natl. Acad. Sci. USA, 98:6759-6764; L. Zagoraiou et al., 2001. Proc. Natl. Acad. Sci. USA, 98:11474-11478; and D. Berg et al. (Eds.), Mobile DNA, Amer. Soc. Microbiol. (Washington, D.C., 1989). However, it should be noted that bacterial transposon-based elements are preferred, as there is less likelihood that a eukaryotic transposase in the recipient species will recognize prokaryotic insertion sequences bracketing the transgene.

Many transposases recognize different insertion sequences, and therefore, it is to be understood that a transposase-based vector will contain insertion sequences recognized by the particular transposase also found in the transposase-based vector. In a preferred embodiment of the invention, the insertion sequences have been shortened to about 70 base pairs in length as compared to those found in wild-type transposons that typically contain insertion sequences of well over 100 base pairs.

While the examples provided below incorporate a "cut and insert" Tn10 based vector that is destroyed following the insertion event, the present invention also encompasses the use of a "rolling replication" type transposon-based vector. Use of a rolling replication type transposon allows multiple copies of the transposon/transgene to be made from a single transgene construct and the copies inserted. This type of transposon-based system thereby provides for insertion of multiple copies of a transgene into a single genome. A rolling replication type transposon-based vector may be preferred when the promoter operably-linked to gene of interest is endogenous to the host cell and present in a high copy number or highly expressed. However, use of a rolling replication system may require tight control to limit the insertion events to non-lethal levels. Tn1, Tn2, Tn3, Tn4, Tn5, Tn9, Tn21, Tn501, Tn551, Tn951, Tn1721, Tn2410 and Tn2603 are examples of a rolling replication type transposon, although Tn5 could be both a rolling replication and a cut and insert type transposon.

Stop Codons and PolyA Sequences

In one embodiment, the transposon-based vector contains two stop codons operably-linked to the transposase and/or to the gene of interest. In an alternate embodiment, one stop codon of UAA or UGA is operably linked to the transposase and/or to the gene of interest.

As used herein an "effective polyA sequence" refers to either a synthetic or non-synthetic sequence that contains multiple and sequential nucleotides containing an adenine base (an A polynucleotide string) and that increases expression of the gene to which it is operably-linked. A polyA sequence may be operably-linked to any gene in the transposon-based vector including, but not limited to, a transposase gene and a gene of interest. A preferred polyA sequence is optimized for use in the host animal or human. In one embodiment, the polyA sequence is optimized for use in an avian species and more specifically, a chicken. An avian optimized polyA sequence generally contains a minimum of 40 base pairs, preferably between approximately 40 and several hundred base pairs, and more preferably approximately 75 base pairs that precede the A polynucleotide string and thereby separate the stop codon from the A polynucleotide string. In one embodiment of the present invention, the polyA sequence comprises a conalbumin polyA sequence as provided in SEQ ID NO:11 and as taken from GenBank accession # Y00407, base pairs 10651-11058. In another embodiment, the polyA sequence comprises a synthetic polynucleotide sequence shown in SEQ ID NO:12. In yet another embodiment, the polyA sequence comprises an avian optimized polyA sequence provided in SEQ ID NO:13. A chicken optimized polyA sequence may also have a reduced amount of CT repeats as compared to a synthetic polyA sequence.

It is a surprising discovery of the present invention that such an avian optimized poly A sequence increases expression of a polynucleotide to which it is operably-linked in an avian as compared to a non-avian optimized polyA sequence. Accordingly, the present invention includes methods of or increasing incorporation of a gene of interest wherein the gene of interest resides in a transposon-based vector containing a transposase gene and wherein the transposase gene is operably linked to an avian optimized polyA sequence. The present invention also includes methods of increasing expression of a gene of interest in an avian that includes administering a gene of interest to the avian, wherein the gene of interest is operably-linked to an avian optimized polyA sequence. An avian optimized polyA nucleotide string is defined herein as a polynucleotide containing an A polynucleotide string and a minimum of 40 base pairs, preferably between approximately 40 and several hundred base pairs, and more preferably approximately 60 base pairs that precede the A polynucleotide string. The present invention further provides transposon-based vectors containing a gene of interest or transposase gene operably linked to an avian optimized polyA sequence.

Promoters and Enhancers

The first promoter operably-linked to the transposase gene and the second promoter operably-linked to the gene of interest can be a constitutive promoter or an inducible promoter. Constitutive promoters include, but are not limited to, immediate early cytomegalovirus (CMV) promoter, herpes simplex virus 1 (HSV1) immediate early promoter, SV40 promoter, lysozyme promoter, early and late CMV promoters, early and late HSV promoters, β-actin promoter, tubulin promoter, Rous-Sarcoma virus (RSV) promoter, and heat-shock protein (HSP) promoter. Inducible promoters include tissue-specific promoters, developmentally-regulated promoters and chemically inducible promoters. Examples of tissue-specific promoters include the glucose 6 phosphate (G6P) promoter, vitellogenin promoter, ovalbumin promoter, ovomucoid promoter, conalbumin promoter, ovotransferrin promoter, prolactin promoter, kidney uromodulin promoter, and placental lactogen promoter. In one embodiment, the vitellogenin promoter includes a polynucleotide sequence of SEQ ID NO: 14. The G6P promoter sequence may be deduced from a rat G6P gene untranslated upstream region provided in GenBank accession number U57552.1. Examples of developmentally-regulated promoters include the homeobox promoters and several hormone induced promoters. Examples of chemically inducible promoters include reproductive hormone induced promoters and antibiotic inducible promoters such as the tetracycline inducible promoter and the zinc-inducible metallothionine promoter.

Other inducible promoter systems include the Lac operator repressor system inducible by IPTG (isopropyl beta-D-thiogalactoside) (Cronin, A. et al. 2001. Genes and Development, v. 15), ecdysone-based inducible systems (Hoppe, U. C. et al. 2000. Mol. Ther. 1:159-164); estrogen-based inducible systems (Braselmann, S. et al. 1993. Proc. Natl. Acad. Sci. 90:1657-1661); progesterone-based inducible systems using a chimeric regulator, GLVP, which is a hybrid protein consisting of the GAL4 binding domain and the herpes simplex virus transcriptional activation domain, VP16, and a truncated form of the human progesterone receptor that retains the ability to bind ligand and can be turned on by RU486 (Wang, et al. 1994. Proc. Natl. Acad. Sci. 91:8180-8184); CID-based inducible systems using chemical inducers of dimerization (CIDs) to regulate gene expression, such as a system wherein rapamycin induces dimerization of the cellular proteins FKBP12 and FRAP (Belshaw, P. J. et al. 1996. J. Chem. Biol. 3:731-738; Fan, L. et al. 1999. Hum. Gene Ther. 10:2273-2285; Shariat, S. F. et al. 2001. Cancer Res. 61:2562-2571; Spencer, D. M. 1996. Curr. Biol. 6:839-847). Chemical substances that activate the chemically inducible promoters can be administered to the animal containing the transgene of interest via any method known to those of skill in the art.

Other examples of cell or tissue-specific and constitutive promoters include but are not limited to smooth-muscle SM22 promoter, including chimeric SM22alpha/telokin promoters (Hoggatt A. M. et al., 2002. Circ Res. 91(12):1151-9); ubiquitin C promoter (Biochim Biophys Acta, 2003. Jan. 3; 1625(1):52-63); Hsf2 promoter; murine COMP (cartilage oligomeric matrix protein) promoter; early B cell-specific mb-1 promoter (Sigvardsson M., et al., 2002. Mol. Cell. Biol. 22(24):8539-51); prostate specific antigen (PSA) promoter (Yoshimura I. et al., 2002, J. Urol. 168(6):2659-64); exorh promoter and pineal expression-promoting element (Asaoka Y., et al., 2002. Proc. Natl. Acad. Sci. 99(24):15456-61); neural and liver ceramidase gene promoters (Okino N. et al., 2002. Biochem. Biophys. Res. Commun. 299(1):160-6); PSP94 gene promoter/enhancer (Gabril M. Y. et al., 2002. Gene Ther. 9(23):1589-99); promoter of the human FAT/CD36 gene (Kuriki C., et al., 2002. Biol. Pharm. Bull. 25(11): 1476-8); VL30 promoter (Staplin W. R. et al., 2002. Blood Oct. 24, 2002); and, IL-10 promoter (Brenner S., et al., 2002. J. Biol. Chem. Dec. 18, 2002).

Examples of avian promoters include, but are not limited to, promoters controlling expression of egg white proteins, such as ovalbumin, ovotransferrin (conalbumin), ovomucoid, lysozyme, ovomucin, g2 ovoglobulin, g3 ovoglobulin, ovoflavoprotein, ovostatin (ovomacroglobin), cystatin, avidin, thiamine-binding protein, glutamyl aminopeptidase minor glycoprotein 1, minor glycoprotein 2; and promoters controlling expression of egg-yolk proteins, such as vitellogenin, very low-density lipoproteins, low density lipoprotein, cobalamin-binding protein, riboflavin-binding protein, biotin-binding protein (Awade, 1996. Z. Lebensm. Unters. Forsch. 202:1-14). An advantage of using the vitellogenin promoter is that it is active during the egg-laying stage of an animal's life-cycle, which allows for the production of the protein of interest to be temporally connected to the import of the protein of interest into the egg yolk when the protein of interest is equipped with an appropriate targeting sequence. In some embodiments, the avian promoter is an oviduct-specific promoter. As used herein, the term "oviduct-specific promoter" includes, but is not limited to, ovalbumin; ovotransferrin (conalbumin); ovomucoid; 01, 02, 03, 04 or 05 avidin; ovomucin; g2 ovoglobulin; g3 ovoglobulin; ovoflavoprotein; and ovostatin (ovomacroglobin) promoters.

When germline transformation occurs via intraovarian administration, liver-specific promoters may be operably-linked to the gene of interest to achieve liver-specific expression of the transgene. Liver-specific promoters of the present invention include, but are not limited to, the following promoters, vitellogenin promoter, G6P promoter, cholesterol-7-alpha-hydroxylase (CYP7A) promoter, phenylalanine hydroxylase (PAH) promoter, protein C gene promoter, insulin-like growth factor I (IGF-I) promoter, bilirubin UDP-glucuronosyltransferase promoter, aldolase B promoter, furin promoter, metallothioneine promoter, albumin promoter, and insulin promoter.

Also included in the present invention are promoters that can be used to target expression of a protein of interest into the milk of a milk-producing animal including, but not limited to, β lactoglobin promoter, whey acidic protein promoter, lactalbumin promoter and casein promoter.

When germline transformation occurs via intraovarian administration, immune system-specific promoters may be operably-linked to the gene of interest to achieve immune system-specific expression of the transgene. Accordingly, promoters associated with cells of the immune system may also be used. Acute phase promoters such as interleukin (IL)-1 and IL-2 may be employed. Promoters for heavy and light chain Ig may also be employed. The promoters of the T cell receptor components CD4 and CD8, B cell promoters and the promoters of CR2 (complement receptor type 2) may also be employed. Immune system promoters are preferably used when the desired protein is an antibody protein.

Also included in this invention are modified promoters/enhancers wherein elements of a single promoter are duplicated, modified, or otherwise changed. In one embodiment, steroid hormone-binding domains of the ovalbumin promoter are moved from about −6.5 kb to within approximately the first 1000 base pairs of the gene of interest. Modifying an existing promoter with promoter/enhancer elements not found naturally in the promoter, as well as building an entirely synthetic promoter, or drawing promoter/enhancer elements from various genes together on a non-natural backbone, are all encompassed by the current invention.

Accordingly, it is to be understood that the promoters contained within the transposon-based vectors of the present invention may be entire promoter sequences or fragments of promoter sequences. For example, in one embodiment, the promoter operably linked to a gene of interest is an approximately 900 base pair fragment of a chicken ovalbumin promoter (SEQ ID NO:15). The constitutive and inducible promoters contained within the transposon-based vectors may also be modified by the addition of one or more modified Kozak sequences of ACCATG (SEQ ID NO:1).

As indicated above, the present invention includes transposon-based vectors containing one or more enhancers. These enhancers may or may not be operably-linked to their native promoter and may be located at any distance from their operably-linked promoter. A promoter operably-linked to an enhancer and a promoter modified to eliminate repressive regulatory effects are referred to herein as an "enhanced promoter." The enhancers contained within the transposon-based vectors are preferably enhancers found in birds, and more preferably, an ovalbumin enhancer, but are not limited to these types of enhancers. In one embodiment, an approximately 675 base pair enhancer element of an ovalbumin promoter is cloned upstream of an ovalbumin promoter with 300 base pairs of spacer DNA separating the enhancer and promoter. In one embodiment, the enhancer used as a part of the present invention comprises base pairs 1-675 of a chicken ovalbumin enhancer from GenBank accession #S82527.1. The polynucleotide sequence of this enhancer is provided in SEQ ID NO:16.

Also included in some of the transposon-based vectors of the present invention are cap sites and fragments of cap sites. In one embodiment, approximately 50 base pairs of a 5' untranslated region wherein the capsite resides are added on the 3' end of an enhanced promoter or promoter. An exemplary 5' untranslated region is provided in SEQ ID NO:17. A putative cap-site residing in this 5' untranslated region preferably comprises the polynucleotide sequence provided in SEQ ID NO:18.

In one embodiment of the present invention, the first promoter operably-linked to the transposase gene is a constitutive promoter and the second promoter operably-linked to the gene of interest is a tissue-specific promoter. In the second embodiment, use of the first constitutive promoter allows for constitutive activation of the transposase gene and incorporation of the gene of interest into virtually all cell types, including the germline of the recipient animal. Although the gene of interest is incorporated into the germline generally, the gene of interest may only be expressed in a tissue-specific manner. A transposon-based vector having a constitutive promoter operably-linked to the transposase gene can be administered by any route, and in one embodiment, the vector is administered to an ovary, to an artery leading to the ovary or to a lymphatic system or fluid proximal to the ovary.

It should be noted that cell- or tissue-specific expression as described herein does not require a complete absence of expression in cells or tissues other than the preferred cell or tissue. Instead, "cell-specific" or "tissue-specific" expression refers to a majority of the expression of a particular gene of interest in the preferred cell or tissue, respectively.

When incorporation of the gene of interest into the germline is not preferred, the first promoter operably-linked to the transposase gene can be a tissue-specific promoter. For example, transfection of a transposon-based vector containing a transposase gene operably-linked to an oviduct specific promoter such as the ovalbumin promoter provides for activation of the transposase gene and incorporation of the gene of interest in the cells of the oviduct but not into the germline and other cells generally. In this embodiment, the second promoter operably-linked to the gene of interest can be a constitutive promoter or an inducible promoter. In a preferred embodiment, both the first promoter and the second promoter are an ovalbumin promoter. In embodiments wherein tissue-specific expression or incorporation is desired, it is preferred that the transposon-based vector is administered directly to the tissue of interest, to an artery leading to the tissue of interest or to fluids surrounding the tissue of interest. In a preferred embodiment, the tissue of interest is the oviduct and administration is achieved by direct injection into the oviduct or an artery leading to the oviduct. In a further preferred embodiment, administration is achieved by direct injection into the lumen of the magnum or the infundibulum of the oviduct. Indirect administration to the oviduct may occur through the cloaca.

Accordingly, cell specific promoters may be used to enhance transcription in selected tissues. In birds, for example, promoters that are found in cells of the fallopian tube, such as ovalbumin, conalbumin, ovomucoid and/or lysozyme, are used in the vectors to ensure transcription of the gene of interest in the epithelial cells and tubular gland cells of the fallopian tube, leading to synthesis of the desired protein encoded by the gene and deposition into the egg white. In mammals, promoters specific for the epithelial cells of the alveoli of the mammary gland, such as prolactin, insulin, beta lactoglobin, whey acidic protein, lactalbumin, casein, and/or placental lactogen, are used in the design of vectors used for transfection of these cells for the production of desired proteins for deposition into the milk. In liver cells, the G6P promoter may be employed to drive transcription of the gene of interest for protein production. Proteins made in the liver of birds may be delivered to the egg yolk.

In order to achieve higher or more efficient expression of the transposase gene, the promoter and other regulatory sequences operably-linked to the transposase gene may be those derived from the host. These host specific regulatory sequences can be tissue specific as described above or can be of a constitutive nature. For example, an avian actin promoter and its associated polyA sequence can be operably-linked to a transposase in a transposase-based vector for transfection into an avian. Examples of other host specific promoters that could be operably-linked to the transposase include the myosin and DNA or RNA polymerase promoters.

Directing Sequences

In some embodiments of the present invention, the gene of interest is operably-linked to a directing sequence or a sequence that provides proper conformation to the desired protein encoded by the gene of interest. As used herein, the term "directing sequence" refers to both signal sequences and targeting sequences. An egg directing sequence includes, but is not limited to, an ovomucoid signal sequence, an ovalbumin signal sequence, a cecropin pre pro signal sequence, and a vitellogenin targeting sequence. The term "signal sequence" refers to an amino acid sequence, or the polynucleotide sequence that encodes the amino acid sequence, that directs the protein to which it is linked to the endoplasmic reticulum in a eukaryote, and more preferably the translocational pores in the endoplasmic reticulum, or the plasma membrane in a prokaryote, or mitochondria, such as for the purpose of gene therapy for mitochondrial diseases. Signal and targeting sequences can be used to direct a desired protein into, for example, the milk, when the transposon-based vectors are administered to a milk-producing animal.

Figure 2:
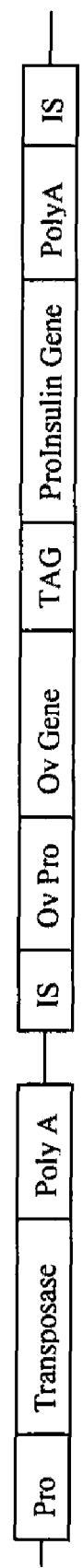
FIG. 2 depicts schematically a transposon-based vector for targeting deposition of a polypeptide in an egg white wherein Ov pro is the ovalbumin promoter, Ov protein is the ovalbumin protein and PolyA is a polyadenylation sequence. The TAG sequence includes a spacer sequence, the gp41 hairpin loop from HIV I and a protease cleavage site.

Signal sequences can also be used to direct a desired protein into, for example, a secretory pathway for incorporation into the egg yolk or the egg white, when the transposon-based vectors are administered to a bird or other egg-laying animal. One example of such a transposon-based vector is provided in FIG. 3 wherein the gene of interest is operably linked to the ovomucoid signal sequence. The present invention also includes a gene of interest operably-linked to a second gene containing a signal sequence. An example of such an embodiment is shown in FIG. 2 wherein the gene of interest is operably-linked to the ovalbumin gene that contains an ovalbumin signal sequence. Other signal sequences that can be included in the transposon-based vectors include, but are not limited to the ovotransferrin and lysozyme signal sequences. In one embodiment, the signal sequence is an ovalbumin signal sequence including a sequence shown in SEQ ID NO:19. In another embodiment, the signal sequence is a modified ovalbumin signal sequence including a sequence shown in SEQ ID NO:20 or SEQ ID NO:21.

As also used herein, the term "targeting sequence" refers to an amino acid sequence, or the polynucleotide sequence encoding the amino acid sequence, which amino acid sequence is recognized by a receptor located on the exterior of a cell. Binding of the receptor to the targeting sequence results in uptake of the protein or peptide operably-linked to the targeting sequence by the cell. One example of a targeting sequence is a vitellogenin targeting sequence that is recognized by a vitellogenin receptor (or the low density lipoprotein receptor) on the exterior of an oocyte. In one embodiment, the vitellogenin targeting sequence includes the polynucleotide sequence of SEQ ID NO:22. In another embodiment, the vitellogenin targeting sequence includes all or part of the vitellogenin gene. Other targeting sequences include VLDL and Apo E, which are also capable of binding the vitellogenin receptor. Since the ApoE protein is not endogenously expressed in birds, its presence may be used advantageously to identify birds carrying the transposon-based vectors of the present invention.

Genes of Interest Encoding Desired Proteins

A gene of interest selected for stable incorporation is designed to encode any desired protein or peptide or to regulate any cellular response. In some embodiments, the desired proteins or peptides are deposited in an egg or in milk. It is to be understood that the present invention encompasses transposon-based vectors containing multiple genes of interest. The multiple genes of interest may each be operably-linked to a separate promoter and other regulatory sequence(s) or may all be operably-linked to the same promoter and other regulatory sequences(s). In one embodiment, multiple gene of interest are linked to a single promoter and other regulatory sequence(s) and each gene of interest is separated by a cleavage site or a pro portion of a signal sequence. A gene of interest may contain modifications of the codons for the first several N-terminal amino acids of the gene of interest, wherein the third base of each codon is changed to an A or a T without changing the corresponding amino acid.

Protein and peptide hormones are a preferred class of proteins in the present invention. Such protein and peptide hormones are synthesized throughout the endocrine system and include, but are not limited to, hypothalamic hormones and hypophysiotropic hormones, anterior, intermediate and posterior pituitary hormones, pancreatic islet hormones, hormones made in the gastrointestinal system, renal hormones, thymic hormones, parathyroid hormones, adrenal cortical and medullary hormones. Specifically, hormones that can be produced using the present invention include, but are not limited to, chorionic gonadotropin, corticotropin, erythropoietin, glucagons, IGF-1, oxytocin, platelet-derived growth factor, calcitonin, follicle-stimulating hormone, luteinizing hormone, thyroid-stimulating hormone, insulin, gonadotropin-releasing hormone and its analogs, vasopressin, octreotide, somatostatin, prolactin, adrenocorticotropic hormone, antidiuretic hormone, thyrotropin-releasing hormone (TRH), growth hormone-releasing hormone (GHRH), dopamine, melatonin, thyroxin ($T_4$), parathyroid hormone (PTH), glucocorticoids such as cortisol, mineralocorticoids such as aldosterone, androgens such as testosterone, adrenaline (epinephrine), noradrenaline (norepinephrine), estrogens such as estradiol, progesterone, glucagons, calcitrol, calciferol, atrial-natriuretic peptide, gastrin, secretin, cholecystokinin (CCK), neuropeptide Y, ghrelin, $PYY_{3-36}$, angiotensinogen, thrombopoietin, and leptin. By using appropriate polynucleotide sequences, species-specific hormones may be made by transgenic animals.

Figure 3:
FIG. 3 depicts schematically a transposon-based vector for targeting deposition of a polypeptide in an egg white wherein Ovo pro is the ovomucoid promoter and Ovo SS is the ovomucoid signal sequence. The TAG sequence includes a spacer, the gp41 hairpin loop from HIV I and a protease cleavage site.

In one embodiment of the present invention, the gene of interest is a proinsulin gene and the desired molecule is insulin. Proinsulin consists of three parts: a C-peptide and two strands of amino acids (the alpha and beta chains) that later become linked together to form the insulin molecule. FIGS. 2 and 3 are schematics of transposon-based vector constructs containing a proinsulin gene operably-linked to an ovalbumin promoter and ovalbumin protein or an ovomucoid promoter and ovomucoid signal sequence, respectively. In these embodiments, proinsulin is expressed in the oviduct tubular gland cells and then deposited in the egg white. One example of a proinsulin polynucleotide sequence is shown in SEQ ID NO:23, wherein the C-peptide cleavage site spans from Arg at position 31 to Arg at position 65.

Serum proteins including lipoproteins such as high density lipoprotein (HDL), HDL-Milano and low density lipoprotein, albumin, clotting cascade factors, factor VIII, factor IX, fibrinogen, and globulins are also included in the group of desired proteins of the present invention. Immunoglobulins are one class of desired globulin molecules and include but are not limited to IgG, IgM, IgA, IgD, IgE, IgY, lambda chains, kappa chains and fragments thereof; Fc fragments, and Fab fragments. Desired antibodies include, but are not limited to, naturally occurring antibodies, human antibodies, humanized antibodies, and hybrid antibodies. Genes encoding modified versions of naturally occurring antibodies or fragments thereof and genes encoding artificially designed antibodies or fragments thereof may be incorporated into the transposon-based vectors of the present invention. Desired antibodies also include antibodies with the ability to bind specific ligands, for example, antibodies against proteins associated with cancer-related molecules, such as anti-her 2, or anti-CA125. Accordingly, the present invention encompasses a transposon-based vector containing one or more genes encoding a heavy immunoglobulin (Ig) chain and a light Ig chain. Further, more than one gene encoding for more than one antibody may be administered in one or more transposon-based vectors of the present invention. In this manner, an egg may contain more than one type of antibody in the egg white, the egg yolk or both. In one embodiment, a transposon-based vector contains a heavy Ig chain and a light Ig chain, both operably linked to a promoter.

Antibodies used as therapeutic reagents include but are not limited to antibodies for use in cancer immunotherapy against specific antigens, or for providing passive immunity to an animal or a human against an infectious disease or a toxic agent. Antibodies used as diagnostic reagents include, but are not limited to antibodies that may be labeled and detected with a detector, for example antibodies with a fluorescent label attached that may be detected following exposure to specific wavelengths. Such labeled antibodies may be primary antibodies directed to a specific antigen, for example, rhodamine-labeled rabbit anti-growth hormone, or may be labeled secondary antibodies, such as fluorescein-labeled goat-anti chicken IgG. Such labeled antibodies are known to one of ordinary skill in the art. Labels useful for attachment to antibodies are also known to one of ordinary skill in the art. Some of these labels are described in the "Handbook of Fluorescent Probes and Research Products", ninth edition, Richard P. Haugland (ed) Molecular Probes, Inc. Eugene, Oreg.), which is incorporated herein in its entirety.

Antibodies produced with using the present invention may be used as laboratory reagents for numerous applications including radioimmunoassay, western blots, dot blots, ELISA, immunoaffinity columns and other procedures requiring antibodies as known to one of ordinary skill in the art. Such antibodies include primary antibodies, secondary antibodies and tertiary antibodies, which may be labeled or unlabeled.

Antibodies that may be made with the practice of the present invention include, but are not limited to primary antibodies, secondary antibodies, designer antibodies, anti-protein antibodies, anti-peptide antibodies, anti-DNA antibodies, anti-RNA antibodies, anti-hormone antibodies, anti-hypophysiotropic peptides, antibodies against non-natural antigens, anti-anterior pituitary hormone antibodies, anti-posterior pituitary hormone antibodies, anti-venom antibodies, anti-tumor marker antibodies, antibodies directed against epitopes associated with infectious disease, including, anti-viral, anti-bacterial, anti-protozoal, anti-fungal, anti-parasitic, anti-receptor, anti-lipid, anti-phospholipid, anti-growth factor, anti-cytokine, anti-monokine, anti-idiotype, and anti-accessory (presentation) protein antibodies. Antibodies made with the present invention, as well as light chains or heavy chains, may also be used to inhibit enzyme activity.

Antibodies that may be produced using the present invention include, but are not limited to, antibodies made against the following proteins: Bovine γ-Globulin, Serum; Bovine IgG, Plasma; Chicken γ-Globulin, Serum; Human γ-Globulin, Serum; Human IgA, Plasma; Human $IgA_1$, Myeloma; Human $IgA_2$, Myeloma; Human $IgA_2$, Plasma; Human IgD, Plasma; Human IgE, Myeloma; Human IgG, Plasma; Human IgG, Fab Fragment, Plasma; Human IgG, F(ab')$_2$ Fragment, Plasma; Human IgG, Fc Fragment, Plasma; Human IgG$_1$, Myeloma; Human IgG$_2$, Myeloma; Human IgG$_3$, Myeloma; Human IgG$_4$, Myeloma; Human IgM, Myeloma; Human IgM, Plasma; Human Immunoglobulin, Light Chain κ, Urine; Human Immunoglobulin, Light Chains κ and λ, Plasma; Mouse γ-Globulin, Serum; Mouse IgG, Serum; Mouse IgM, Myeloma; Rabbit γ-Globulin, Serum; Rabbit IgG, Plasma; and Rat γ-Globulin, Serum. In one embodiment, the transposon-based vector comprises the coding sequence of light and heavy chains of a murine monoclonal antibody that shows specificity for human seminoprotein (GenBank Accession numbers AY129006 and AY129304 for the light and heavy chains, respectively).

A further non-limiting list of antibodies that recognize other antibodies is as follows: Anti-Chicken IgG, heavy (H) & light (L) Chain Specific (Sheep); Anti-Goat γ-Globulin (Donkey); Anti-Goat IgG, Fc Fragment Specific (Rabbit); Anti-Guinea Pig γ-Globulin (Goat); Anti-Human Ig, Light Chain, Type κ Specific; Anti-Human Ig, Light Chain, Type λ Specific; Anti-Human IgA, α-Chain Specific (Goat); Anti-Human IgA, Fab Fragment Specific; Anti-Human IgA, Fc Fragment Specific; Anti-Human IgA, Secretory; Anti-Human IgE, ε-Chain Specific (Goat); Anti-Human IgE, Fc Fragment Specific; Anti-Human IgG, Fc Fragment Specific (Goat); Anti-Human IgG, γ-Chain Specific (Goat); Anti-Human IgG, Fc Fragment Specific; Anti-Human IgG, Fd Fragment Specific; Anti-Human IgG, H & L Chain Specific (Goat); Anti-Human IgG, Fc Fragment Specific; Anti-Human IgG$_2$, Fc Fragment Specific; Anti-Human IgG$_2$, Fd Fragment Specific; Anti-Human IgG$_3$, Hinge Specific; Anti-Human IgG$_4$, Fc Fragment Specific; Anti-Human IgM, Fc Fragment Specific; Anti-Human IgM, μ-Chain Specific; Anti-Mouse IgE, ε-Chain Specific; Anti-Mouse γ-Globulin (Goat); Anti-Mouse IgG, γ-Chain Specific (Goat); Anti-Mouse IgG, γ-Chain Specific (Goat) F(ab')$_2$ Fragment; Anti-Mouse IgG, H & L Chain Specific (Goat); Anti-Mouse IgM, μ-Chain Specific (Goat); Anti-Mouse IgM, H & L Chain Specific (Goat); Anti-Rabbit γ-Globulin (Goat); Anti-Rabbit IgG, Fc Fragment Specific (Goat); Anti-Rabbit IgG, H & L Chain Specific (Goat); Anti-Rat γ-Globulin (Goat); Anti-Rat IgG, H & L Chain Specific; Anti-Rhesus Monkey γ-Globulin (Goat); and, Anti-Sheep IgG, H & L Chain Specific.

Another non-limiting list of the antibodies that may be produced using the present invention is provided in product catalogs of companies such as Phoenix Pharmaceuticals, Inc. (530 Harbor Boulevard, Belmont, Calif.), Peninsula Labs (San Carlos Calif.), SIGMA (St. Louis, Mo.), Cappel ICN (Irvine, Calif.), Calbiochem (La Jolla, Calif.), which are all available electronically via the internet and which are incorporated herein by reference in their entirety. The polynucleotide sequences encoding these antibodies may be obtained from the scientific literature, from patents, and from databases such as GenBank. Alternatively, one of ordinary skill in the art may design the polynucleotide sequence to be incorporated into the genome by choosing the codons that encode for each amino acid in the desired antibody. Antibodies made by the transgenic animals of the present invention include antibodies that may be used as therapeutic reagents, for example in cancer immunotherapy against specific antigens, as diagnostic reagents and as laboratory reagents for numerous applications including immunoneutralization, radioimmunoassay, western blots, dot blots, ELISA, immunoprecipitation and immunoaffinity columns. Some of these antibodies include, but are not limited to, antibodies which bind the following ligands: adrenomedulin, amylin, calcitonin, amyloid, calcitonin gene-related peptide, cholecystokinin, gastrin, gastric inhibitory peptide, gastrin releasing peptide, interleukin, interferon, cortistatin, somatostatin, endothelin, sarafotoxin, glucagon, glucagon-like peptide, insulin, atrial natriuretic peptide, BNP, CNP, neurokinin, substance P, leptin, neuropeptide Y, melanin concentrating hormone, melanocyte stimulating hormone, orphanin, endorphin, dynorphin, enkephalin, enkephalin, leumorphin, peptide F, PACAP, PACAP-related peptide, parathyroid hormone, urocortin, corticotrophin releasing hormone, PHM, PHI, vasoactive intestinal polypeptide, secretin, ACTH, angiotensin, angiostatin, bombesin, endostatin, bradykinin, FMRF amide, galanin, gonadotropin releasing hormone (GnRH) associated peptide, GnRH, growth hormone releasing hormone, inhibin, granulocyte-macrophage colony stimulating factor (GM-CSF), motilin, neurotensin, oxytocin, vasopressin, osteocalcin, pancreastatin, pancreatic polypeptide, peptide YY, proopiomelanocortin, transforming growth factor, vascular endothelial growth factor, vesicular monoamine transporter, vesicular acetylcholine transporter, ghrelin, NPW, NPB, C3d, prokinetican, thyroid stimulating hormone, luteinizing hormone, follicle stimulating hormone, prolactin, growth hormone, beta-lipotropin, melatonin, kallikriens, kinins, prostaglandins, erythropoietin, p146 (SEQ ID NO:24 amino acid sequence, SEQ ID NO:25, nucleotide sequence), estrogen, testosterone, corticosteroids, mineralocorticoids, thyroid hormone, thymic hormones, connective tissue proteins, nuclear proteins, actin, avidin, activin, agrin, albumin, and prohormones, propeptides, splice variants, fragments and analogs thereof.

The following is yet another non-limiting list of antibodies that can be produced by the methods of present invention: abciximab (ReoPro), abciximab anti-platelet aggregation monoclonal antibody, anti-CD11a (hu1124), anti-CD18 antibody, anti-CD20 antibody, anti-cytomegalovirus (CMV) antibody, anti-digoxin antibody, anti-hepatitis B antibody, anti-HER-2 antibody, anti-idiotype antibody to GD3 glycolipid, anti-IgE antibody, anti-IL-2R antibody, antimetastatic cancer antibody (mAb 17-1A), anti-rabies antibody, anti-respiratory syncytial virus (RSV) antibody, anti-Rh antibody, anti-TCR, anti-TNF antibody, anti-VEGF antibody and fab fragment thereof, rattlesnake venom antibody, black widow spider venom antibody, coral snake venom antibody, antibody against very late antigen-4 (VLA-4), C225 humanized antibody to EGF receptor, chimeric (human & mouse) antibody against TNFα, antibody directed against GPIIb/IIIa receptor on human platelets, gamma globulin, anti-hepatitis B immunoglobulin, human anti-D immunoglobulin, human antibodies against *S. aureus*, human tetanus immunoglobulin, humanized antibody against the epidermal growth receptor-2, humanized antibody against the a subunit of the interleukin-2 receptor, humanized antibody CTLA4IG, humanized antibody to the IL-2 R α-chain, humanized anti-CD40-ligand monoclonal antibody (5c8), humanized mAb against the epidermal growth receptor-2, humanized mAb to rous sarcoma virus, humanized recombinant antibody (IgG1k) against respiratory syncytial virus (RSV), lymphocyte immunoglobulin (anti-thymocyte antibody), lymphocyte immunoglobulin, mAb against factor VII, MDX-210 bi-specific antibody against HER-2, MDX-22, MDX-220 bi-specific antibody against TAG-72 on tumors, MDX-33 antibody to FcγR1 receptor, MDX-447 bi-specific antibody against EGF receptor, MDX-447 bispecific humanized antibody to EGF receptor, MDX-RA immunotoxin (ricin A linked) antibody, Medi-507 antibody (humanized form of BTI-322) against CD2 receptor on T-cells, monoclonal antibody LDP-02, muromonab-CD3(OKT3) antibody, OKT3 ("muromomab- CD3") antibody, PRO542 antibody, ReoPro ("abciximab") antibody, and TNF-IgG fusion protein.

The antibodies prepared using the methods of the present invention may also be designed to possess specific labels that may be detected through means known to one of ordinary skill in the art. The antibodies may also be designed to possess specific sequences useful for purification through means known to one of ordinary skill in the art. Specialty antibodies designed for binding specific antigens may also be made in transgenic animals using the transposon-based vectors of the present invention.

Production of a monoclonal antibody using the transposon-based vectors of the present invention can be accomplished in a variety of ways. In one embodiment, two vectors may be constructed: one that encodes the light chain, and a second vector that encodes the heavy chain of the monoclonal antibody. These vectors may then be incorporated into the genome of the target animal by methods disclosed herein. In an alternative embodiment, the sequences encoding light and heavy chains of a monoclonal antibody may be included on a single DNA construct. For example, the coding sequence of light and heavy chains of a murine monoclonal antibody that show specificity for human seminoprotein can be expressed using transposon-based constructs of the present invention (GenBank Accession numbers AY129006 and AY129304 for the light and heavy chains, respectively).

Further included in the present invention are proteins and peptides synthesized by the immune system including those synthesized by the thymus, lymph nodes, spleen, and the gastrointestinal associated lymph tissues (GALT) system. The immune system proteins and peptides proteins that can be made in transgenic animals using the transposon-based vectors of the present invention include, but are not limited to, alpha-interferon, beta-interferon, gamma-interferon, alpha-interferon A, alpha-interferon 1, G-CSF, GM-CSF, interlukin-1 (IL-1), IL-2, IL-3, IL-4, IL-5, IL-6, IL-7, IL-8, IL-9, IL-10, IL-11, IL-12, IL-13, TNF-α, and TNF-β. Other cytokines included in the present invention include cardiotrophin, stromal cell derived factor, macrophage derived chemokine (MDC), melanoma growth stimulatory activity (MGSA), macrophage inflammatory proteins 1 alpha (MIP-1 alpha), 2, 3 alpha, 3 beta, 4 and 5.

Lytic peptides such as p146 are also included in the desired molecules of the present invention. In one embodiment, the p146 peptide comprises an amino acid sequence of SEQ ID NO:24. The present invention also encompasses a transposon-based vector comprising a p146 nucleic acid comprising a polynucleotide sequence of SEQ ID NO:25.

Enzymes are another class of proteins that may be made through the use of the transposon-based vectors of the present invention. Such enzymes include but are not limited to adenosine deaminase, alpha-galactosidase, cellulase, collagenase, dnaseI, hyaluronidase, lactase, L-asparaginase, pancreatin, papain, streptokinase B, subtilisin, superoxide dismutase, thrombin, trypsin, urokinase, fibrinolysin, glucocerebrosidase and plasminogen activator. In some embodiments wherein the enzyme could have deleterious effects, additional amino acids and a protease cleavage site are added to the carboxy end of the enzyme of interest in order to prevent expression of a functional enzyme. Subsequent digestion of the enzyme with a protease results in activation of the enzyme.

Extracellular matrix proteins are one class of desired proteins that may be made through the use of the present invention. Examples include but are not limited to collagen, fibrin, elastin, laminin, and fibronectin and subtypes thereof. Intracellular proteins and structural proteins are other classes of desired proteins in the present invention.

Growth factors are another desired class of proteins that may be made through the use of the present invention and include, but are not limited to, transforming growth factor-α ("TGF-α"), transforming growth factor-β (TGF-β), platelet-derived growth factors (PDGF), fibroblast growth factors (FGF), including FGF acidic isoforms 1 and 2, FGF basic form 2 and FGF 4, 8, 9 and 10, nerve growth factors (NGF) including NGF 2.5s, NGF 7.0s and beta NGF and neurotrophins, brain derived neurotrophic factor, cartilage derived factor, growth factors for stimulation of the production of red blood cells, growth factors for stimulation of the production of white blood cells, bone growth factors (BGF), basic fibroblast growth factor, vascular endothelial growth factor (VEGF), granulocyte colony stimulating factor (G-CSF), insulin like growth factor (IGF) I and II, hepatocyte growth factor, glial neurotrophic growth factor (GDNF), stem cell factor (SCF), keratinocyte growth factor (KGF), transforming growth factors (TGF), including TGFs alpha, beta, beta1, beta2, beta3, skeletal growth factor, bone matrix derived growth factors, bone derived growth factors, erythropoietin (EPO) and mixtures thereof.

Another desired class of proteins that may be made may be made through the use of the present invention include, but are not limited to, leptin, leukemia inhibitory factor (LIF), tumor necrosis factor alpha and beta, ENBREL, angiostatin, endostatin, thrombospondin, osteogenic protein-1, bone morphogenetic proteins 2 and 7, osteonectin, somatomedin-like peptide, and osteocalcin.

Yet another desired class of proteins are blood proteins or clotting cascade protein including albumin, Prekallikrein, High molecular weight kininogen (HMWK) (contact activation cofactor; Fitzgerald, Flaujeac Williams factor), Factor I (Fibrinogen), Factor II (prothrombin), Factor III (Tissue Factor), Factor IV (calcium), Factor V (proaccelerin, labile factor, accelerator (Ac-) globulin), Factor VI (Va) (accelerin), Factor VII (proconvertin), serum prothrombin conversion accelerator (SPCA), cothromboplastin), Factor VIII (antihemophiliac factor A, antihemophilic globulin (AHG)), Factor IX (Christmas Factor, antihemophilic factor B, plasma thromboplastin component (PTC)), Factor X (Stuart-Prower Factor), Factor XI (Plasma thromboplastin antecedent (PTA)), Factor XII (Hageman Factor), Factor XIII (rotransglutaminase, fibrin stabilizing factor (FSF), fibrinoligase), von Willebrand factor, Protein C, Protein S, Thrombomodulin, Antithrombin III.

A non-limiting list of the peptides and proteins that may be made may be made through the use of the present invention is provided in product catalogs (electronically available over the internet) of companies such as Phoenix Pharmaceuticals, Inc. (530 Harbor Boulevard, Belmont, Calif.), Peninsula Labs (San Carlos Calif.), SIGMA (St. Louis, Mo.), Cappel ICN (Irvine, Calif.), and Calbiochem (La Jolla, Calif.). The polynucleotide sequences encoding these proteins and peptides of interest may be obtained from the scientific literature, from patents, and from databases such as GenBank. Alternatively, one of ordinary skill in the art may design the polynucleotide sequence to be incorporated into the genome by choosing the codons that encode for each amino acid in the desired protein or peptide.

Some of these desired proteins or peptides that may be made through the use of the present invention include but are not limited to the following: adrenomedulin, amylin, calcitonin, amyloid, calcitonin gene-related peptide, cholecystokinin, gastrin, gastric inhibitory peptide, gastrin releasing peptide, interleukin, interferon, cortistatin, somatostatin, endothelin, sarafotoxin, glucagon, glucagon-like peptide, insulin, atrial natriuretic peptide, BNP, CNP, neurokinin, substance P, leptin, neuropeptide Y, melanin concentrating hormone, melanocyte stimulating hormone, orphanin, endorphin, dynorphin, enkephalin, leumorphin, peptide F, PACAP, PACAP-related peptide, parathyroid hormone, urocortin, corticotrophin releasing hormone, PHM, PHI, vasoactive intestinal polypeptide, secretin, ACTH, angiotensin, angiostatin, bombesin, endostatin, bradykinin, FMRF amide, galanin, gonadotropin releasing hormone (GnRH) associated peptide, GnRH, growth hormone releasing hormone, inhibin, granulocyte-macrophage colony stimulating factor (GM-CSF), motilin, neurotensin, oxytocin, vasopressin, osteocalcin, pancreastatin, pancreatic polypeptide, peptide YY, proopiomelanocortin, transforming growth factor, vascular endothelial growth factor, vesicular monoamine transporter, vesicular acetylcholine transporter, ghrelin, NPW, NPB, C3d, prokinetican, thyroid stimulating hormone, luteinizing hormone, follicle stimulating hormone, prolactin, growth hormone, beta-lipotropin, melatonin, kallikriens, kinins, prostaglandins, erythropoietin, p146 (SEQ ID NO:24, amino acid sequence, SEQ ID NO:25, nucleotide sequence), thymic hormones, connective tissue proteins, nuclear proteins, actin, avidin, activin, agrin, albumin, apolipoproteins, apolipoprotein A, apolipoprotein B, and prohormones, propeptides, splice variants, fragments and analogs thereof.

Other desired proteins that may be made by the transgenic animals of the present invention include bacitracin, polymixin b, vancomycin, cyclosporine, anti-RSV antibody, alpha-1 antitrypsin (AAT), anti-cytomegalovirus antibody, anti-hepatitis antibody, anti-inhibitor coagulant complex, anti-rabies antibody, anti-Rh(D) antibody, adenosine deaminase, anti-digoxin antibody, antivenin crotalidae (rattlesnake venom antibody), antivenin latrodectus (black widow spider venom antibody), antivenin micrurus (coral snake venom antibody), aprotinin, corticotropin (ACTH), diphtheria antitoxin, lymphocyte immune globulin (anti-thymocyte antibody), protamine, thyrotropin, capreomycin, α-galactosidase, gramicidin, streptokinase, tetanus toxoid, tyrothricin, IGF-1, proteins of varicella vaccine, anti-TNF antibody, anti-IL-2r antibody, anti-HER-2 antibody, OKT3 ("muromonab-CD3") antibody, TNF-IgG fusion protein, ReoPro ("abciximab") antibody, ACTH fragment 1-24, desmopressin, gonadotropin-releasing hormone, histrelin, leuprolide, lypressin, nafarelin, peptide that binds GPIIb/MPIIIa on platelets (integrilin), goserelin, capreomycin, colistin, anti-respiratory syncytial virus, lymphocyte immune globulin (Thymoglovin, Atgam), panorex, alpha-antitrypsin, botulinin, lung surfactant protein, tumor necrosis receptor-IgG fusion protein (enbrel), gonadorelin, proteins of influenza vaccine, proteins of rotavirus vaccine, proteins of haemophilus b conjugate vaccine, proteins of poliovirus vaccine, proteins of pneumococcal conjugate vaccine, proteins of meningococcal C vaccine, proteins of influenza vaccine, megakaryocyte growth and development factor (MGDF), neuroimmunophilin ligand-A (NIL-A), brain-derived neurotrophic factor (BDNF), glial cell line-derived neurotrophic factor (GDNF), leptin (native), leptin B, leptin C, IL-IRA (interleukin-IRA), R-568, novel erythropoiesis-stimulating protein (NESP), humanized mAb to rous sarcoma virus (MEDI-493), glutamyl-tryptophan dipeptide IM862, LFA-3TIP immunosuppressive, humanized anti-CD40-ligand monoclonal antibody (5c8), gelsonin enzyme, tissue factor pathway inhibitor (TFPI), proteins of meningitis B vaccine, antimetastatic cancer antibody (mAb 17-1A), chimeric (human & mouse) mAb against TNFα, mAb against factor VII, relaxin, capreomycin, glycopeptide (LY333328), recombi- nant human activated protein C (rhAPC), humanized mAb against the epidermal growth receptor-2, altepase, anti-CD20 antigen, C2B8 antibody, insulin-like growth factor-1, atrial natriuretic peptide (anaritide), tenectaplase, anti-CD11a antibody (hu 1124), anti-CD18 antibody, mAb LDP-02, anti-VEGF antibody, fab fragment of anti-VEGF Ab, APO2 ligand (tumor necrosis factor-related apoptosis-inducing ligand), rTGF-β (transforming growth factor-β), alpha-antitrypsin, ananain (a pineapple enzyme), humanized mAb CTLA4IG, PRO542 (mAb), D2E7 (mAb), calf intestine alkaline phosphatase, α-L-iduronidase, α-L-galactosidase (humanglutamic acid decarboxylase, acid sphingomyelinase, bone morphogenetic protein-2 (rhBMP-2), proteins of HIV vaccine, T cell receptor (TCR) peptide vaccine, TCR peptides, V beta 3 and V beta 13.1. (IR502), (IR501), BI 1050/1272 mAb against very late antigen-4 (VLA-4), C225 humanized mAb to EGF receptor, anti-idiotype antibody to GD3 glycolipid, antibacterial peptide against *H. pylori*, MDX-447 bispecific humanized mAb to EGF receptor, anti-cytomegalovirus (CMV), Medi-491 B 19 parvovirus vaccine, humanized recombinant mAb (IgG1k) against respiratory syncytial virus (RSV), urinary tract infection vaccine (against "pili" on *Escherechia coli* strains), proteins of lyme disease vaccine against *B. burgdorferi* protein (DbpA), proteins of Medi-501 human papilloma virus-11 vaccine (HPV), *Streptococcus pneumoniae* vaccine, Medi-507 mAb (humanized form of BTI-322) against CD2 receptor on T-cells, MDX-33 mAb to FcγR1 receptor, MDX-RA immunotoxin (ricin A linked) mAb, MDX-210 bi-specific mAb against HER-2, MDX-447 bi-specific mAb against EGF receptor, MDX-22, MDX-220 bi-specific mAb against TAG-72 on tumors, colony-stimulating factor (CSF) (molgramostim), humanized mAb to the IL-2 R α-chain (basiliximab), mAb to IgE (IGE 025A), myelin basic protein-altered peptide (MSP771A), humanized mAb against the epidermal growth receptor-2, humanized mAb against the α subunit of the interleukin-2 receptor, low molecular weight heparin, anti-hemophillic factor, and bactericidal/permeability-increasing protein (r-BPI).

The peptides and proteins made using the present invention may be labeled using labels and techniques known to one of ordinary skill in the art. Some of these labels are described in the "Handbook of Fluorescent Probes and Research Products", ninth edition, Richard P. Haugland (ed) Molecular Probes, Inc. Eugene, Oreg.), which is incorporated herein in its entirety. Some of these labels may be genetically engineered into the polynucleotide sequence for the expression of the selected protein or peptide. The peptides and proteins may also have label-incorporation "handles" incorporated to allow labeling of an otherwise difficult or impossible to label protein.

It is to be understood that the various classes of desired peptides and proteins, as well as specific peptides and proteins described in this section may be modified as described below by inserting selected codons for desired amino acid substitutions into the gene incorporated into the transgenic animal.

The present invention may also be used to produce desired molecules other than proteins and peptides including, but not limited to, lipoproteins such as high density lipoprotein (HDL), HDL-Milano, and low density lipoprotein, lipids, carbohydrates, siRNA and ribozymes. In these embodiments, a gene of interest encodes a nucleic acid molecule or a protein that directs production of the desired molecule.

The present invention further encompasses the use of inhibitory molecules to inhibit endogenous (i.e., non-vector) protein production. These inhibitory molecules include antisense nucleic acids, siRNA and inhibitory proteins. In a preferred embodiment, the endogenous protein whose expression is inhibited is an egg white protein including, but not limited to ovalbumin, ovotransferrin, and ovomucin. In one embodiment, a transposon-based vector containing an ovalbumin DNA sequence, that upon transcription forms a double stranded RNA molecule, is transfected into an animal such as a bird and the bird's production of endogenous ovalbumin protein is reduced by the interference RNA mechanism (RNAi). In other embodiments, a transposon-based vector encodes an inhibitory RNA molecule that inhibits the expression of more than one egg white protein. One exemplary construct is provided in FIG. 4 wherein "Ovgen" indicates approximately 60 base pairs of an ovalbumin gene, "Ovotrans" indicates approximately 60 base pairs of an ovotransferrin gene and "Ovomucin" indicates approximately 60 base pairs of an ovomucin gene. These ovalbumin, ovotransferrin and ovomucin can be from any avian species, and in some embodiments, are from a chicken or quail. The term "pro" indicates the pro portion of a prepro sequence. One exemplary prepro sequence is that of cecropin and comprising base pairs 563-733 of the Cecropin cap site and Prepro provided in Genbank accession number X07404. Additional cecropin prepro and pro sequences are provided in SEQ ID NO:48, SEQ ID NO:49, SEQ ID NO:50, and SEQ ID NO:51. Additionally, inducible knockouts or knockdowns of the endogenous protein may be created to achieve a reduction or inhibition of endogenous protein production. Endogenous egg white production can be inhibited in an avian at any time, but is preferably inhibited preceding, or immediately preceding, the harvest of eggs.

Modified Desired Proteins and Peptides

"Proteins", "peptides," "polypeptides" and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the protein, or to the alpha-amino group (imino group when participating in a peptide bond) of an amino acid at any other location within the protein. Similarly, the term "carboxy terminus" (abbreviated C-terminus) refers to the free carboxyl group on the amino acid at the carboxy terminus of a protein, or to the carboxyl group of an amino acid at any other location within the protein.

Typically, the amino acids making up a protein are numbered in order, starting at the amino terminal and increasing in the direction toward the carboxy terminal of the protein. Thus, when one amino acid is said to "follow" another, that amino acid is positioned closer to the carboxy terminal of the protein than the preceding amino acid.

The term "residue" is used herein to refer to an amino acid (D or L) or an amino acid mimetic that is incorporated into a protein by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

Furthermore, one of skill will recognize that, as mentioned above, individual substitutions, deletions or additions which alter, add or delete a single amino acid or a small percentage of amino acids (typically less than about 5%, more typically less than about 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

A conservative substitution is a substitution in which the substituting amino acid (naturally occurring or modified) is structurally related to the amino acid being substituted, i.e., has about the same size and electronic properties as the amino acid being substituted. Thus, the substituting amino acid would have the same or a similar functional group in the side chain as the original amino acid. A "conservative substitution" also refers to utilizing a substituting amino acid which is identical to the amino acid being substituted except that a functional group in the side chain is protected with a suitable protecting group.

Suitable protecting groups are described in Green and Wuts, "Protecting Groups in Organic Synthesis", John Wiley and Sons, Chapters 5 and 7, 1991, the teachings of which are incorporated herein by reference. Preferred protecting groups are those which facilitate transport of the peptide through membranes, for example, by reducing the hydrophilicity and increasing the lipophilicity of the peptide, and which can be cleaved, either by hydrolysis or enzymatically (Ditter et al., 1968. J. Pharm. Sci. 57:783; Ditter et al., 1968. J. Pharm. Sci. 57:828; Ditter et al., 1969. J. Pharm. Sci. 58:557; King et al., 1987. Biochemistry 26:2294; Lindberg et al., 1989. Drug Metabolism and Disposition 17:311; Tunek et al., 1988. Biochem. Pharm. 37:3867; Anderson et al., 1985 Arch. Biochem. Biophys. 239:538; and Singhal et al., 1987. FASEB J. 1:220). Suitable hydroxyl protecting groups include ester, carbonate and carbamate protecting groups. Suitable amine protecting groups include acyl groups and alkoxy or aryloxy carbonyl groups, as described above for N-terminal protecting groups. Suitable carboxylic acid protecting groups include aliphatic, benzyl and aryl esters, as described below for C-terminal protecting groups. In one embodiment, the carboxylic acid group in the side chain of one or more glutamic acid or aspartic acid residues in a peptide of the present invention is protected, preferably as a methyl, ethyl, benzyl or substituted benzyl ester, more preferably as a benzyl ester.

Provided below are groups of naturally occurring and modified amino acids in which each amino acid in a group has similar electronic and steric properties. Thus, a conservative substitution can be made by substituting an amino acid with another amino acid from the same group. It is to be understood that these groups are non-limiting, i.e. that there are additional modified amino acids which could be included in each group.

Group I includes leucine, isoleucine, valine, methionine and modified amino acids having the following side chains: ethyl, n-propyl n-butyl. Preferably, Group I includes leucine, isoleucine, valine and methionine.

Group II includes glycine, alanine, valine and a modified amino acid having an ethyl side chain. Preferably, Group II includes glycine and alanine.

Group III includes phenylalanine, phenylglycine, tyrosine, tryptophan, cyclohexylmethyl glycine, and modified amino residues having substituted benzyl or phenyl side chains. Preferred substituents include one or more of the following: halogen, methyl, ethyl, nitro, —NH$_2$, methoxy, ethoxy and —CN. Preferably, Group III includes phenylalanine, tyrosine and tryptophan.

Group IV includes glutamic acid, aspartic acid, a substituted or unsubstituted aliphatic, aromatic or benzylic ester of glutamic or aspartic acid (e.g., methyl, ethyl, n-propyl isopropyl, cyclohexyl, benzyl or substituted benzyl), glutamine, asparagine, —CO—NH— alkylated glutamine or asparagines (e.g., methyl, ethyl, n-propyl and iso-propyl) and modified amino acids having the side chain —(CH$_2$)$_3$—COOH, an ester thereof (substituted or unsubstituted aliphatic, aromatic or benzylic ester), an amide thereof and a substituted or unsubstituted N-alkylated amide thereof. Preferably, Group IV includes glutamic acid, aspartic acid, methyl aspartate, ethyl aspartate, benzyl aspartate and methyl glutamate, ethyl glutamate and benzyl glutamate, glutamine and asparagine.

Group V includes histidine, lysine, ornithine, arginine, N-nitroarginine, β-cycloarginine,γ-hydroxyarginine, N-amidinocitruline and 2-amino-4-guanidinobutanoic acid, homologs of lysine, homologs of arginine and homologs of ornithine. Preferably, Group V includes histidine, lysine, arginine and ornithine. A homolog of an amino acid includes from 1 to about 3 additional or subtracted methylene units in the side chain.

Group VI includes serine, threonine, cysteine and modified amino acids having C1-C5 straight or branched alkyl side chains substituted with —OH or —SH, for example, —CH$_2$CH$_2$OH, —CH$_2$CH$_2$CH$_2$OH or —CH$_2$CH$_2$OHCH$_3$. Preferably, Group VI includes serine, cysteine or threonine.

In another aspect, suitable substitutions for amino acid residues include "severe" substitutions. A "severe substitution" is a substitution in which the substituting amino acid (naturally occurring or modified) has significantly different size and/or electronic properties compared with the amino acid being substituted. Thus, the side chain of the substituting amino acid can be significantly larger (or smaller) than the side chain of the amino acid being substituted and/or can have functional groups with significantly different electronic properties than the amino acid being substituted. Examples of severe substitutions of this type include the substitution of phenylalanine or cyclohexylmethyl glycine for alanine, isoleucine for glycine, a D amino acid for the corresponding L amino acid, or —NH—CH[(—CH$_2$)$_5$—COOH]—CO— for aspartic acid. Alternatively, a functional group may be added to the side chain, deleted from the side chain or exchanged with another functional group. Examples of severe substitutions of this type include adding of valine, leucine or isoleucine, exchanging the carboxylic acid in the side chain of aspartic acid or glutamic acid with an amine, or deleting the amine group in the side chain of lysine or ornithine. In yet another alternative, the side chain of the substituting amino acid can have significantly different steric and electronic properties that the functional group of the amino acid being substituted. Examples of such modifications include tryptophan for glycine, lysine for aspartic acid and —(CH$_2$)$_4$COOH for the side chain of serine. These examples are not meant to be limiting.

In another embodiment, for example in the synthesis of a peptide 26 amino acids in length, the individual amino acids may be substituted according in the following manner:

$AA_1$ is serine, glycine, alanine, cysteine or threonine;
$AA_2$ is alanine, threonine, glycine, cysteine or serine;
$AA_3$ is valine, arginine, leucine, isoleucine, methionine, ornithine, lysine, N-nitroarginine, β-cycloarginine, γ-hydroxyarginine, N-amidinocitruline or 2-amino-4-guanidinobutanoic acid;
$AA_4$ is proline, leucine, valine, isoleucine or methionine;
$AA_5$ is tryptophan, alanine, phenylalanine, tyrosine or glycine;
$AA_6$ is serine, glycine, alanine, cysteine or threonine;
$AA_7$ is proline, leucine, valine, isoleucine or methionine;
$AA_8$ is alanine, threonine, glycine, cysteine or serine;
$AA_9$ is alanine, threonine, glycine, cysteine or serine;
$AA_{10}$ is leucine, isoleucine, methionine or valine;
$AA_{11}$ is serine, glycine, alanine, cysteine or threonine;
$AA_{12}$ is leucine, isoleucine, methionine or valine;
$AA_{13}$ is leucine, isoleucine, methionine or valine;
$AA_{14}$ is glutamine, glutamic acid, aspartic acid, asparagine, or a substituted or unsubstituted aliphatic or aryl ester of glutamic acid or aspartic acid;
$AA_{15}$ is arginine, N-nitroarginine, β-cycloarginine, γ-hydroxy-arginine, N-amidinocitruline or 2-amino-4-guanidinobutanoic acid
$AA_{16}$ is proline, leucine, valine, isoleucine or methionine;
$AA_{17}$ is serine, glycine, alanine, cysteine or threonine;
$AA_{18}$ is glutamic acid, aspartic acid, asparagine, glutamine or a substituted or unsubstituted aliphatic or aryl ester of glutamic acid or aspartic acid;
$AA_{19}$ is aspartic acid, asparagine, glutamic acid, glutamine, leucine, valine, isoleucine, methionine or a substituted or unsubstituted aliphatic or aryl ester of glutamic acid or aspartic acid;
$AA_{20}$ is valine, arginine, leucine, isoleucine, methionine, ornithine, lysine, N-nitroarginine, β-cycloarginine, γ-hydroxyarginine, N-amidinocitruline or 2-amino-4-guanidinobutanoic acid;
$AA_{21}$ is alanine, threonine, glycine, cysteine or serine;
$AA_{22}$ is alanine, threonine, glycine, cysteine or serine;
$AA_{23}$ is histidine, serine, threonine, cysteine, lysine or ornithine;
$AA_{24}$ is threonine, aspartic acid, serine, glutamic acid or a substituted or unsubstituted aliphatic or aryl ester of glutamic acid or aspartic acid;
$AA_{25}$ is asparagine, aspartic acid, glutamic acid, glutamine, leucine, valine, isoleucine, methionine or a substituted or unsubstituted aliphatic or aryl ester of glutamic acid or aspartic acid; and
$AA_{26}$ is cysteine, histidine, serine, threonine, lysine or ornithine.

It is to be understood that these amino acid substitutions may be made for longer or shorter peptides than the 26 mer in the preceding example above, and for proteins.

In one embodiment of the present invention, codons for the first several N-terminal amino acids of the transposase are modified such that the third base of each codon is changed to an A or a T without changing the corresponding amino acid. It is preferable that between approximately 1 and 20, more preferably 3 and 15, and most preferably between 4 and 12 of the first N-terminal codons of the gene of interest are modified such that the third base of each codon is changed to an A or a T without changing the corresponding amino acid. In one embodiment, the first ten N-terminal codons of the gene of interest are modified in this manner.

When several desired proteins, protein fragments or peptides are encoded in the gene of interest to be incorporated into the genome, one of skill in the art will appreciate that the proteins, protein fragments or peptides may be separated by a spacer molecule such as, for example, a peptide, consisting of one or more amino acids. Generally, the spacer will have no specific biological activity other than to join the desired proteins, protein fragments or peptides together, or to preserve some minimum distance or other spatial relationship between them. However, the constituent amino acids of the spacer may be selected to influence some property of the molecule such as the folding, net charge, or hydrophobicity. The spacer may also be contained within a nucleotide sequence with a purification handle or be flanked by cleavage sites, such as proteolytic cleavage sites.

Such polypeptide spacers may have from about 5 to about 40 amino acid residues. The spacers in a polypeptide are independently chosen, but are preferably all the same. The spacers should allow for flexibility of movement in space and are therefore typically rich in small amino acids, for example, glycine, serine, proline or alanine. Preferably, peptide spacers contain at least 60%, more preferably at least 80% glycine or alanine. In addition, peptide spacers generally have little or no biological and antigenic activity. Preferred spacers are (Gly-Pro-Gly-Gly)$_x$ (SEQ ID NO:26) and (Gly$_4$-Ser)$_y$, wherein x is an integer from about 3 to about 9 and y is an integer from about 1 to about 8. Specific examples of suitable spacers include (Gly-Pro-Gly-Gly)$_3$ SEQ ID NO: 27
Gly Pro Gly Gly Gly Pro Gly Gly Gly Pro Gly Gly (Gly$_4$-Ser)$_3$ SEQ ID NO: 28
Gly Gly Gly Gly Ser Gly Gly Gly Gly Ser Gly Gly Gly Gly Ser
or (Gly$_4$-Ser)$_4$ SEQ ID NO: 29
Gly Gly Gly Gly Ser Gly Gly Gly Gly Ser Gly Gly Gly Gly Ser Gly Gly Gly Gly Ser.

Nucleotide sequences encoding for the production of residues which may be useful in purification of the expressed recombinant protein may also be built into the vector. Such sequences are known in the art and include the glutathione binding domain from glutathione S-transferase, polylysine, hexa-histidine or other cationic amino acids, thioredoxin, hemagglutinin antigen and maltose binding protein.

Additionally, nucleotide sequences may be inserted into the gene of interest to be incorporated so that the protein or peptide can also include from one to about six amino acids that create signals for proteolytic cleavage. In this manner, if a gene is designed to make one or more peptides or proteins of interest in the transgenic animal, specific nucleotide sequences encoding for amino acids recognized by enzymes may be incorporated into the gene to facilitate cleavage of the large protein or peptide sequence into desired peptides or proteins or both. For example, nucleotides encoding a proteolytic cleavage site can be introduced into the gene of interest so that a signal sequence can be cleaved from a protein or peptide encoded by the gene of interest. Nucleotide sequences encoding other amino acid sequences which display pH sensitivity or chemical sensitivity may also be added to the vector to facilitate separation of the signal sequence from the peptide or protein of interest.

Proteolytic cleavage sites include cleavage sites recognized by exopeptidases such as carboxypeptidase A, carboxypeptidase B, aminopeptidase I, and dipeptidylaminopeptidase; endopeptidases such as trypsin, V8-protease, enterokinase, factor Xa, collagenase, endoproteinase, subtilisin, and thombin; and proteases such as Protease 3C IgA protease (Igase) Rhinovirus 3C(preScission) protease. Chemical cleavage sites are also included in the definition of cleavage site as used herein. Chemical cleavage sites include, but are not limited to, site cleaved by cyanogen bromide, hydroxylamine, formic acid, and acetic acid.

In one embodiment of the present invention, a TAG sequence is linked to the gene of interest. The TAG sequence serves three purposes: 1) it allows free rotation of the peptide or protein to be isolated so there is no interference from the native protein or signal sequence, i.e. vitellogenin, 2) it provides a "purification handle" to isolate the protein using column purification, and 3) it includes a cleavage site to remove the desired protein from the signal and purification sequences. Accordingly, as used herein, a TAG sequence includes a spacer sequence, a purification handle and a cleavage site. The spacer sequences in the TAG proteins contain one or more repeats shown in SEQ ID NO:30. A preferred spacer sequence comprises the sequence provided in SEQ ID NO:31. One example of a purification handle is the gp41 hairpin loop from HIV I. Exemplary gp41 polynucleotide and polypeptide sequences are provided in SEQ ID NO:32 and SEQ ID NO:33, respectively. However, it should be understood that any antigenic region may be used as a purification handle, including any antigenic region of gp41. Preferred purification handles are those that elicit highly specific antibodies. Additionally, the cleavage site can be any protein cleavage site known to one of ordinary skill in the art and includes an enterokinase cleavage site comprising the Asp Asp Asp Asp Lys sequence (SEQ ID NO:34) and a furin cleavage site. Constructs containing a TAG sequence are shown in FIGS. 2 and 3. In one embodiment of the present invention, the TAG sequence comprises a polynucleotide sequence of SEQ ID NO:35.

Methods of Administering Transposon-Based Vectors

In addition to the transposon-based vectors described above, the present invention also includes methods of administering the transposon-based vectors to an animal, methods of producing a transgenic animal wherein a gene of interest is incorporated into the germline of the animal and methods of producing a transgenic animal wherein a gene of interest is incorporated into cells other than the germline cells (somatic cells) of the animal. The transposon-based vectors of the present invention are administered to a reproductive organ of an animal via any method known to those of skill in the art. Preferred reproductive organs include an ovary, an oviduct, a mammary gland, and a fallopian tube.

In some embodiments, a transposon-based vector is directly administered to the reproductive organ. Direct administration encompasses injection into the organ, and in a preferred embodiment, a transposon-based vector is injected into the lumen of the oviduct, and more preferably, the lumen of the magnum or the infundibulum of the oviduct. The transposon-based vectors may additionally or alternatively be placed in an artery supplying the reproductive organ. Administering the vectors to the artery supplying the ovary results in transfection of follicles and oocytes in the ovary to create a germline transgenic animal. Alternatively, supplying the vectors through an artery leading to the oviduct would preferably transfect the tubular gland and epithelial cells. Such transfected cells could manufacture a desired protein or peptide for deposition in the egg white. In one embodiment, a transposon-based vector is administered into the lumen of the magnum or the infundibulum of the oviduct and to an artery supplying the oviduct. Indirect administration to the oviduct epithelium may occur through the cloaca. Direct administration into the mammary gland comprises introduction into the duct system of the mammary gland.

Administration of transposon-based vectors may occur in arteries supplying the ovary and or through direct intrathecal administration into the ovary through injection.

The transposon-based vectors may be administered in a single administration, multiple administrations, continuously, or intermittently. The transposon-based vectors may be administered by injection, via a catheter, an osmotic minipump or any other method. In some embodiments, the transposon-based vector is administered to an animal in multiple administrations, each administration containing the vector and a different transfecting reagent.

The transposon-based vectors may be administered to the animal at any point during the lifetime of the animal, however, it is preferable that the vectors are administered prior to the animal reaching sexual maturity. The transposon-based vectors are preferably administered to a chicken between approximately 14 and 16 weeks of age and to a quail between approximately 5 and 10 weeks of age, more preferably 5 and 8 weeks of age, and most preferably between 5 and 6 weeks of age, when standard poultry rearing practices are used. The vectors may be administered at earlier ages when exogenous hormones are used to induce early sexual maturation in the bird. In some embodiments, the transposon-based vector is administered to an animal following an increase in proliferation of the oviduct epithelial cells and/or the tubular gland cells. Such an increase in proliferation normally follows an influx of reproductive hormones in the area of the oviduct. When the animal is an avian, the transposon-based vector is administered following an increase in proliferation of the oviduct epithelial cells and before the avian begins to produce egg white constituents.

In a preferred embodiment, the animal is an egg-laying animal, and more preferably, an avian. In one embodiment, between approximately 1 and 150 µg, 1 and 100 µg, 1 and 50 µg, preferably between 1 and 20 µg, and more preferably between 5 and 10 µg of transposon-based vector DNA is administered to the oviduct of a bird. Optimal ranges depend upon the type of bird and the bird's stage of sexual maturity. In a chicken, it is preferred that between approximately 1 and 100 µg, or 5 and 50 µg are administered. In a quail, it is preferred that between approximately 5 and 10 µg are administered. Intraoviduct administration of the transposon-based vectors of the present invention result in incorporation of the gene of interest into the cells of the oviduct as evidenced by a PCR positive signal in the oviduct tissue. In other embodiments, the transposon-based vector is administered to an artery that supplies the oviduct. These methods of administration may also be combined with any methods for facilitating transfection, including without limitation, electroporation, gene guns, injection of naked DNA, and use of dimethyl sulfoxide (DMSO).

According to the present invention, the transposon-based vector is administered in conjunction with an acceptable carrier and/or transfection reagent. Acceptable carriers include, but are not limited to, water, saline, Hanks Balanced Salt Solution (HBSS), Tris-EDTA (TE) and lyotropic liquid crystals. Transfection reagents commonly known to one of ordinary skill in the art that may be employed include, but are not limited to, the following: cationic lipid transfection reagents, cationic lipid mixtures, polyamine reagents, liposomes and combinations thereof; SUPERFECT®, Cytofectene, BioPORTER®, GenePORTER®, NeuroPORTER®, and perfectin from Gene Therapy Systems; lipofectamine, cellfectin, DMRIE-C oligofectamine, TROJENE® and PLUS reagent from InVitrogen; Xtreme gene, fugene, DOSPER and DOTAP from Roche; Lipotaxi and Genejammer from Strategene; and Escort from SIGMA. In one embodiment, the transfection reagent is SUPERFECT®. The ratio of DNA to transfection reagent may vary based upon the method of administration. In one embodiment, the transposon-based vector is administered to the oviduct and the ratio of DNA to transfection reagent can be from 1:1.5 to 1:15, preferably 1:2 to 1:5, all expressed as wt/vol. Transfection may also be accomplished using other means known to one of ordinary skill in the art, including without limitation electroporation, gene guns, injection of naked DNA, and use of dimethyl sulfoxide (DMSO).

Depending upon the cell or tissue type targeted for transfection, the form of the transposon-based vector may be important. Plasmids harvested from bacteria are generally closed circular supercoiled molecules, and this is the preferred state of a vector for gene delivery because of the ease of preparation. In some instances, transposase expression and insertion may be more efficient in a relaxed, closed circular configuration or in a linear configuration. In still other instances, a purified transposase protein may be co-injected with a transposon-based vector containing the gene of interest for more immediate insertion. This could be accomplished by using a transfection reagent complexed with both the purified transposase protein and the transposon-based vector.

Testing for and Breeding Animals Carrying the Transgene

Figure 5:
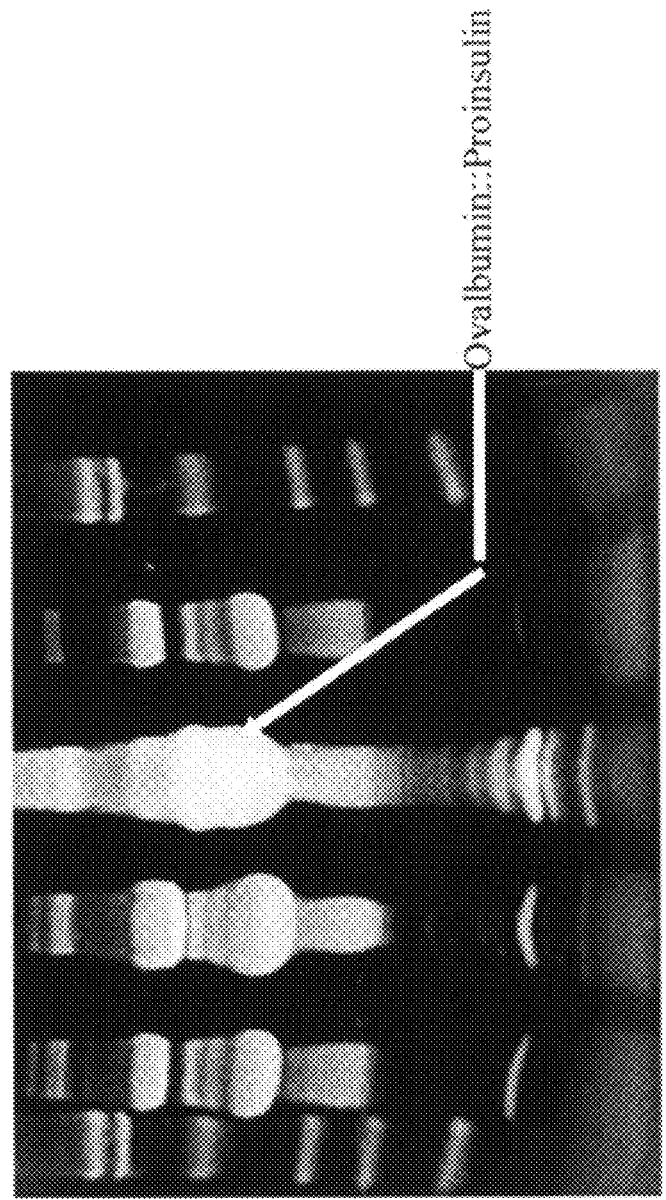
FIG. 5 is a picture of an SDS-PAGE gel wherein a pooled fraction of an isolated proinsulin fusion protein was run in lanes 4 and 6. Lanes 1 and 10 of the gel contain molecular weight standards, lanes 2 and 8 contain non-transgenic chicken egg white, and lanes 3, 5, 7 and 9 are blank.

Following administration of a transposon-based vector to an animal, DNA is extracted from the animal to confirm integration of the gene of interest. Advantages provided by the present invention include the high rates of integration, or incorporation, and transcription of the gene of interest when administered to a bird via an intraoviduct or intraovarian route (including intraarterial administrations to arteries leading to the oviduct or ovary). Example 6 below describes isolation of a proinsulin/ENT TAG protein from a transgenic hen following ammonium sulfate precipitation and ion exchange chromatography. FIG. 5 demonstrates successful administration of a transposon-based vector to a hen, successful integration of the gene of interest, successful production of a protein encoded by the gene of interest, and successful deposition of the protein in egg white produced by the transgenic hen.

Actual frequencies of integration may be estimated both by comparative strength of the PCR signal, and by histological evaluation of the tissues by quantitative PCR. Another method for estimating the rate of transgene insertion is the so-called primed in situ hybridization technique (PRINS). This method determines not only which cells carry a transgene of interest, but also into which chromosome the gene has inserted, and even what portion of the chromosome. Briefly, labeled primers are annealed to chromosome spreads (affixed to glass slides) through one round of PCR, and the slides are then developed through normal in situ hybridization procedures. This technique combines the best features of in situ PCR and fluorescence in situ hybridization (FISH) to provide distinct chromosome location and copy number of the gene in question.

Breeding experiments are also conducted to determine if germline transmission of the transgene has occurred. In a general bird breeding experiment performed according to the present invention, each male bird was exposed to 2-3 different adult female birds for 3-4 days each. This procedure was continued with different females for a total period of 6-12 weeks. Eggs are collected daily for up to 14 days after the last exposure to the transgenic male, and each egg is incubated in a standard incubator. The resulting embryos are examined for transgene presence at day 3 or 4 using PCR. It is to be understood that the above procedure can be modified to suit animals other than birds and that selective breeding techniques may be performed to amplify gene copy numbers and protein output.

Production of Desired Proteins or Peptides in Egg White

In one embodiment, the transposon-based vectors of the present invention may be administered to a bird for production of desired proteins or peptides in the egg white. These transposon-based vectors preferably contain one or more of an ovalbumin promoter, an ovomucoid promoter, an ovalbumin signal sequence and an ovomucoid signal sequence. Oviduct-specific ovalbumin promoters are described in B. O'Malley et al., 1987. EMBO J., vol. 6, pp. 2305-12; A. Qiu et al., 1994. Proc. Nat. Acad. Sci. (USA), vol. 91, pp. 4451-4455; D. Monroe et al., 2000. Biochim. Biophys. Acta, 1517 (1):27-32; H. Park et al., 2000. Biochem., 39:8537-8545; and T. Muramatsu et al., 1996. Poult. Avian Biol. Rev., 6:107-123. Examples of transposon-based vectors designed for production of a desired protein in an egg white are shown in FIGS. 2 and 3.

Production of Desired Proteins or Peptides in Egg Yolk

The present invention is particularly advantageous for production of recombinant peptides and proteins of low solubility in the egg yolk. Such proteins include, but are not limited to, membrane-associated or membrane-bound proteins, lipophilic compounds; attachment factors, receptors, and components of second messenger transduction machinery. Low solubility peptides and proteins are particularly challenging to produce using conventional recombinant protein production techniques (cell and tissue cultures) because they aggregate in water-based, hydrophilic environments. Such aggregation necessitates denaturation and re-folding of the recombinantly-produced proteins, which may deleteriously affect their structure and function. Moreover, even highly soluble recombinant peptides and proteins may precipitate and require denaturation and renaturation when produced in sufficiently high amounts in recombinant protein production systems. The present invention provides an advantageous resolution of the problem of protein and peptide solubility during production of large amounts of recombinant proteins.

In one embodiment of the present invention wherein germ line transfection is obtained via intraovarian administration of the transposon-based vector, deposition of a desired protein into the egg yolk is accomplished in offspring by attaching a sequence encoding a protein capable of binding to the yolk vitellogenin receptor to a gene of interest that encodes a desired protein. This transposon-based vector can be used for the receptor-mediated uptake of the desired protein by the oocytes. In a preferred embodiment, the sequence ensuring the binding to the vitellogenin receptor is a targeting sequence of a vitellogenin protein. The invention encompasses various vitellogenin proteins and their targeting sequences. In a preferred embodiment, a chicken vitellogenin protein targeting sequence is used, however, due to the high degree of conservation among vitellogenin protein sequences and known cross-species reactivity of vitellogenin targeting sequences with their egg-yolk receptors, other vitellogenin targeting sequences can be substituted. One example of a construct for use in the transposon-based vectors of the present invention and for deposition of an insulin protein in an egg yolk is a transposon-based vector containing a vitellogenin promoter, a vitellogenin targeting sequence, a TAG sequence, a pro-insulin sequence and a synthetic polyA sequence. The present invention includes, but is not limited to, vitellogenin targeting sequences residing in the N-terminal domain of vitellogenin, particularly in lipovitellin I. In one embodiment, the vitellogenin targeting sequence contains the polynucleotide sequence of SEQ ID NO:22. In a preferred embodiment, the transposon-based vector contains a transposase gene operably-linked to a constitutive promoter and a gene of interest operably-linked to a liver-specific promoter and a vitellogenin targeting sequence.

Isolation and Purification of Desired Protein or Peptide

For large-scale production of protein, an animal breeding stock that is homozygous for the transgene is preferred. Such homozygous individuals are obtained and identified through, for example, standard animal breeding procedures or PCR protocols.

Once expressed, peptides, polypeptides and proteins can be purified according to standard procedures known to one of ordinary skill in the art, including ammonium sulfate precipitation, affinity columns, column chromatography, gel electrophoresis, high performance liquid chromatography, immunoprecipitation and the like. Substantially pure compositions of about 50 to 99% homogeneity are preferred, and 80 to 95% or greater homogeneity are most preferred for use as therapeutic agents.

In one embodiment of the present invention, the animal in which the desired protein is produced is an egg-laying animal. In a preferred embodiment of the present invention, the animal is an avian and a desired peptide, polypeptide or protein is isolated from an egg white. Egg white containing the exogenous protein or peptide is separated from the yolk and other egg constituents on an industrial scale by any of a variety of methods known in the egg industry. See, e.g., W. Stadelman et al. (Eds.), Egg Science & Technology, Haworth Press, Binghamton, N.Y. (1995). Isolation of the exogenous peptide or protein from the other egg white constituents is accomplished by any of a number of polypeptide isolation and purification methods well known to one of ordinary skill in the art. These techniques include, for example, chromatographic methods such as gel permeation, ion exchange, affinity separation, metal chelation, HPLC, and the like, either alone or in combination. Another means that may be used for isolation or purification, either in lieu of or in addition to chromatographic separation methods, includes electrophoresis. Successful isolation and purification is confirmed by standard analytic techniques, including HPLC, mass spectroscopy, and spectrophotometry. These separation methods are often facilitated if the first step in the separation is the removal of the endogenous ovalbumin fraction of egg white, as doing so will reduce the total protein content to be further purified by about 50%.

To facilitate or enable purification of a desired protein or peptide, transposon-based vectors may include one or more additional epitopes or domains. Such epitopes or domains include DNA sequences encoding enzymatic or chemical cleavage sites including, but not limited to, an enterokinase cleavage site; the glutathione binding domain from glutathione S-transferase; polylysine; hexa-histidine or other cationic amino acids; thioredoxin; hemagglutinin antigen; maltose binding protein; a fragment of gp41 from HIV; and other purification epitopes or domains commonly known to one of skill in the art.

In one representative embodiment, purification of desired proteins from egg white utilizes the antigenicity of the ovalbumin carrier protein and particular attributes of a TAG linker sequence that spans ovalbumin and the desired protein. The TAG sequence is particularly useful in this process because it contains 1) a highly antigenic epitope, a fragment of gp41 from HIV, allowing for stringent affinity purification, and, 2) a recognition site for the protease enterokinase immediately juxtaposed to the desired protein. In a preferred embodiment, the TAG sequence comprises approximately 50 amino acids. A representative TAG sequence is provided below.

```
                                          (SEQ ID NO: 35)
Pro Ala Asp Asp Ala Pro Ala Asp Asp Ala Pro Ala

Asp Asp Ala Pro Ala Asp Asp Ala Pro Ala Asp Asp

Ala Pro Ala Asp Asp Ala Thr Thr Cys Ile Leu Lys

Gly Ser Cys Gly Trp Ile Gly Leu Leu Asp Asp Asp

Asp Lys
```

The underlined sequences were taken from the hairpin loop domain of HIV gp-41 (SEQ ID NO:33). Sequences in italics represent the cleavage site for enterokinase (SEQ ID NO:34). The spacer sequence upstream of the loop domain was made from repeats of (Pro Ala Asp Asp Ala) (SEQ ID NO:31) to provide free rotation and promote surface availability of the hairpin loop from the ovalbumin carrier protein.

Isolation and purification of a desired protein is performed as follows:

1. Enrichment of the egg white protein fraction containing ovalbumin and the transgenic ovalbumin-TAG-desired protein.
2. Size exclusion chromatography to isolate only those proteins within a narrow range of molecular weights (a further enrichment of step 1).
3. Ovalbumin affinity chromatography. Highly specific antibodies to ovalbumin will eliminate virtually all extraneous egg white proteins except ovalbumin and the transgenic ovalbumin-TAG-desired protein.
4. gp41 affinity chromatography using anti-gp41 antibodies. Stringent application of this step will result in virtually pure transgenic ovalbumin-TAG-desired protein.
5. Cleavage of the transgene product can be accomplished in at least one of two ways:
   a. The transgenic ovalbumin-TAG-desired protein is left attached to the gp41 affinity resin (beads) from step 4 and the protease enterokinase is added. This liberates the transgene target protein from the gp41 affinity resin while the ovalbumin-TAG sequence is retained. Separation by centrifugation (in a batch process) or flow through (in a column purification), leaves the desired protein together with enterokinase in solution. Enterokinase is recovered and reused.
   b. Alternatively, enterokinase is immobilized on resin (beads) by the addition of poly-lysine moieties to a non-catalytic area of the protease. The transgenic ovalbumin-TAG-desired protein eluted from the affinity column of step 4 is then applied to the protease resin. Protease action cleaves the ovalbumin-TAG sequence from the desired protein and leaves both entities in solution. The immobilized enterokinase resin is recharged and reused.
   c. The choice of these alternatives is made depending upon the size and chemical composition of the transgene target protein.
6. A final separation of either of these two (5a or 5b) protein mixtures is made using size exclusion, or enterokinase affinity chromatography. This step allows for desalting, buffer exchange and/or polishing, as needed.

Cleavage of the transgene product (ovalbumin-TAG-desired protein) by enterokinase, then, results in two products: ovalbumin-TAG and the desired protein. More specific methods for isolation using the TAG label is provided in the Examples. Some desired proteins may require additions or modifications of the above-described approach as known to one of ordinary skill in the art. The method is scaleable from the laboratory bench to pilot and production facility largely because the techniques applied are well documented in each of these settings.

In another representative embodiment, egg whites containing a protein of interest were pooled and separated, in any order, from the yolks and other egg constituents by methods known to one skilled in the art. A variety of such methods is described in manuals known in the art, such as Egg Science & Technology, W. Stadelman, et al. (Eds.), Haworth Press, Binghamton, N.Y. (1995).

One non-limiting example of a method for isolating a desired peptide, polypeptide or protein from an egg white is as follows. It is to be understood that this method may be employed to isolate any desired peptide, polypeptide or protein from the eggs of transgenic animals of the present invention. This present example involved transgenes that used a portion of or the entire ovalbumin protein, or specific ovalbumin epitopes, as a carrier, linked to the protein of interest via the specified TAG sequence, or another affinity/cleavage sequence. The TAG sequence contains the hairpin loop epitope from HIV I followed by an enterokinase cleavage site.

First, the viscosity of the egg white was lowered by subjecting the egg white to low shear forces of 3140 cps (Tung et al., 1969). The resulting pourable solution was then filtered to remove chalazae. An ammonium sulfate precipitation was then used to enrich the fraction of transgenic protein (see, for example, *Practical Protein Chemistry A Handbook* A. Darbre (Ed.), John Wiley & Sons Ltd., 1986). Other methods of crude fractionation known in the art are also used as needed. The supernatant of this separation was then fractionated using size-exclusion chromatography, further enriching the transgenic fusion protein fraction and eliminating the ammonium sulfate from the material. The fusion protein was isolated by anti-ovalbumin affinity chromatography (batch or column) using methods known to one skilled in the art. This step may capture native ovalbumin in addition to an ovalbumin-transgene fusion protein. After elution from the anti-ovalbumin affinity resin, the transgenic protein was specifically isolated using anti-gp41 affinity chromatography (batch or column) using methods known to one skilled in the art.

Cleavage of the transgene product from the carrier and the TAG sequences was accomplished in one of at least two ways:

1) The transgenic ovalbumin-TAG-transgene target protein was left attached to the gp41 affinity resin and the protease enterokinase was added. Cleavage of the transgene by enterokinase liberated the transgene target protein from the gp41 affinity resin while the ovalbumin-TAG sequence was retained. Separation by centrifugation (in a batch process) or flow through (in a column purification), kept the transgene target protein together with enterokinase in solution. Enterokinase was recovered and reused.

2) Alternatively, enterokinase was immobilized on resin (beads) by the addition of poly-lysine moieties to a non-catalytic area of the protease. The transgenic ovalbumin-TAG-transgene target protein was eluted from the gp41 affinity chromatography resin and then applied to the protease resin. Protease action cleaved the ovalbumin-TAG sequence from the transgene target protein and left both entities in solution. The immobilized enterokinase resin was recharged and reused. The choice between these alternatives is made on a case-by case basis, depending upon the size and chemical composition of the transgene target protein.

A final separation of either of these two (process 1 or 2) protein mixtures was made using size exclusion chromatography, or enterokinase affinity chromatography. This step also allows for desalting, concentrating, buffer exchange and/or polishing, as needed.

It is believed that a typical chicken egg produced by a transgenic animal of the present invention will contain at least 0.001 mg, from about 0.001 to 1.0 mg, or from about 0.001 to 100.0 mg of exogenous protein, peptide or polypeptide, in addition to the normal constituents of egg white (or possibly replacing a small fraction of the latter). In some embodiments, a chicken egg will contain between 50 and 75 mg of exogenous protein.

One of skill in the art will recognize that after biological expression or purification, the desired proteins, fragments thereof and peptides may possess a conformation substantially different than the native conformations of the proteins, fragments thereof and peptides. In this case, it is often necessary to denature and reduce protein and then to cause the protein to re-fold into the preferred conformation. Methods of reducing and denaturing proteins and inducing re-folding are well known to those of skill in the art.

Production of Protein or Peptide in Milk

In addition to methods of producing eggs containing transgenic proteins or peptides, the present invention encompasses methods for the production of milk containing transgenic proteins or peptides. These methods include the administration of a transposon-based vector described above to a mammal through the duct system. In one embodiment, the transposon-based vector contains a transposase operably-linked to a constitutive promoter and a gene of interest operably-linked to mammary specific promoter. Genes of interest can include, but are not limited to antiviral and antibacterial proteins and immunoglobulins. In other embodiments, a transposon-based vector is administered to the ovary of an animal and germline transformation is obtained. In these embodiments, offspring of the transfected animal express a gene of interest in the mammary gland under the control of a mammary gland-specific promoter.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

EXAMPLE 1

IntraOviduct Administration of Transposon-Based Vectors

Quail or chicken were selected for administration of the transposon-based vectors of the present invention. Feathers were removed from the area where surgery was performed and the area was cleansed and sterilized by rinsing it with ethanol (alcohol) and 0.5% chlorhexidine. Using the scalpel, a dorsolateral incision was made through the skin over the ovary approximately 2 cm in length. Using blunt scissors, a second incision was made through the muscle between the last two ribs to expose the oviduct beneath. A small animal retractor was used to spread the last two ribs, exposing the oviduct beneath. The oviduct was further exposed using retractors to pull the intestines to one side.

A delivery solution containing a transposon-based vector and SUPERFECT® was prepared fresh immediately before surgery. Specific ratios of vector and SUPERFECT® that were used in each experiment are provided in the Examples below. The delivery solution was warmed to room temperature prior to injection into the bird. Approximately 250-500 µl of the delivery solution was injected into the lumen of the magnum of the oviduct using a 1 cc syringe with a 27 gauge needle attached. The wound was closed and antibiotic cream liberally applied to the area surrounding the wound.

EXAMPLE 2

Preparation of Transposon-Based Vector pTnMod

A vector was designed for inserting a desired coding sequence into the genome of eukaryotic cells, given below as SEQ ID NO:3. The vector of SEQ ID NO:3, termed pTnMod, was constructed and its sequence verified.

This vector employed a cytomegalovirus (CMV) promoter. A modified Kozak sequence (ACCATG) (SEQ ID NO:1) was added to the promoter. The nucleotide in the wobble position in nucleotide triplet codons encoding the first 10 amino acids of transposase was changed to an adenine (A) or thymine (T), which did not alter the amino acid encoded by this codon. Two stop codons were added and a synthetic polyA was used to provide a strong termination sequence. This vector uses a promoter designed to be active soon after entering the cell (without any induction) to increase the likelihood of stable integration. The additional stop codons and synthetic polyA insures proper termination without read through to potential genes downstream.

The first step in constructing this vector was to modify the transposase to have the desired changes. Modifications to the transposase were accomplished with the primers High Efficiency forward primer (Hef) Altered transposase (ATS)-Hef 5' ATCTCGAGACCATGTGTGAACT TGATATTTTACATGATTCTCTTTACC 3' (SEQ ID NO:36) and Altered transposase-High efficiency reverse primer (Her) 5' GATTGATCATTATCATAATTTC-CCCAAAGCGTAACC 3' (SEQ ID NO:37, a reverse complement primer). In the 5' forward primer ATS-Hef, the sequence CTCGAG (SEQ ID NO:38) is the recognition site for the restriction enzyme Xho I, which permits directional cloning of the amplified gene. The sequence ACCATG (SEQ ID NO:1) contains the Kozak sequence and start codon for the transposase and the underlined bases represent changes in the wobble position to an A or T of codons for the first 10 amino acids (without changing the amino acid coded by the codon). Primer ATS-Her (SEQ ID NO:37) contains an additional stop codon TAA in addition to native stop codon TGA and adds a Bcl I restriction site, TGATCA (SEQ ID NO:39), to allow directional cloning. These primers were used in a PCR reaction with pTnLac (p defines plasmid, tn defines transposon, and lac defines the beta fragment of the lactose gene, which contains a multiple cloning site) as the template for the transposase and a FailSafe™ PCR System (which includes enzyme, buffers, dNTP's, $MgCl_2$ and PCR Enhancer; Epicentre Technologies, Madison, Wis.). Amplified PCR product was electrophoresed on a 1% agarose gel, stained with ethidium bromide, and visualized on an ultraviolet transilluminator. A band corresponding to the expected size was excised from the gel and purified from the agarose using a Zymo Clean Gel Recovery Kit (Zymo Research, Orange, Calif.). Purified DNA was digested with restriction enzymes Xho 1 (5') and Bcl I (3') (New England Biolabs, Beverly, Mass.) according to the manufacturer's protocol. Digested DNA was purified from restriction enzymes using a Zymo DNA Clean and Concentrator kit (Zymo Research).

Plasmid gwhiz (Gene Therapy Systems, San Diego, Calif.) was digested with restriction enzymes Sal I and BamH I (New England Biolabs), which are compatible with Xho I and Bcl I, but destroy the restriction sites. Digested gwhiz was separated on an agarose gel, the desired band excised and purified as described above. Cutting the vector in this manner facilitated directional cloning of the modified transposase (mATS) between the CMV promoter and synthetic polyA.

To insert the mATS between the CMV promoter and synthetic polyA in gWhiz, a Stratagene T4 Ligase Kit (Stratagene, Inc. La Jolla, Calif.) was used and the ligation set up according to the manufacturer's protocol. Ligated product was transformed into *E. coli* Top10 competent cells (Invitrogen Life Technologies, Carlsbad, Calif.) using chemical transformation according to Invitrogen's protocol. Transformed bacteria were incubated in 1 ml of SOC (GIBCO BRL, CAT#15544-042) medium for 1 hour at 37° C. before being spread to LB (Luria-Bertani media (broth or agar)) plates supplemented with 100 µg/ml ampicillin (LB/amp plates). These plates were incubated overnight at 37° C. and resulting colonies picked to LB/amp broth for overnight growth at 37° C. Plasmid DNA was isolated using a modified alkaline lysis protocol (Sambrook et al., 1989), electrophoresed on a 1% agarose gel, and visualized on a U.V. transilluminator after ethidium bromide staining. Colonies producing a plasmid of the expected size (approximately 6.4 kbp) were cultured in at least 250 ml of LB/amp broth and plasmid DNA harvested using a Qiagen Maxi-Prep Kit (column purification) according to the manufacturer's protocol (Qiagen, Inc., Chatsworth, Calif.). Column purified DNA was used as template for sequencing to verify the changes made in the transposase were the desired changes and no further changes or mutations occurred due to PCR amplification. For sequencing, Perkin-Elmer's Big Dye Sequencing Kit was used. All samples were sent to the Gene Probes and Expression Laboratory (LSU School of Veterinary Medicine) for sequencing on a Perkin-Elmer Model 377 Automated Sequencer.

Once a clone was identified that contained the desired mATS in the correct orientation, primers CMVf-NgoM IV (5' TTGCCGGCATCAGATTGGCTAT (SEQ ID NO:40); underlined bases denote a NgoM IV recognition site) and Syn-polyA-BstE II (5' AGA GGTCACCGGGTCAATTCTTCAGCACCTGGTA (SEQ ID NO:41); underlined bases denote a BstE II recognition site) were used to PCR amplify the entire CMV promoter, mATS, and synthetic polyA for cloning upstream of the transposon in pTnLac. The PCR was conducted with FailSafe™ as described above, purified using the Zymo Clean and Concentrator kit, the ends digested with NgoM IV and BstE II (New England Biolabs), purified with the Zymo kit again and cloned upstream of the transposon in pTnLac as described below.

Plasmid pTnLac was digested with NgoM IV and BstE II to remove the ptac promoter and transposase and the fragments separated on an agarose gel. The band corresponding to the vector and transposon was excised, purified from the agarose, and dephosphorylated with calf intestinal alkaline phosphatase (New England Biolabs) to prevent self-annealing. The enzyme was removed from the vector using a Zymo DNA Clean and Concentrator-5. The purified vector and CMVp/mATS/polyA were ligated together using a Stratagene T4 Ligase Kit and transformed into *E. coli* as described above.

Colonies resulting from this transformation were screened (mini-preps) as describe above and clones that were the correct size were verified by DNA sequence analysis as described above. The vector was given the name pTnMod (SEQ ID NO:3) and includes the following components:

Base pairs 1-130 are a remainder of F1(−) on from pBluescriptII sk(−) (Stratagene), corresponding to base pairs 1-130 of pBluescriptII sk(−).

Base pairs 131-132 are a residue from ligation of restriction enzyme sites used in constructing the vector.

Base pairs 133-1777 are the CMV promoter/enhancer taken from vector pGWiz (Gene Therapy Systems), corresponding to bp 229-1873 of pGWiz. The CMV promoter was modified by the addition of an ACC sequence upstream of ATG.

Base pairs 1778-1779 are a residue from ligation of restriction enzyme sites used in constructing the vector.

Base pairs 1780-1785 are the Kozak sequence of SEQ ID NO: 1, and base pairs 1783-2987 are the coding sequence for the transposase, modified from Tn10 (GenBank accession J01829) by optimizing codons for stability of the transposase mRNA and for the expression of protein. More specifically, in each of the codons for the first ten amino acids of the transposase, G or C was changed to A or T when such a substitution would not alter the amino acid that was encoded.

Base pairs 2988-2993 are two engineered stop codons.

Base pair 2994 is a residue from ligation of restriction enzyme sites used in constructing the vector.

Base pairs 2995-3410 are a synthetic polyA sequence taken from the pGWiz vector (Gene Therapy Systems), corresponding to bp 1922-2337 of 10 pGWiz.

Base pairs 3415-3718 are non-coding DNA that is residual from vector pNK2859.

Base pairs 3719-3761 are non-coding λ DNA that is residual from pNK2859.

Base pairs 3762-3831 are the 70 bp of the left insertion sequence recognized by the transposon Tn10.

Base pairs 3832-3837 are a residue from ligation of restriction enzyme sites used in constructing the vector.

Base pairs 3838-4527 are the multiple cloning site from pBluescriptII sk(20), corresponding to bp 924-235 of pBluescriptII sk(−). This multiple cloning site may be used to insert any coding sequence of interest into the vector.

Base pairs 4528-4532 are a residue from ligation of restriction enzyme sites used in constructing the vector.

Base pairs 4533-4602 are the 70 bp of the right insertion sequence recognized by the transposon Tn10.

Base pairs 4603-4644 are non-coding λ DNA that is residual from pNK2859.

Base pairs 4645-5488 are non-coding DNA that is residual from pNK2859.

Base pairs 5489-7689 are from the pBluescriptII sk(−) base vector—(Stratagene, Inc.), corresponding to bp 761-2961 of pBluescriptII sk(−).

Completing pTnMod is a pBlueScript backbone that contains a colE I origin of replication and an antibiotic resistance marker (ampicillin).

It should be noted that all non-coding DNA sequences described above can be replaced with any other non-coding DNA sequence(s). Missing nucleotide sequences in the above construct represent restriction site remnants.

All plasmid DNA was isolated by standard procedures. Briefly, *Escherichia coli* containing the plasmid was grown in 500 mL aliquots of LB broth (supplemented with an appropriate antibiotic) at 37° C. overnight with shaking. Plasmid DNA was recovered from the bacteria using a Qiagen Maxi-Prep kit (Qiagen, Inc., Chatsworth, Calif.) according to the

EXAMPLE 3

Transposon-Based Vector pTnMCS

Another transposon-based vector was designed for inserting a desired coding sequence into the genome of eukaryotic cells. This vector was termed pTnMCS and its constituents are provided below. The sequence of the pTnMCS vector is provided in SEQ ID NO:2. The pTnMCS vector contains an avian optimized polyA sequence operably-linked to the transposase gene. The avian optimized polyA sequence contains approximately 40 nucleotides that precede the A nucleotide string.

Bp 1-130 Remainder of F1 (−) ori of pBluescriptII sk(−) (Stratagene) bp1-130
Bp 133-1777 CMV promoter/enhancer taken from vector pGWIZ (Gene Therapy Systems) bp 229-1873
Bp 1783-2991 Transposase, from Tn10 (GenBank accession #J01829) bp 108-1316
Bp 2992-3344 Non coding DNA from vector pNK2859
Bp 3345-3387 Lambda DNA from pNK2859
Bp 3388-3457 70 bp of IS10 left insertion sequence from Tn10
Bp 3464-3670 Multiple cloning site from pBluescriptII sk(−), thru the XmaI site bp 924-718
Bp 3671-3715 Multiple cloning site from pBluescriptII sk(−), from the XmaI site thru the XhoI site. These base pairs are usually lost when cloning into pTnMCS bp 717-673
Bp 3716-4153 Multiple cloning site from pBluescriptII sk(−), from the XhoI site bp 672-235
Bp 4159-4228 70 bp of IS10 right insertion sequence from Tn10
Bp 4229-4270 Lambda DNA from pNK2859
Bp 4271-5114 Non-coding DNA from pNK2859
Bp 5115-7315 pBluescript sk (−) base vector (Stratagene, Inc.) bp 761-2961.

EXAMPLE 4

Preparation of Transposon-Based Vector pTnMod(Oval/ENT TAG/ProIns/PA)—Chicken

A vector was designed to insert a human proinsulin coding sequence under the control of a chicken ovalbumin promoter, and a ovalbumin gene including an ovalbumin signal sequence, into the genome of a bird given below as SEQ ID NO:42.

Base pairs 1-130 are a remainder of F1(−) ori of pBluescriptII sk(−) (Stratagene) corresponding to base pairs 1-130 of pBluescriptII sk(−).

Base pairs 133-1777 are a CMV promoter/enhancer taken from vector pGWiz (Gene Therapy Systems) corresponding to base pairs 229-1873 of pGWiz.

Base pairs 1780-1785 are the Kozak sequence of SEQ ID NO: 1, and base pairs 1783-2987 are the coding sequence for the a transposase, modified from Tn10 (GenBank accession number J01829).

Base pairs 2988-2993 are two engineered stop codons.

Base pairs 2995-3410 are a synthetic polyA from pGWiz (Gene Therapy Systems) corresponding to base pairs 1922-2337 of pGWiz.

Base pairs 3415-37.18 are non coding DNA that is residual from vector pNK2859.

Base pairs 3719-3761 are λ DNA that is residual from pNK2859.

Base pairs 3762-3831 are the 70 base pairs of the left insertion sequence (IS10) recognized by the transposon Tn10.

Base pairs 3838-4044 are a multiple cloning site from pBlueScriptII sk(−) corresponding to base pairs 924-718 of pBluescriptII sk(−).

Base pairs 4050-4951 are a chicken ovalbumin promoter (including SDRE) that corresponds to base pairs 431-1332 of the chicken ovalbumin promoter in GenBank Accession Number J00895 M24999.

Base pairs 4958-6115 are a chicken ovalbumin signal sequence and ovalbumin gene that correspond to base pairs 66-1223 of GenBank Accession Number V00383.1. (The STOP codon being omitted).

Base pairs 6122-6271 are a TAG sequence containing a gp41 hairpin loop from HIV I, an enterokinase cleavage site and a spacer (synthetic).

Base pairs 6272-6531 are a proinsulin gene.

Base pairs 6539-6891 are a synthetic polyadenylation sequence from pGWiz (Gene Therapy Systems) corresponding to base pairs 1920-2272 of pGWiz.

Base pairs 6897-7329 are a multiple cloning site from pBlueScriptII sk(−) corresponding to base pairs 667-235 of pBluescriptII sk(−).

Base pairs 7335-7404 are the 70 base pairs of the right insertion sequence (IS10) recognized by the transposon Tn10.

Base pairs 7405-7446 are λ DNA that is residual from pNK2859.

Base pairs 7447-8311 are non coding DNA that is residual from pNK2859.

Base pairs 8312-10512 are pBlueScript sk(−) base vector (Stratagene, Inc.) corresponding to base pairs 761-2961 of pBluescriptII sk(−).

It should be noted that all non-coding DNA sequences described above can be replaced with any other non-coding DNA sequence(s). Missing nucleotide sequences in the above construct represent restriction site remnants.

EXAMPLE 5

Transposon-Based Vector pTnMOD (CMV-CHOVg-ent-ProInsulin-synPA)

A vector was designed to insert a proinsulin coding sequence under the control of a quail ovalbumin promoter, and a ovalbumin gene including an ovalbumin signal sequence, into the genome of a bird given below as SEQ ID NO:43.

Bp 1-4045 from vector pTnMod, bp 1-4045
Bp 4051-5695 CMV promoter/enhancer taken from vector pGWIZ (Gene therapy systems), bp 230-1864
Bp 5702-6855 Chicken ovalbumin gene taken from GenBank accession # V00383, bp 66-1219
Bp 6862-7011 Synthetic spacer sequence and hairpin loop of HIV gp41 with an added enterokinase cleavage site
Bp 7012-7272 Human Proinsulin taken from GenBank accession # NM000207, bp 117-377
Bp 7273-7317 Spacer DNA, derived as an artifact from the cloning vectors pTOPO Blunt II (Invitrogen) and pGWIZ (Gene Therapy Systems)
Bp 7318-7670 Synthetic polyA from the cloning vector pGWIZ (Gene Therapy Systems), bp 1920-2271
Bp 7672-11271 from cloning vector pTnMCS, bp 3716-7315

EXAMPLE 6

Transfection of Japanese Quail Using a Transposon-Based Vector Containing a Proinsulin Gene Via Oviduct Injections Two experiments were conducted in Japanese quail using transposon-based vectors containing either Oval promoter/Oval gene/GP41 Enterokinase TAG/Proinsulin/Poly A (SEQ ID NO:42) or CMV promoter/Oval gene/GP41 Enterokinase TAG/Proinsulin/Poly A (SEQ ID NO:43).

In the first experiment, the Oval promoter/Oval gene/GP41 Enterokinase TAG/Proinsulin/Poly A containing construct was injected into the lumen of the oviduct of sexually mature quail; three hens received 5 µg at a 1:3 SUPERFECT® ratio and three received 10 µg at a 1:3 SUPERFECT® ratio. As of the writing of the present application, at least one bird that received above-mentioned construct was producing human proinsulin in egg white (other birds remain to be tested). This experiment indicates that 1) the DNA has been stable for at least 3 months; 2) protein levels are comparable to those observed with a constitutive promoter such as the CMV promoter; and 3) sexually mature birds can be injected and results obtained without the need for cell culture. It is estimated that each quail egg contains approximately 1.4 mg/ml of the proinsulin protein. It is also estimated that each transgenic chicken egg contains 50-75 mg of protein encoded by the gene of interest.

In the second experiment, the transposon-based vector containing CMV promoter/Oval gene/GP41 Enterokinase TAG/Proinsulin/Poly A was injected into the lumen of the oviduct of sexually immature Japanese quail. A total of 9 birds were injected. Of the 8 survivors, 3 produced human proinsulin in the white of their eggs for over 6 weeks. An ELISA assay described in detail below was developed to detect GP41 in the fusion peptide (Oval gene/GP41 Enterokinase TAG/Proinsulin) since the GP41 peptide sequence is unique and not found as part of normal egg white protein. In all ELISA assays, the same birds produced positive results and all controls worked as expected.

ELISA Procedure: Individual egg white samples were diluted in sodium carbonate buffer, pH 9.6, and added to individual wells of 96 well microtiter ELISA plates at a total volume of 0.1 ml. These plates were then allowed to coat overnight at 4° C. Prior to ELISA development, the plates were allowed warm to room temperature. Upon decanting the coating solutions and blotting away any excess, non-specific binding of antibodies was blocked by adding a solution of phosphate buffered saline (PBS), 1% (w/v) BSA, and 0.05% (v/v) Tween 20 and allowing it to incubate with shaking for a minimum of 45 minutes. This blocking solution was subsequently decanted and replaced with a solution of the primary antibody (Goat Anti-GP41 TAG) diluted in fresh PBS/BSA/Tween 20. After a two hour period of incubation with the primary antibody, each plate was washed with a solution of PBS and 0.05% Tween 20 in an automated plate washer to remove unbound antibody. Next, the secondary antibody, Rabbit anti-Goat Alkaline Phosphatase-conjugated, was diluted in PBS/BSA/Tween 20 and allowed to incubate 1 hour. The plates were then subjected to a second wash with PBS/Tween 20. Antigen was detected using a solution of p-Nitrophenyl Phosphate in Diethanolamine Substrate Buffer for Alkaline Phosphatase and measuring the absorbance at 30 minutes and 1 hour.

Additionally, a proinsulin fusion protein produced using a construct described above was isolated from egg white using ammonium sulfate precipitation and ion exchange chromatography. A pooled fraction of the isolated fusion protein was run on an SDS-PAGE gel shown in FIG. 5, lanes 4 and 6. Lanes 1 and 10 of the gel contain molecular weight standards, lanes 2 and 8 contain non-transgenic chicken egg white, whereas lanes 3, 5, 7 and 9 are blank.

EXAMPLE 7

Isolation of Human Proinsulin Using Anti-Tag Column Chromotography

A HiTrap NHS-activated 1 mL column (Amersham) was charged with a 30 amino acid peptide that contained the gp-41 epitope containing gp-41's native disulfide bond that stabilizes the formation of the gp-41 hairpin loop. The 30 amino acid gp41 peptide is provided as SEQ ID NO:32. Approximately 10 mg of the peptide was dissolved in coupling buffer (0.2 M NaHCO3, 0.5 M NaCl, pH 8.3 and the ligand was circulated on the column for 2 hours at room temperature at 0.5 mL/minute. Excess active groups were then deactivated using 6 column volumes of 0.5 M ethanolamine, 0.5 M NaCl, pH 8.3 and the column was washed alternately with 6 column volumes of acetate buffer (0.1 M acetate, 0.5 M NaCl, pH 4.0) and ethanolamine (above). The column was neutralized using 1×PBS. The column was then washed with buffers to be used in affinity purification: 75 mM Tris, pH 8.0 and elution buffer, 100 mM glycine-HCl, 0.5 M NaCl, pH 2.7. Finally, the column was equilibrated in 75 mM Tris buffer, pH 8.0.

Antibodies to gp-41 were raised in goats by inoculation with the gp-41 peptide described above. More specifically, goats were inoculated, given a booster injection of the gp-41 peptide and blood samples were obtained by veinupuncture. Serum was harvested by centrifugation. Approximately 30 mL of goat serum was filtered to 0.45 uM and passed over a TAG column at a rate of 0.5 mL/min. The column was washed with 75 mM Tris, pH 8.0 until absorbance at 280 nm reached a baseline. Three column volumes (3 mL) of elution buffer (100 mM glycine, 0.5 M NaCl, pH 2.7) was applied, followed by 75 mM Tris buffer, pH 8.0, all at a rate of 0.5 mL/min. One milliliter fractions were collected. Fractions were collected into 200 uL 1 M Tris, pH 9.0 to neutralize acidic factions as rapidly as possible. A large peak eluted from the column, coincident with the application the elution buffer. Fractions were pooled. Analysis by SDS-PAGE showed a high molecular weight species that separated into two fragments under reducing condition, in keeping with the heavy and light chain structure of IgG.

Pooled antibody fractions were used to charge two 1 mL HiTrap NHS-activated columns, attached in series. Coupling was carried out in the same manner as that used for charging the TAG column.

Isolation of Ovalbumin-TAG-Proinsulin from Egg White

Egg white from quail and chickens treated by intra-oviduct injection of the CMV-ovalbumin-TAG-proinsulin construct were pooled. Viscosity was lowered by subjecting the allantoid fluid to successively finer pore sizes using negative pressure filtration, finishing with a 0.22 µM pore size. Through the process, egg white was diluted approximately 1:16. The clarified sample was loaded on the Anti-TAG column and eluted in the same manner as described for the purification of the anti-TAG antibodies. A peak of absorbance at 280 nm, coincident with the application of the elution buffer, indicated that protein had been specifically eluted from the Anti-TAG column. Fractions containing the eluted peak were pooled for analysis.

The pooled fractions from the Anti-TAG affinity column were characterized by SDS-PAGE and western blot analysis.

SDS-PAGE of the pooled fractions revealed a 60 kDal molecular weight band not present in control egg white fluid, consistent with the predicted molecular weight of the transgenic protein. Although some contaminating bands were observed, the 60 kDal species was greatly enriched compared to the other proteins. An aliquot of the pooled fractions was cleaved overnight at room temperature with the protease, enterokinase. SDS-PAGE analysis of the cleavage product, revealed a band not present in the uncut material that co-migrated with a commercial human proinsulin positive control. Western blot analysis showed specific binding to the 60 kDal species under non-reducing condition (which preserved the hairpin epitope of gp-41 by retaining the disulfide bond). Western analysis of the low molecular weight species that appeared upon cleavage with an anti-human proinsulin antibody, conclusively identified the cleaved fragment as human proinsulin.

EXAMPLE 8

Purification Procedures for Insulin

I. ELISA Data for Egg Characterization/Identification

An ELISA was employed for the initial screening of eggs and, thereby, identification of hens producing positive eggs. With further modifications this procedure was used for the initial quantification of recombinant protein amounts. These procedures were aided by the successful purification of an initial stock of the recombinant proinsulin (RPI). This stock of protein is used in the development of a double antibody assay that increases the sensitivity and reduces the background in the assay. Subsequent identification of hens producing positive eggs obviate the need to screen each egg collected. Only periodic checks are needed to determine if production levels are consistent.

II. Egg White (EW) or Albumin Preparation

A. Clarification—Ovomucin Precipitation

Eggs from hens positively identified as producing RPI are pooled for RPI purification. The initial purification step involved diluting the pool 1:1 with 100 mM Tris-HCl, pH 8 for a final concentration of 50 mM Tris-HCl. The pH of this solution was then adjusted to 6 and ovomucin was allowed to precipitate at 4° C. for a minimum of 3 hrs (preferably overnight) with constant stirring. The precipitated ovomucin was then pelleted and removed by centrifugation at 2400×g. After collection of the RPI containing supernatant, the pH of this solution was readjusted to 8.

B. Filtration

To prepare the egg white for loading onto the column and, thereby, minimize the potential for clogging the columns during loading, the egg white solution was filtered to at least 0.45 um.

Initially, the ovomucin precipitated egg white solution was subjected to successive filtration steps with the pore size of the filtration membrane decreasing at each step. This procedure involved time and dilution of the egg white solution to reach 0.45 um filtration.

Amersham's hollow-fiber ultrafiltration apparatus was used to produced a column-ready solution filtered down to <0.2 um with an undiluted starting solution. This approach minimized the time and the solution dilution needed to prepare the egg white solution for column loading.

III. Purification

A. Affinity Chromatography—

Using antibody with specificity to a synthetic peptide modeled after the enterokinase recognition site, initial purification schemes involved developing a one-step column purification procedure for the RPI.

Goats immunized with the synthetic Ent peptide were employed to produce anti-Ent Tag antiserum which was used in the egg screening ELISAs followed by antibody purification. The purified goat Anti-Ent Tag antibodies were covalently bound to the matrix of HiTrap NHS-activated HP columns (Amersham) and subsequently used to specifically bind and purify the RPI.

An initial attempt was made to direct the first purification step against the ovalbumin portion of the recombinant protein using an antibody specific for the ovalbumin portion. The present purification scheme employed a combination of classical techniques such as ammonium sulfate precipitation, ion exchange, and gel filtration chromatography.

After the initial ovomucin precipitation, the egg white solution was subjected to protein precipitation using a 40% ammonium sulfate fractionation. The precipitated protein was subsequently collected via centrifugation and resuspended in 50 mM Tris-HCl, pH 8. The resuspended protein solution was dialyzed to remove residual $(NH_4)_2SO_4$ or subjected to gel filtration to remove the $(NH_4)_2SO_4$ and partially isolate the RPI from the remaining egg white protein. The RPI was further isolated via anion exchange chromatography using a 0 to 0.5M NaCl gradient in 50 mM Tris-HCl, pH 8. Two possible elution profiles were observed. One at approximately 25% of the 0.5 M NaCl gradient without $(NH_4)_2SO_4$ precipitation. The second was observed at less than 16% gradient (approximately 7%) following 40% $(NH_4)_2SO_4$ precipitation and a longer gradient. Fractions containing RPI were identified by SDS-PAGE analysis and pooled.

Three gel filtration columns, differing by column size and fractionation range, were employed in RPI purification and/or desalting: Superdex 75 10/300 GL, Hiload 26/60 Superdex 75, and Hiload 26/60 Superdex 200. Using these individual columns at different steps in the purification scheme increased the efficiency of the process. Fractions containing RPI were identified by SDS-PAGE analysis and pooled.

Cleavage of the RPI Enterokinase recognition site was accomplished using purified enterokinase from Sigma. Enterokinase, 0.004 Unit/µl per reaction, was applied to the pooled and, if necessary, concentrated protein solution. The digestion reaction was incubated at room temperature (up to 30° C. in a rolling hybridization oven) for a minimum of 16 h and in some cases up to 48 hrs of incubation. The digestion efficiency was followed using 16.5% Tris-Tricine SDS-PAGE peptide gels. All gel staining utilized Simply Blue Coomassie Staining Solutions. Free Proinsulin was observed on gels after digestion.

A subsequent gel filtration separation was employed to obtain purified Proinsulin, and to remove the remaining Ovalbumin portion of the RPI and residual native EW proteins. Select steps in the purification process were analyzed using the 2-dimensional Beckman Coulter ProteomeLab PF2D Protein Fractionation System.

EXAMPLE 9

Optimization of Intra-Oviduct and Intra-Ovarian Arterial Injections

Overall transfection rates of oviduct cells in a flock of chicken or quail hens are enhanced by synchronizing the development of the oviduct and ovary within the flock. When the development of the oviducts and ovaries are uniform across a group of hens and when the stage of oviduct and ovarian development can be determined or predicted, timing of injections is optimized to transfect the greatest number of cells. Accordingly, oviduct development is synchronized as described below to ensure that a large and uniform proportion of oviduct secretory cells are transfected with the gene of interest.

Hens are treated with estradiol to stimulate oviduct maturation as described in Oka and Schimke (T. Oka and R T Schimke, J. Cell Biol., 41, 816 (1969)), Palmiter, Christensen and Schimke (J. Biol. Chem. 245(4):833-845, 1970). Specifically, repeated daily injections of 1 mg estradiol benzoate are performed sometime before the onset of sexual maturation, a period ranging from 1-14 weeks of age. After a stimulation period sufficient to maximize development of the oviduct, hormone treatment is withdrawn thereby causing regression in oviduct secretory cell size but not cell number. At an optimum time after hormone withdrawal, the lumens of the oviducts of treated hens are injected with the transposon-based vector. Hens are subjected to additional estrogen stimulation after an optimized time during which the transposon-based vector is taken up into oviduct secretory cells. Re-stimulation by estrogen activates transposon expression, causing the integration of the gene of interest into the host genome. Estrogen stimulation is then withdrawn and hens continue normal sexual development. If a developmentally regulated promoter such as the ovalbumin promoter is used, expression of the transposon-based vector initiates in the oviduct at the time of sexual maturation. Intra-ovarian artery injection during this window allows for high and uniform transfection efficiencies of ovarian follicles to produce germ-line transfections and possibly oviduct expression.

Other means are also used to synchronize the development, or regression, of the oviduct and ovary to allow high and uniform transfection efficiencies. Alterations of lighting and/or feed regimens, for example, cause hens to 'molt' during which time the oviduct and ovary regress. Molting is used to synchronize hens for transfection, and may be used in conjunction with other hormonal methods to control regression and/or development of the oviduct and ovary.

EXAMPLE 10

Preparation of Transposon-Based Vector pTnMod(Oval/ENT TAG/ProIns/PA)—Quail

A vector is designed for inserting a proinsulin gene under the control of a quail ovalbumin promoter, and a ovalbumin gene including an ovalbumin signal sequence, into the genome of a bird given below as SEQ ID NO:44.

Base pairs 1-130 are a remainder of F1(−) ori of pBluescriptII sk(−) (Stratagene) corresponding to base pairs 1-130 of pBluescriptII sk(−).

Base pairs 133-1777 are a CMV promoter/enhancer taken from vector pGWiz (Gene Therapy Systems) corresponding to base pairs 229-1873 of pGWiz.

Base pairs 1780-1785 are the Kozak sequence of SEQ ID NO: 1, and base pairs 1783-2987 are the coding sequence for the a transposase, modified from Tn10 (GenBank accession number J01829).

Base pairs 2988-2993 are an engineered stop codon.

Base pairs 2995-3410 are a synthetic polyA from pGWiz (Gene Therapy Systems) corresponding to base pairs 1922-2337 of pGWiz.

Base pairs 3415-3718 are non coding DNA that is residual from vector pNK2859.

Base pairs 3719-3761 are λ DNA that is residual from pNK2859.

Base pairs 3762-3831 are the 70 base pairs of the left insertion sequence (IS10) recognized by the transposon Tn10.

Base pairs 3838-4044 are a multiple cloning site from pBlueScriptII sk(−) corresponding to base pairs 924-718 of pBluescriptII sk(−).

Base pairs 4050-4938 are the Japanese quail ovalbumin promoter (including SDRE, steroid-dependent response element). The Japanese quail ovalbumin promoter was isolated by its high degree of homology to the chicken ovalbumin promoter (GenBank accession number J00895 M24999, base pairs 431-1332). Some deletions were noted in the quail sequence, as compared to the chicken sequence.

Base pairs 4945-6092 are a quail ovalbumin signal sequence and ovalbumin gene that corresponds to base pairs 54-1201 of GenBank accession number X53964.1. (The STOP codon being omitted).

Base pairs 6093-6246 are a TAG sequence containing a gp41 hairpin loop from HIV I an enterokinase cleavage site and a spacer (synthetic).

Base pairs 6247-6507 are a proinsulin gene.

Base pairs 6514-6866 are a synthetic polyadenylation sequence from pGWiz (Gene Therapy Systems) corresponding to base pairs 1920-2272 of pGWiz.

Base pairs 6867-7303 are a multiple cloning site from pBlueScriptII sk(−) corresponding to base pairs 667-235 of pBluescriptII sk(−).

Base pairs 7304-7379 are the 70 base pairs of the right insertion sequence (IS10) recognized by the transposon Tn10.

Base pairs 7380-7421 are λ DNA that is residual from pNK2859.

Base pairs 7422-8286 are non coding DNA that is residual from pNK2859.

Base pairs 8287-10487 are pBlueScript sk(−) base vector (Stratagene, Inc.) corresponding to base pairs 761-2961 of pBluescriptII sk(−).

It should be noted that all non-coding DNA sequences described above can be replaced with any other non-coding DNA sequence(s). Missing nucleotide sequences in the above construct represent restriction site remnants.

EXAMPLE 11

Preparation of Transposon-Based Vector pTnMod(Oval/ENT TAG/p146/PA)—Chicken

A vector was designed for inserting a p146 gene under the control of a chicken ovalbumin promoter, and a ovalbumin gene including an ovalbumin signal sequence, into the genome of a bird. The vector sequence is provided below as SEQ ID NO:45.

Base pairs 1-130 are a remainder of F1(−) ori of pBluescriptII sk(−) (Stratagene) corresponding to base pairs 1-130 of pBluescriptII sk(−).

Base pairs 133-1777 are a CMV promoter/enhancer taken from vector pGWiz (Gene Therapy Systems) corresponding to base pairs 229-1873 of pGWiz.

Base pairs 1780-1785 are the Kozak sequence of SEQ ID NO: 1, and base pairs 1783-2987 are the coding sequence for the a transposase, modified from Tn10 (GenBank accession number J01829).

Base pairs 2988-2993 are an engineered stop codon.

Base pairs 2995-3410 are a synthetic polyA from pGWiz (Gene Therapy Systems) corresponding to base pairs 1922-2337 of pGWiz.

Base pairs 3415-3718 are non coding DNA that is residual from vector pNK2859.

Base pairs 3719-3761 are λ DNA that is residual from pNK2859.

Base pairs 3762-3831 are the 70 base pairs of the left insertion sequence (IS10) recognized by the transposon Tn10.

Base pairs 3838-4044 are a multiple cloning site from pBlueScriptII sk(-) corresponding to base pairs 924-718 of pBluescriptII sk(-).

Base pairs 4050-4951 are a chicken ovalbumin promoter (including SDRE, steroid-dependent response element) that corresponds to base pairs 431-1332 of the chicken ovalbumin promoter in GenBank Accession Number J00895 M24999.

Base pairs 4958-6115 are a chicken ovalbumin signal sequence and Ovalbumin gene that correspond to base pairs 66-1223 of GenBank Accession Number V00383.1 (The STOP codon being omitted).

Base pairs 6122-6271 are a TAG sequence containing a gp41 hairpin loop from HIV I, an enterokinase cleavage site and a spacer (synthetic).

Base pairs 6272-6316 are a p146 sequence (synthetic) with 2 added stop codons.

Base pairs 6324-6676 are a synthetic polyadenylation sequence from pGWiz (Gene Therapy Systems) corresponding to base pairs 1920-2272 of pGWiz.

Base pairs 6682-7114 are a multiple cloning site from pBlueScriptII sk(-) corresponding to base pairs 667-235 of pBluescriptII sk(-).

Base pairs 7120-7189 are the 70 base pairs of the right insertion sequence (IS10) recognized by the transposon Tn10.

Base pairs 7190-7231 are λ DNA that is residual from pNK2859.

Base pairs 7232-8096 are non coding DNA that is residual from pNK2859.

Base pairs 8097-10297 are pBlueScript sk(-) base vector (Stratagene, Inc.) corresponding to base pairs 761-2961 of pBluescriptII sk(-).

It should be noted that all non-coding DNA sequences described above can be replaced with any other non-coding DNA sequence(s). Missing nucleotide sequences in the above construct represent restriction site remnants.

EXAMPLE 12

Preparation of Transposon-Based Vector pTnMod(Oval/ENT TAG/p146/PA)—Quail

A vector was designed for inserting a p146 gene under the control of a quail ovalbumin promoter, and a ovalbumin gene including an ovalbumin signal sequence, into the genome of a bird. The vector sequence is given below as SEQ ID NO:46.

Base pairs 1-130 are a remainder of F1(-) ori of pBluescriptII sk(-) (Stratagene) corresponding to base pairs 1-130 of pBluescriptII sk(-).

Base pairs 133-1777 are a CMV promoter/enhancer taken from vector pGWiz (Gene Therapy Systems) corresponding to base pairs 229-1873 of pGWiz.

Base pairs 1780-1785 are the Kozak sequence of SEQ ID NO: 1, and base pairs 1783-2987 are the coding sequence for the a transposase, modified from Tn10 (GenBank accession number J01829).

Base pairs 2988-2993 are an engineered stop codon.

Base pairs 2995-3410 are a synthetic polyA from pGWiz (Gene Therapy Systems) corresponding to base pairs 1922-2337 of pGWiz.

Base pairs 3415-3718 are non coding DNA that is residual from vector pNK2859.

Base pairs 3719-3761 are λ DNA that is residual from pNK2859.

Base pairs 3762-3831 are the 70 base pairs of the left insertion sequence (IS10) recognized by the transposon Tn10.

Base pairs 3838-4044 are a multiple cloning site from pBlueScriptII sk(-) corresponding to base pairs 924-718 of pBluescriptII sk(-).

Base pairs 4050-4938 are the Japanese quail ovalbumin promoter (including SDRE, steroid-dependent response element). The Japanese quail ovalbumin promoter was isolated by its high degree of homology to the chicken ovalbumin promoter (GenBank accession number J00895 M24999, base pairs 431-1332).

Bp 4945-6092 are a quail ovalbumin signal sequence and ovalbumin gene that corresponds to base pairs 54-1201 of GenBank accession number X53964.1. (The STOP codon being omitted).

Base pairs 6097-6246 are a TAG sequence containing a gp41 hairpin loop from HIV I, an enterokinase cleavage site and a spacer (synthetic).

Base pairs 6247-6291 are a p146 sequence (synthetic) with 2 added stop codons.

Base pairs 6299-6651 are a synthetic polyadenylation sequence from pGWiz (Gene Therapy Systems) corresponding to base pairs 1920-2272 of pGWiz.

Base pairs 6657-7089 are a multiple cloning site from pBlueScriptII sk(-) corresponding to base pairs 667-235 of pBluescriptII sk(-).

Base pairs 7095-7164 are the 70 base pairs of the right insertion sequence (IS10) recognized by the transposon Tn10.

Base pairs 7165-7206 are λ DNA that is residual from pNK2859.

Base pairs 7207-8071 are non coding DNA that is residual from pNK2859.

Base pairs 8072-10272 are pBlueScript sk(-) base vector (Stratagene, Inc.) corresponding to base pairs 761-2961 of pBluescriptII sk(-).

It should be noted that all non-coding DNA sequences described above can be replaced with any other non-coding DNA sequence(s). Missing nucleotide sequences in the above construct represent restriction site remnants.

EXAMPLE 13

Additional Transposon-Based Vectors for Administration to an Animal

The following example provides a description of various transposon-based vectors of the present invention and several constructs that have been made for insertion into the transposon-based vectors of the present invention. These examples are not meant to be limiting in any way. The constructs for insertion into a transposon-based vector are provided in a cloning vector pTnMCS or pTnMod, both described above. pTnMCS (CMV-CHOVg-ent-ProInsulin-synPA) (SEQ ID NO:47)
Bp 1-3670 from vector PTnMCS, bp 1-3670
Bp 3676-5320 CMV promoter/enhancer taken from vector pGWIZ (Gene Therapy Systems), bp 230-1864

Bp 5327-6480 Chicken ovalbumin gene taken from GenBank accession # V00383, bp 66-1219
Bp 6487-6636 Synthetic spacer sequence and hairpin loop of HIV gp41 with an added enterokinase cleavage site
Bp 6637-6897 Human Proinsulin taken from GenBank accession # NM000207, bp 117-377
Bp 6898-6942 Spacer DNA, derived as an artifact from the cloning vectors pTOPO Blunt II (Invitrogen) and pGWIZ (Gene Therapy Systems)
Bp 6943-7295 Synthetic polyA from the cloning vector pGWIZ (Gene Therapy Systems), bp 1920-2271
Bp 7296-10895 from cloning vector pTnMCS, bp 3716-7315
pTnMCS (CMV-prepro-ent-ProInsulin-synPA)
Bp 1-3670 from vector PTnMCS, bp 1-3670
Bp 3676-5320 CMV promoter/enhancer taken from vector pGWIZ (Gene Therapy Systems), bp 230-1864
Bp 5326-5496 Capsite/prepro taken from GenBank accession # X07404, bp 563-733
Bp 5504-5652 Synthetic spacer sequence and hairpin loop of HIV gp41 with an added enterokinase cleavage site
Bp 5653-5913 Human Proinsulin taken from GenBank accession # NM000207, bp 117-377
Bp 5914-5958 Spacer DNA, derived as an artifact from the cloning vectors pTOPO Blunt II (Invitrogen) and pGWIZ (Gene Therapy Systems)
Bp 5959-6310 Synthetic polyA from the cloning vector pGWIZ (Gene Therapy Systems), bp 1920-2271
Bp 6313-9912 from cloning vector pTnMCS, bp 3716-7315
pTnMCS(Chicken OVep+OVg'+ENT+proins+syn polyA)
Bp 1-3670 from vector pTnMCS, bp 1-3670
Bp 3676-4350 Chicken Ovalbumin enhancer taken from GenBank accession #S82527.1 bp 1-675
Bp 4357-5692 Chicken Ovalbumin promoter taken from GenBank accession # J00895M24999 bp 1-1336
Bp 5699-6917 Chicken Ovalbumin gene from GenBank Accession # V00383.1 bp 2-1220. (This sequence includes the 5'UTR, containing putative cap site, bp 5699-5762.)
Bp 6924-7073 Synthetic spacer sequence and hairpin loop of HIV gp41 with an added enterokinase cleavage site
Bp 7074-7334 Human proinsulin GenBank Accession # NM000207 bp 117-377
Bp 7335-7379 Spacer DNA, derived as an artifact from the cloning vectors pTOPO Blunt II (Invitrogen) and gWIZ (Gene Therapy Systems)
Bp 7380-7731 Synthetic polyA from the cloning vector gWIZ (Gene Therapy Systems) bp 1920-2271
Bp 7733-11332 from vector pTnMCS, bp 3716-7315
pTnMCS(Chicken OVep+prepro+ENT+proins+syn polyA)
Bp 1-3670 from cloning vector pTnMCS, bp 1-3670
Bp 3676-4350 Chicken Ovalbumin enhancer taken from GenBank accession # S82527.1 bp 1-675
Bp 4357-5692 Chicken Ovalbumin promoter taken from GenBank accession # J00895-M24999 bp 1-1336
Bp 5699-5869 Cecropin cap site and prepro, Genbank accession # X07404 bp 563-733
Bp 5876-6025 Synthetic spacer sequence and hairpin loop of HIV gp41 with an added enterokinase cleavage site
Bp 6026-6286 Human proinsulin GenBank Accession # NM000207 bp 117-377
Bp 6287-6331 Spacer DNA, derived as an artifact from the cloning vectors pTOPO Blunt II (Invitrogen) and gWIZ (Gene Therapy Systems)
Bp 6332-6683 Synthetic polyA from the cloning vector gWIZ (Gene Therapy Systems) bp 1920-2271
Bp 6685-10284 from cloning vector pTnMCS, bp 3716-7315
pTnMCS(Quail OVep+OVg'+ENT+proins+syn polyA)
Bp 1-3670 from cloning vector pTnMCS, bp 1-3670
Bp 3676-4333 Quail Ovalbumin enhancer: 658 bp sequence, amplified in-house from quail genomic DNA, roughly equivalent to the far-upstream chicken ovalbumin enhancer, GenBank accession # S82527.1, bp 1-675. (There are multiple base pair substitutions and deletions in the quail sequence, relative to chicken, so the number of bases does not correspond exactly.)
Bp 4340-5705 Quail Ovalbumin promoter: 1366 bp sequence, amplified in-house from quail genomic DNA, roughly corresponding to chicken ovalbumin promoter, GenBank accession # J00895-M24999 bp 1-1336. (There are multiple base pair substitutions and deletions between the quail and chicken sequences, so the number of bases does not correspond exactly.)
Bp 5712-6910 Quail Ovalbumin gene, EMBL accession # X53964, bp 1-1199. (This sequence includes the 5'UTR, containing putative cap site bp 5712-5764.)
Bp 6917-7066 Synthetic spacer sequence and hairpin loop of HIV gp41 with an added enterokinase cleavage site
Bp 7067-7327 Human proinsulin GenBank Accession # NM000207 bp 117-377
Bp 7328-7372 Spacer DNA, derived as an artifact from the cloning vectors pTOPO Blunt II (Invitrogen) and gWIZ (Gene Therapy Systems)
Bp 7373-7724 Synthetic polyA from the cloning vector gWIZ (Gene Therapy Systems) bp 1920-2271
Bp 7726-11325 from cloning vector pTnMCS, bp 3716-7315
pTnMCS(Quail OVep+prepro+ENT+proins+syn polyA)
Bp 1-3670 from cloning vector pTnMCS, bp 1-3670
Bp 3676-4333 Quail Ovalbumin enhancer: 658 bp sequence, amplified from quail genomic DNA, roughly equivalent to the far-upstream chicken ovalbumin enhancer, GenBank accession #S82527.1, bp 1-675. (There are multiple base pair substitutions and deletions in the quail sequence, relative to chicken, so the number of bases does not correspond exactly.)
Bp 4340-5705 Quail Ovalbumin promoter: 1366 bp sequence, amplified from quail genomic DNA, roughly corresponding to chicken ovalbumin promoter, GenBank accession # J00895-M24999 bp 1-1336. (There are multiple base pair substitutions and deletions between the quail and chicken sequences, so the number of bases does not correspond exactly.)
Bp 5712-5882 Cecropin cap site and prepro, Genbank accession # X07404 bp 563-733
Bp 5889-6038 Synthetic spacer sequence and hairpin loop of HIV gp41 with an added enterokinase cleavage site
Bp 6039-6299 Human proinsulin GenBank Accession # NM000207 bp 117-377
Bp 6300-6344 Spacer DNA, derived as an artifact from the cloning vectors pTOPO Blunt II (Invitrogen) and gWIZ (Gene Therapy Systems)
Bp 6345-6696 Synthetic polyA from the cloning vector gWIZ (Gene Therapy Systems) bp 1920-2271
Bp 6698-10297 from cloning vector pTnMCS, bp 3716-7315.
pTnMOD (CMV-prepro-ent-proins-synPA)
Bp 1-4045 from vector pTnMOD, bp 1-4045
Bp 4051-5695 CMV promoter/enhancer taken from vector pGWIZ (Gene therapy systems), bp 230-1864
Bp 5701-5871 Capsite/prepro taken from GenBank accession # X07404, bp 563-733
Bp 5879-6027 Synthetic spacer sequence and hairpin loop of HIV gp41 with an added enterokinase cleavage site
Bp 6028-6288 Human Proinsulin taken from GenBank accession # NM000207, bp 117-377

Bp 6289-6333 Spacer DNA, derived as an artifact from the cloning vectors pTOPO Blunt II (Invitrogen) and pGWIZ (Gene Therapy Systems)
Bp 6334-6685 Synthetic polyA from the cloning vector pGWIZ (Gene Therapy Systems), bp 1920-2271
Bp 6687-10286 from cloning vector pTnMOD, bp 3716-7315
pTnMOD(Chicken OVep+OVg'+ENT+proins+syn polyA)
Bp 1-4045 from cloning vector pTnMod, bp 1-4045
Bp 4051-4725 Chicken Ovalbumin enhancer taken from GenBank accession # S82527.1 bp 1-675
Bp 4732-6067 Chicken Ovalbumin promoter taken from GenBank accession # J00895-M24999 bp 1-1336
Bp 6074-7292 Chicken Ovalbumin gene from GenBank Accession # V00383.1 bp 2-1220. (This sequence includes the 5'UTR, containing putative cap site bp 6074-6137.)
Bp 7299-7448 Synthetic spacer sequence and hairpin loop of HIV gp41 with an added enterokinase cleavage site
Bp 7449-7709 Human proinsulin GenBank Accession # NM000207 bp 117-377
Bp 7710-7754 Spacer DNA, derived as an artifact from the cloning vectors pTOPO Blunt II (Invitrogen) and gWIZ (Gene Therapy Systems)
Bp 7755-8106 Synthetic polyA from the cloning vector gWIZ (Gene Therapy Systems) bp 1920-2271
Bp 8108-11707 from cloning vector pTnMod, bp 3716-7315
pTnMOD(Chicken OVep+prepro+ENT+proins+syn polyA)
Bp 1-4045 from cloning vector pTnMOD, bp 1-4045
Bp 4051-4725 Chicken Ovalbumin enhancer taken from GenBank accession # S82527.1 bp 1-675
Bp 4732-6067 Chicken Ovalbumin promoter taken from GenBank accession # J00895-M24999 bp 1-1336
Bp 6074-6244 Cecropin cap site and prepro, Genbank accession # X07404 bp 563-733
Bp 6251-6400 Synthetic spacer sequence and hairpin loop of HIV gp41 with an added enterokinase cleavage site
Bp 6401-6661 Human proinsulin GenBank Accession # NM000207 bp 117-377
Bp 6662-6706 Spacer DNA, derived as an artifact from the cloning vectors pTOPO Blunt II (Invitrogen) and gWIZ (Gene Therapy Systems)
Bp 6707-7058 Synthetic polyA from the cloning vector gWIZ (Gene Therapy Systems) bp 1920-2271
Bp 7060-10659 from cloning vector pTnMOD, bp 3716-7315
pTnMOD(Quail OVep+OVg'+ENT+proins+syn polyA)
Bp 1-4045 from cloning vector pTnMOD, bp 1-4045
Bp 4051-4708 Quail Ovalbumin enhancer: 658 bp sequence, amplified in-house from quail genomic DNA, roughly equivalent to the far-upstream chicken ovalbumin enhancer, GenBank accession # S82527.1, bp 1-675. (There are multiple base pair substitutions and deletions in the quail sequence, relative to chicken, so the number of bases does not correspond exactly.)
Bp 4715-6080 Quail Ovalbumin promoter: 1366 bp sequence, amplified in-house from quail genomic DNA, roughly corresponding to chicken ovalbumin promoter, GenBank accession # J00895-M24999 bp 1-1336. (There are multiple base pair substitutions and deletions between the quail and chicken sequences, so the number of bases does not correspond exactly.)
Bp 6087-7285 Quail Ovalbumin gene, EMBL accession # X53964, bp 1-1199. (This sequence includes the 5'UTR, containing putative cap site by 6087-6139.)
Bp 7292-7441 Synthetic spacer sequence and hairpin loop of HIV gp41 with an added enterokinase cleavage site
Bp 7442-7702 Human proinsulin GenBank Accession # NM000207 bp 117-377
Bp 7703-7747 Spacer DNA, derived as an artifact from the cloning vectors pTOPO Blunt II (Invitrogen) and gWIZ (Gene Therapy Systems)
Bp 7748-8099 Synthetic polyA from the cloning vector gWIZ (Gene Therapy Systems) bp 1920-2271
Bp 8101-11700 from cloning vector pTnMOD, bp 3716-7315
pTnMOD(Quail OVep+prepro+ENT+proins+syn polyA
Bp 1-4045 from cloning vector pTnMOD, bp 1-4045
Bp 4051-4708 Quail Ovalbumin enhancer: 658 bp sequence, amplified in-house from quail genomic DNA, roughly equivalent to the far-upstream chicken ovalbumin enhancer, GenBank accession #S82527.1, bp 1-675. (There are multiple base pair substitutions and deletions in the quail sequence, relative to chicken, so the number of bases does not correspond exactly.)
Bp 4715-6080 Quail Ovalbumin promoter: 1366 bp sequence, amplified in-house from quail genomic DNA, roughly corresponding to chicken ovalbumin promoter, GenBank accession # J00895-M24999 bp 1-1336. (There are multiple base pair substitutions and deletions between the quail and chicken sequences, so the number of bases does not correspond exactly.)
Bp 6087-6257 Cecropin cap site and Prepro, Genbank accession # X07404 bp 563-733
Bp 6264-6413 Synthetic spacer sequence and hairpin loop of HIV gp41 with an added enterokinase cleavage site
Bp 6414-6674 Human proinsulin GenBank Accession # NM000207 bp 117-377
Bp 6675-6719 Spacer DNA, derived as an artifact from the cloning vectors pTOPO Blunt II (Invitrogen) and gWIZ (Gene Therapy Systems)
Bp 6720-7071 Synthetic polyA from the cloning vector gWIZ (Gene Therapy Systems) bp 1920-2271
Bp 7073-10672 from cloning vector pTnMOD pTnMCS, bp 3716-7315
pTnMOD (CMV-prepro-ent-hGH-CPA)
Bp 1-4045 from vector PTnMOD, bp 1-4045
Bp 4051-5694 CMV promoter/enhancer taken from vector pGWIZ (Gene therapy systems), bp 230-1873
Bp 5701-5871 Capsite/Prepro taken from GenBank accession # X07404, bp 563-733
Bp 5878-6012 Synthetic spacer sequence and hairpin loop of HIV gp41 with an added enterokinase cleavage site
Bp 6013-6666 Human growth hormone taken from GenBank accession # V00519, bp 1-654
Bp 6673-7080 Conalbumin polyA taken from GenBank accession # Y00407, bp 10651-11058
Bp 7082-10681 from cloning vector pTnMOD, bp 4091-7690
pTnMCS(CHOVep-prepro-ent-hGH-CPA)
Bp 1-3670 from vector PTnMCS, bp 1-3670
Bp 3676-4350 Chicken Ovalbumin enhancer taken from GenBank accession # S82527.1, bp 1-675
Bp 4357-5692 Chicken Ovalbumin promoter taken from GenBank accession # J00899-M24999, bp 1-1336
Bp 5699-5869 Capsite/Prepro taken from GenBank accession # X07404, bp 563-733
Bp 5876-6010 Synthetic spacer sequence and hairpin loop of HIV gp41 with an added enterokinase cleavage site
Bp 6011-6664 Human growth hormone taken from GenBank accession # V00519, bp 1-654
Bp 6671-7078 Conalbumin polyA taken from GenBank accession # Y00407, bp 10651-11058
Bp 7080-10679 from cloning vector pTnMCS, bp 3716-7315 pTnMCS (CMV-prepro-ent-hGH-CPA)
Bp 1-3670 from vector PTnMCS, bp 1-3670
Bp 3676-5319 CMV promoter/enhancer taken from vector pGWIZ (Gene therapy systems), bp 230-1873
Bp 5326-5496 Capsite/Prepro taken from GenBank accession # X07404, bp 563-733
Bp 5503-5637 Synthetic spacer sequence and hairpin loop of HIV gp41 with an added enterokinase cleavage site
Bp 5638-6291 Human growth hormone taken from GenBank accession # V00519, bp 1-654
Bp 6298-6705 Conalbumin polyA taken from GenBank accession # Y00407, bp 10651-11058
Bp 6707-10306 from cloning vector pTnMCS, bp 3716-7315
pTnMOD (CHOVep-prepro-ent-hGH-CPA)
Bp 1-4045 from vector PTnMOD, bp 1-4045
Bp 4051-4725 Chicken Ovalbumin enhancer taken from GenBank accession # S82527.1, bp 1-675
Bp 4732-6067 Chicken Ovalbumin promoter taken from GenBank accession # J00899-M24999, bp 1-1336
Bp 60746244 Capsite/Prepro taken from GenBank accession # X07404, bp 563-733
Bp 6251-6385 Synthetic spacer sequence and hairpin loop of HIV gp41 with an added enterokinase cleavage site
Bp 6386-7039 Human growth hormone taken from GenBank accession # V00519, bp 1-654
Bp 7046-7453 Conalbumin polyA taken from GenBank accession # Y00407, bp 10651-11058
Bp 7455-11054 from cloning vector pTnMOD, bp 4091-7690
PTnMod(CMV/Transposase/ChickOvep/prepro/ProteinA/ConpolyA
BP 1-130 remainder of F1 (−) ori of pBluescriptII sk(−) (Stragagene) bp 1-130.
BP 133-1777 CMV promoter/enhancer taken from vector pGWIZ (Gene Therapy Systems) bp 229-1873.
BP 1780-2987 Transposase, modified from Tn10 (GenBank #J01829).
BP 2988-2993 Engineered DOUBLE stop codon.
BP 2994-3343 non coding DNA from vector pNK2859.
BP 3344-3386 Lambda DNA from pNK2859.
BP 3387-3456 70 bp of IS10 left from Tn10.
BP 3457-3674 multiple cloning site from pBluescriptII sk(−) bp 924-707.
BP 3675-5691 Chicken Ovalbumin enhancer plus promoter from a Topo Clone 10 maxi 040303 (5' XmaI, 3' BamHI)
BP 5698-5865 prepro with Cap site amplified from cecropin of pMON200 GenBank # X07404 (5'BamHI, 3'KpnI)
BP 5872-7338 Protein A gene from GenBank# J01786, mature peptide bp 292-1755 (5'KpnI, 3'SacII)
BP 7345-7752 ConPolyA from Chicken conalbumin polyA from GenBank # Y00407 bp 10651-11058. (5'SacII, 3'XhoI)
BP 7753-8195 multiple cloning site from pBluescriptII sk(−) bp 677-235.
BP 8196-8265 70 bp of IS 10 left from Tn10.
BP 8266-8307 Lamda DNA from pNK2859
BP 8308-9151 noncoding DNA from pNK2859
BP 9152-11352 pBluescriptII sk(−) base vector (Stratagene, INC.) bp 761-2961

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

APPENDIX A

```
SEQ ID NO: 1 (modified Kozak sequence)
ACCATG

SEQ ID NO: 2 (pTnMCS)
    1 ctgacgcgcc ctgtagcggc gcattaagcg cggcgggtgt ggtggttacg cgcagcgtga 61 ccgctacact tgccagcgcc ctagcgcccg ctcctttcgc tttcttccct tcctttctcg 121 ccacgttcgc cggcatcaga ttggctattg gccattgcat acgttgtatc catatcataa 181 tatgtacatt tatattggct catgtccaac attaccgcca tgttgacatt gattattgac 241 tagttattaa tagtaatcaa ttacggggtc attagttcat agcccatata tggagttccg 301 cgttacataa cttacggtaa atggcccgcc tggctgaccg cccaacgacc cccgcccatt 361 gacgtcaata atgacgtatg ttcccatagt aacgccaata gggactttcc attgacgtca 421 atgggtggag tatttacggt aaactgccca cttggcagta catcaagtgt atcatatgcc 481 aagtacgccc cctattgacg tcaatgacgg taaatggccc gcctggcatt atgcccagta 541 catgacctta tgggactttc ctacttggca gtacatctac gtattagtca tcgctattac 601 catggtgatg cggttttggc agtacatcaa tgggcgtgga tagcggtttg actcacgggg 661 atttccaagt ctccacccca ttgacgtcaa tgggagtttg ttttggcacc aaaatcaacg 721 ggactttcca aaatgtcgta caactccgc cccattgacg caaatgggcg gtaggcgtgt 781 acggtgggag gtctatataa gcagagctcg tttagtgaac cgtcagatcg cctggagacg 841 ccatccacgc tgttttgacc tccatagaag acaccgggac cgatccagcc tccgcggccg 901 ggaacggtgc attggaacgc ggattccccg tgccaagagt gacgtaagta ccgcctatag 961 actctatagg cacacccctt tggctcttat gcatgctata ctgtttttgg cttggggcct
```

```
1021  atacaccccc gcttccttat gctataggtg atggtatagc ttagcctata ggtgtgggtt
1081  attgaccatt attgaccact cccctattgg tgacgatact ttccattact aatccataac
1141  atggctcttt gccacaacta tctctattgg ctatatgcca atactctgtc cttcagagac
1201  tgacacggac tctgtatttt tacaggatgg ggtcccattt attatttaca aattcacata
1261  tacaacaacg ccgtcccccg tgcccgcagt ttttattaaa catagcgtgg gatctccacg
1321  cgaatctcgg gtacgtgttc cggacatggg ctcttctccg gtagcggcgg agcttccaca
1381  tccgagccct ggtcccatgc ctccagcggc tcatggtcgc tcggcagctc cttgctccta
1441  acagtggagg ccagacttag gcacagcaca atgcccacca ccaccagtgt gccgcacaag
1501  gccgtggcgg tagggtatgt gtctgaaaat gagcgtggag attgggctcg cacggctgac
1561  gcagatggaa gacttaaggc agcggcagaa gaagatgcag gcagctgagt tgttgtattc
1621  tgataagagt cagaggtaac tcccgttgcg gtgctgttaa cggtggaggg cagtgtagtc
1681  tgagcagtac tcgttgctgc cgcgcgcgcc accagacata atagctgaca gactaacaga
1741  ctgttccttt ccatgggtct tttctgcagt caccgtcgga ccatgtgcga actcgatatt
1801  ttacacgact ctctttacca attctgcccc gaattacact taaaacgact caacagctta
1861  acgttggctt gccacgcatt acttgactgt aaaactctca ctcttaccga acttggccgt
1921  aacctgccaa ccaaagcgag aacaaaacat aacatcaaac gaatcgaccg attgttaggt
1981  aatcgtcacc tccacaaaga gcgactcgct gtataccgtt ggcatgctag ctttatctgt
2041  tcgggcaata cgatgcccat tgtacttgtt gactggtctg atattcgtga gcaaaaacga
2101  cttatggtat tgcgagcttc agtcgcacta cacggtcgtt ctgttactct ttatgagaaa
2161  gcgttcccgc tttcagagca atgttcaaag aaagctcatg accaatttct agccgacctt
2221  gcgagcattc taccgagtaa caccacaccg ctcattgtca gtgatgctgg ctttaaagtg
2281  ccatggtata aatccgttga gaagctgggt tggtactggt taagtcgagt aagaggaaaa
2341  gtacaatatg cagacctagg agcggaaaac tggaaaccta tcagcaactt acatgatatg
2401  tcatctagtc actcaaagac tttaggctat aagaggctga ctaaaagcaa tccaatctca
2461  tgccaaattc tattgtataa atctcgctct aaaggccgaa aaaatcagcg ctcgacacgg
2521  actcattgtc accacccgtc acctaaaatc tactcagcgt cggcaaagga gccatgggtt
2581  ctagcaacta acttacctgt tgaaattcga acacccaaac aacttgttaa tatctattcg
2641  aagcgaatgc agattgaaga aaccttccga gacttgaaaa gtcctgccta cggactaggc
2701  ctacgccata gccgaacgag cagctcagag cgttttgata tcatgctgct aatcgccctg
2761  atgcttcaac taacatgttg gcttgcgggc gttcatgctc agaaacaagg ttgggacaag
2821  cacttccagg ctaacacagt cagaaatcga aacgtactct caacagttcg cttaggcatg
2881  gaagttttgc ggcattctgg ctacacaata acaagggaag acttactcgt ggctgcaacc
2941  ctactagctc aaaatttatt cacacatggt tacgctttgg ggaaattatg agggatcgc
3001  tctagagcga tccgggatct cgggaaaagc gttggtgacc aaaggtgcct tttatcatca
3061  ctttaaaaat aaaaaacaat tactcagtgc ctgttataag cagcaattaa ttatgattga
3121  tgcctacatc acaacaaaaa ctgatttaac aaatggttgg tctgccttag aaagtatatt
3181  tgaacattat cttgattata ttattgataa taataaaaac cttatcccta tccaagaagt
3241  gatgcctatc attggttgga atgaacttga aaaaattag ccttgaatac attactggta
3301  aggtaaacgc cattgtcagc aaattgatcc aagagaacca acttaaagct ttcctgacgg
3361  aatgttaatt ctcgttgacc ctgagcactg atgaatcccc taatgatttt ggtaaaaatc
3421  attaagttaa ggtggataca catcttgtca tatgatcccg gtaatgtgag ttagctcact
```

-continued

```
3481 cattaggcac cccaggcttt acactttatg cttccggctc gtatgttgtg tggaattgtg
3541 agcggataac aatttcacac aggaaacagc tatgaccatg attacgccaa gcgcgcaatt
3601 aaccctcact aaagggaaca aaagctggag ctccaccgcg gtggcggccg ctctagaact
3661 agtggatccc ccgggctgca ggaattcgat atcaagctta tcgataccgc tgacctcgag
3721 gggggggcccg gtacccaatt cgccctatag tgagtcgtat tacgcgcgct cactggccgt
3781 cgttttacaa cgtcgtgact gggaaaaccc tggcgttacc caacttaatc gccttgcagc
3841 acatccccct ttcgccagct ggcgtaatag cgaagaggcc cgcaccgatc gcccttccca
3901 acagttgcgc agcctgaatg gcgaatggaa attgtaagcg ttaatatttt gttaaaattc
3961 gcgttaaatt tttgttaaat cagctcattt tttaaccaat aggccgaaat cggcaaaatc
4021 ccttataaat caaagaata gaccgagata gggttgagtg ttgttccagt ttggaacaag
4081 agtccactat taaagaacgt ggactccaac gtcaaagggc gaaaaaccgt ctatcagggc
4141 gatggcccac tactccggga tcatatgaca agatgtgtat ccaccttaac ttaatgattt
4201 ttaccaaaat cattagggga ttcatcagtg ctcagggtca acgagaatta acattccgtc
4261 aggaaagctt atgatgatga tgtgcttaaa aacttactca atggctggtt atgcatatcg
4321 caatacatgc gaaaaaccta aaagagcttg ccgataaaaa aggccaattt attgctattt
4381 accgcggctt tttattgagc ttgaaagata aataaaatag ataggtttta tttgaagcta
4441 aatcttcttt atcgtaaaaa atgccctctt gggttatcaa gagggtcatt atatttcgcg
4501 gaataacatc atttggtgac gaataactaa agcacttgtc tcctgtttac tcccctgagc
4561 ttgaggggtt aacatgaagg tcatcgatag caggataata atacagtaaa acgctaaacc
4621 aataatccaa atccagccat cccaaattgg tagtgaatga ttataaataa cagcaaacag
4681 taatgggcca ataacaccgg ttgcattggt aaggctcacc aataatccct gtaaagcacc
4741 ttgctgatga ctctttgttt ggatagacat cactccctgt aatgcaggta aagcgatccc
4801 accaccagcc aataaaatta aaacagggaa aactaaccaa ccttcagata taaacgctaa
4861 aaaggcaaat gcactactat ctgcaataaa tccgagcagt actgccgttt tttcgcccat
4921 ttagtggcta ttcttcctgc cacaaaggct tggaatactg agtgtaaaag accaagaccc
4981 gtaatgaaaa gccaaccatc atgctattca tcatcacgat ttctgtaata gcaccacacc
5041 gtgctggatt ggctatcaat gcgctgaaat aataatcaac aaatggcatc gttaaataag
5101 tgatgtatac cgatcagctt tgttcccctt tagtgagggt taattgcgcg cttggcgtaa
5161 tcatggtcat agctgtttcc tgtgtgaaat tgttatccgc tcacaattcc acacaacata
5221 cgagccggaa gcataaagtg taaagcctgg ggtgcctaat gagtgagcta actcacatta
5281 attgcgttgc gctcactgcc cgctttccag tcgggaaacc tgtcgtgcca gctgcattaa
5341 tgaatcggcc aacgcgcggg gagaggcggt ttgcgtattg ggcgctcttc cgcttcctcg
5401 ctcactgact cgctgcgctc ggtcgttcgg ctgcggcgag cggtatcagc tcactcaaag
5461 gcggtaatac ggttatccac agaatcaggg gataacgcag gaaagaacat gtgagcaaaa
5521 ggccagcaaa aggccaggaa ccgtaaaaag gccgcgttgc tggcgttttt ccataggctc
5581 cgcccccctg acgagcatca caaaaatcga cgctcaagtc agaggtggcg aaacccgaca
5641 ggactataaa gataccaggc gtttccccct ggaagctccc tcgtgcgctc tcctgttccg
5701 accctgccgc ttaccggata cctgtccgcc tttctccctt cgggaagcgt ggcgctttct
5761 catagctcac gctgtaggta tctcagttcg gtgtaggtcg ttcgctccaa gctgggctgt
5821 gtgcacgaac cccccgttca gcccgaccgc tgcgccttat ccggtaacta tcgtcttgag
```

```
5881 tccaacccgg taagacacga cttatcgcca ctggcagcag ccactggtaa caggattagc 5941 agagcgaggt atgtaggcgg tgctacagag ttcttgaagt ggtggcctaa ctacggctac 6001 actagaagga cagtatttgg tatctgcgct ctgctgaagc cagttacctt cggaaaaaga 6061 gttggtagct cttgatccgg caaacaaacc accgctggta gcggtggttt ttttgtttgc 6121 aagcagcaga ttacgcgcag aaaaaaagga tctcaagaag atcctttgat cttttctacg 6181 gggtctgacg ctcagtggaa cgaaaactca cgttaaggga ttttggtcat gagattatca 6241 aaaaggatct tcacctagat ccttttaaat taaaaatgaa gttttaaatc aatctaaagt 6301 atatatgagt aaacttggtc tgacagttac caatgcttaa tcagtgaggc acctatctca 6361 gcgatctgtc tatttcgttc atccatagtt gcctgactcc ccgtcgtgta gataactacg 6421 atacgggagg gcttaccatc tggccccagt gctgcaatga taccgcgaga cccacgctca 6481 ccggctccag atttatcagc aataaaccag ccagccggaa gggccgagcg cagaagtggt 6541 cctgcaactt tatccgcctc catccagtct attaattgtt gccgggaagc tagagtaagt 6601 agttcgccag ttaatagttt gcgcaacgtt gttgccattg ctacaggcat cgtggtgtca 6661 cgctcgtcgt ttggtatggc ttcattcagc tccggttccc aacgatcaag gcgagttaca 6721 tgatccccca tgttgtgcaa aaaagcggtt agctccttcg gtcctccgat cgttgtcaga 6781 agtaagttgg ccgcagtgtt atcactcatg gttatggcag cactgcataa ttctcttact 6841 gtcatgccat ccgtaagatg cttttctgtg actggtgagt actcaaccaa gtcattctga 6901 gaatagtgta tgcggcgacc gagttgctct tgcccggcgt caatacggga taataccgcg 6961 ccacatagca gaactttaaa agtgctcatc attggaaaac gttcttcggg gcgaaaactc 7021 tcaaggatct taccgctgtt gagatccagt tcgatgtaac ccactcgtgc acccaactga 7081 tcttcagcat cttttacttt caccagcgtt tctgggtgag caaaaacagg aaggcaaaat 7141 gccgcaaaaa agggaataag ggcgacacgg aaatgttgaa tactcatact cttcctttt 7201 caatattatt gaagcattta tcagggttat tgtctcatga gcggatacat atttgaatgt 7261 atttagaaaa ataaacaaat aggggttccg cgcacatttc cccgaaaagt gccac
```

SEQ ID NO: 3 (pTnMod)
```
CTGACGCGCC CTGTAGCGGC GCATTAAGCG CGGCGGGTGT GGTGGTTACG    50

CGCAGCGTGA CCGCTACACT TGCCAGCGCC CTAGCGCCCG CTCCTTTCGC   100

TTTCTTCCCT TCCTTTCTCG CCACGTTCGC CGGCATCAGA TTGGCTATTG   150

GCCATTGCAT ACGTTGTATC CATATCATAA TATGTACATT TATATTGGCT   200

CATGTCCAAC ATTACCGCCA TGTTGACATT GATTATTGAC TAGTTATTAA   250

TAGTAATCAA TTACGGGGTC ATTAGTTCAT AGCCCATATA TGGAGTTCCG   300

CGTTACATAA CTTACGGTAA ATGGCCCGCC TGGCTGACCG CCCAACGACC   350

CCCGCCCATT GACGTCAATA ATGACGTATG TTCCCATAGT AACGCCAATA   400

GGGACTTTCC ATTGACGTCA ATGGGTGGAG TATTTACGGT AAACTGCCCA   450

CTTGGCAGTA CATCAAGTGT ATCATATGCC AAGTACGCCC CCTATTGACG   500

TCAATGACGG TAAATGGCCC GCCTGGCATT ATGCCCAGTA CATGACCTTA   550

TGGGACTTTC CTACTTGGCA GTACATCTAC GTATTAGTCA TCGCTATTAC   600

CATGGTGATG CGGTTTTGGC AGTACATCAA TGGGCGTGGA TAGCGGTTTG   650

ACTCACGGGG ATTTCCAAGT CTCCACCCCA TTGACGTCAA TGGGAGTTTG   700

TTTTGGCACC AAAATCAACG GGACTTTCCA AAATGTCGTA ACAACTCCGC   750

CCCATTGACG CAAATGGGCG GTAGGCGTGT ACGGTGGGAG GTCTATATAA   800
```

```
GCAGAGCTCG TTTAGTGAAC CGTCAGATCG CCTGGAGACG CCATCCACGC   850
TGTTTTGACC TCCATAGAAG ACACCGGGAC CGATCCAGCC TCCGCGGCCG   900
GGAACGGTGC ATTGGAACGC GGATTCCCCG TGCCAAGAGT GACGTAAGTA   950
CCGCCTATAG ACTCTATAGG CACACCCCTT TGGCTCTTAT GCATGCTATA  1000
CTGTTTTTGG CTTGGGGCCT ATACACCCCC GCTTCCTTAT GCTATAGGTG  1050
ATGGTATAGC TTAGCCTATA GGTGTGGGTT ATTGACCATT ATTGACCACT  1100
CCCCTATTGG TGACGATACT TTCCATTACT AATCCATAAC ATGGCTCTTT  1150
GCCACAACTA TCTCTATTGG CTATATGCCA ATACTCTGTC CTTCAGAGAC  1200
TGACACGGAC TCTGTATTTT TACAGGATGG GGTCCCATTT ATTATTTACA  1250
AATTCACATA TACAACAACG CCGTCCCCCG TGCCCGCAGT TTTTATTAAA  1300
CATAGCGTGG GATCTCCACG CGAATCTCGG GTACGTGTTC CGGACATGGG  1350
CTCTTCTCCG GTAGCGGCGG AGCTTCCACA TCCGAGCCCT GGTCCCATGC  1400
CTCCAGCGGC TCATGGTCGC TCGGCAGCTC CTTGCTCCTA ACAGTGGAGG  1450
CCAGACTTAG GCACAGCACA ATGCCCACCA CCACCAGTGT GCCGCACAAG  1500
GCCGTGGCGG TAGGGTATGT GTCTGAAAAT GAGCGTGGAG ATTGGGCTCG  1550
CACGGCTGAC GCAGATGGAA GACTTAAGGC AGCGGCAGAA GAAGATGCAG  1600
GCAGCTGAGT TGTTGTATTC TGATAAGAGT CAGAGGTAAC TCCCGTTGCG  1650
GTGCTGTTAA CGGTGGAGGG CAGTGTAGTC TGAGCAGTAC TCGTTGCTGC  1700
CGCGCGCGCC ACCAGACATA ATAGCTGACA GACTAACAGA CTGTTCCTTT  1750
CCATGGGTCT TTTCTGCAGT CACCGTCGGA CCATGTGTGA ACTTGATATT  1800
TTACATGATT CTCTTTACCA ATTCTGCCCC GAATTACACT TAAAACGACT  1850
CAACAGCTTA ACGTTGGCTT GCCACGCATT ACTTGACTGT AAAACTCTCA  1900
CTCTTACCGA ACTTGGCCGT AACCTGCCAA CCAAAGCGAG AACAAAACAT  1950
AACATCAAAC GAATCGACCG ATTGTTAGGT AATCGTCACC TCCACAAAGA  2000
GCGACTCGCT GTATACCGTT GGCATGCTAG CTTTATCTGT TCGGGAATAC  2050
GATGCCCATT GTACTTGTTG ACTGGTCTGA TATTCGTGAG CAAAAACGAC  2100
TTATGGTATT GCGAGCTTCA GTCGCACTAC ACGGTCGTTC TGTTACTCTT  2150
TATGAGAAAG CGTTCCCGCT TTCAGAGCAA TGTTCAAAGA AAGCTCATGA  2200
CCAATTTCTA GCCGACCTTG CGAGCATTCT ACCGAGTAAC ACCACACCGC  2250
TCATTGTCAG TGATGCTGGC TTTAAAGTGC CATGGTATAA ATCCGTTGAG  2300
AAGCTGGGTT GGTACTGGTT AAGTCGAGTA AGAGGAAAAG TACAATATGC  2350
AGACCTAGGA GCGGAAAACT GGAAACCTAT CAGCAACTTA CATGATATGT  2400
CATCTAGTCA CTCAAAGACT TTAGGCTATA AGAGGCTGAC TAAAAGCAAT  2450
CCAATCTCAT GCCAAATTCT ATTGTATAAA TCTCGCTCTA AAGGCCGAAA  2500
AAATCAGCGC TCGACACGGA CTCATTGTCA CCACCCGTCA CCTAAAATCT  2550
ACTCAGCGTC GGCAAAGGAG CCATGGGTTC TAGCAACTAA CTTACCTGTT  2600
GAAATTCGAA CACCCAAACA ACTTGTTAAT ATCTATTCGA AGCGAATGCA  2650
GATTGAAGAA ACCTTCCGAG ACTTGAAAAG TCCTGCCTAC GGACTAGGCC  2700
TACGCCATAG CCGAACGAGC AGCTCAGAGC GTTTTGATAT CATGCTGCTA  2750
ATCGCCCTGA TGCTTCAACT AACATGTTGG CTTGCGGGCG TTCATGCTCA  2800
GAAACAAGGT TGGGACAAGC ACTTCCAGGC TAACACAGTC AGAAATCGAA  2850
```

```
ACGTACTCTC AACAGTTCGC TTAGGCATGG AAGTTTTGCG GCATTCTGGC 2900
TACACAATAA CAAGGGAAGA CTTACTCGTG GCTGCAACCC TACTAGCTCA 2950
AAATTTATTC ACACATGGTT ACGCTTTGGG GAAATTATGA TAATGATCCA 3000
GATCACTTCT GGCTAATAAA AGATCAGAGC TCTAGAGATC TGTGTGTTGG 3050
TTTTTTGTGG ATCTGCTGTG CCTTCTAGTT GCCAGCCATC TGTTGTTTGC 3100
CCCTCCCCCG TGCCTTCCTT GACCCTGGAA GGTGCCACTC CCACTGTCCT 3150
TTCCTAATAA AATGAGGAAA TTGCATCGCA TTGTCTGAGT AGGTGTCATT 3200
CTATTCTGGG GGGTGGGGTG GGGCAGCACA GCAAGGGGGA GGATTGGGAA 3250
GACAATAGCA GGCATGCTGG GGATGCGGTG GGCTCTATGG GTACCTCTCT 3300
CTCTCTCTCT CTCTCTCTCT CTCTCTCTCT CTCTCGGTAC CTCTCTCTCT 3350
CTCTCTCTCT CTCTCTCTCT CTCTCTCTCT CGGTACCAGG TGCTGAAGAA 3400
TTGACCCGGT GACCAAAGGT GCCTTTTATC ATCACTTTAA AAATAAAAAA 3450
CAATTACTCA GTGCCTGTTA TAAGCAGCAA TTAATTATGA TTGATGCCTA 3500
CATCACAACA AAAACTGATT TAACAAATGG TTGGTCTGCC TTAGAAAGTA 3550
TATTTGAACA TTATCTTGAT TATATTATTG ATAATAATAA AAACCTTATC 3600
CCTATCCAAG AAGTGATGCC TATCATTGGT TGGAATGAAC TTGAAAAAAA 3650
TTAGCCTTGA ATACATTACT GGTAAGGTAA ACGCCATTGT CAGCAAATTG 3700
ATCCAAGAGA ACCAACTTAA AGCTTTCCTG ACGGAATGTT AATTCTCGTT 3750
GACCCTGAGC ACTGATGAAT CCCCTAATGA TTTTGGTAAA AATCATTAAG 3800
TTAAGGTGGA TACACATCTT GTCATATGAT CCCGGTAATG TGAGTTAGCT 3850
CACTCATTAG GCACCCCAGG CTTTACACTT TATGCTTCCG GCTCGTATGT 3900
TGTGTGGAAT TGTGAGCGGA TAACAATTTC ACACAGGAAA CAGCTATGAC 3950
CATGATTACG CCAAGCGCGC AATTAACCCT CACTAAAGGG AACAAAAGCT 4000
GGAGCTCCAC CGCGGTGGCG GCCGCTCTAG AACTAGTGGA TCCCCCGGGC 4050
TGCAGGAATT CGATATCAAG CTTATCGATA CCGCTGACCT CGAGGGGGGG 4100
CCCGGTACCC AATTCCCCCT ATAGTGAGTC GTATTACGCG CGCTCACTGG 4150
CCGTCGTTTT ACAACGTCGT GACTGGGAAA ACCCTGGCGT TACCCAACTT 4200
AATCGCCTTG CAGCACATCC CCCTTTCGCC AGCTGGCGTA ATAGCGAAGA 4250
GGCCCGCACC GATCGCCCTT CCCAACAGTT GCGCAGCCTG AATGGCGAAT 4300
GGAAATTGTA AGCGTTAATA TTTTGTTAAA ATTCGCGTTA AATTTTTGTT 4350
AAATCAGCTC ATTTTTTAAC CAATAGGCCG AAATCGGCAA AATCCCTTAT 4400
AAATCAAAAG AATAGACCGA GATAGGGTTG AGTGTTGTTC CAGTTTGGAA 4450
CAAGAGTCCA CTATTAAAGA ACGTGGACTC CAACGTCAAA GGGCGAAAAA 4500
CCGTCTATCA GGGCGATGGC CCACTACTCC GGGATCATAT GACAAGATGT 4550
GTATCCACCT TAACTTAATG ATTTTTACCA AATCATTAG GGGATTCATC 4600
AGTGCTCAGG GTCAACGAGA ATTAACATTC CGTCAGGAAA GCTTATGATG 4650
ATGATGTGCT TAAAAACTTA CTCAATGGCT GGTTATGCAT ATCGCAATAC 4700
ATGCGAAAAA CCTAAAAGAG CTTGCCGATA AAAAAGGCCA ATTTATTGCT 4750
ATTTACCGCG GCTTTTTATT GAGCTTGAAA GATAAATAAA ATAGATAGGT 4800
TTTATTTGAA GCTAAATCTT CTTTATCGTA AAAAATGCCC TCTTGGGTTA 4850
```

```
TCAAGAGGGT CATTATATTT CGCGGAATAA CATCATTTGG TGACGAAATA 4900

ACTAAGCACT TGTCTCCTGT TTACTCCCCT GAGCTTGAGG GGTTAACATG 4950

AAGGTCATCG ATAGCAGGAT AATAATACAG TAAAACGCTA AACCAATAAT 5000

CCAAATCCAG CCATCCCAAA TTGGTAGTGA ATGATTATAA ATAACAGCAA 5050

ACAGTAATGG GCCAATAACA CCGGTTGCAT TGGTAAGGCT CACCAATAAT 5100

CCCTGTAAAG CACCTTGCTG ATGACTCTTT GTTTGGATAG ACATCACTCC 5150

CTGTAATGCA GGTAAAGCGA TCCCACCACC AGCCAATAAA ATTAAAACAG 5200

GGAAAACTAA CCAACCTTCA GATATAAACG CTAAAAAGGC AAATGCACTA 5250

CTATCTGCAA TAAATCCGAG CAGTACTGCC GTTTTTTCGC CCATTTAGTG 5300

GCTATTCTTC CTGCCACAAA GGCTTGGAAT ACTGAGTGTA AAAGACCAAG 5350

ACCCGTAATG AAAAGCCAAC CATCATGCTA TTCATCATCA CGATTTCTGT 5400

AATAGCACCA CACCGTGCTG GATTGGCTAT CAATGCGCTG AAATAATAAT 5450

CAACAAATGG CATCGTTAAA TAAGTGATGT ATACCGATCA GCTTTTGTTC 5500

CCTTTAGTGA GGGTTAATTG CGCGCTTGGC GTAATCATGG TCATAGCTGT 5550

TTCCTGTGTG AAATTGTTAT CCGCTCACAA TTCCACACAA CATACGAGCC 5600

GGAAGCATAA AGTGTAAAGC CTGGGGTGCC TAATGAGTGA GCTAACTCAC 5650

ATTAATTGCG TTGCGCTCAC TGCCCGCTTT CCAGTCGGGA AACCTGTCGT 5700

GCCAGCTGCA TTAATGAATC GGCCAACGCG CGGGGAGAGG CGGTTTGCGT 5750

ATTGGGCGCT CTTCCGCTTC CTCGCTCACT GACTCGCTGC GCTCGGTCGT 5800

TCGGCTGCGG CGAGCGGTAT CAGCTCACTC AAAGGCGGTA ATACGGTTAT 5850

CCACAGAATC AGGGGATAAC GCAGGAAAGA ACATGTGAGC AAAAGGCCAG 5900

CAAAAGGCCA GGAACCGTAA AAAGGCCGCG TTGCTGGCGT TTTTCCATAG 5950

GCTCCGCCCC CCTGACGAGC ATCACAAAAA TCGACGCTCA AGTCAGAGGT 6000

GGCGAAACCC GACAGGACTA TAAAGATACC AGGCGTTTCC CCCTGGAAGC 6050

TCCCTCGTGC GCTCTCCTGT TCCGACCCTG CCGCTTACCG GATACCTGTC 6100

CGCCTTTCTC CCTTCGGGAA GCGTGGCGCT TTCTCATAGC TCACGCTGTA 6150

GGTATCTCAG TTCGGTGTAG GTCGTTCGCT CCAAGCTGGG CTGTGTGCAC 6200

GAACCCCCCG TTCAGCCCGA CCGCTGCGCC TTATCCGGTA ACTATCGTCT 6250

TGAGTCCAAC CCGGTAAGAC ACGACTTATC GCCACTGGCA GCAGCCACTG 6300

GTAACAGGAT TAGCAGAGCG AGGTATGTAG GCGGTGCTAC AGAGTTCTTG 6350

AAGTGGTGGC CTAACTACGG CTACACTAGA AGGACAGTAT TTGGTATCTG 6400

CGCTCTGCTG AAGCCAGTTA CCTTCGGAAA AAGAGTTGGT AGCTCTTGAT 6450

CCGGCAAACA AACCACCGCT GGTAGCGGTG GTTTTTTTGT TTGCAAGCAG 6500

CAGATTACGC GCAGAAAAAA AGGATCTCAA GAAGATCCTT TGATCTTTTC 6550

TACGGGGTCT GACGCTCAGT GGAACGAAAA CTCACGTTAA GGGATTTTGG 6600

TCATGAGATT ATCAAAAAGG ATCTTCACCT AGATCCTTTT AAATTAAAAA 6650

TGAAGTTTTA AATCAATCTA AAGTATATAT GAGTAAACTT GGTCTGACAG 6700

TTACCAATGC TTAATCAGTG AGGCACCTAT CTCAGCGATC TGTCTATTTC 6750

GTTCATCCAT AGTTGCCTGA CTCCCCGTCG TGTAGATAAC TACGATACGG 6800

GAGGGCTTAC CATCTGGCCC CAGTGCTGCA ATGATACCGC GAGACCCACG 6850

CTCACCGGCT CCAGATTTAT CAGCAATAAA CCAGCCAGCC GGAAGGGCCG 6900
```

```
AGCGCAGAAG TGGTCCTGCA ACTTTATCCG CCTCCATCCA GTCTATTAAT   6950

TGTTGCCGGG AAGCTAGAGT AAGTAGTTCG CCAGTTAATA GTTTGCGCAA   7000

CGTTGTTGCC ATTGCTACAG GCATCGTGGT GTCACGCTCG TCGTTTGGTA   7050

TGGCTTCATT CAGCTCCGGT TCCCAACGAT CAAGGCGAGT TACATGATCC   7100

CCCATGTTGT GCAAAAAAGC GGTTAGCTCC TTCGGTCCTC CGATCGTTGT   7150

CAGAAGTAAG TTGGCCGCAG TGTTATCACT CATGGTTATG GCAGCACTGC   7200

ATAATTCTCT TACTGTCATG CCATCCGTAA GATGCTTTTC TGTGACTGGT   7250

GAGTACTCAA CCAAGTCATT CTGAGAATAG TGTATGCGGC GACCGAGTTG   7300

CTCTTGCCCG GCGTCAATAC GGGATAATAC CGCGCCACAT AGCAGAACTT   7350

TAAAAGTGCT CATCATTGGA AAACGTTCTT CGGGGCGAAA ACTCTCAAGG   7400

ATCTTACCGC TGTTGAGATC CAGTTCGATG TAACCCACTC GTGCACCCAA   7450

CTGATCTTCA GCATCTTTTA CTTTCACCAG CGTTTCTGGG TGAGCAAAAA   7500

CAGGAAGGCA AAATGCCGCA AAAAAGGGAA TAAGGGCGAC ACGGAAATGT   7550

TGAATACTCA TACTCTTCCT TTTTCAATAT TATTGAAGCA TTTATCAGGG   7600

TTATTGTCTC ATGAGCGGAT ACATATTTGA ATGTATTTAG AAAAATAAAC   7650

AAATAGGGGT TCCGCGCACA TTTCCCCGAA AAGTGCCAC               7689
```

SEQ ID NO: 4 (a Kozak sequence)
ACCATGG

SEQ ID NO: 52 (a Kozak sequence)
ACCATGT

SEQ ID NO: 5 (a Kozak sequence)
AAGATGT

SEQ ID NO: 6 (a Kozak sequence)
ACGATGA

SEQ ID NO: 7 (a Kozak sequence)
AAGATGG

SEQ ID NO: 8 (a Kozak sequence)
GACATGA

SEQ ID NO: 9 (a Kozak sequence)
ACCATGA

SEQ ID NO: 11 (conalbumin polyA)
tctgccattg ctgcttcctc tgcccttcct cgtcactctg aatgtggctt cttcgctact gccacagcaa gaaataaaat ctcaacatct aaatgggttt cctgaggttt ttcaagagtc gttaagcaca ttccttcccc agcacccctt gctgcaggcc agtgccaggc accaacttgg ctactgctgc ccatgagaga aatccagttc aatattttcc aaagcaaaat ggattacata tgccctagat cctgattaac aggcgtttgt attatctagt gctttcgctt cacccagatt atcccattgc ctccc SEQ ID NO: 12 (synthetic polyA)
GGCGCCTGGATCCAGATCACTTCTGGCTAATAAAAGATCAGAGCTCTAGAGATCTGTGTGTTGGTTTTT

TGTGGATCTGCTGTGCCTTCTAGTTGCCAGCCATCTGTTGTTTGCCCCTCCCCCGTGCCTTCCTTGACC

CTGGAAGGTGCCACTCCCACTGTCCTTTCCTAATAAAATGAGGAAATTGCATCGCATTGTCTGAGTAGG

TGTCATTCTATTCTGGGGGGTGGGGTGGGGCAGCACAGCAAGGGGGAGGATTGGGAAGACAATAGCAGG

CATGCTGGGGATGCGGTGGGCTCTATGGGTACCTCTCTCTCTCTCTCTCTCTCTCTCTCTCTCTCTCTC

TCTCGGTACCTCTCTC

SEQ ID NO: 13 (avian optimized polyA)

-continued gggatcgc tctagagcga tccgggatct cgggaaaagc gttggtgacc aaaggtgcct tttatcatca ctttaaaaat aaaaaacaat tactcagtgc ctgttataag cagcaattaa ttatgattga tgcctacatc acaacaaaaa ctgatttaac aaatggttgg tctgccttag aaagtatatt tgaacattat cttgattata ttattgataa taataaaaac cttatcccta tccaagaagt gatgcctatc attggttgga atgaacttga aaaaaattag ccttgaatac attactggta aggtaaacgc cattgtcagc aaattgatcc aagagaacca a SEQ ID NO: 14 (vitellogenin promoter)
TGAATGTGTT CTTGTGTTAT CAATATAAAT CACAGTTAGT GATGAAGTTG GCTGCAAGCC

TGCATCAGTT CAGCTACTTG GCTGCATTTT GTATTTGGTT CTGTAGGAAA TGCAAAAGGT

TCTAGGCTGA CCTGCACTTC TATCCCTCTT GCCTTACTGC TGAGAATCTC TGCAGGTTTT

AATTGTTCAC ATTTTGCTCC CATTTACTTT GGAAGATAAA ATATTTACAG AATGCTTATG

AAACCTTTGT TCATTTAAAA ATATTCCTGG TCAGCGTGAC CGGAGCTGAA AGAACACATT

GATCCCGTGA TTTCAATAAA TACATATGTT CCATATATTG TTTCTCAGTA GCCTCTTAAA

TCATGTGCGT TGGTGCACAT ATGAATACAT GAATAGCAAA GGTTTATCTG GATTACGCTC

TGGCCTGCAG AATGGCCAT AAACCAAAGC TGAGGGAAGA GGGAGAGTAT AGTCAATGTA

GATTATACTG ATTGCTGATT GGGTTATTAT CAGCTAGATA ACAACTTGGG TCAGGTGCCA

GGTCAACATA ACCTGGGCAA AACCAGTCTC ATCTGTGGCA GGACCATGTA CCAGCAGCCA

GCCGTGACCC AATCTAGGAA AGCAAGTAGC ACATCAATTT TAAATTTATT GTAAATGCCG

TAGTAGAAGT GTTTTACTGT GATACATTGA AACTTCTGGT CAATCAGAAA AAGGTTTTTT

ATCAGAGATG CCAAGGTATT ATTTGATTTT CTTTATTCGC CGTGAAGAGA ATTTATGATT

GCAAAAAGAG GAGTGTTTAC ATAAACTGAT AAAAAACTTG AGGAATTCAG CAGAAAACAG

CCACGTGTTC CTGAACATTC TTCCATAAAA GTCTCACCAT GCCTGGCAGA GCCCTATTCA

CCTTCGCT

SEQ ID NO: 15 (fragment of ovalbumin promoter - chicken)
GAGGTCAGAAT GGTTTCTTTA CTGTTTGTCA ATTCTATTAT TTCAATACAG

AACAATAGCT TCTATAACTG AAATATATTT GCTATTGTAT ATTATGATTG

TCCCTCGAAC CATGAACACT CCTCCAGCTG AATTTCACAA TTCCTCTGTC

ATCTGCCAGG CCATTAAGTT ATTCATGGAA GATCTTTGAG GAACACTGCA

AGTTCATATC ATAAACACAT TTGAAATTGA GTATTGTTTT GCATTGTATG

GAGCTATGTT TTGCTGTATC CTCAGAAAAA AAGTTTGTTA TAAAGCATTC

ACACCCATAA AAAGATAGAT TTAAATATTC CAGCTATAGG AAAGAAAGTG

CGTCTGCTCT TCACTCTAGT CTCAGTTGGC TCCTTCACAT GCATGCTTCT

TTATTTCTCC TATTTTGTCA AGAAAATAAT AGGTCACGTC TTGTTCTCAC

TTATGTCCTG CCTAGCATGG CTCAGATGCA CGTTGTAGAT ACAAGAAGGA

TCAAATGAAA CAGACTTCTG GTCTGTTACT ACAACCATAG TAATAAGCAC

ACTAACTAAT AATTGCTAAT TATGTTTTCC ATCTCTAAGG TTCCCACATT

TTTCTGTTTT CTTAAAGATC CCATTATCTG GTTGTAACTG AAGCTCAATG

GAACATGAGC AATATTTCCC AGTCTTCTCT CCCATCCAAC AGTCCTGATG

GATTAGCAGA ACAGGCAGAA AACACATTGT TACCCAGAAT TAAAAACTAA

TATTTGCTCT CCATTCAATC CAAAATGGAC CTATTGAAAC TAAAATCTAA

CCCAATCCCA TTAAATGATT TCTATGGCGT CAAAGGTCAA ACTTCTGAAG

GGAACCTGTG GGTGGGTCAC AATTCAGGCT ATATATTCCC CAGGGCTCAG

SEQ ID NO: 16 (chicken ovalbumin ehancer)
ccgggctgca gaaaaatgcc aggtggacta tgaactcaca tccaaaggag cttgacctga tacctgattt tcttcaaact ggggaaacaa cacaatccca caaacagct cagagagaaa ccatcactga tggctacagc accaaggtat gcaatggcaa tccattcgac attcatctgt gacctgagca aaatgattta tctctccatg aatggttgct tctttccctc atgaaaaggc aatttccaca ctcacaatat gcaacaaaga caaacagaga acaattaatg tgctccttcc taatgtcaaa attgtagtgg caaagaggag aacaaaatct caagttctga gtaggtttta gtgattggat aagaggcttt gacctgtgag ctcacctgga cttcatatcc ttttggataa aaagtgcttt tataactttc aggtctccga gtctttattc atgagactgt tggtttaggg acagacccac aatgaaatgc ctggcatagg aaagggcagc agagccttag ctgacctttt cttgggacaa gcattgtcaa acaatgtgtg acaaaactat ttgtactgct ttgcacagct gtgctgggca gggcaatcca ttgccaccta tcccaggtaa ccttccaact gcaagaagat tgttgcttac tctctctaga SEQ ID NO: 17 (5' untranslated region)
GTGGATCAACATACAGCTAGAAAGCTGTATTGCCTTTAGCACTCAAGCTCAAAAGACAACTCAGAGTTC

ACC

SEQ ID NO: 18 (putative cap site)
ACATACAGCTAG AAAGCTGTAT TGCCTTTAGC ACTCAAGCTC AAAAGACAAC TCAGAGTTCA SEQ ID NO: 19 (Chicken Ovalbumin Signal Sequence)
ATG GGCTCCATCG GCGCAGCAAG CATGGAATTT TGTTTTGATG TATTCAAGGA GCTCAAAGTC

CACCATGCCA ATGAGAACAT CTTCTACTGC CCCATTGCCA TCATGTCAGC TCTAGCCATG

GTATACCTGG GTGCAAAAGA CAGCACCAGG ACACAGATAA ATAAGGTTGT TCGCTTTGAT

AAACTTCCAG GATTCGGAGA CAGTATTGAA GCTCAGTGTG GCACATCTGT AAACGTTCAC

TCTTCACTTA GAGACATCCT CAACCAAATC ACCAAACCAA ATGATGTTTA TTCGTTCAGC

CTTGCCAGTA GACTTTATGC TGAAGAGAGA TACCCAATCC TGCCAGAATA CTTGCAGTGT

GTGAAGGAAC TGTATAGAGG AGGCTTGGAA CCTATCAACT TCAAACAGC TGCAGATCAA

GCCAGAGAGC TCATCAATTC CTGGGTAGAA AGTCAGACAA ATGGAATTAT CAGAAATGTC

CTTCAGCCAA GCTCCGTGGA TTCTCAAACT GCAATGGTTC TGGTTAATGC CATTGTCTTC

AAAGGACTGT GGGAGAAAAC ATTTAAGGAT GAAGACACAC AAGCAATGCC TTTCAGAGTG

ACTGAGCAAG AAAGCAAACC TGTGCAGATG ATGTACCAGA TTGGTTTATT TAGAGTGGCA

TCAATGGCTT CTGAGAAAAT GAAGATCCTG GAGCTTCCAT TGCCAGTGG ACAATGAGC

ATGTTGGTGC TGTTGCCTGA TGAAGTCTCA GGCCTTGAGC AGCTTGAGAG TATAATCAAC

TTTGAAAAAC TGACTGAATG GACCAGTTCT AATGTTATGG AAGAGAGGAA GATCAAAGTG

TACTTACCTC GCATGAAGAT GGAGGAAAAA TACAACCTCA CATCTGTCTT AATGGCTATG

GGCATTACTG ACGTGTTTAG CTCTTCAGCC AATCTGTCTG GCATCTCCTC AGCAGAGAGC

CTGAAGATAT CTCAAGCTGT CCATGCAGCA CATGCAGAAA TCAATGAAGC AGGCAGAGAG

GTGGTAGGGT CAGCAGAGGC TGGAGTGGAT GCTGCAAGCG TCTCTGAAGA ATTTAGGGCT

GACCATCCAT TCCTCTTCTG TATCAAGCAC ATCGCAACCA ACGCCGTTCT CTTCTTTGGC

AGATGTGTTT CCCCT

SEQ ID NO: 20 (Chicken Ovalbumin Signal Sequence - shortened 50 bp)
ATG GGCTCCATCG GCGCAGCAAG CATGGAATTT TGTTTTGATG TATTCAAGGA SEQ ID NO: 21 (Chicken Ovalbumin Signal Sequence - shortened 100 bp)
ATG GGCTCCATCG GCGCAGCAAG CATGGAATTT TGTTTTGATG TATTCAAGGA GCTCAAAGTC

```
-continued
CACCATGCCA ATGAGAACAT CTTCTACTGC CCCATTGCCA

SEQ ID NO: 22 (vitellogenin targeting sequence)
ATGAGGGGGATCATACTGGCATTAGTGCTCACCCTTGTAGGCAGCCAGAAGTTTGACATTGGT SEQ ID NO: 23 (pro-insulin sequence)
TTTGTGAACCAACACCTGTGCGGCTCACACCTGGTGGAAGCTCTCTACCTAGTGTGCGGGGAACGAGGC

TTCTTCTACACACCCAAGACCCGCCGGGAGGCAGAGGACCTGCAGGTGGGGCAGGTGGAGCTGGGCGGG

GGCCCTGGTGCAGGCAGCCTGCAGCCCTTGGCCCTGGAGGGGTCCCTGCAGAAGCGTGGCATTGTGGAA

CAATGCTGTACCAGCATCTGCTCCCTCTACCAGCTGGAGAACTCTGCAACTAG

SEQ ID NO: 24 (p146 protein)
KYKKALKKLAKLL

SEQ ID NO: 25 (p146 coding sequence)
AAATACAAAAAAGCACTGAAAAAACTGGCAAAACTGCTG

SEQ ID NO: 26 (spacer)
(GPGG)ₓ

SEQ ID NO: 27 (spacer)
GPGGGPGGGPGG

SEQ ID NO: 28 (spacer)
GGGGSGGGGSGGGGS

SEQ ID NO: 29 (spacer)
GGGGSGGGGSGGGGSGGGGS

SEQ ID NO: 30 (repeat domain in TAG spacer sequence)
Pro Ala Asp Asp Ala

SEQ ID NO: 31 (TAG spacer sequence)
Pro Ala Asp Asp Ala Pro Ala Asp Asp Ala Pro Ala Asp Asp Ala Pro Ala Asp Asp Ala Pro Ala Asp Asp Ala Pro Ala Asp Asp SEQ ID NO: 32 (gp41 epitope)
Ala Thr Thr Cys Ile Leu Lys Gly Ser Cys Gly Trp Ile Gly Leu Leu SEQ ID NO: 33 (polynucleotide sequence encoding gp41 epitope)
Pro Ala Asp Asp Ala Pro Ala Asp Asp Ala Thr Thr Cys Ile Leu Lys Gly Ser Cys Gly Trp Ile Gly Leu Leu Asp Asp Asp Asp Lys SEQ ID NO: 34 (enterokinase cleavage site)
DDDDK SEQ ID NO: 35 (TAG sequence)
Pro Ala Asp Asp Ala Pro Ala Asp Asp Ala Pro Ala Asp Asp Ala Pro Ala Asp Asp Ala Pro Ala Asp Asp Ala Pro Ala Asp Asp Ala Thr Thr Cys Ile Leu Lys Gly Ser Cys Gly Trp Ile Gly Leu Leu Asp Asp Asp Asp Lys SEQ ID NO: 36 (altered transposase Hef forward primer)
ATCTCGAGACCATGTGTGAACTTGATATTTTACATGATTCTCTTTACC SEQ ID NO: 37 (altered transposase Her reverse primer)
GATTGATCATTATCATAATTTCCCCAAAGCGTAACC SEQ ID NO: 38 (Xho I restriction site)
CTCGAG SEQ ID NO: 39 (Bcl I restriction site)
TGATCA SEQ ID NO: 40 (CMVf-NgoM IV primer)
TTGCCGGCATCAGATTGGTAT SEQ ID NO: 41 (Syn-polyAr-BstE II primer)
AGAGGTCACCGGGTCAATTCTTCAGCACCTGGTA SEQ ID NO: 42 (pTnMod(Oval/ENT tag/ProIns/PA) - Chicken)
CTGACGCGCC CTGTAGCGGC GCATTAAGCG CGGCGGGTGT GGTGGTTACG        50

CGCAGCGTGA CCGCTACACT TGCCAGCGCC CTAGCGCCCG CTCCTTTCGC       100
```

-continued

```
TTTCTTCCCT TCCTTTCTCG CCACGTTCGC CGGCATCAGA TTGGCTATTG    150

GCCATTGCAT ACGTTGTATC CATATCATAA TATGTACATT TATATTGGCT    200

CATGTCCAAC ATTACCGCCA TGTTGACATT GATTATTGAC TAGTTATTAA    250

TAGTAATCAA TTCGGGGTC ATTAGTTCAT AGCCCATATA TGGAGTTCCG     300

CGTTACATAA CTTACGGTAA ATGGCCCGCC TGGCTGACCG CCCAACGACC    350

CCCGCCCATT GACGTCAATA ATGACGTATG TTCCCATAGT AACGCCAATA    400

GGGACTTTCC ATTGACGTCA ATGGGTGGAG TATTTACGGT AAACTGCCCA    450

CTTGGCAGTA CATCAAGTGT ATCATATGCC AAGTACGCCC CCTATTGACG    500

TCAATGACGG TAAATGGCCC GCCTGGCATT ATGCCCAGTA CATGACCTTA    550

TGGGACTTTC CTACTTGGCA GTACATCTAC GTATTAGTCA TCGCTATTAC    600

CATGGTGATG CGGTTTTGGC AGTACATCAA TGGGCGTGGA TAGCGGTTTG    650

ACTCACGGGG ATTTCCAAGT CTCCACCCCA TTGACGTCAA TGGGAGTTTG    700

TTTTGGCACC AAAATCAACG GGACTTTCCA AAATGTCGTA ACAACTCCGC    750

CCCATTGACG CAAATGGGCG GTAGGCGTGT ACGGTGGGAG GTCTATATAA    800

GCAGAGCTCG TTTAGTGAAC CGTCAGATCG CCTGGAGACG CCATCCACGC    850

TGTTTTGACC TCCATAGAAG ACACCGGGAC CGATCCAGCC TCCGCGGCCG    900

GGAACGGTGC ATTGGAACGC GGATTCCCCG TGCCAAGAGT GACGTAAGTA    950

CCGCCTATAG ACTCTATAGG CACACCCCTT TGGCTCTTAT GCATGCTATA    1000

CTGTTTTTGG CTTGGGGCCT ATACACCCCC GCTTCCTTAT GCTATAGGTG    1050

ATGGTATAGC TTAGCCTATA GGTGTGGGTT ATTGACCATT ATTGACCACT    1100

CCCCTATTGG TGACGATACT TTCCATTACT AATCCATAAC ATGGCTCTTT    1150

GCCACAACTA TCTCTATTGG CTATATGCCA ATACTCTGTC CTTCAGAGAC    1200

TGACACGGAC TCTGTATTTT TACAGGATGG GGTCCCATTT ATTATTTACA    1250

AATTCACATA TACAACAACG CCGTCCCCCG TGCCCGCAGT TTTTATTAAA    1300

CATAGCGTGG GATCTCCACG CGAATCTCGG GTACGTGTTC CGGACATGGG    1350

CTCTTCTCCG GTAGCGGCGG AGCTTCCACA TCCGAGCCCT GGTCCCATGC    1400

CTCCAGCGGC TCATGGTCGC TCGGCAGCTC CTTGCTCCTA ACAGTGGAGG    1450

CCAGACTTAG GCACAGCACA ATGCCCACCA CCACCAGTGT GCCGCACAAG    1500

GCCGTGGCGG TAGGGTATGT GTCTGAAAAT GAGCGTGGAG ATTGGGCTCG    1550

CACGGCTGAC GCAGATGGAA GACTTAAGGC AGCGGCAGAA GAAGATGCAG    1600

GCAGCTGAGT TGTTGTATTC TGATAAGAGT CAGAGGTAAC TCCCGTTGCG    1650

GTGCTGTTAA CGGTGGAGGG CAGTGTAGTC TGAGCAGTAC TCGTTGCTGC    1700

CGCGCGCGCC ACCAGACATA ATAGCTGACA GACTAACAGA CTGTTCCTTT    1750

CCATGGGTCT TTTCTGCAGT CACCGTCGGA CCATGTGTGA ACTTGATATT    1800

TTACATGATT CTCTTTACCA ATTCTGCCCC GAATTACACT TAAAACGACT    1850

CAACAGCTTA ACGTTGGCTT GCCACGCATT ACTTGACTGT AAAACTCTCA    1900

CTCTTACCGA ACTTGGCCGT AACCTGCCAA CCAAAGCGAG AACAAAACAT    1950

AACATCAAAC GAATCGACCG ATTGTTAGGT AATCGTCACC TCCACAAAGA    2000

GCGACTCGCT GTATACCGTT GGCATGCTAG CTTTATCTGT TCGGGAATAC    2050

GATGCCCATT GTACTTGTTG ACTGGTCTGA TATTCGTGAG CAAAAACGAC    2100

TTATGGTATT GCGAGCTTCA GTCGCACTAC ACGGTCGTTC TGTTACTCTT    2150
```

```
TATGAGAAAG CGTTCCCGCT TTCAGAGCAA TGTTCAAAGA AAGCTCATGA  2200
CCAATTTCTA GCCGACCTTG CGAGCATTCT ACCGAGTAAC ACCACACCGC  2250
TCATTGTCAG TGATGCTGGC TTTAAAGTGC CATGGTATAA ATCCGTTGAG  2300
AAGCTGGGTT GGTACTGGTT AAGTCGAGTA AGAGGAAAAG TACAATATGC  2350
AGACCTAGGA GCGGAAAACT GGAAACCTAT CAGCAACTTA CATGATATGT  2400
CATCTAGTCA CTCAAAGACT TTAGGCTATA AGAGGCTGAC TAAAAGCAAT  2450
CCAATCTCAT GCCAAATTCT ATTGTATAAA TCTCGCTCTA AAGGCCGAAA  2500
AAATCAGCGC TCGACACGGA CTCATTGTCA CCACCCGTCA CCTAAAATCT  2550
ACTCAGCGTC GGCAAAGGAG CCATGGGTTC TAGCAACTAA CTTACCTGTT  2600
GAAATTCGAA CACCCAAACA ACTTGTTAAT ATCTATTCGA AGCGAATGCA  2650
GATTGAAGAA ACCTTCCGAG ACTTGAAAAG TCCTGCCTAC GGACTAGGCC  2700
TACGCCATAG CCGAACGAGC AGCTCAGAGC GTTTTGATAT CATGCTGCTA  2750
ATCGCCCTGA TGCTTCAACT AACATGTTGG CTTGCGGGCG TTCATGCTCA  2800
GAAACAAGGT TGGGACAAGC ACTTCCAGGC TAACACAGTC AGAAATCGAA  2850
ACGTACTCTC AACAGTTCGC TTAGGCATGG AAGTTTTGCG GCATTCTGGC  2900
TACACAATAA CAAGGGAAGA CTTACTCGTG GCTGCAACCC TACTAGCTCA  2950
AAATTTATTC ACACATGGTT ACGCTTTGGG GAAATTATGA TAATGATCCA  3000
GATCACTTCT GGCTAATAAA AGATCAGAGC TCTAGAGATC TGTGTGTTGG  3050
TTTTTTGTGG ATCTGCTGTG CCTTCTAGTT GCCAGCCATC TGTTGTTTGC  3100
CCCTCCCCCG TGCCTTCCTT GACCCTGGAA GGTGCCACTC CCACTGTCCT  3150
TTCCTAATAA AATGAGGAAA TTGCATCGCA TTGTCTGAGT AGGTGTCATT  3200
CTATTCTGGG GGGTGGGGTG GGGCAGCACA GCAAGGGGGA GGATTGGGAA  3250
GACAATAGCA GGCATGCTGG GGATGCGGTG GGCTCTATGG GTACCTCTCT  3300
CTCTCTCTCT CTCTCTCTCT CTCTCTCTCT CTCTCGGTAC CTCTCTCTCT  3350
CTCTCTCTCT CTCTCTCTCT CTCTCTCTCT CGGTACCAGG TGCTGAAGAA  3400
TTGACCCGGT GACCAAAGGT GCCTTTTATC ATCACTTTAA AAATAAAAAA  3450
CAATTACTCA GTGCCTGTTA TAAGCAGCAA TTAATTATGA TTGATGCCTA  3500
CATCACAACA AAAACTGATT TAACAAATGG TTGGTCTGCC TTAGAAAGTA  3550
TATTTGAACA TTATCTTGAT TATATTATTG ATAATAATAA AAACCTTATC  3600
CCTATCCAAG AAGTGATGCC TATCATTGGT TGGAATGAAC TTGAAAAAAA  3650
TTAGCCTTGA ATACATTACT GGTAAGGTAA ACGCCATTGT CAGCAAATTG  3700
ATCCAAGAGA ACCAACTTAA AGCTTTCCTG ACGGAATGTT AATTCTCGTT  3750
GACCCTGAGC ACTGATGAAT CCCCTAATGA TTTTGGTAAA AATCATTAAG  3800
TTAAGGTGGA TACACATCTT GTCATATGAT CCCGGTAATG TGAGTTAGCT  3850
CACTCATTAG GCACCCCAGG CTTTACACTT TATGCTTCCG GCTCGTATGT  3900
TGTGTGGAAT TGTGAGCGGA TAACAATTTC ACACAGGAAA CAGCTATGAC  3950
CATGATTACG CCAAGCGCGC AATTAACCCT CACTAAAGGG AACAAAAGCT  4000
GGAGCTCCAC CGCGGTGGCG GCCGCTCTAG AACTAGTGGA TCCCCCGGGG  4050
AGGTCAGAAT GGTTTCTTTA CTGTTTGTCA ATTCTATTAT TTCAATACAG  4100
AACAATAGCT TCTATAACTG AAATATATTT GCTATTGTAT ATTATGATTG  4150
```

```
TCCCTCGAAC CATGAACACT CCTCCAGCTG AATTTCACAA TTCCTCTGTC     4200

ATCTGCCAGG CCATTAAGTT ATTCATGGAA GATCTTTGAG GAACACTGCA    4250

AGTTCATATC ATAAACACAT TTGAAATTGA GTATTGTTTT GCATTGTATG    4300

GAGCTATGTT TTGCTGTATC CTCAGAAAAA AAGTTTGTTA TAAAGCATTC    4350

ACACCCATAA AAAGATAGAT TTAAATATTC CAGCTATAGG AAAGAAAGTG    4400

CGTCTGCTCT TCACTCTAGT CTCAGTTGGC TCCTTCACAT GCATGCTTCT    4450

TTATTTCTCC TATTTTGTCA AGAAAATAAT AGGTCACGTC TTGTTCTCAC    4500

TTATGTCCTG CCTAGCATGG CTCAGATGCA CGTTGTAGAT ACAAGAAGGA    4550

TCAAATGAAA CAGACTTCTG GTCTGTTACT ACAACCATAG TAATAAGCAC    4600

ACTAACTAAT AATTGCTAAT TATGTTTTCC ATCTCTAAGG TTCCCACATT    4650

TTTCTGTTTT CTTAAAGATC CCATTATCTG GTTGTAACTG AAGCTCAATG    4700

GAACATGAGC AATATTTCCC AGTCTTCTCT CCCATCCAAC AGTCCTGATG    4750

GATTAGCAGA ACAGGCAGAA AACACATTGT TACCCAGAAT TAAAAACTAA    4800

TATTTGCTCT CCATTCAATC CAAAATGGAC CTATTGAAAC TAAAATCTAA    4850

CCCAATCCCA TTAAATGATT TCTATGGCGT CAAAGGTCAA ACTTCTGAAG    4900

GGAACCTGTG GGTGGGTCAC AATTCAGGCT ATATATTCCC CAGGGCTCAG    4950

CGGATCCATG GGCTCCATCG GCGCAGCAAG CATGGAATTT TGTTTTGATG    5000

TATTCAAGGA GCTCAAAGTC CACCATGCCA ATGAGAACAT CTTCTACTGC    5050

CCCATTGCCA TCATGTCAGC TCTAGCCATG GTATACCTGG GTGCAAAAGA    5100

CAGCACCAGG ACACAGATAA ATAAGGTTGT TCGCTTTGAT AAACTTCCAG    5150

GATTCGGAGA CAGTATTGAA GCTCAGTGTG GCACATCTGT AAACGTTCAC    5200

TCTTCACTTA GAGACATCCT CAACCAAATC ACCAAACCAA ATGATGTTTA    5250

TTCGTTCAGC CTTGCCAGTA GACTTTATGC TGAAGAGAGA TACCCAATCC    5300

TGCCAGAATA CTTGCAGTGT GTGAAGGAAC TGTATAGAGG AGGCTTGGAA    5350

CCTATCAACT TTCAAACAGC TGCAGATCAA GCCAGAGAGC TCATCAATTC    5400

CTGGGTAGAA AGTCAGACAA ATGGAATTAT CAGAAATGTC CTTCAGCCAA    5450

GCTCCGTGGA TTCTCAAACT GCAATGGTTC TGGTTAATGC CATTGTCTTC    5500

AAAGGACTGT GGGAGAAAAC ATTTAAGGAT GAAGACACAC AAGCAATGCC    5550

TTTCAGAGTG ACTGAGCAAG AAAGCAAACC TGTGCAGATG ATGTACCAGA    5600

TTGGTTTATT TAGAGTGGCA TCAATGGCTT CTGAGAAAAT GAAGATCCTG    5650

GAGCTTCCAT TTGCCAGTGG GACAATGAGC ATGTTGGTGC TGTTGCCTGA    5700

TGAAGTCTCA GGCCTTGAGC AGCTTGAGAG TATAATCAAC TTTGAAAAAC    5750

TGACTGAATG GACCAGTTCT AATGTTATGG AAGAGAGGAA GATCAAAGTG    5800

TACTTACCTC GCATGAAGAT GGAGGAAAAA TACAACCTCA CATCTGTCTT    5850

AATGGCTATG GGCATTACTG ACGTGTTTAG CTCTTCAGCC AATCTGTCTG    5900

GCATCTCCTC AGCAGAGAGC CTGAAGATAT CTCAAGCTGT CCATGCAGCA    5950

CATGCAGAAA TCAATGAAGC AGGCAGAGAG GTGGTAGGGT CAGCAGAGGC    6000

TGGAGTGGAT GCTGCAAGCG TCTCTGAAGA ATTTAGGGCT GACCATCCAT    6050

TCCTCTTCTG TATCAAGCAC ATCGCAACCA ACGCCGTTCT CTTCTTTGGC    6100

AGATGTGTTT CCCCTCCGCG GCCAGCGATG ACGCACCAG CAGATGACGC    6150

ACCAGCAGAT GACGCACCAG CAGATGACGC ACCAGCAGAT GACGCACCAG    6200
```

```
CAGATGACGC AACAACATGT ATCCTGAAAG GCTCTTGTGG CTGGATCGGC    6250

CTGCTGGATG ACGATGACAA ATTTGTGAAC CAACACCTGT GCGGCTCACA    6300

CCTGGTGGAA GCTCTCTACC TAGTGTGCGG GGAACGAGGC TTCTTCTACA    6350

CACCCAAGAC CCGCCGGGAG GCAGAGGACC TGCAGGTGGG GCAGGTGGAG    6400

CTGGGCGGGG GCCCTGGTGC AGGCAGCCTG CAGCCCTTGG CCCTGGAGGG    6450

GTCCCTGCAG AAGCGTGGCA TTGTGGAACA ATGCTGTACC AGCATCTGCT    6500

CCCTCTACCA GCTGGAGAAC TACTGCAACT AGGGCGCCTG GATCCAGATC    6550

ACTTCTGGCT AATAAAAGAT CAGAGCTCTA GAGATCTGTG TGTTGGTTTT    6600

TTGTGGATCT GCTGTGCCTT CTAGTTGCCA GCCATCTGTT GTTTGCCCCT    6650

CCCCCGTGCC TTCCTTGACC CTGGAAGGTG CCACTCCCAC TGTCCTTTCC    6700

TAATAAAATG AGGAAATTGC ATCGCATTGT CTGAGTAGGT GTCATTCTAT    6750

TCTGGGGGGT GGGGTGGGGC AGCACAGCAA GGGGGAGGAT TGGGAAGACA    6800

ATAGCAGGCA TGCTGGGGAT GCGGTGGGCT CTATGGGTAC CTCTCTCTCT    6850

CTCTCTCTCT CTCTCTCTCT CTCTCTCTCT CGGTACCTCT CTCGAGGGGG    6900

GGCCCGGTAC CCAATTCGCC CTATAGTGAG TCGTATTACG CGCGCTCACT    6950

GGCCGTCGTT TTACAACGTC GTGACTGGGA AAACCCTGGC GTTACCCAAC    7000

TTAATCGCCT TGCAGCACAT CCCCCTTTCG CCAGCTGGCG TAATAGCGAA    7050

GAGGCCCGCA CCGATCGCCC TTCCCAACAG TTGCGCAGCC TGAATGGCGA    7100

ATGGAAATTG TAAGCGTTAA TATTTTGTTA AAATTCGCGT TAAATTTTTG    7150

TTAAATCAGC TCATTTTTTA ACCAATAGGC CGAAATCGGC AAAATCCCTT    7200

ATAAATCAAA AGAATAGACC GAGATAGGGT TGAGTGTTGT TCCAGTTTGG    7250

AACAAGAGTC CACTATTAAA GAACGTGGAC TCCAACGTCA AAGGGCGAAA    7300

AACCGTCTAT CAGGGCGATG GCCCACTACT CCGGGATCAT ATGACAAGAT    7350

GTGTATCCAC CTTAACTTAA TGATTTTTAC CAAAATCATT AGGGGATTCA    7400

TCAGTGCTCA GGGTCAACGA GAATTAACAT TCCGTCAGGA AAGCTTATGA    7450

TGATGATGTG CTTAAAAACT TACTCAATGG CTGGTTATGC ATATCGCAAT    7500

ACATGCGAAA AACCTAAAAG AGCTTGCCGA TAAAAAGGC CAATTTATTG    7550

CTATTTACCG CGGCTTTTTA TTGAGCTTGA AAGATAAATA AAATAGATAG    7600

GTTTTATTTG AAGCTAAATC TTCTTTATCG TAAAAAATG CCTCTTGGGT    7650

TATCAAGAGG GTCATTATAT TTCGCGGAAT AACATCATTT GGTGACGAAA    7700

TAACTAAGCA CTTGTCTCCT GTTTACTCCC CTGAGCTTGA GGGGTAACA    7750

TGAAGGTCAT CGATAGCAGG ATAATAATAC AGTAAAACGC TAAACCAATA    7800

ATCCAAATCC AGCCATCCCA AATTGGTAGT GAATGATTAT AAATAACAGC    7850

AAACAGTAAT GGGCCAATAA CACCGGTTGC ATTGGTAAGG CTCACCAATA    7900

ATCCCTGTAA AGCACCTTGC TGATGACTCT TTGTTTGGAT AGACATCACT    7950

CCCTGTAATG CAGGTAAAGC GATCCCACCA CCAGCCAATA AAATTAAAAC    8000

AGGGAAAACT AACCAACCTT CAGATATAAA CGCTAAAAAG GCAAATGCAC    8050

TACTATCTGC AATAAATCCG AGCAGTACTG CCGTTTTTTC GCCCCATTTA    8100

GTGGCTATTC TTCCTGCCAC AAAGGCTTGG AATACTGAGT GTAAAAGACC    8150

AAGACCCGCT AATGAAAGC CAACCATCAT GCTATTCCAT CCAAAACGAT    8200
```

```
TTTCGGTAAA TAGCACCCAC ACCGTTGCGG GAATTTGGCC TATCAATTGC 8250

GCTGAAAAAT AAATAATCAA CAAAATGGCA TCGTTTTAAA TAAAGTGATG 8300

TATACCGAAT TCAGCTTTTG TTCCCTTTAG TGAGGGTTAA TTGCGCGCTT 8350

GGCGTAATCA TGGTCATAGC TGTTTCCTGT GTGAAATTGT TATCCGCTCA 8400

CAATTCCACA CAACATACGA GCCGGAAGCA TAAAGTGTAA AGCCTGGGGT 8450

GCCTAATGAG TGAGCTAACT CACATTAATT GCGTTGCGCT CACTGCCCGC 8500

TTTCCAGTCG GGAAACCTGT CGTGCCAGCT GCATTAATGA ATCGGCCAAC 8550

GCGCGGGGAG AGGCGGTTTG CGTATTGGGC GCTCTTCCGC TTCCTCGCTC 8600

ACTGACTCGC TGCGCTCGGT CGTTCGGCTG CGGCGAGCGG TATCAGCTCA 8650

CTCAAAGGCG GTAATACGGT TATCCACAGA ATCAGGGGAT AACGCAGGAA 8700

AGAACATGTG AGCAAAAGGC CAGCAAAAGG CCAGGAACCG TAAAAAGGCC 8750

GCGTTGCTGG CGTTTTTCCA TAGGCTCCGC CCCCCTGACG AGCATCACAA 8800

AAATCGACGC TCAAGTCAGA GGTGGCGAAA CCCGACAGGA CTATAAAGAT 8850

ACCAGGCGTT TCCCCCTGGA AGCTCCCTCG TGCGCTCTCC TGTTCCGACC 8900

CTGCCGCTTA CCGGATACCT GTCCGCCTTT CTCCCTTCGG GAAGCGTGGC 8950

GCTTTCTCAT AGCTCACGCT GTAGGTATCT CAGTTCGGTG TAGGTCGTTC 9000

GCTCCAAGCT GGGCTGTGTG CACGAACCCC CCGTTCAGCC CGACCGCTGC 9050

GCCTTATCCG GTAACTATCG TCTTGAGTCC AACCCGGTAA GACACGACTT 9100

ATCGCCACTG GCAGCAGCCA CTGGTAACAG GATTAGCAGA GCGAGGTATG 9150

TAGGCGGTGC TACAGAGTTC TTGAAGTGGT GGCCTAACTA CGGCTACACT 9200

AGAAGGACAG TATTTGGTAT CTGCGCTCTG CTGAAGCCAG TTACCTTCGG 9250

AAAAAGAGTT GGTAGCTCTT GATCCGGCAA ACAAACCACC GCTGGTAGCG 9300

GTGGTTTTTT TGTTTGCAAG CAGCAGATTA CGCGCAGAAA AAAAGGATCT 9350

CAAGAAGATC CTTTGATCTT TTCTACGGGG TCTGACGCTC AGTGGAACGA 9400

AAACTCACGT TAAGGGATTT TGGTCATGAG ATTATCAAAA AGGATCTTCA 9450

CCTAGATCCT TTTAAATTAA AAATGAAGTT TTAAATCAAT CTAAAGTATA 9500

TATGAGTAAA CTTGGTCTGA CAGTTACCAA TGCTTAATCA GTGAGGCACC 9550

TATCTCAGCG ATCTGTCTAT TTCGTTCATC CATAGTTGCC TGACTCCCCG 9600

TCGTGTAGAT AACTACGATA CGGGAGGGCT TACCATCTGG CCCCAGTGCT 9650

GCAATGATAC CGCGAGACCC ACGCTCACCG GCTCCAGATT TATCAGCAAT 9700

AAACCAGCCA GCCGGAAGGG CCGAGCGCAG AAGTGGTCCT GCAACTTTAT 9750

CCGCCTCCAT CCAGTCTATT AATTGTTGCC GGGAAGCTAG AGTAAGTAGT 9800

TCGCCAGTTA ATAGTTTGCG CAACGTTGTT GCCATTGCTA CAGGCATCGT 9850

GGTGTCACGC TCGTCGTTTG GTATGGCTTC ATTCAGCTCC GGTTCCCAAC 9900

GATCAAGGCG AGTTACATGA TCCCCCATGT TGTGCAAAAA AGCGGTTAGC 9950

TCCTTCGGTC CTCCGATCGT TGTCAGAAGT AAGTTGGCCG CAGTGTTATC 10000

ACTCATGGTT ATGGCAGCAC TGCATAATTC TCTTACTGTC ATGCCATCCG 10050

TAAGATGCTT TTCTGTGACT GGTGAGTACT CAACCAAGTC ATTCTGAGAA 10100

TAGTGTATGC GGCGACCGAG TTGCTCTTGC CCGGCGTCAA TACGGGATAA 10150

TACCGCGCCA CATAGCAGAA CTTTAAAAGT GCTCATCATT GGAAAACGTT 10200

CTTCGGGGCG AAAACTCTCA AGGATCTTAC CGCTGTTGAG ATCCAGTTCG 10250
```

```
ATGTAACCCA CTCGTGCACC CAACTGATCT TCAGCATCTT TTACTTTCAC    10300
CAGCGTTTCT GGGTGAGCAA AACAGGAAG  GCAAATGCC  GCAAAAAAGG    10350
GAATAAGGGC GACACGGAAA TGTTGAATAC TCATACTCTT CCTTTTTCAA    10400
TATTATTGAA GCATTTATCA GGGTTATTGT CTCATGAGCG GATACATATT    10450
TGAATGTATT TAGAAAAATA AACAAATAGG GGTTCCGCGC ACATTTCCCC    10500
GAAAAGTGCC AC                                            10512
```

SEQ ID NO: 43 (pTnMOD (CMV-CHOVg-ent-ProInsulin-synPA))

```
   1 ctgacgcgcc ctgtagcggc gcattaagcg cggcgggtgt ggtggttacg cgcagcgtga
  61 ccgctacact tgccagcgcc ctagcgcccg ctcctttcgc tttcttccct tcctttctcg
 121 ccacgttcgc cggcatcaga ttggctattg gccattgcat acgttgtatc catatcataa
 181 tatgtacatt tatattggct catgtccaac attaccgcca tgttgacatt gattattgac
 241 tagttattaa tagtaatcaa ttacggggtc attagttcat agcccatata tggagttccg
 301 cgttacataa cttacggtaa atggcccgcc tggctgaccg cccaacgacc cccgcccatt
 361 gacgtcaata atgacgtatg ttcccatagt aacgccaata gggactttcc attgacgtca
 421 atgggtggag tatttacggt aaactgccca cttggcagta catcaagtgt atcatatgcc
 481 aagtacgccc cctattgacg tcaatgacgg taaatggccc gcctggcatt atgcccagta
 541 catgacctta tgggactttc ctacttggca gtacatctac gtattagtca tcgctattac
 601 catggtgatg cggttttggc agtacatcaa tgggcgtgga tagcggtttg actcacgggg
 661 atttccaagt ctccacccca ttgacgtcaa tgggagtttg ttttggcacc aaaatcaacg
 721 ggactttcca aaatgtcgta acaactccgc cccattgacg caaatgggcg gtaggcgtgt
 781 acggtgggag gtctatataa gcagagctcg tttagtgaac cgtcagatcc cctggagacg
 841 ccatccacgc tgttttgacc tccatagaag acaccgggac cgatccagcc tccgcggccg
 901 ggaacggtgc attggaacgc ggattccccg tgccaagagt gacgtaagta ccgcctatag
 961 actctatagg cacccccttt ggctcttat gcatgctata ctgttttgg cttggggcct
1021 atacaccccc gcttccttat gctataggtg atggtatagc ttagcctata ggtgtgggtt
1081 attgaccatt attgaccact cccctattgg tgacgatact tccattact aatccataac
1141 atggctcttt gccacaacta tctctattgg ctatatgcca atactctgtc cttcagagac
1201 tgacacggac tctgtatttt tacaggatgg ggtcccattt attatttaca aattcacata
1261 tacaacaacg ccgtcccccg tgcccgcagt tttattaaa catagcgtgg gatctccacg
1321 cgaatctcgg gtacgtgttc cggacatggg ctcttctccg gtagcggcgg agcttccaca
1381 tccgagccct ggtcccatgc ctccagcggc tcatggtcgc tcggcagctc cttgctccta
1441 acagtggagg ccagacttag gcacagcaca atgcccacca ccaccagtgt gccgcacaag
1501 gccgtggcgg tagggtatgt gtctgaaaat gagcgtggag attgggctcg cacggctgac
1561 gcagatggaa gacttaaggc agcggcagaa gaagatgcag gcagctgagt tgttgtattc
1621 tgataagagt cagaggtaac tcccgttgcg gtgctgttaa cggtggaggg cagtgtagtc
1681 tgagcagtac tcgttgctgc cgcgcgcgcc accagacata atagctgaca gactaacaga
1741 ctgttccttt ccatgggtct tttctgcagt caccgtcgga ccatgtgtga acttgatatt
1801 ttacatgatt ctcttacca attctgcccc gaattacact aaaacgact caacagctta
1861 acgttggctt gccacgcatt acttgactgt aaaactctca ctcttaccga acttggccgt
1921 aacctgccaa ccaaagcgag aacaaaacat aacatcaaac gaatcgaccg attgttaggt
1981 aatcgtcacc tccacaaaga gcgactcgct gtataccgtt ggcatgctag ctttatctgt
```

```
2041  tcgggcaata cgatgcccat tgtacttgtt gactggtctg atattcgtga gcaaaaacga
2101  cttatggtat tgcgagcttc agtcgcacta cacggtcgtt ctgttactct ttatgagaaa
2161  gcgttcccgc tttcagagca atgttcaaag aaagctcatg accaatttct agccgacctt
2221  gcgagcattc taccgagtaa caccacaccg ctcattgtca gtgatgctgg ctttaaagtg
2281  ccatggtata atccgttgaa gaagctgggt tggtactggt taagtcgagt aagaggaaaa
2341  gtacaatatg cagacctagg agcggaaaac tggaaaccta tcagcaactt acatgatatg
2401  tcatctagtc actcaaagac tttaggctat aagaggctga ctaaaagcaa tccaatctca
2461  tgccaaattc tattgtataa atctcgctct aaaggccgaa aaaatcagcg ctcgacacgg
2521  actcattgtc accacccgtc acctaaaatc tactcagcgt cggcaaagga gccatgggtt
2581  ctagcaacta acttacctgt tgaaattcga acacccaaac aacttgttaa tatctattcg
2641  aagcgaatgc agattgaaga aaccttccga gacttgaaaa gtcctgccta cggactaggc
2701  ctacgccata gccgaacgag cagctcagag cgttttgata tcatgctgct aatcgccctg
2761  atgcttcaac taacatgttg gcttgcgggc gttcatgctc agaaacaagg ttgggacaag
2821  cacttccagg ctaacacagt cagaaatcga aacgtactct caacagttcg cttaggcatg
2881  gaagttttgc ggcattctgg ctacacaata caagggaag acttactcgt ggctgcaacc
2941  ctactagctc aaaatttatt cacacatggt tacgctttgg ggaaattatg ataatgatcc
3001  agatcacttc tggctaataa aagatcagag ctctagagat ctgtgtgttg gttttttgtg
3061  gatctgctgt gccttctagt tgccagccat ctgttgtttg cccctcccc gtgccttcct
3121  tgaccctgga aggtgccact cccactgtcc tttcctaata aaatgaggaa attgcatcgc
3181  attgtctgag taggtgtcat tctattctgg ggggtggggt ggggcagcac agcaaggggg
3241  aggattggga agacaatagc aggcatgctg gggatgcggt gggctctatg ggtacctctc
3301  tctctctctc tctctctctc tctctctctc tctctcggta cctctctctc tctctctctc
3361  tctctctctc tctctctctc tcggtaccag gtgctgaaga attgacccgg tgaccaaagg
3421  tgcctttat catcacttta aaaataaaaa acaattactc agtgcctgtt ataagcagca
3481  attaattatg attgatgcct acatcacaac aaaaactgat ttaacaaatg gttggtctgc
3541  cttagaaagt atatttgaac attatcttga ttatattatt gataataata aaaaccttat
3601  ccctatccaa gaagtgatgc ctatcattgg ttggaatgaa cttgaaaaaa attagccttg
3661  aatacattac tggtaaggta aacgccattg tcagcaaatt gatccaagag aaccaactta
3721  aagcttttcct gacggaatgt taattctcgt tgaccctgag cactgatgaa tcccctaatg
3781  attttggtaa aaatcattaa gttaaggtgg atacacatct tgtcatatga tcccggtaat
3841  gtgagttagc tcactcatta ggcaccccag gctttacact ttatgcttcc ggctcgtatg
3901  ttgtgtggaa ttgtgagcgg ataacaattt cacacaggaa acagctatga ccatgattac
3961  gccaagcgcg caattaaccc tcactaaagg gaacaaaagc tggagctcca ccgcggtggc
4021  ggccgctcta gaactagtgg atccccgggg catcagattg gctattggcc attgcatacg
4081  ttgtatccat atcataatat gtacatttat attggctcat gtccaacatt accgccatgt
4141  tgacattgat tattgactag ttattaatag taatcaatta cggggtcatt agttcatagc
4201  ccatatatgg agttccgcgt tacataactt acggtaaatg gcccgcctgg ctgaccgccc
4261  aacgaccccc gcccattgac gtcaataatg acgtatgttc ccatagtaac gccaataggg
4321  actttccatt gacgtcaatg ggtggagtat ttacggtaaa ctgcccactt ggcagtacat
4381  caagtgtatc atatgccaag tacgccccct attgacgtca atgacggtaa atggcccgcc
```

-continued

```
4441 tggcattatg cccagtacat gaccttatgg gactttccta cttggcagta catctacgta 4501 ttagtcatcg ctattaccat ggtgatgcgg ttttggcagt acatcaatgg gcgtggatag 4561 cggtttgact cacggggatt ccaagtctc caccccattg acgtcaatgg gagtttgttt 4621 tggcaccaaa atcaacggga ctttccaaaa tgtcgtaaca actccgcccc attgacgcaa 4681 atgggcggta ggcgtgtacg gtgggaggtc tatataagca gagctcgttt agtgaaccgt 4741 cagatcgcct ggagacgcca tccacgctgt tttgacctcc atagaagaca ccgggaccga 4801 tccagcctcc gcggccggga acggtgcatt ggaacgcgga ttccccgtgc caagagtgac 4861 gtaagtaccg cctatagact ctataggcac acccctttgg ctcttatgca tgctatactg 4921 tttttggctt ggggcctata cacccccgct tccttatgct ataggtgatg gtatagctta 4981 gcctataggt gtgggttatt gaccattatt gaccactccc tattggtga cgatactttc 5041 cattactaat ccataacatg gctctttgcc acaactatct ctattggcta tatgccaata 5101 ctctgtcctt cagagactga cacggactct gtattttac aggatggggt cccatttatt 5161 atttacaaat tcacatatac aacaacgccg tcccccgtgc ccgcagtttt tattaaacat 5221 agcgtgggat ctccacgcga atctcgggta cgtgttccgg acatgggctc ttctccggta 5281 gcggcggagc ttccacatcc gagccctggt cccatgcctc cagcggctca tggtcgctcg 5341 gcagctcctt gctcctaaca gtggaggcca gacttaggca cagcacaatg cccaccacca 5401 ccagtgtgcc gcacaaggcc gtggcggtag ggtatgtgtc tgaaaatgag cgtggagatt 5461 gggctcgcac ggctgacgca gatggaagac ttaaggcagc ggcagaagaa gatgcaggca 5521 gctgagttgt tgtattctga taagagtcag aggtaactcc cgttgcggtg ctgttaacgg 5581 tggagggcag tgtagtctga gcagtactcg ttgctgccgc gcgcgccacc agacataata 5641 gctgacagac taacagactg ttcctttcca tgggtctttt ctgcagtcac cgtcggatca 5701 atgggctcca tcggtgcagc aagcatggaa ttttgttttg atgtattcaa ggagctcaaa 5761 gtccaccatg ccaatgagaa catcttctac tgccccattg ccatcatgtc agctctagcc 5821 atggtatacc tgggtgcaaa agacagcacc aggacacaaa taataaggt tgttcgcttt 5881 gataaacttc caggattcgg agacagtatt gaagctcagt gtggcacatc tgtaaacgtt 5941 cactcttcac ttagagacat cctcaaccaa atcaccaaac caaatgatgt ttattcgttc 6001 agccttgcca gtagacttta tgctgaagag agatacccaa tcctgccaga atacttgcag 6061 tgtgtgaagg aactgtatag aggaggcttg gaacctatca actttcaaac agctgcagat 6121 caagccagag agctcatcaa ttcctgggta gaaagtcaga caaatggaat tatcagaaat 6181 gtccttcagc caagctccgt ggattctcaa actgcaatgg ttctggttaa tgccattgtc 6241 ttcaaaggac tgtgggagaa agcatttaag gatgaagaca cacaagcaat gcctttcaga 6301 gtgactgagc aagaaagcaa acctgtgcag atgatgtacc agattggttt atttagagtg 6361 gcatcaatgg cttctgagaa aatgaagatc ctggagcttc catttgccag tgggacaatg 6421 agcatgttgg tgctgttgcc tgatgaagtc tcaggccttg agcagcttga gagtataatc 6481 aactttgaaa aactgactga atggaccagt tctaatgtta tggaagagaa aagatcaaag 6541 tgtacttacc tcgcatgaag atggaggaaa aatacaacct cacatctgtc ttaatggcta 6601 tgggcattac tgacgtgttt agctcttcag ccaatctgtc tggcatctcc tcagcagaga 6661 gcctgaagat atctcaagct gtccatgcag cacatgcaga atcaatgaa gcaggcagag 6721 aggtggtagg gtcagcagag gctggagtgg atgctgcaag cgtctctgaa gaatttaggg 6781 ctgaccatcc attcctcttc tgtatcaagc acatcgcaac caacgccgtt ctcttctttt 6841 ggcagatgtg tttcccgcgg ccagcagatg acgcaccagc agatgacgca ccagcagatg
```

-continued

```
6901 acgcaccagc agatgacgca ccagcagatg acgcaacaac atgtatcctg aaaggctctt
6961 gtggctggat cggcctgctg gatgacgatg acaaatttgt gaaccaacac ctgtgcggct
7021 cacacctggt ggaagctctc tacctagtgt gcggggaacg aggcttcttc tacacaccca
7081 agacccgccg ggaggcagag gacctgcagg tggggcaggt ggagctgggc gggggccctg
7141 gtgcaggcag cctgcagccc ttggccctgg aggggtccct gcagaagcgt ggcattgtgg
7201 aacaatgctg taccagcatc tgctccctct accagctgga gaactactgc aactagggcg
7261 cctaaagggc gaattatcgc ggccgctcta gaccaggcgc ctggatccag atcacttctg
7321 gctaataaaa gatcagagct ctagagatct gtgtgttggt ttttgtgga tctgctgtgc
7381 cttctagttg ccagccatct gttgtttgcc cctcccccgt gccttccttg accctggaag
7441 gtgccactcc cactgtcctt tcctaataaa atgaggaaat tgcatcgcat tgtctgagta
7501 ggtgtcattc tattctgggg gtgggtgg ggcagcacag caaggggag gattgggaag
7561 acaatagcag gcatgctggg gatgcggtgg gctctatggg tacctctctc tctctctctc
7621 tctctctcac tctctctctc tctcggtacc tctcctcgag ggggggcccg gtacccaatt
7681 cgccctatag tgagtcgtat tacgcgcgct cactggccgt cgttttacaa cgtcgtgact
7741 gggaaaaccc tggcgttacc caacttaatc gccttgcagc acatccccct ttcgccagct
7801 ggcgtaatag cgaagaggcc cgcaccgatc gcccttccca acagttgcgc agcctgaatg
7861 gcgaatggaa attgtaagcg ttaatatttt gttaaaattc gcgttaaatt tttgttaaat
7921 cagctcattt tttaaccaat aggccgaaat cggcaaaatc ccttataaat caaagaata
7981 gaccgagata gggttgagtg ttgttccagt ttggaacaag agtccactat taaagaacgt
8041 ggactccaac gtcaaggggc gaaaaaccgt ctatcagggc gatggcccac tactccggga
8101 tcatatgaca agatgtgtat ccaccttaac ttaatgattt ttaccaaaat cattagggga
8161 ttcatcagtg ctcagggtca acgagaatta acattccgtc aggaaagctt atgatgatga
8221 tgtgcttaaa aacttactca atggctggtt atgcatatcg caatacatgc gaaaaaccta
8281 aaagagcttg ccgataaaaa aggccaattt attgctattt accgcgcgctt tttattgagc
8341 ttgaaagata aataaaatag ataggtttta tttgaagcta aatcttcttt atcgtaaaaa
8401 atgccctctt gggttatcaa gagggtcatt atatttcgcg gaataacatc atttggtgac
8461 gaaataacta agcacttgtc tcctgtttac tcccctgagc ttgaggggt aacatgaagg
8521 tcatcgatag caggataata atacagtaaa acgctaaacc aataatccaa atccagccat
8581 cccaaattgg tagtgaatga ttataaataa cagcaaacag taatgggcca ataacaccgg
8641 ttgcattggt aaggctcacc aataatccct gtaaagcacc ttgctgatga ctctttgttt
8701 ggatagacat cactccctgt aatgcaggta aagcgatccc accaccagcc aataaaatta
8761 aaacagggaa aactaaccaa ccttcagata taaacgctaa aaaggcaaat gcactactat
8821 ctgcaataaa tccgagcagt actgccgttt tttcgcccat ttagtggcta ttcttcctgc
8881 cacaaaggct tggaatactg agtgtaaaag accaagaccc gtaatgaaaa gccaaccatc
8941 atgctattca tcatcacgat ttctgtaata gcaccacacc gtgctggatt ggctatcaat
9001 gcgctgaaat aataatcaac aaatggcatc gttaaataag tgatgtatac cgatcagctt
9061 ttgttccctt tagtgagggt taattgcgcg cttggcgtaa tcatggtcat agctgtttcc
9121 tgtgtgaaat tgttatccgc tcacaattcc acacaacata cgagccggaa gcataaagtg
9181 taaagcctgg ggtgcctaat gagtgagcta actcacatta attgcgttgc gctcactgcc
9241 cgctttccag tcgggaaacc tgtcgtgcca gctgcattaa tgaatcggcc aacgcgcggg
```

```
9301 gagaggcggt ttgcgtattg ggcgctcttc cgcttcctcg ctcactgact cgctgcgctc 9361 ggtcgttcgg ctgcggcgag cggtatcagc tcactcaaag gcggtaatac ggttatccac 9421 agaatcaggg gataacgcag gaaagaacat gtgagcaaaa ggccagcaaa aggccaggaa 9481 ccgtaaaaag gccgcgttgc tggcgttttt ccataggctc cgcccccctg acgagcatca 9541 caaaaatcga cgctcaagtc agaggtggcg aaacccgaca ggactataaa gataccaggc 9601 gtttccccct ggaagctccc tcgtgcgctc tcctgttccg accctgccgc ttaccggata 9661 cctgtccgcc tttctccctt cgggaagcgt ggcgctttct catagctcac gctgtaggta 9721 tctcagttcg gtgtaggtcg ttcgctccaa gctgggctgt gtgcacgaac cccccgttca 9781 gcccgaccgc tgcgccttat ccggtaacta tcgtcttgag tccaacccgg taagacacga 9841 cttatcgcca ctggcagcag ccactggtaa caggattagc agagcgaggt atgtaggcgg 9901 tgctacagag ttcttgaagt ggtggcctaa ctacggctac actagaagga cagtatttgg 9961 tatctgcgct ctgctgaagc cagttacctt cggaaaaaga gttggtagct cttgatccgg 10021 caaacaaacc accgctggta gcggtggttt ttttgtttgc aagcagcaga ttacgcgcag 10081 aaaaaaagga tctcaagaag atcctttgat cttttctacg gggtctgacg ctcagtggaa 10141 cgaaaactca cgttaaggga ttttggtcat gagattatca aaaaggatct tcacctagat 10201 ccttttaaat taaaaatgaa gttttaaatc aatctaaagt atatatgagt aaacttggtc 10261 tgacagttac caatgcttaa tcagtgaggc acctatctca gcgatctgtc tatttcgttc 10321 atccatagtt gcctgactcc ccgtcgtgta gataactacg atacgggagg gcttaccatc 10381 tggccccagt gctgcaatga taccgcgaga cccacgctca ccggctccag atttatcagc 10441 aataaaccag ccagccggaa gggccgagcg cagaagtggt cctgcaactt tatccgcctc 10501 catccagtct attaattgtt gccgggaagc tagagtaagt agttcgccag ttaatagttt 10561 gcgcaacgtt gttgccattg ctacaggcat cgtggtgtca cgctcgtcgt ttggtatggc 10621 ttcattcagc tccggttccc aacgatcaag gcgagttaca tgatcccccca tgttgtgcaa 10681 aaaagcggtt agctccttcg gtcctccgat cgttgtcaga agtaagttgg ccgcagtgtt 10741 atcactcatg gttatggcag cactgcataa ttctcttact gtcatgccat ccgtaagatg 10801 cttttctgtg actggtgagt actcaaccaa gtcattctga atagtgta tgcggcgacc 10861 gagttgctct tgcccggcgt caatacggga taataccgcg ccacatagca gaactttaaa 10921 agtgctcatc attggaaaac gttcttcggg gcgaaaactc tcaaggatct taccgctgtt 10981 gagatccagt tcgatgtaac ccactcgtgc acccaactga tcttcagcat cttttacttt 11041 caccagcgtt tctgggtgag caaaaacagg aaggcaaaat gccgcaaaaa agggaataag 11101 ggcgacacgg aaatgttgaa tactcatact cttcctttt caatattatt gaagcattta 11161 tcagggttat tgtctcatga gcggatacat atttgaatgt atttagaaaa ataaacaaat 11221 aggggttccg cgcacatttc cccgaaaagt gccac
```

SEQ ID NO: 44 (pTnMod (Oval/ENT tag/Proins/PA) - QUAIL)
```
CTGACGCGCC CTGTAGCGGC GCATTAAGCG CGGCGGGTGT GGTGGTTACG     50

CGCAGCGTGA CCGCTACACT TGCCAGCGCC CTAGCGCCCG CTCCTTTCGC    100

TTTCTTCCCT TCCTTTCTCG CCACGTTCGC CGGCATCAGA TTGGCTATTG    150

GCCATTGCAT ACGTTGTATC CATATCATAA TATGTACATT TATATTGGCT    200

CATGTCCAAC ATTACCGCCA TGTTGACATT GATTATTGAC TAGTTATTAA    250

TAGTAATCAA TTACGGGGTC ATTAGTTCAT AGCCCATATA TGGAGTTCCG    300

CGTTACATAA CTTACGGTAA ATGGCCCGCC TGGCTGACCG CCCAACGACC    350
```

```
CCCGCCCATT GACGTCAATA ATGACGTATG TTCCCATAGT AACGCCAATA    400
GGGACTTTCC ATTGACGTCA ATGGGTGGAG TATTTACGGT AAACTGCCCA    450
CTTGGCAGTA CATCAAGTGT ATCATATGCC AAGTACGCCC CCTATTGACG    500
TCAATGACGG TAAATGGCCC GCCTGGCATT ATGCCCAGTA CATGACCTTA    550
TGGGACTTTC CTACTTGGCA GTACATCTAC GTATTAGTCA TCGCTATTAC    600
CATGGTGATG CGGTTTTGGC AGTACATCAA TGGGCGTGGA TAGCGGTTTG    650
ACTCACGGGG ATTTCCAAGT CTCCACCCCA TTGACGTCAA TGGGAGTTTG    700
TTTTGGCACC AAAATCAACG GGACTTTCCA AAATGTCGTA ACAACTCCGC    750
CCCATTGACG CAAATGGGCG GTAGGCGTGT ACGGTGGGAG GTCTATATAA    800
GCAGAGCTCG TTTAGTGAAC CGTCAGATCG CCTGGAGACG CCATCCACGC    850
TGTTTTGACC TCCATAGAAG ACACCGGGAC CGATCCAGCC TCCGCGGCCG    900
GGAACGGTGC ATTGGAACGC GGATTCCCCG TGCCAAGAGT GACGTAAGTA    950
CCGCCTATAG ACTCTATAGG CACACCCCTT TGGCTCTTAT GCATGCTATA   1000
CTGTTTTTGG CTTGGGGCCT ATACACCCCC GCTTCCTTAT GCTATAGGTG   1050
ATGGTATAGC TTAGCCTATA GGTGTGGGTT ATTGACCATT ATTGACCACT   1100
CCCCTATTGG TGACGATACT TTCCATTACT AATCCATAAC ATGGCTCTTT   1150
GCCACAACTA TCTCTATTGG CTATATGCCA ATACTCTGTC CTTCAGAGAC   1200
TGACACGGAC TCTGTATTTT TACAGGATGG GGTCCCATTT ATTATTTACA   1250
AATTCACATA TACAACAACG CCGTCCCCCG TGCCCGCAGT TTTTATTAAA   1300
CATAGCGTGG GATCTCCACG CGAATCTCGG GTACGTGTTC CGGACATGGG   1350
CTCTTCTCCG GTAGCGGCGG AGCTTCCACA TCCGAGCCCT GGTCCCATGC   1400
CTCCAGCGGC TCATGGTCGC TCGGCAGCTC CTTGCTCCTA ACAGTGGAGG   1450
CCAGACTTAG GCACAGCACA ATGCCCACCA CCACCAGTGT GCCGCACAAG   1500
GCCGTGGCGG TAGGGTATGT GTCTGAAAAT GAGCGTGGAG ATTGGGCTCG   1550
CACGGCTGAC GCAGATGGAA GACTTAAGGC AGCGGCAGAA GAAGATGCAG   1600
GCAGCTGAGT TGTTGTATTC TGATAAGAGT CAGAGGTAAC TCCCGTTGCG   1650
GTGCTGTTAA CGGTGGAGGG CAGTGTAGTC TGAGCAGTAC TCGTTGCTGC   1700
CGCGCGCGCC ACCAGACATA ATAGCTGACA GACTAACAGA CTGTTCCTTT   1750
CCATGGGTCT TTTCTGCAGT CACCGTCGGA CCATGTGTGA ACTTGATATT   1800
TTACATGATT CTCTTTACCA ATTCTGCCCC GAATTACACT TAAAACGACT   1850
CAACAGCTTA ACGTTGGCTT GCCACGCATT ACTTGACTGT AAAACTCTCA   1900
CTCTTACCGA ACTTGGCCGT AACCTGCCAA CCAAAGCGAG AACAAAACAT   1950
AACATCAAAC GAATCGACCG ATTGTTAGGT AATCGTCACC TCCACAAAGA   2000
GCGACTCGCT GTATACCGTT GGCATGCTAG CTTTATCTGT TCGGGAATAC   2050
GATGCCCATT GTACTTGTTG ACTGGTCTGA TATTCGTGAG CAAAAACGAC   2100
TTATGGTATT GCGAGCTTCA GTCGCACTAC ACGGTCGTTC TGTTACTCTT   2150
TATGAGAAAG CGTTCCCGCT TTCAGAGCAA TGTTCAAAGA AAGCTCATGA   2200
CCAATTTCTA GCCGACCTTG CGAGCATTCT ACCGAGTAAC ACCACACCGC   2250
TCATTGTCAG TGATGCTGGC TTTAAAGTGC CATGGTATAA ATCCGTTGAG   2300
AAGCTGGGTT GGTACTGGTT AAGTCGAGTA AGAGGAAAAG TACAATATGC   2350
AGACCTAGGA GCGGAAAACT GGAAACCTAT CAGCAACTTA CATGGATATGT  2400
```

```
CATCTAGTCA CTCAAAGACT TTAGGCTATA AGAGGCTGAC TAAAAGCAAT    2450

CCAATCTCAT GCCAAATTCT ATTGTATAAA TCTCGCTCTA AAGGCCGAAA    2500

AAATCAGCGC TCGACACGGA CTCATTGTCA CCACCCGTCA CCTAAAATCT    2550

ACTCAGCGTC GGCAAAGGAG CCATGGGTTC TAGCAACTAC CTTACCTGTT    2600

GAAATTCGAA CACCCAAACA ACTTGTTAAT ATCTATTCGA AGCGAATGCA    2650

GATTGAAGAA ACCTTCCGAG ACTTGAAAAG TCCTGCCTAC GGACTAGGCC    2700

TACGCCATAG CCGAACGAGC AGCTCAGAGC GTTTTGATAT CATGCTGCTA    2750

ATCGCCCTGA TGCTTCAACT AACATGTTGG CTTGCGGGCG TTCATGCTCA    2800

GAAACAAGGT TGGGACAAGC ACTTCCAGGC TAACACAGTC AGAAATCGAA    2850

ACGTACTCTC AACAGTTCGC TTAGGCATGG AAGTTTTGCG GCATTCTGGC    2900

TACACAATAA CAAGGGAAGA CTTACTCGTG GCTGCAACCC TACTAGCTCA    2950

AAATTTATTC ACACATGGTT ACGCTTTGGG GAAATTATGA TAATGATCCA    3000

GATCACTTCT GGCTAATAAA AGATCAGAGC TCTAGAGATC TGTGTGTTGG    3050

TTTTTTGTGG ATCTGCTGTG CCTTCTAGTT GCCAGCCATC TGTTGTTTGC    3100

CCCTCCCCCG TGCCTTCCTT GACCCTGGAA GGTGCCACTC CCACTGTCCT    3150

TTCCTAATAA AATGAGGAAA TTGCATCGCA TTGTCTGAGT AGGTGTCATT    3200

CTATTCTGGG GGGTGGGGTG GGGCAGCACA GCAAGGGGGA GGATTGGGAA    3250

GACAATAGCA GGCATGCTGG GGATGCGGTG GGCTCTATGG GTACCTCTCT    3300

CTCTCTCTCT CTCTCTCTCT CTCTCTCTCT CTCTCGGTAC CTCTCTCTCT    3350

CTCTCTCTCT CTCTCTCTCT CTCTCTCTCT CGGTACCAGG TGCTGAAGAA    3400

TTGACCCGGT GACCAAAGGT GCCTTTTATC ATCACTTTAA AAATAAAAAA    3450

CAATTACTCA GTGCCTGTTA TAAGCAGCAA TTAATTATGA TTGATGCCTA    3500

CATCACAACA AAAACTGATT TAACAAATGG TTGGTCTGCC TTAGAAAGTA    3550

TATTTGAACA TTATCTTGAT TATATTATTG ATAATAATAA AAACCTTATC    3600

CCTATCCAAG AAGTGATGCC TATCATTGGT TGGAATGAAC TTGAAAAAAA    3650

TTAGCCTTGA ATACATTACT GGTAAGGTAA ACGCCATTGT CAGCAAATTG    3700

ATCCAAGAGA ACCAACTTAA AGCTTTCCTG ACGGAATGTT AATTCTCGTT    3750

GACCCTGAGC ACTGATGAAT CCCCTAATGA TTTTGGTAAA AATCATTAAG    3800

TTAAGGTGGA TACACATCTT GTCATATGAT CCCGGTAATG TGAGTTAGCT    3850

CACTCATTAG GCACCCCAGG CTTTACACTT TATGCTTCCG GCTCGTATGT    3900

TGTGTGGAAT TGTGAGCGGA TAACAATTTC ACACAGGAAA CAGCTATGAC    3950

CATGATTACG CCAAGCGCGC AATTAACCCT CACTAAAGGG AACAAAAGCT    4000

GGAGCTCCAC CGCGGTGGCG GCCGCTCTAG AACTAGTGGA TCCCCCGGGG    4050

AGGTCAGAAT GGTTTCTTTA CTGTTTGTCA ATTCTATTAT TTCAATACAG    4100

AACAAAAGCT TCTATAACTG AAATATATTT GCTATTGTAT ATTATGATTG    4150

TCCCTCGAAC CATGAACACT CCTCCAGCTG AATTTCACAA TTCCTCTGTC    4200

ATCTGCCAGG CTGGAAGATC ATGGAAGATC TCTGAGGAAC ATTGCAAGTT    4250

CATACCATAA ACTCATTTGG AATTGAGTAT TATTTTGCTT TGAATGGAGC    4300

TATGTTTTGC AGTTCCCTCA GAAGAAAAGC TTGTTATAAA GCGTCTACAC    4350

CCATCAAAAG ATATATTTAA ATATTCCAAC TACAGAAAGA TTTTGTCTGC    4400
```

```
TCTTCACTCT GATCTCAGTT GGTTTCTTCA CGTACATGCT TCTTTATTTG   4450

CCTATTTTGT CAAGAAAATA ATAGGTCAAG TCCTGTTCTC ACTTATCTCC   4500

TGCCTAGCAT GGCTTAGATG CACGTTGTAC ATTCAAGAAG GATCAAATGA   4550

AACAGACTTC TGGTCTGTTA CAACAACCAT AGTAATAAAC AGACTAACTA   4600

ATAATTGCTA ATTATGTTTT CCATCTCTAA GGTTCCCACA TTTTTCTGTT   4650

TTAAGATCCC ATTATCTGGT TGTAACTGAA GCTCAATGGA ACATGAACAG   4700

TATTTCTCAG TCTTTTCTCC AGCAATCCTG ACGGATTAGA AGAACTGGCA   4750

GAAAACACTT TGTTACCCAG AATTAAAAAC TAATATTTGC TCTCCCTTCA   4800

ATCCAAAATG GACCTATTGA AACTAAAATC TGACCCAATC CCATTAAATT   4850

ATTTCTATGG CGTCAAAGGT CAAACTTTTG AAGGGAACCT GTGGGTGGGT   4900

CCCAATTCAG GCTATATATT CCCCAGGGCT CAGCCAGTGG ATCCATGGGC   4950

TCCATCGGTG CAGCAAGCAT GGAATTTTGT TTTGATGTAT TCAAGGAGCT   5000

CAAAGTCCAC CATGCCAATG ACAACATGCT CTACTCCCCC TTTGCCATCT   5050

TGTCAACTCT GGCCATGGTC TTCCTAGGTG CAAAAGACAG CACCAGGACC   5100

CAGATAAATA AGGTTGTTCA CTTTGATAAA CTTCCAGGAT TCGGAGACAG   5150

TATTGAAGCT CAGTGTGGCA CATCTGTAAA TGTTCACTCT TCACTTAGAG   5200

ACATACTCAA CCAAATCACC AAACAAAATG ATGCTTATTC GTTCAGCCTT   5250

GCCAGTAGAC TTTATGCTCA AGAGACATAC ACAGTCGTGC CGGAATACTT   5300

GCAATGTGTG AAGGAACTGT ATAGAGGAGG CTTAGAATCC GTCAACTTTC   5350

AAACAGCTGC AGATCAAGCC AGAGGCCTCA TCAATGCCTG GGTAGAAAGT   5400

CAGACAAACG GAATTATCAG AAACATCCTT CAGCCAAGCT CCGTGGATTC   5450

TCAAACTGCA ATGGTCCTGG TTAATGCCAT TGCCTTCAAG GGACTGTGGG   5500

AGAAAGCATT TAAGGCTGAA GACACGCAAA CAATACCTTT CAGAGTGACT   5550

GAGCAAGAAA GCAAACCTGT GCAGATGATG TACCAGATTG GTTCATTTAA   5600

AGTGGCATCA ATGGCTTCTG AGAAAATGAA GATCCTGGAG CTTCCATTTG   5650

CCAGTGGAAC AATGAGCATG TTGGTGCTGT TGCCTGATGA TGTCTCAGGC   5700

CTTGAGCAGC TTGAGAGTAT AATCAGCTTT GAAAAACTGA CTGAATGGAC   5750

CAGTTCTAGT ATTATGGAAG AGAGGAAGGT CAAAGTGTAC TTACCTCGCA   5800

TGAAGATGGA GGAGAAATAC AACCTCACAT CTCTCTTAAT GGCTATGGGA   5850

ATTACTGACC TGTTCAGCTC TTCAGCCAAT CTGTCTGGCA TCTCCTCAGT   5900

AGGGAGCCTG AAGATATCTC AAGCTGTCCA TGCAGCACAT GCAGAAATCA   5950

ATGAAGCGGG CAGAGATGTG GTAGGCTCAG CAGAGGCTGG AGTGGATGCT   6000

ACTGAAGAAT TTAGGGCTGA CCATCCATTC CTCTTCTGTG TCAAGCACAT   6050

CGAAACCAAC GCCATTCTCC TCTTTGGCAG ATGTGTTTCT CCGCGGCCAG   6100

CAGATGACGC ACCAGCAGAT GACGCACCAG CAGATGACGC ACCAGCAGAT   6150

GACGCACCAG CAGATGACGC ACCAGCAGAT GACGCAACAA CATGTATCCT   6200

GAAAGGCTCT TGTGGCTGGA TCGGCCTGCT GGATGACGAT GACAAATTTG   6250

TGAACCAACA CCTGTGCGGC TCACACCTGG TGGAAGCTCT CTACCTAGTG   6300

TGCGGGGAAC GAGGCTTCTT CTACACACCC AAGACCCGCC GGGAGGCAGA   6350

GGACCTGCAG GTGGGGCAGG TGGAGCTGGG CGGGGGCCCT GGTGCAGGCA   6400

GCCTGCAGCC CTTGGCCCTG GAGGGGTCCC TGCAGAAGCG TGGCATTGTG   6450
```

```
                                       -continued
GAACAATGCT GTACCAGCAT CTGCTCCCTC TACCAGCTGG AGAACTACTG    6500

CAACTAGGGC GCCTGGATCC AGATCACTTC TGGCTAATAA AAGATCAGAG    6550

CTCTAGAGAT CTGTGTGTTG GTTTTTTGTG GATCTGCTGT GCCTTCTAGT    6600

TGCCAGCCAT CTGTTGTTTG CCCCTCCCCC GTGCCTTCCT TGACCCTGGA    6650

AGGTGCCACT CCCACTGTCC TTTCCTAATA AAATGAGGAA ATTGCATCGC    6700

ATTGTCTGAG TAGGTGTCAT TCTATTCTGG GGGGTGGGGT GGGGCAGCAC    6750

AGCAAGGGGG AGGATTGGGA AGACAATAGC AGGCATGCTG GGGATGCGGT    6800

GGGCTCTATG GGTACCTCTC TCTCTCTCTC TCTCTCTCTC TCTCTCTCTC    6850

TCTCTCGGTA CCTCTCTCGA GGGGGGGCCC GGTACCCAAT TCGCCCTATA    6900

GTGAGTCGTA TTACGCGCGC TCACTGGCCG TCGTTTTACA ACGTCGTGAC    6950

TGGGAAAACC CTGGCGTTAC CCAACTTAAT CGCCTTGCAG CACATCCCCC    7000

TTTCGCCAGC TGGCGTAATA GCGAAGAGGC CCGCACCGAT CGCCCTTCCC    7050

AACAGTTGCG CAGCCTGAAT GGCGAATGGA AATTGTAAGC GTTAATATTT    7100

TGTTAAAATT CGCGTTAAAT TTTTGTTAAA TCAGCTCATT TTTTAACCAA    7150

TAGGCCGAAA TCGGCAAAAT CCCTTATAAA TCAAAGAAT AGACCGAGAT    7200

AGGGTTGAGT GTTGTTCCAG TTTGGAACAA GAGTCCACTA TTAAAGAACG    7250

TGGACTCCAA CGTCAAAGGG CGAAAAACCG TCTATCAGGG CGATGGCCCA    7300

CTACTCCGGG ATCATATGAC AAGATGTGTA TCCACCTTAA CTTAATGATT    7350

TTTACCAAAA TCATTAGGGG ATTCATCAGT GCTCAGGGTC AACGAGAATT    7400

AACATTCCGT CAGGAAAGCT TATGATGATG ATGTGCTTAA AAACTTACTC    7450

AATGGCTGGT TATGCATATC GCAATACATG CGAAAAACCT AAAAGAGCTT    7500

GCCGATAAAA AAGGCCAATT TATTGCTATT TACCGCGGCT TTTTATTGAG    7550

CTTGAAAGAT AAATAAAATA GATAGGTTTT ATTTGAAGCT AAATCTTCTT    7600

TATCGTAAAA AATGCCCTCT TGGGTTATCA AGAGGGTCAT TATATTTCGC    7650

GGAATAACAT CATTTGGTGA CGAAATAACT AAGCACTTGT CTCCTGTTTA    7700

CTCCCCTGAG CTTGAGGGGT TAACATGAAG GTCATCGATA GCAGGATAAT    7750

AATACAGTAA AACGCTAAAC CAATAATCCA AATCCAGCCA TCCCAAATTG    7800

GTAGTGAATG ATTATAAATA ACAGCAAACA GTAATGGGCC AATAACACCG    7850

GTTGCATTGG TAAGGCTCAC CAATAATCCC TGTAAAGCAC CTTGCTGATG    7900

ACTCTTTGTT TGGATAGACA TCACTCCCTG TAATGCAGGT AAAGCGATCC    7950

CACCACCAGC CAATAAAATT AAAACAGGGA AAACTAACCA ACCTTCAGAT    8000

ATAAACGCTA AAAGGCAAA TGCACTACTA TCTGCAATAA ATCCGAGCAG    8050

TACTGCCGTT TTTTCGCCCC ATTTAGTGGC TATTCTTCCT GCCACAAAGG    8100

CTTGGAATAC TGAGTGTAAA AGACCAAGAC CCGCTAATGA AAAGCCAACC    8150

ATCATGCTAT TCCATCCAAA ACGATTTTCG GTAAATAGCA CCCACACCGT    8200

TGCGGGAATT TGGCCTATCA ATTGCGCTGA AAAATAAATA ATCAACAAAA    8250

TGGCATCGTT TTAAATAAAG TGATGTATAC CGAATTCAGC TTTTGTTCCC    8300

TTTAGTGAGG GTTAATTGCG CGCTTGGCGT AATCATGGTC ATAGCTGTTT    8350

CCTGTGTGAA ATTGTTATCC GCTCACAATT CCACACAACA TACGAGCCGG    8400

AAGCATAAAG TGTAAAGCCT GGGGTGCCTA ATGAGTGAGC TAACTCACAT    8450
```

-continued

```
TAATTGCGTT GCGCTCACTG CCCGCTTTCC AGTCGGGAAA CCTGTCGTGC   8500

CAGCTGCATT AATGAATCGG CCAACGCGCG GGGAGAGGCG GTTTGCGTAT   8550

TGGGCGCTCT TCCGCTTCCT CGCTCACTGA CTCGCTGCGC TCGGTCGTTC   8600

GGCTGCGGCG AGCGGTATCA GCTCACTCAA AGGCGGTAAT ACGGTTATCC   8650

ACAGAATCAG GGGATAACGC AGGAAAGAAC ATGTGAGCAA AAGGCCAGCA   8700

AAAGGCCAGG AACCGTAAAA AGGCCGCGTT GCTGGCGTTT TTCCATAGGC   8750

TCCGCCCCCC TGACGAGCAT CACAAAAATC GACGCTCAAG TCAGAGGTGG   8800

CGAAACCCGA CAGGACTATA AAGATACCAG GCGTTTCCCC CTGGAAGCTC   8850

CCTCGTGCGC TCTCCTGTTC CGACCCTGCC GCTTACCGGA TACCTGTCCG   8900

CCTTTCTCCC TTCGGGAAGC GTGGCGCTTT CTCATAGCTC ACGCTGTAGG   8950

TATCTCAGTT CGGTGTAGGT CGTTCGCTCC AAGCTGGGCT GTGTGCACGA   9000

ACCCCCCGTT CAGCCCGACC GCTGCGCCTT ATCCGGTAAC TATCGTCTTG   9050

AGTCCAACCC GGTAAGACAC GACTTATCGC CACTGGCAGC AGCCACTGGT   9100

AACAGGATTA GCAGAGCGAG GTATGTAGGC GGTGCTACAG AGTTCTTGAA   9150

GTGGTGGCCT AACTACGGCT ACACTAGAAG GACAGTATTT GGTATCTGCG   9200

CTCTGCTGAA GCCAGTTACC TTCGGAAAAA GAGTTGGTAG CTCTTGATCC   9250

GGCAAACAAA CCACCGCTGG TAGCGGTGGT TTTTTTGTTT GCAAGCAGCA   9300

GATTACGCGC AGAAAAAAAG GATCTCAAGA AGATCCTTTG ATCTTTTCTA   9350

CGGGGTCTGA CGCTCAGTGG AACGAAAACT CACGTTAAGG GATTTTGGTC   9400

ATGAGATTAT CAAAAAGGAT CTTCACCTAG ATCCTTTTAA ATTAAAAATG   9450

AAGTTTTAAA TCAATCTAAA GTATATATGA GTAAACTTGG TCTGACAGTT   9500

ACCAATGCTT AATCAGTGAG GCACCTATCT CAGCGATCTG TCTATTTCGT   9550

TCATCCATAG TTGCCTGACT CCCCGTCGTG TAGATAACTA CGATACGGGA   9600

GGGCTTACCA TCTGGCCCCA GTGCTGCAAT GATACCGCGA GACCCACGCT   9650

CACCGGCTCC AGATTTATCA GCAATAAACC AGCCAGCCGG AAGGGCCGAG   9700

CGCAGAAGTG GTCCTGCAAC TTTATCCGCC TCCATCCAGT CTATTAATTG   9750

TTGCCGGGAA GCTAGAGTAA GTAGTTCGCC AGTTAATAGT TTGCGCAACG   9800

TTGTTGCCAT TGCTACAGGC ATCGTGGTGT CACGCTCGTC GTTTGGTATG   9850

GCTTCATTCA GCTCCGGTTC CCAACGATCA AGGCGAGTTA CATGATCCCC   9900

CATGTTGTGC AAAAAAGCGG TTAGCTCCTT CGGTCCTCCG ATCGTTGTCA   9950

GAAGTAAGTT GGCCGCAGTG TTATCACTCA TGGTTATGGC AGCACTGCAT  10000

AATTCTCTTA CTGTCATGCC ATCCGTAAGA TGCTTTTCTG TGACTGGTGA  10050

GTACTCAACC AAGTCATTCT GAGAATAGTG TATGCGGCGA CCGAGTTGCT  10100

CTTGCCCGGC GTCAATACGG GATAATACCG CGCCACATAG CAGAACTTTA  10150

AAAGTGCTCA TCATTGGAAA ACGTTCTTCG GGGCGAAAAC TCTCAAGGAT  10200

CTTACCGCTG TTGAGATCCA GTTCGATGTA ACCCACTCGT GCACCCAACT  10250

GATCTTCAGC ATCTTTTACT TTCACCAGCG TTTCTGGGTG AGCAAAAACA  10300

GGAAGGCAAA ATGCCGCAAA AAAGGGAATA AGGGCGACAC GGAAATGTTG  10350

AATACTCATA CTCTTCCTTT TTCAATATTA TTGAAGCATT TATCAGGGTT  10400

ATTGTCTCAT GAGCGGATAC ATATTTGAAT GTATTTAGAA AAATAAACAA  10450

TAGGGGTTC CGCGCACATT TCCCCGAAAA GTGCCAC                10487
```

SEQ ID NO: 45 (pTnMod (Oval/ENT tag/P146/PA) - Chicken)
```
CTGACGCGCC CTGTAGCGGC GCATTAAGCG CGGCGGGTGT GGTGGTTACG    50
CGCAGCGTGA CCGCTACACT TGCCAGCGCC CTAGCGCCCG CTCCTTTCGC   100
TTTCTTCCCT TCCTTTCTCG CCACGTTCGC CGGCATCAGA TTGGCTATTG   150
GCCATTGCAT ACGTTGTATC CATATCATAA TATGTACATT TATATTGGCT   200
CATGTCCAAC ATTACCGCCA TGTTGACATT GATTATTGAC TAGTTATTAA   250
TAGTAATCAA TTACGGGGTC ATTAGTTCAT AGCCCATATA TGGAGTTCCG   300
CGTTACATAA CTTACGGTAA ATGGCCCGCC TGGCTGACCG CCCAACGACC   350
CCCGCCCATT GACGTCAATA ATGACGTATG TTCCCATAGT AACGCCAATA   400
GGGACTTTCC ATTGACGTCA ATGGGTGGAG TATTTACGGT AAACTGCCCA   450
CTTGGCAGTA CATCAAGTGT ATCATATGCC AAGTACGCCC CCTATTGACG   500
TCAATGACGG TAAATGGCCC GCCTGGCATT ATGCCCAGTA CATGACCTTA   550
TGGGACTTTC CTACTTGGCA GTACATCTAC GTATTAGTCA TCGCTATTAC   600
CATGGTGATG CGGTTTTGGC AGTACATCAA TGGGCGTGGA TAGCGGTTTG   650
ACTCACGGGG ATTTCCAAGT CTCCACCCCA TTGACGTCAA TGGGAGTTTG   700
TTTTGGCACC AAAATCAACG GGACTTTCCA AAATGTCGTA ACAACTCCGC   750
CCCATTGACG CAAATGGGCG GTAGGCGTGT ACGGTGGGAG GTCTATATAA   800
GCAGAGCTCG TTTAGTGAAC CGTCAGATCG CCTGGAGACG CCATCCACGC   850
TGTTTTGACC TCCATAGAAG ACACCGGGAC CGATCCAGCC TCCGCGGCCG   900
GGAACGGTGC ATTGGAACGC GGATTCCCCG TGCCAAGAGT GACGTAAGTA   950
CCGCCTATAG ACTCTATAGG CACACCCCTT TGGCTCTTAT GCATGCTATA  1000
CTGTTTTTGG CTTGGGGCCT ATACACCCCC GCTTCCTTAT GCTATAGGTG  1050
ATGGTATAGC TTAGCCTATA GGTGTGGGTT ATTGACCATT ATTGACCACT  1100
CCCCTATTGG TGACGATACT TTCCATTACT AATCCATAAC ATGGCTCTTT  1150
GCCACAACTA TCTCTATTGG CTATATGCCA ATACTCTGTC CTTCAGAGAC  1200
TGACACGGAC TCTGTATTTT TACAGGATGG GGTCCCATTT ATTATTTACA  1250
AATTCACATA TACAACAACG CCGTCCCCCG TGCCCGCAGT TTTTATTAAA  1300
CATAGCGTGG GATCTCCACG CGAATCTCGG GTACGTGTTC CGGACATGGG  1350
CTCTTCTCCG GTAGCGGCGG AGCTTCCACA TCCGAGCCCT GGTCCCATGC  1400
CTCCAGCGGC TCATGGTCGC TCGGCAGCTC CTTGCTCCTA ACAGTGGAGG  1450
CCAGACTTAG GCACAGCACA ATGCCCACCA CCACCAGTGT GCCGCACAAG  1500
GCCGTGGCGG TAGGGTATGT GTCTGAAAAT GAGCGTGGAG ATTGGGCTCG  1550
CACGGCTGAC GCAGATGGAA GACTTAAGGC AGCGGCAGAA GAAGATGCAG  1600
GCAGCTGAGT TGTTGTATTC TGATAAGAGT CAGAGGTAAC TCCCGTTGCG  1650
GTGCTGTTAA CGGTGGAGGG CAGTGTAGTC TGAGCAGTAC TCGTTGCTGC  1700
CGCGCGCGCC ACCAGACATA ATAGCTGACA GACTAACAGA CTGTTCCTTT  1750
CCATGGGTCT TTTCTGCAGT CACCGTCGGA CCATGTGTGA ACTTGATATT  1800
TTACATGATT CTCTTTACCA ATTCTGCCCC GAATTACACT TAAAACGACT  1850
CAACAGCTTA ACGTTGGCTT GCCACGCATT ACTTGACTGT AAAACTCTCA  1900
CTCTTACCGA ACTTGGCCGT AACCTGCCAA CCAAAGCGAG AACAAAACAT  1950
AACATCAAAC GAATCGACCG ATTGTTAGGT AATCGTCACC TCCACAAAGA  2000
```

```
                                  -continued
GCGACTCGCT GTATACCGTT GGCATGCTAG CTTTATCTGT TCGGGAATAC       2050

GATGCCCATT GTACTTGTTG ACTGGTCTGA TATTCGTGAG CAAAAACGAC       2100

TTATGGTATT GCGAGCTTCA GTCGCACTAC ACGGTCGTTC TGTTACTCTT       2150

TATGAGAAAG CGTTCCCGCT TTCAGAGCAA TGTTCAAAGA AAGCTCATGA       2200

CCAATTTCTA GCCGACCTTG CGAGCATTCT ACCGAGTAAC ACCACACCGC       2250

TCATTGTCAG TGATGCTGGC TTTAAAGTGC CATGGTATAA ATCCGTTGAG       2300

AAGCTGGGTT GGTACTGGTT AAGTCGAGTA AGAGGAAAAG TACAATATGC       2350

AGACCTAGGA GCGGAAAACT GGAAACCTAT CAGCAACTTA CATGATATGT       2400

CATCTAGTCA CTCAAAGACT TTAGGCTATA AGAGGCTGAC TAAAAGCAAT       2450

CCAATCTCAT GCCAAATTCT ATTGTATAAA TCTCGCTCTA AAGGCCGAAA       2500

AAATCAGCGC TCGACACGGA CTCATTGTCA CCACCCGTCA CCTAAAATCT       2550

ACTCAGCGTC GGCAAAGGAG CCATGGGTTC TAGCAACTAA CTTACCTGTT       2600

GAAATTCGAA CACCCAAACA ACTTGTTAAT ATCTATTCGA AGCGAATGCA       2650

GATTGAAGAA ACCTTCCGAG ACTTGATAAG TCCTGCCTAC GGACTAGGCC       2700

TACGCCATAG CCGAACGAGC AGCTCAGAGC GTTTTGATAT CATGCTGCTA       2750

ATCGCCCTGA TGCTTCAACT AACATGTTGG CTTGCGGGCG TTCATGCTCA       2800

GAAACAAGGT TGGGACAAGC ACTTCCAGGC TAACACAGTC AGAAATCGAA       2850

ACGTACTCTC AACAGTTCGC TTAGGCATGG AAGTTTTGCG GCATTCTGGC       2900

TACACAATAA CAAGGGAAGA CTTACTCGTG GCTGCAACCC TACTAGCTCA       2950

AAATTTATTC ACACATGGTT ACGCTTTGGG GAAATTATGA TAATGATCCA       3000

GATCACTTCT GGCTAATAAA AGATCAGAGC TCTAGAGATC TGTGTGTTGG       3050

TTTTTTGTGG ATCTGCTGTG CCTTCTAGTT GCCAGCCATC TGTTGTTTGC       3100

CCCTCCCCCG TGCCTTCCTT GACCCTGGAA GGTGCCACTC CCACTGTCCT       3150

TTCCTAATAA AATGAGGAAA TTGCATCGCA TTGTCTGAGT AGGTGTCATT       3200

CTATTCTGGG GGGTGGGGTG GGGCAGCACA GCAAGGGGGA GGATTGGGAA       3250

GACAATAGCA GGCATGCTGG GGATGCGGTG GGCTCTATGG GTACCTCTCT       3300

CTCTCTCTCT CTCTCTCTCT CTCTCTCTCT CTCTCGGTAC CTCTCTCTCT       3350

CTCTCTCTCT CTCTCTCTCT CTCTCTCTCT CGGTACCAGG TGCTGAAGAA       3400

TTGACCCGGT GACCAAAGGT GCCTTTTATC ATCACTTTAA AAATAAAAAA       3450

CAATTACTCA GTGCCTGTTA TAAGCAGCAA TTAATTATGA TTGATGCCTA       3500

CATCACAACA AAAACTGATT TAACAAATGG TTGGTCTGCC TTAGAAAGTA       3550

TATTTGAACA TTATCTTGAT TATATTATTG ATAATAATAA AAACCTTATC       3600

CCTATCCAAG AAGTGATGCC TATCATTGGT TGGAATGAAC TTGAAAAAAA       3650

TTAGCCTTGA ATACATTACT GGTAAGGTAA ACGCCATTGT CAGCAAATTG       3700

ATCCAAGAGA ACCAACTTAA AGCTTTCCTG ACGGAATGTT AATTCTCGTT       3750

GACCCTGAGC ACTGATGAAT CCCCTAATGA TTTTGGTAAA AATCATTAAG       3800

TTAAGGTGGA TACACATCTT GTCATATGAT CCCGGTAATG TGAGTTAGCT       3850

CACTCATTAG GCACCCCAGG CTTTACACTT TATGCTTCCG GCTCGTATGT       3900

TGTGTGGAAT TGTGAGCGGA TAACAATTTC ACACAGGAAA CAGCTATGAC       3950

CATGATTACG CCAAGCGCGC AATTAACCCT CACTAAAGGG AACAAAAGCT       4000
```

```
GGAGCTCCAC CGCGGTGGCG GCCGCTCTAG AACTAGTGGA TCCCCCGGGG   4050

AGGTCAGAAT GGTTTCTTTA CTGTTTGTCA ATTCTATTAT TTCAATACAG   4100

AACAATAGCT TCTATAACTG AAATATATTT GCTATTGTAT ATTATGATTG   4150

TCCCTCGAAC CATGAACACT CCTCCAGCTG AATTTCACAA TTCCTCTGTC   4200

ATCTGCCAGG CCATTAAGTT ATTCATGGAA GATCTTTGAG GAACACTGCA   4250

AGTTCATATC ATAAACACAT TTGAAATTGA GTATTGTTTT GCATTGTATG   4300

GAGCTATGTT TTGCTGTATC CTCAGAAAAA AAGTTTGTTA TAAAGCATTC   4350

ACACCCATAA AAAGATAGAT TTAAATATTC CAGCTATAGG AAAGAAAGTG   4400

CGTCTGCTCT TCACTCTAGT CTCAGTTGGC TCCTTCACAT GCATGCTTCT   4450

TTATTTCTCC TATTTTGTCA AGAAAATAAT AGGTCACGTC TTGTTCTCAC   4500

TTATGTCCTG CCTAGCATGG CTCAGATGCA CGTTGTAGAT ACAAGAAGGA   4550

TCAAATGAAA CAGACTTCTG GTCTGTTACT ACAACCATAG TAATAAGCAC   4600

ACTAACTAAT AATTGCTAAT TATGTTTTCC ATCTCTAAGG TTCCCACATT   4650

TTTCTGTTTT CTTAAAGATC CCATTATCTG GTTGTAACTG AAGCTCAATG   4700

GAACATGAGC AATATTTCCC AGTCTTCTCT CCCATCCAAC AGTCCTGATG   4750

GATTAGCAGA ACAGGCAGAA AACACATTGT TACCCAGAAT TAAAAACTAA   4800

TATTTGCTCT CCATTCAATC CAAAATGGAC CTATTGAAAC TAAAATCTAA   4850

CCCAATCCCA TTAAATGATT TCTATGGCGT CAAAGGTCAA ACTTCTGAAG   4900

GGAACCTGTG GGTGGGTCAC AATTCAGGCT ATATATTCCC CAGGGCTCAG   4950

CGGATCCATG GGCTCCATCG GCGCAGCAAG CATGGAATTT TGTTTTGATG   5000

TATTCAAGGA GCTCAAAGTC CACCATGCCA ATGAGAACAT CTTCTACTGC   5050

CCCATTGCCA TCATGTCAGC TCTAGCCATG GTATACCTGG GTGCAAAAGA   5100

CAGCACCAGG ACACAGATAA ATAAGGTTGT TCGCTTTGAT AAACTTCCAG   5150

GATTCGGAGA CAGTATTGAA GCTCAGTGTG GCACATCTGT AAACGTTCAC   5200

TCTTCACTTA GAGACATCCT CAACCAAATC ACCAAACCAA ATGATGTTTA   5250

TTCGTTCAGC CTTGCCAGTA GACTTTATGC TGAAGAGAGA TACCCAATCC   5300

TGCCAGAATA CTTGCAGTGT GTGAAGGAAC TGTATAGAGG AGGCTTGGAA   5350

CCTATCAACT TTCAAACAGC TGCAGATCAA GCCAGAGAGC TCATCAATTC   5400

CTGGGTAGAA AGTCAGACAA ATGGAATTAT CAGAAATGTC CTTCAGCCAA   5450

GCTCCGTGGA TTCTCAAACT GCAATGGTTC TGGTTAATGC CATTGTCTTC   5500

AAAGGACTGT GGGAGAAAAC ATTTAAGGAT GAAGACACAC AAGCAATGCC   5550

TTTCAGAGTG ACTGAGCAAG AAAGCAAACC TGTGCAGATG ATGTACCAGA   5600

TTGGTTTATT TAGAGTGGCA TCAATGGCTT CTGAGAAAAT GAAGATCCTG   5650

GAGCTTCCAT TTGCCAGTGG GACAATGAGC ATGTTGGTGC TGTTGCCTGA   5700

TGAAGTCTCA GGCCTTGAGC AGCTTGAGAG TATAATCAAC TTTGAAAAAC   5750

TGACTGAATG GACCAGTTCT AATGTTATGG AAGAGAGGAA GATCAAAGTG   5800

TACTTACCTC GCATGAAGAT GGAGGAAAAA TACAACCTCA CATCTGTCTT   5850

AATGGCTATG GGCATTACTG ACGTGTTTAG CTCTTCAGCC AATCTGTCTG   5900

GCATCTCCTC AGCAGAGAGC CTGAAGATAT CTCAAGCTGT CCATGCAGCA   5950

CATGCAGAAA TCAATGAAGC AGGCAGAGAG GTGGTAGGGT CAGCAGAGGC   6000

TGGAGTGGAT GCTGCAAGCG TCTCTGAAGA ATTTAGGGCT GACCATCCAT   6050
```

```
TCCTCTTCTG TATCAAGCAC ATCGCAACCA ACGCCGTTCT CTTCTTTGGC    6100
AGATGTGTTT CCCCTCCGCG GCCAGCAGAT GACGCACCAG CAGATGACGC    6150
ACCAGCAGAT GACGCACCAG CAGATGACGC ACCAGCAGAT GACGCACCAG    6200
CAGATGACGC AACAACATGT ATCCTGAAAG GCTCTTGTGG CTGGATCGGC    6250
CTGCTGGATG ACGATGACAA AAAATACAAA AAAGCACTGA AAAAACTGGC    6300
AAAACTGCTG TAATGAGGGC GCCTGGATCC AGATCACTTC TGGCTAATAA    6350
AAGATCAGAG CTCTAGAGAT CTGTGTGTTG GTTTTTTGTG GATCTGCTGT    6400
GCCTTCTAGT TGCCAGCCAT CTGTTGTTTG CCCCTCCCCC GTGCCTTCCT    6450
TGACCCTGGA AGGTGCCACT CCCACTGTCC TTTCCTAATA AAATGAGGAA    6500
ATTGCATCGC ATTGTCTGAG TAGGTGTCAT TCTATTCTGG GGGGTGGGGT    6550
GGGGCAGCAC AGCAAGGGGG AGGATTGGGA AGACAATAGC AGGCATGCTG    6600
GGGATGCGGT GGGCTCTATG GGTACCTCTC TCTCTCTCTC TCTCTCTCTC    6650
TCTCTCTCTC TCTCTCGGTA CCTCTCTCGA GGGGGGGCCC GGTACCCAAT    6700
TCGCCCTATA GTGAGTCGTA TTACGCGCGC TCACTGGCCG TCGTTTTACA    6750
ACGTCGTGAC TGGGAAAACC CTGGCGTTAC CCAACTTAAT CGCCTTGCAG    6800
CACATCCCCC TTTCGCCAGC TGGCGTAATA GCGAAGAGGC CCGCACCGAT    6850
CGCCCTTCCC AACAGTTGCG CAGCCTGAAT GGCGAATGGA AATTGTAAGC    6900
GTTAATATTT TGTTAAAATT CGCGTTAAAT TTTGTTAAA TCAGCTCATT    6950
TTTTAACCAA TAGGCCGAAA TCGGCAAAAT CCCTTATAAA TCAAAAGAAT    7000
AGACCGAGAT AGGGTTGAGT GTTGTTCCAG TTTGGAACAA GAGTCCACTA    7050
TTAAAGAACG TGGACTCCAA CGTCAAAGGG CGAAAAACCG TCTATCAGGG    7100
CGATGGCCCA CTACTCCGGG ATCATATGAC AAGATGTGTA TCCACCTTAA    7150
CTTAATGATT TTTACCAAAA TCATTAGGGG ATTCATCAGT GCTCAGGGTC    7200
AACGAGAATT AACATTCCGT CAGGAAAGCT TATGATGATG ATGTGCTTAA    7250
AAACTTACTC AATGGCTGGT TATGCATATC GCAATACATG CGAAAAACCT    7300
AAAAGAGCTT GCCGATAAAA AAGGCCAATT TATTGCTATT TACCGCGGCT    7350
TTTTATTGAG CTTGAAAGAT AAATAAAATA GATAGGTTTT ATTTGAAGCT    7400
AAATCTTCTT TATCGTAAAA AATGCCCTCT TGGGTTATCA AGAGGGTCAT    7450
TATATTTCGC GGAATAACAT CATTTGGTGA CGAAATAACT AAGCACTTGT    7500
CTCCTGTTTA CTCCCCTGAG CTTGAGGGGT TAACATGAAG GTCATCGATA    7550
GCAGGATAAT AATACAGTAA AACGCTAAAC CAATAATCCA AATCCAGCCA    7600
TCCCAAATTG GTAGTGAATG ATTATAAATA ACAGCAAACA GTAATGGGCC    7650
AATAACACCG GTTGCATTGG TAAGGCTCAC CAATAATCCC TGTAAAGCAC    7700
CTTGCTGATG ACTCTTTGTT TGGATAGACA TCACTCCCTG TAATGCAGGT    7750
AAAGCGATCC CACCACCAGC CAATAAAATT AAAACAGGGA AAACTAACCA    7800
ACCTTCAGAT ATAAACGCTA AAAGGCAAA TGCACTACTA TCTGCAATAA    7850
ATCCGAGCAG TACTGCCGTT TTTTCGCCCC ATTTAGTGGC TATTCTTCCT    7900
GCCACAAAGG CTTGGAATAC TGAGTGTAAA AGACCAAGAC CCGCTAATGA    7950
AAAGCCAACC ATCATGCTAT TCCATCCAAA ACGATTTTCG GTAAATAGCA    8000
CCCACACCGT TGCGGGAATT TGGCCTATCA ATTGCGCTGA AAAATAAATA    8050
```

```
ATCAACAAAA TGGCATCGTT TTAAATAAAG TGATGTATAC CGAATTCAGC   8100

TTTTGTTCCC TTTAGTGAGG GTTAATTGCG CGCTTGGCGT AATCATGGTC   8150

ATAGCTGTTT CCTGTGTGAA ATTGTTATCC GCTCACAATT CCACACAACA   8200

TACGAGCCGG AAGCATAAAG TGTAAAGCCT GGGGTGCCTA ATGAGTGAGC   8250

TAACTCACAT TAATTGCGTT GCGCTCACTG CCCGCTTTCC AGTCGGGAAA   8300

CCTGTCGTGC CAGCTGCATT AATGAATCGG CCAACGCGCG GGGAGAGGCG   8350

GTTTGCGTAT TGGGCGCTCT TCCGCTTCCT CGCTCACTGA CTCGCTGCGC   8400

TCGGTCGTTC GGCTGCGGCG AGCGGTATCA GCTCACTCAA AGGCGGTAAT   8450

ACGGTTATCC ACAGAATCAG GGGATAACGC AGGAAAGAAC ATGTGAGCAA   8500

AAGGCCAGCA AAAGGCCAGG AACCGTAAAA AGGCCGCGTT GCTGGCGTTT   8550

TTCCATAGGC TCCGCCCCCC TGACGAGCAT CACAAAAATC GACGCTCAAG   8600

TCAGAGGTGG CGAAACCCGA CAGGACTATA AAGATACCAG GCGTTTCCCC   8650

CTGGAAGCTC CCTCGTGCGC TCTCCTGTTC CGACCCTGCC GCTTACCGGA   8700

TACCTGTCCG CCTTTCTCCC TTCGGGAAGC GTGGCGCTTT CTCATAGCTC   8750

ACGCTGTAGG TATCTCAGTT CGGTGTAGGT CGTTCGCTCC AAGCTGGGCT   8800

GTGTGCACGA ACCCCCCGTT CAGCCCGACC GCTGCGCCTT ATCCGGTAAC   8850

TATCGTCTTG AGTCCAACCC GGTAAGACAC GACTTATCGC CACTGGCAGC   8900

AGCCACTGGT AACAGGATTA GCAGAGCGAG GTATGTAGGC GGTGCTACAG   8950

AGTTCTTGAA GTGGTGGCCT AACTACGGCT ACACTAGAAG GACAGTATTT   9000

GGTATCTGCG CTCTGCTGAA GCCAGTTACC TTCGGAAAAA GAGTTGGTAG   9050

CTCTTGATCC GGCAAACAAA CCACCGCTGG TAGCGGTGGT TTTTTTGTTT   9100

GCAAGCAGCA GATTACGCGC AGAAAAAAAG GATCTCAAGA AGATCCTTTG   9150

ATCTTTTCTA CGGGGTCTGA CGCTCAGTGG AACGAAAACT CACGTTAAGG   9200

GATTTTGGTC ATGAGATTAT CAAAAAGGAT CTTCACCTAG ATCCTTTTAA   9250

ATTAAAAATG AAGTTTTAAA TCAATCTAAA GTATATATGA GTAAACTTGG   9300

TCTGACAGTT ACCAATGCTT AATCAGTGAG GCACCTATCT CAGCGATCTG   9350

TCTATTTCGT TCATCCATAG TTGCCTGACT CCCCGTCGTG TAGATAACTA   9400

CGATACGGGA GGGCTTACCA TCTGGCCCCA GTGCTGCAAT GATACCGCGA   9450

GACCCACGCT CACCGGCTCC AGATTTATCA GCAATAAACC AGCCAGCCGG   9500

AAGGGCCGAG CGCAGAAGTG GTCCTGCAAC TTTATCCGCC TCCATCCAGT   9550

CTATTAATTG TTGCCGGGAA GCTAGAGTAA GTAGTTCGCC AGTTAATAGT   9600

TTGCGCAACG TTGTTGCCAT TGCTACAGGC ATCGTGGTGT CACGCTCGTC   9650

GTTTGGTATG GCTTCATTCA GCTCCGGTTC CCAACGATCA AGGCGAGTTA   9700

CATGATCCCC CATGTTGTGC AAAAAAGCGG TTAGCTCCTT CGGTCCTCCG   9750

ATCGTTGTCA GAAGTAAGTT GGCCGCAGTG TTATCACTCA TGGTTATGGC   9800

AGCACTGCAT AATTCTCTTA CTGTCATGCC ATCCGTAAGA TGCTTTTCTG   9850

TGACTGGTGA GTACTCAACC AAGTCATTCT GAGAATAGTG TATGCGGCGA   9900

CCGAGTTGCT CTTGCCCGGC GTCAATACGG GATAATACCG CGCCACATAG   9950

CAGAACTTTA AAAGTGCTCA TCATTGGAAA ACGTTCTTCG GGGCGAAAAC  10000

TCTCAAGGAT CTTACCGCTG TTGAGATCCA GTTCGATGTA ACCCACTCGT  10050

GCACCCAACT GATCTTCAGC ATCTTTTACT TTCACCAGCG TTTCTGGGTG  10100
```

```
AGCAAAAACA GGAAGGCAAA ATGCCGCAAA AAGGGAATA  AGGGCGACAC    10150

GGAAATGTTG AATACTCATA CTCTTCCTTT TCAATATTA  TTGAAGCATT    10200

TATCAGGGTT ATTGTCTCAT GAGCGGATAC ATATTTGAAT GTATTTAGAA    10250

AAATAAACAA ATAGGGGTTC CGCGCACATT TCCCCGAAAA GTGCCAC       10297

SEQ ID NO: 46 (pTnMod (Oval/ENT tag/P146/PA) - QUAIL)
CTGACGCGCC CTGTAGCGGC GCATTAAGCG CGGCGGGTGT GGTGGTTACG       50

CGCAGCGTGA CCGCTACACT TGCCAGCGCC CTAGCGCCCG CTCCTTTCGC      100

TTTCTTCCCT TCCTTTCTCG CCACGTTCGC CGGCATCAGA TTGGCTATTG      150

GCCATTGCAT ACGTTGTATC CATATCATAA TATGTACATT TATATTGGCT      200

CATGTCCAAC ATTACCGCCA TGTTGACATT GATTATTGAC TAGTTATTAA      250

TAGTAATCAA TTACGGGGTC ATTAGTTCAT AGCCCATATA TGGAGTTCCG      300

CGTTACATAA CTTACGGTAA ATGGCCCGCC TGGCTGACCG CCCAACGACC      350

CCCGCCCATT GACGTCAATA ATGACGTATG TTCCCATAGT AACGCCAATA      400

GGGACTTTCC ATTGACGTCA ATGGGTGGAG TATTTACGGT AAACTGCCCA      450

CTTGGCAGTA CATCAAGTGT ATCATATGCC AAGTACGCCC CCTATTGACG      500

TCAATGACGG TAAATGGCCC GCCTGGCATT ATGCCCAGTA CATGACCTTA      550

TGGGACTTTC CTACTTGGCA GTACATCTAC GTATTAGTCA TCGCTATTAC      600

CATGGTGATG CGGTTTTGGC AGTACATCAA TGGGCGTGGA TAGCGGTTTG      650

ACTCACGGGG ATTTCCAAGT CTCCACCCCA TTGACGTCAA TGGGAGTTTG      700

TTTTGGCACC AAAATCAACG GGACTTTCCA AAATGTCGTA ACAACTCCGC      750

CCCATTGACG CAAATGGGCG GTAGGCGTGT ACGGTGGGAG GTCTATATAA      800

GCAGAGCTCG TTTAGTGAAC CGTCAGATCG CCTGGAGACG CCATCCACGC      850

TGTTTTGACC TCCATAGAAG ACACCGGGAC CGATCCAGCC TCCGCGGCCG      900

GGAACGGTGC ATTGGAACGC GGATTCCCCG TGCCAAGAGT GACGTAAGTA      950

CCGCCTATAG ACTCTATAGG CACACCCCTT TGGCTCTTAT GCATGCTATA     1000

CTGTTTTTGG CTTGGGGCCT ATACACCCCC GCTTCCTTAT GCTATAGGTG     1050

ATGGTATAGC TTAGCCTATA GGTGTGGGTT ATTGACCATT ATTGACCACT     1100

CCCCTATTGG TGACGATACT TTCCATTACT AATCCATAAC ATGGCTCTTT     1150

GCCACAACTA TCTCTATTGG CTATATGCCA ATACTCTGTC CTTCAGAGAC     1200

TGACACGGAC TCTGTATTTT TACAGGATGG GGTCCCATTT ATTATTTACA     1250

AATTCACATA TACAACAACG CCGTCCCCCG TGCCCGCAGT TTTTATTAAA     1300

CATAGCGTGG GATCTCCACG CGAATCTCGG GTACGTGTTC CGGACATGGG     1350

CTCTTCTCCG GTAGCGGCGG AGCTTCCACA TCCGAGCCCT GGTCCCATGC     1400

CTCCAGCGGC TCATGGTCGC TCGGCAGCTC CTTGCTCCTA ACAGTGGAGG     1450

CCAGACTTAG GCACAGCACA ATGCCCACCA CCACCAGTGT GCCGCACAAG     1500

GCCGTGGCGG TAGGGTATGT GTCTGAAAAT GAGCGTGGAG ATTGGGCTCG     1550

CACGGCTGAC GCAGATGGAA GACTTAAGGC AGCGGCAGAA GAAGATGCAG     1600

GCAGCTGAGT TGTTGTATTC TGATAAGAGT CAGAGGTAAC TCCCGTTGCG     1650

GTGCTGTTAA CGGTGGAGGG CAGTGTAGTC TGAGCAGTAC TCGTTGCTGC     1700

CGCGCGCGCC ACCAGACATA ATAGCTGACA GACTAACAGA CTGTTCCTTT     1750

CCATGGGTCT TTTCTGCAGT CACCGTCGGA CCATGTGTGA ACTTGATATT     1800
```

-continued

```
TTACATGATT CTCTTTACCA ATTCTGCCCC GAATTACACT TAAAACGACT   1850

CAACAGCTTA ACGTTGGCTT GCCACGCATT ACTTGACTGT AAAACTCTCA   1900

CTCTTACCGA ACTTGGCCGT AACCTGCCAA CCAAAGCGAG AACAAAACAT   1950

AACATCAAAC GAATCGACCG ATTGTTAGGT AATCGTCACC TCCACAAAGA   2000

GCGACTCGCT GTATACCGTT GGCATGCTAG CTTTATCTGT TCGGGAATAC   2050

GATGCCCATT GTACTTGTTG ACTGGTCTGA TATTCGTGAG CAAAAACGAC   2100

TTATGGTATT GCGAGCTTCA GTCGCACTAC ACGGTCGTTC TGTTACTCTT   2150

TATGAGAAAG CGTTCCCGCT TTCAGAGCAA TGTTCAAAGA AAGCTCATGA   2200

CCAATTTCTA GCCGACCTTG CGAGCATTCT ACCGAGTAAC ACCACACCGC   2250

TCATTGTCAG TGATGCTGGC TTTAAAGTGC CATGGTATAA ATCCGTTGAG   2300

AAGCTGGGTT GGTACTGGTT AAGTCGAGTA AGAGGAAAAG TACAATATGC   2350

AGACCTAGGA GCGAAAAACT GGAAACCTAT CAGCAACTTA CATGATATGT   2400

CATCTAGTCA CTCAAAGACT TTAGGCTATA AGAGGCTGAC TAAAAGCAAT   2450

CCAATCTCAT GCCAAATTCT ATTGTATAAA TCTCGCTCTA AAGGCCGAAA   2500

AAATCAGCGC TCGACACGGA CTCATTGTCA CCACCCGTCA CCTAAAATCT   2550

ACTCAGCGTC GGCAAAGGAG CCATGGGTTC TAGCAACTAA CTTACCTGTT   2600

GAAATTCGAA CACCCAAACA ACTTGTTAAT ATCTATTCGA AGCGAATGCA   2650

GATTGAAGAA ACCTTCCGAG ACTTGAAAAG TCCTGCCTAC GGACTAGGCC   2700

TACGCCATAG CCGAACGAGC AGCTCAGAGC GTTTTGATAT CATGCTGCTA   2750

ATCGCCCTGA TGCTTCAACT AACATGTTGG CTTGCGGGCG TTCATGCTCA   2800

GAAACAAGGT TGGGACAAGC ACTTCCAGGC TAACACAGTC AGAAATCGAA   2850

ACGTACTCTC AACAGTTCGC TTAGGCATGG AAGTTTTGCG GCATTCTGGC   2900

TACACAATAA CAAGGGAAGA CTTACTCGTG GCTGCAACCC TACTAGCTCA   2950

AAATTTATTC ACACATGGTT ACGCTTTGGG GAAATTATGA TAATGATCCA   3000

GATCACTTCT GGCTAATAAA AGATCAGAGC TCTAGAGATC TGTGTGTTGG   3050

TTTTTTGTGG ATCTGCTGTG CCTTCTAGTT GCCAGCCATC TGTTGTTTGC   3100

CCCTCCCCCG TGCCTTCCTT GACCCTGGAA GGTGCCACTC CCACTGTCCT   3150

TTCCTAATAA AATGAGGAAA TTGCATCGCA TTGTCTGAGT AGGTGTCATT   3200

CTATTCTGGG GGGTGGGGTG GGGCAGCACA GCAAGGGGGA GGATTGGGAA   3250

GACAATAGCA GGCATGCTGG GGATGCGGTG GGCTCTATGG GTACCTCTCT   3300

CTCTCTCTCT CTCTCTCTCT CTCTCTCTCT CTCTCGGTAC CTCTCTCTCT   3350

CTCTCTCTCT CTCTCTCTCT CTCTCTCTCT CGGTACCAGG TGCTGAAGAA   3400

TTGACCCGGT GACCAAGGGT GCCTTTTATC ATCACTTTAA AAATAAAAAA   3450

CAATTACTCA GTGCCTGTTA TAAGCAGCAA TTAATTATGA TTGATGCCTA   3500

CATCACAACA AAAACTGATT TAACAAATGG TTGGTCTGCC TTAGAAAGTA   3550

TATTTGAACA TTATCTTGAT TATATTATTG ATAATAATAA AAACCTTATC   3600

CCTATCCAAG AAGTGATGCC TATCATTGGT TGGAATGAAC TTGAAAAAAA   3650

TTAGCCTTGA ATACATTACT GGTAAGGTAA ACGCCATTGT CAGCAAATTG   3700

ATCCAAGAGA ACCAACTTAA AGCTTTCCTG ACGGAATGTT AATTCTCGTT   3750

GACCCTGAGC ACTGATGAAT CCCCTAATGA TTTTGGTAAA AATCATTAAG   3800
```

-continued

```
TTAAGGTGGA TACACATCTT GTCATATGAT CCCGGTAATG TGAGTTAGCT    3850

CACTCATTAG GCACCCCAGG CTTTACACTT TATGCTTCCG GCTCGTATGT    3900

TGTGTGGAAT TGTGAGCGGA TAACAATTTC ACACAGGAAA CAGCTATGAC    3950

CATGATTACG CCAAGCGCGC AATTAACCCT CACTAAAGGG AACAAAAGCT    4000

GGAGCTCCAC CGCGGTGGCG GCCGCTCTAG AACTAGTGGA TCCCCCGGGG    4050

AGGTCAGAAT GGTTTCTTTA CTGTTTGTCA ATTCTATTAT TTCAATACAG    4100

AACAAAAGCT TCTATAACTG AAATATATTT GCTATTGTAT ATTATGATTG    4150

TCCCTCGAAC CATGAACACT CCTCCAGCTG AATTTCACAA TTCCTCTGTC    4200

ATCTGCCAGG CTGGAAGATC ATGGAAGATC TCTGAGGAAC ATTGCAAGTT    4250

CATACCATAA ACTCATTTGG AATTGAGTAT TATTTTGCTT TGAATGGAGC    4300

TATGTTTTGC AGTTCCCTCA GAAGAAAGC TTGTTATAAA GCGTCTACAC     4350

CCATCAAAAG ATATATTTAA ATATTCCAAC TACAGAAAGA TTTTGTCTGC    4400

TCTTCACTCT GATCTCAGTT GGTTTCTTCA CGTACATGCT TCTTTATTTG    4450

CCTATTTTGT CAAGAAAATA ATAGGTCAAG TCCTGTTCTC ACTTATCTCC    4500

TGCCTAGCAT GGCTTAGATG CACGTTGTAC ATTCAAGAAG GATCAAATGA    4550

AACAGACTTC TGGTCTGTTA CAACAACCAT AGTAATAAAC AGACTAACTA    4600

ATAATTGCTA ATTATGTTTT CCATCTCTAA GGTTCCCACA TTTTTCTGTT    4650

TTAAGATCCC ATTATCTGGT TGTAACTGAA GCTCAATGGA ACATGAACAG    4700

TATTTCTCAG TCTTTTCTCC AGCAATCCTG ACGGATTAGA AGAACTGGCA    4750

GAAAACACTT TGTTACCCAG AATTAAAAAC TAATATTTGC TCTCCCTTCA    4800

ATCCAAAATG GACCTATTGA AACTAAAATC TGACCCAATC CCATTAAATT    4850

ATTTCTATGG CGTCAAAGGT CAAACTTTTG AAGGGAACCT GTGGGTGGGT    4900

CCCAATTCAG GCTATATATT CCCCAGGGCT CAGCCAGTGG ATCCATGGGC    4950

TCCATCGGTG CAGCAAGCAT GGAATTTTGT TTTGATGTAT TCAAGGAGCT    5000

CAAAGTCCAC CATGCCAATG ACAACATGCT CTACTCCCCC TTTGCCATCT    5050

TGTCAACTCT GGCCATGGTC TTCCTAGGTG CAAAAGACAG CACCAGGACC    5100

CAGATAAATA AGGTTGTTCA CTTTGATAAA CTTCCAGGAT TCGGAGACAG    5150

TATTGAAGCT CAGTGTGGCA CATCTGTAAA TGTTCACTCT TCACTTAGAG    5200

ACATACTCAA CCAAATCACC AAACAAAATG ATGCTTATTC GTTCAGCCTT    5250

GCCAGTAGAC TTTATGCTCA AGAGACATAC ACAGTCGTGC CGGAATACTT    5300

GCAATGTGTG AAGGAACTGT ATAGAGGAGG CTTAGAATCC GTCAACTTTC    5350

AAACAGCTGC AGATCAAGCC AGAGGCCTCA TCAATGCCTG GGTAGAAAGT    5400

CAGACAAACG GAATTATCAG AAACATCCTT CAGCCAAGCT CCGTGGATTC    5450

TCAAACTGCA ATGGTCCTGG TTAATGCCAT TGCCTTCAAG GGACTGTGGG    5500

AGAAAGCATT TAAGGCTGAA GACACGCAAA CAATACCTTT CAGAGTGACT    5550

GAGCAAGAAA GCAAACCTGT GCAGATGATG TACCAGATTG GTTCATTTAA    5600

AGTGGCATCA ATGGCTTCTG AGAAAATGAA GATCCTGGAG CTTCCATTTG    5650

CCAGTGGAAC AATGAGCATG TTGGTGCTGT TGCCTGATGA TGTCTCAGGC    5700

CTTGAGCAGC TTGAGAGTAT AATCAGCTTT GAAAAACTGA CTGAATGGAC    5750

CAGTTCTAGT ATTATGGAAG AGAGGAAGGT CAAAGTGTAC TTACCTCGCA    5800

TGAAGATGGA GGAGAAATAC AACCTCACAT CTCTCTTAAT GGCTATGGGA    5850
```

```
                                         -continued
ATTACTGACC TGTTCAGCTC TTCAGCCAAT CTGTCTGGCA TCTCCTCAGT   5900

AGGGAGCCTG AAGATATCTC AAGCTGTCCA TGCAGCACAT GCAGAAATCA   5950

ATGAAGCGGG CAGAGATGTG GTAGGCTCAG CAGAGGCTGG AGTGGATGCT   6000

ACTGAAGAAT TTAGGGCTGA CCATCCATTC CTCTTCTGTG TCAAGCACAT   6050

CGAAACCAAC GCCATTCTCC TCTTTGGCAG ATGTGTTTCT CCGCGGCCAG   6100

CAGATGACGC ACCAGCAGAT GACGCACCAG CAGATGACGC ACCAGCAGAT   6150

GACGCACCAG CAGATGACGC ACCAGCAGAT GACGCAACAA CATGTATCCT   6200

GAAAGGCTCT TGTGGCTGGA TCGGCCTGCT GGATGACGAT GACAAAAAAT   6250

ACAAAAAAGC ACTGAAAAAA CTGGCAAAAC TGCTGTAATG AGGGCGCCTG   6300

GATCCAGATC ACTTCTGGCT AATAAAAGAT CAGAGCTCTA GAGATCTGTG   6350

TGTTGGTTTT TTGTGGATCT GCTGTGCCTT CTAGTTGCCA GCCATCTGTT   6400

GTTTGCCCCT CCCCCGTGCC TTCCTTGACC CTGGAAGGTG CCACTCCCAC   6450

TGTCCTTTCC TAATAAAATG AGGAAATTGC ATCGCATTGT CTGAGTAGGT   6500

GTCATTCTAT TCTGGGGGGT GGGGTGGGGC AGCACAGCAA GGGGGAGGAT   6550

TGGGAAGACA ATAGCAGGCA TGCTGGGGAT GCGGTGGGCT CTATGGGTAC   6600

CTCTCTCTCT CTCTCTCTCT CTCTCTCTCT CTCTCTCTCT CGGTACCTCT   6650

CTCGAGGGGG GGCCCGGTAC CCAATTCGCC CTATAGTGAG TCGTATTACG   6700

CGCGCTCACT GGCCGTCGTT TTACAACGTC GTGACTGGGA AAACCCTGGC   6750

GTTACCCAAC TTAATCGCCT TGCAGCACAT CCCCCTtTCG CCAGCTGGCG   6800

TAATAGCGAA GAGGCCCGCA CCGATCGCCC TTCCCAACAG TTGCGCAGCC   6850

TGAATGGCGA ATGGAAATTG TAAGCGTTAA TATTTTGTTA AAATTCGCGT   6900

TAAATTTTTG TTAAATCAGC TCATTTTTTA ACCAATAGGC CGAAATCGGC   6950

AAAATCCCTT ATAAATCAAA AGAATAGACC GAGATAGGGT TGAGTGTTGT   7000

TCCAGTTTGG AACAAGAGTC CACTATTAAA GAACGTGGAC TCCAACGTCA   7050

AAGGGCGAAA AACCGTCTAT CAGGGCGATG GCCCACTACT CCGGGATCAT   7100

ATGACAAGAT GTGTATCCAC CTTAACTTAA TGATTTTTAC CAAAATCATT   7150

AGGGGATTCA TCAGTGCTCA GGGTCAACGA GAATTAACAT TCCGTCAGGA   7200

AAGCTTATGA TGATGATGTG CTTAAAAACT TACTCAATGG CTGGTTATGC   7250

ATATCGCAAT ACATGCGAAA AACCTAAAAG AGCTTGCCGA TAAAAAAGGC   7300

CAATTTATTG CTATTTACCG CGGCTTTTTA TTGAGCTTGA AGATAAATA   7350

AAATAGATAG GTTTTATTTG AAGCTAAATC TTCTTTATCG TAAAAAATGC   7400

CCTCTTGGGT TATCAAGAGG GTCATTATAT TTCGCGGAAT AACATCATTT   7450

GGTGACGAAA TAACTAAGCA CTTGTCTCCT GTTTACTCCC CTGAGCTTGA   7500

GGGGTTAACA TGAAGGTCAT CGATAGCAGG ATAATAATAC AGTAAAACGC   7550

TAAACCAATA ATCCAAATCC AGCCATCCCA AATTGGTAGT GAATGATTAT   7600

AAATAACAGC AAACAGTAAT GGGCCAATAA CACCGGTTGC ATTGGTAAGG   7650

CTCACCAATA ATCCCTGTAA AGCACCTTGC TGATGACTCT TTGTTTGGAT   7700

AGACATCACT CCCTGTAATG CAGGTAAAGC GATCCCACCA CCAGCCAATA   7750

AAATTAAAAC AGGGAAAACT AACCAACCTT CAGATATAAA CGCTAAAAAG   7800

GCAAATGCAC TACTATCTGC AATAAATCCG AGCAGTACTG CCGTTTTTTC   7850
```

```
GCCCCATTTA GTGGCTATTC TTCCTGCCAC AAAGGCTTGG AATACTGAGT    7900

GTAAAAGACC AAGACCCGCT AATGAAAAGC CAACCATCAT GCTATTCCAT    7950

CCAAAACGAT TTTCGGTAAA TAGCACCCAC ACCGTTGCGG GAATTTGGCC    8000

TATCAATTGC GCTGAAAAAT AAATAATCAA CAAATGGCA TCGTTTTAAA     8050

TAAAGTGATG TATACCGAAT TCAGCTTTTG TTCCCTTTAG TGAGGGTTAA    8200

TTGCGCGCTT GGCGTAATCA TGGTCATAGC TGTTTCCTGT GTGAAATTGT    8150

TATCCGCTCA CAATTCCACA CAACATACGA GCCGGAAGCA TAAAGTGTAA    8200

AGCCTGGGGT GCCTAATGAG TGAGCTAACT CACATTAATT GCGTTGCGCT    8250

CACTGCCCGC TTTCCAGTCG GGAAACCTGT CGTGCCAGCT GCATTAATGA    8300

ATCGGCCAAC GCGCGGGGAG AGGCGGTTTG CGTATTGGGC GCTCTTCCGC    8350

TTCCTCGCTC ACTGACTCGC TGCGCTCGGT CGTTCGGCTG CGGCGAGCGG    8400

TATCAGCTCA CTCAAAGGCG GTAATACGGT TATCCACAGA ATCAGGGGAT    8450

AACGCAGGAA AGAACATGTG AGCAAAAGGC CAGCAAAAGG CCAGGAACCG    8500

TAAAAAGGCC GCGTTGCTGG CGTTTTTCCA TAGGCTCCGC CCCCCTGACG    8550

AGCATCACAA AAATCGACGC TCAAGTCAGA GGTGGCGAAA CCCGACAGGA    8600

CTATAAAGAT ACCAGGCGTT TCCCCCTGGA AGCTCCCTCG TGCGCTCTCC    8650

TGTTCCGACC CTGCCGCTTA CCGGATACCT GTCCGCCTTT CTCCCTTCGG    8700

GAAGCGTGGC GCTTTCTCAT AGCTCACGCT GTAGGTATCT CAGTTCGGTG    8750

TAGGTCGTTC GCTCCAAGCT GGGCTGTGTG CACGAACCCC CCGTTCAGCC    8800

CGACCGCTGC GCCTTATCCG GTAACTATCG TCTTGAGTCC AACCCGGTAA    8850

GACACGACTT ATCGCCACTG GCAGCAGCCA CTGGTAACAG GATTAGCAGA    8900

GCGAGGTATG TAGGCGGTGC TACAGAGTTC TTGAAGTGGT GGCCTAACTA    8950

CGGCTACACT AGAAGGACAG TATTTGGTAT CTGCGCTCTG CTGAAGCCAG    9000

TTACCTTCGG AAAAAGAGTT GGTAGCTCTT GATCCGGCAA ACAAACCACC    9050

GCTGGTAGCG GTGGTTTTTT TGTTTGCAAG CAGCAGATTA CGCGCAGAAA    9100

AAAAGGATCT CAAGAAGATC CTTTGATCTT TTCTACGGGG TCTGACGCTC    9250

AGTGGAACGA AAACTCACGT TAAGGGATTT TGGTCATGAG ATTATCAAAA    9200

AGGATCTTCA CCTAGATCCT TTTAAATTAA AAATGAAGTT TTAAATCAAT    9250

CTAAAGTATA TATGAGTAAA CTTGGTCTGA CAGTTACCAA TGCTTAATCA    9300

GTGAGGCACC TATCTCAGCG ATCTGTCTAT TTCGTTCATC CATAGTTGCC    9350

TGACTCCCCG TCGTGTAGAT AACTACGATA CGGGAGGGCT TACCATCTGG    9400

CCCCAGTGCT GCAATGATAC CGCGAGACCC ACGCTCACCG GCTCCAGATT    9450

TATCAGCAAT AAACCAGCCA GCCGGAAGGG CCGAGCGCAG AAGTGGTCCT    9500

GCAACTTTAT CCGCCTCCAT CCAGTCTATT AATTGTTGCC GGGAAGCTAG    9550

AGTAAGTAGT TCGCCAGTTA ATAGTTTGCG CAACGTTGTT GCCATTGCTA    9600

CAGGCATCGT GGTGTCACGC TCGTCGTTTG GTATGGCTTC ATTCAGCTCC    9650

GGTTCCCAAC GATCAAGGCG AGTTACATGA TCCCCCATGT TGTGCAAAAA    9700

AGCGGTTAGC TCCTTCGGTC CTCCGATCGT TGTCAGAAGT AAGTTGGCCG    9750

CAGTGTTATC ACTCATGGTT ATGGCAGCAC TGCATAATTC TCTTACTGTC    9800

ATGCCATCCG TAAGATGCTT TTCTGTGACT GGTGAGTACT CAACCAAGTC    9850

ATTCTGAGAA TAGTGTATGC GGCGACCGAG TTGCTCTTGC CCGGCGTCAA    9900
```

-continued

```
TACGGGATAA TACCGCGCCA CATAGCAGAA CTTTAAAAGT GCTCATCATT      9950

GGAAAACGTT CTTCGGGGCG AAAACTCTCA AGGATCTTAC CGCTGTTGAG     10000

ATCCAGTTCG ATGTAACCCA CTCGTGCACC CAACTGATCT TCAGCATCTT     10050

TTACTTTCAC CAGCGTTTCT GGGTGAGCAA AAACAGGAAG GCAAAATGCC     10100

GCAAAAAAGG GAATAAGGGC GACACGGAAA TGTTGAATAC TCATACTCTT     10150

CCTTTTTCAA TATTATTGAA GCATTTATCA GGGTTATTGT CTCATGAGCG     10200

GATACATaTT TGAATGTATT TAGAAAAATA AACAAATAGG GGTTCCGCGC     10250

ACATTTCCCC GAAAAGTGCC AC                                   10272
```

SEQ ID NO: 47 pTnMCS (CMV-CHOVg-ent-ProInsulin-synPA)

```
   1 ctgacgcgcc ctgtagcggc gcattaagcg cggcgggtgt ggtggttacg cgcagcgtga
  61 ccgctacact tgccagcgcc ctagcgcccg ctcctttcgc tttcttccct tcctttctcg
 121 ccacgttcgc cggcatcaga ttggctattg gccattgcat acgttgtatc catatcataa
 181 tatgtacatt tatattggct catgtccaac attaccgcca tgttgacatt gattattgac
 241 tagttattaa tagtaatcaa ttacggggtc attagttcat agcccatata tggagttccg
 301 cgttacataa cttacggtaa atggcccgcc tggctgaccg cccaacgacc cccgcccatt
 361 gacgtcaata atgacgtatg ttcccatagt aacgccaata gggactttcc attgacgtca
 421 atgggtggag tatttacggt aaactgccca cttggcagta catcaagtgt atcatatgcc
 481 aagtacgccc cctattgacg tcaatgacgg taaatggccc gcctggcatt atgcccagta
 541 catgacctta tgggactttc ctacttggca gtacatctac gtattagtca tcgctattac
 601 catggtgatg cggttttggc agtacatcaa tgggcgtgga tagcggtttg actcacgggg
 661 atttccaagt ctccacccca ttgacgtcaa tgggagtttg ttttggcacc aaaatcaacg
 721 ggactttcca aaatgtcgta acaactccgc cccattgacg caaatgggcg gtaggcgtgt
 781 acggtgggag gtctatataa gcagagctcg tttagtgaac cgtcagatcc ctggagacg
 841 ccatccacgc tgttttgacc tccatagaag acaccgggac cgatccagcc tccgcggccg
 901 ggaacggtgc attggaacgc ggattccccg tgccaagagt gacgtaagta ccgcctatag
 961 actctatagg cacacccctt ggctcttat gcatgctata ctgttttggg cttggggcct
1021 atacaccccc gcttccttat gctataggtg atggtatagc ttagcctata ggtgtgggtt
1081 attgaccatt attgaccact cccctattgg tgacgatact ttccattact aatccataac
1141 atggctcttt gccacaacta tctctattgg ctatatgcca atactctgtc cttcagagac
1201 tgacacggac tctgtatttt tacaggatgg ggtcccattt attatttaca aattcacata
1261 tacaacaacg ccgtcccccg tgcccgcagt ttttattaaa catagcgtgg gatctccacg
1321 cgaatctcgg gtacgtgttc cggacatggg ctcttctccg gtagcggcg agcttccaca
1381 tccgagccct ggtcccatgc ctccagcggc tcatggtcgc tcggcagctc cttgctccta
1441 acagtggagg ccagacttag gcacagcaca atgcccacca ccaccagtgt gccgcacaag
1501 gccgtggcgg tagggtatgt gtctgaaaat gagcgtggag attgggctcg cacggctgac
1561 gcagatggaa gacttaaggc agcggcagaa gaagatgcag gcagctgagt tgttgtattc
1621 tgataagagt cagaggtaac tcccgttgcg gtgctgttaa cggtggaggg cagtgtagtc
1681 tgagcagtac tcgttgctgc cgcgcgcgcc accagacata atagctgaca gactaacaga
1741 ctgttccttt ccatgggtct tttctgcagt caccgtcgga ccatgtgcga actcgatatt
1801 ttacacgact ctctttacca attctgcccc gaattacact taaaacgact caacagctta
1861 acgttggctt gccacgcatt acttgactgt aaaactctca ctcttaccga acttggccgt
```

-continued

```
1921  aacctgccaa ccaaagcgag aacaaaacat aacatcaaac gaatcgaccg attgttaggt
1981  aatcgtcacc tccacaaaga gcgactcgct gtataccgtt ggcatgctag ctttatctgt
2041  tcgggcaata cgatgcccat tgtacttgtt gactggtctg atattcgtga gcaaaaacga
2101  cttatggtat tgcgagcttc agtcgcacta cacggtcgtt ctgttactct ttatgagaaa
2161  gcgttccgc  tttcagagca atgttcaaag aaagctcatg accaatttct agccgacctt
2221  gcgagcattc taccgagtaa caccacaccg ctcattgtca gtgatgctgc ctttaaagtg
2281  ccatggtata aatccgttga gaagctgggt tggtactggt taagtcgagt aagaggaaaa
2341  gtacaatatg cagacctagg agcggaaaac tggaaaccta tcagcaactt acatgatatg
2401  tcatctagtc actcaaagac tttaggctat aagaggctga ctaaaagcaa tccaatctca
2461  tgccaaattc tattgtataa atctcgctct aaaggccgaa aaaatcagcg ctcgacacgg
2521  actcattgtc accacccgtc acctaaaatc tactcagcgt cggcaaagga gccatgggtt
2581  ctagcaacta acttacctgt tgaaattcga acacccaaac aacttgttaa tatctattcg
2641  aagcgaatgc agattgaaga aaccttccga gacttgaaaa gtcctgccta cggactaggc
2701  ctacgccata gccgaacgag cagctcagag cgttttgata tcatgctgct aatcgccctg
2761  atgcttcaac taacatgttg gcttgcgggc gttcatgctc agaaacaagg ttgggacaag
2821  cacttccagg ctaacacagt cagaaatcga aacgtactct caacagttcg cttaggcatg
2881  gaagttttgc ggcattctgg ctacacaata caagggaag acttactcgt ggctgcaacc
2941  ctactagctc aaaatttatt cacacatggt tacgctttgg ggaaattatg aggggatcgc
3001  tctagagcga tccgggatct cgggaaaagc gttggtgacc aaaggtgcct tttatcatca
3061  cttttaaaaat aaaaaacaat tactcagtgc ctgttataag cagcaattaa ttatgattga
3121  tgcctacatc acaacaaaaa ctgatttaac aaatggttgg tctgccttag aaagtatatt
3181  tgaacattat cttgattata ttattgataa taataaaaac cttatcccta tccaagaagt
3241  gatgcctatc attggttgga atgaacttga aaaaaattag ccttgaatac attactggta
3301  aggtaaacgc cattgtcagc aaattgatcc aagagaacca acttaaagct ttcctgacgg
3361  aatgttaatt ctcgttgacc ctgagcactg atgaatcccc taatgatttt ggtaaaaatc
3421  attaagttaa ggtggataca catcttgtca tatgatcccg gtaatgtgag ttagctcact
3481  cattaggcac cccaggcttt acactttatg cttccggctc gtatgttgtg tggaattgtg
3541  agcggataac aatttcacac aggaaacagc tatgaccatg attacgccaa gcgcgcaatt
3601  aaccctcact aaagggaaca aaagctggag ctccaccgcg gtggcggccg ctctagaact
3661  agtggatccc ccgggcatca gattggctat tggccattgc atacgttgta tccatatcat
3721  aatatgtaca tttatattgg ctcatgtcca acattaccgc catgttgaca ttgattattg
3781  actagttatt aatagtaatc aattacgggg tcattagttc atagcccata tggagttc
3841  cgcgttacat aacttacggt aaatggcccg cctggctgac cgcccaacga ccccgccca
3901  ttgacgtcaa taatgacgta tgttcccata gtaacgccaa tagggacttt ccattgacgt
3961  caatgggtgg agtatttacg gtaaactgcc cacttggcag tacatcaagt gtatcatatg
4021  ccaagtacgc cccctattga cgtcaatgac ggtaaatggc ccgcctggca ttatgcccag
4081  tacatgacct tatgggactt tcctacttgg cagtacatct acgtattagt catcgctatt
4141  accatggtga tgcggttttg gcagtacatc aatgggcgtg gatagcggtt tgactcacgg
4201  ggatttccaa gtctccaccc cattgacgtc aatgggagtt tgttttggca ccaaaatcaa
4261  cgggactttc caaaatgtcg taacaactcc gccccattga cgcaaatggg cggtaggcgt
```

```
4321  gtacggtggg aggtctatat aagcagagct cgtttagtga accgtcagat cgcctggaga
4381  cgccatccac gctgttttga cctccataga agacaccggg accgatccag cctccgcggc
4441  cgggaacggt gcattggaac gcggattccc cgtgccaaga gtgacgtaag taccgcctat
4501  agactctata ggcacacccc tttggctctt atgcatgcta tactgttttt ggcttgggc
4561  ctatacaccc ccgcttcctt atgctatagg tgatggtata gcttagccta taggtgtggg
4621  ttattgacca ttattgacca ctcccctatt ggtgacgata ctttccatta ctaatccata
4681  acatggctct ttgccacaac tatctctatt ggctatatgc caatactctg tccttcagag
4741  actgacacgg actctgtatt tttacaggat ggggtcccat ttattattta caaattcaca
4801  tatacaacaa cgccgtcccc cgtgcccgca gtttttatta aacatagcgt gggatctcca
4861  cgcgaatctc gggtacgtgt tccggacatg ggctcttctc cggtagcggc ggagcttcca
4921  catccgagcc ctggtcccat gcctccagcg gctcatggtc gctcggcagc tccttgctcc
4981  taacagtgga ggccagactt aggcacagca caatgcccac caccaccagt gtgccgcaca
5041  aggccgtggc ggtagggtat gtgtctgaaa atgagcgtgg agattgggct cgcacggctg
5101  acgcagatgg aagacttaag gcagcggcag aagaagatgc aggcagctga gttgttgtat
5161  tctgataaga gtcagaggta actcccgttg cggtgctgtt aacggtggag ggcagtgtag
5221  tctgagcagt actcgttgct gccgcgcgcg ccaccagaca taatagctga cagactaaca
5281  gactgttcct ttccatgggt cttttctgca gtcaccgtcg gatcaatggg ctccatcggt
5341  gcagcaagca tggaattttg ttttgatgta ttcaaggagc tcaaagtcca ccatgccaat
5401  gagaacatct tctactgccc cattgccatc atgtcagctc tagccatggt atacctgggt
5461  gcaaaagaca gcaccaggac acaaataaat aaggttgttc gctttgataa acttccagga
5521  ttcggagaca gtattgaagc tcagtgtggc acatctgtaa acgttcactc ttcacttaga
5581  gacatcctca accaaatcac caaaccaaat gatgtttatt cgttcagcct tgccagtaga
5641  ctttatgctg aagagagata cccaatcctg ccagaatact tgcagtgtgt gaaggaactg
5701  tatagaggag cttggaacc tatcaacttt caaacagctg cagatcaagc cagagagctc
5761  atcaattcct gggtagaaag tcagacaaat ggaattatca gaaatgtcct tcagccaagc
5821  tccgtggatt ctcaaactgc aatggttctg gttaatgcca ttgtcttcaa aggactgtgg
5881  gagaaagcat ttaaggatga agacacacaa gcaatgcctt tcagagtgac tgagcaagaa
5941  agcaaacctg tgcagatgat gtaccagatt ggtttattta gagtggcatc aatggcttct
6001  gagaaaatga agatcctgga gcttccattt gccagtggga caatgagcat gttggtgctg
6061  ttgcctgatg aagtctcagg ccttgagcag cttgagagta taatcaactt tgaaaaactg
6121  actgaatgga ccagttctaa tgttatggaa gagagaagat caaagtgtac ttacctcgca
6181  tgaagatgga ggaaaaatac aacctcacat ctgtcttaat ggctatgggc attactgacg
6241  tgtttagctc ttcagccaat ctgtctggca tctcctcagc agagagcctg aagatatctc
6301  aagctgtcca tgcagcacat gcagaaatca atgaagcagg cagagaggtg gtagggtcag
6361  cagaggctgg agtggatgct gcaagcgtct ctgaagaatt tagggctgac catccattcc
6421  tcttctgtat caagcacatc gcaaccaacg ccgttctctt cttttggcag atgtgtttcc
6481  cgcggccagc agatgacgca ccagcagatg acgcaccagc agatgacgca ccagcagatg
6541  acgcaccagc agatgacgca acaacatgta tcctgaaagg ctcttgtggc tggatcggcc
6601  tgctggatga cgatgacaaa tttgtgaacc aacacctgtg cggctcacac ctggtggaag
6661  ctctctacct agtgtgcggg gaacgaggct tcttctacac acccaagacc cgccgggagg
6721  cagaggacct gcaggtgggg caggtggagc tgggcggggg ccctggtgca ggcagcctgc
```

```
6781 agcccttggc cctggagggg tccctgcaga agcgtggcat tgtggaacaa tgctgtacca 6841 gcatctgctc cctctaccag ctggagaact actgcaacta gggcgcctaa agggcgaatt 6901 atcgcggccg ctctagacca ggcgcctgga tccagatcac ttctggctaa taaaagatca 6961 gagctctaga gatctgtgtg ttggttttt gtggatctgc tgtgccttct agttgccagc 7021 catctgttgt ttgcccctcc cccgtgcctt ccttgaccct ggaaggtgcc actcccactg 7081 tcctttccta ataaaatgag gaaattgcat cgcattgtct gagtaggtgt cattctattc 7141 tggggggtgg ggtggggcag cacagcaagg gggaggattg ggaagacaat agcaggcatg 7201 ctgggatgc ggtgggctct atgggtacct ctctctctct ctctctctct ctcactctct 7261 ctctctctcg gtacctctcc tcgagggggg gcccggtacc caattcgccc tatagtgagt 7321 cgtattacgc gcgctcactg gccgtcgttt tacaacgtcg tgactgggaa accctggcg 7381 ttacccaact taatcgcctt gcagcacatc cccctttcgc cagctggcgt aatagcgaag 7441 aggcccgcac cgatcgccct tcccaacagt tgcgcagcct gaatggcgaa tggaaattgt 7501 aagcgttaat attttgttaa aattcgcgtt aaattttgt taaatcagct catttttaa 7561 ccaataggcc gaaatcggca aaatcccta taaatcaaaa gaatagaccg atagggtt 7621 gagtgttgtt ccagtttgga acaagagtcc actattaaag aacgtggact ccaacgtcaa 7681 agggcgaaaa accgtctatc agggcgatgg cccactactc cgggatcata tgacaagatg 7741 tgtatccacc ttaacttaat gatttttacc aaaatcatta ggggattcat cagtgctcag 7801 ggtcaacgag aattaacatt ccgtcaggaa agcttatgat gatgatgtgc ttaaaaactt 7861 actcaatggc tggttatgca tatcgcaata catgcgaaaa acctaaaaga gcttgccgat 7921 aaaaaaggcc aatttattgc tatttaccgc ggcttttat tgagcttgaa agataaataa 7981 aatagatagg ttttatttga agctaaatct tctttatcgt aaaaaatgcc ctcttgggtt 8041 atcaagaggg tcattatatt tcgcggaata acatcatttg gtgacgaaat aactaagcac 8101 ttgtctcctg tttactcccc tgagcttgag gggttaacat gaaggtcatc gatagcagga 8161 taataataca gtaaaacgct aaaccaataa tccaaatcca gccatcccaa attggtagtg 8221 aatgattata ataacagca aacagtaatg ggccaataac accggttgca ttggtaaggc 8281 tcaccaataa tccctgtaaa gcaccttgct gatgactctt tgtttggata gacatcactc 8341 cctgtaatgc aggtaaagcg atcccaccac cagccaataa aattaaaaca gggaaaacta 8401 accaaccttc agatataaac gctaaaaagg caaatgcact actatctgca ataaatccga 8461 gcagtactgc cgtttttcg cccatttagt ggctattctt cctgccacaa aggcttggaa 8521 tactgagtgt aaaagaccaa gacccgtaat gaaaagccaa ccatcatgct attcatcatc 8581 acgatttctg taatagcacc acaccgtgct ggattggcta tcaatgcgct gaaataataa 8641 tcaacaaatg gcatcgttaa ataagtgatg tataccgatc agcttttgtt ccctttagtg 8701 agggttaatt gcgcgcttgg cgtaatcatg gtcatagctg tttcctgtgt gaaattgtta 8761 tccgctcaca attccacaca acatacgagc cggaagcata aagtgtaaag cctggggtgc 8821 ctaatgagtg agctaactca cattaattgc gttgcgctca ctgcccgctt tccagtcggg 8881 aaacctgtcg tgccagctgc attaatgaat cggccaacgc gcggggagag cggtttgcg 8941 tattgggcgc tcttccgctt cctcgctcac tgactcgctg cgctcggtcg ttcggctgcg 9001 gcgagcggta tcagctcact caaaggcggt aatacggtta tccacagaat cagggataa 9061 cgcaggaaag aacatgtgag caaaaggcca gcaaaaggcc aggaaccgta aaaaggccgc 9121 gttgctggcg ttttccata ggctccgccc ccctgacgag catcacaaaa atcgacgctc
```

```
9181 aagtcagagg tggcgaaacc cgacaggact ataaagatac caggcgtttc ccctggaag
9241 ctccctcgtg cgctctcctg ttccgaccct gccgcttacc ggatacctgt ccgcctttct
9301 cccttcggga agcgtggcgc tttctcatag ctcacgctgt aggtatctca gttcggtgta
9361 ggtcgttcgc tccaagctgg gctgtgtgca cgaaccccccg gttcagcccg accgctgcgc
9421 cttatccggt aactatcgtc ttgagtccaa cccggtaaga cacgacttat cgccactggC
9481 agcagccact ggtaacagga ttagcagagc gaggtatgta ggcggtgcta cagagttctt
9541 gaagtggtgg cctaactacg gctacactag aaggacagta tttggtatct gcgctctgct
9601 gaagccagtt accttcggaa aaagagttgg tagctcttga tccggcaaac aaaccaccgc
9661 tggtagcggt ggtttttttg tttgcaagca gcagattacg cgcagaaaaa aaggatctca
9721 agaagatcct ttgatctttt ctacggggtc tgacgctcag tggaacgaaa actcacgtta
9781 agggattttg gtcatgagat tatcaaaaag gatcttcacc tagatccttt taaattaaaa
9841 atgaagtttt aaatcaatct aaagtatata tgagtaaact tggtctgaca gttaccaatg
9901 cttaatcagt gaggcaccta tctcagcgat ctgtctattt cgttcatcca tagttgcctg
9961 actccccgtc gtgtagataa ctacgatacg ggagggctta ccatctggcc ccagtgctgc
10021 aatgataccg cgagacccac gctcaccggc tccagattta tcagcaataa accagccagc
10081 cggaagggcc gagcgcagaa gtggtcctgc aactttatcc gcctccatcc agtctattaa
10141 ttgttgccgg gaagctagag taagtagttc gccagttaat agtttgcgca acgttgttgc
10201 cattgctaca ggcatcgtgg tgtcacgctc gtcgtttggt atggcttcat tcagctccgg
10261 ttcccaacga tcaaggcgag ttacatgatc ccccatgttg tgcaaaaaag cggttagctc
10321 cttcggtcct ccgatcgttg tcagaagtaa gttggccgca gtgttatcac tcatggttat
10381 ggcagcactg cataattctc ttactgtcat gccatccgta agatgctttt ctgtgactgg
10441 tgagtactca accaagtcat tctgagaata gtgtatgcgg cgaccgagtt gctcttgccc
10501 ggcgtcaata cgggataata ccgcgccaca tagcagaact ttaaaagtgc tcatcattgg
10561 aaaacgttct cggggcgaaa actctcaag gatcttaccg ctgttgagat ccagttcgat
10621 gtaacccact cgtgcaccca actgatcttc agcatctttt actttcacca gcgtttctgg
10681 gtgagcaaaa acaggaaggc aaaatgccgc aaaaaaggga ataagggcga cacggaaatg
10741 ttgaatactc atactcttcc ttttttcaata ttattgaagc atttatcagg gttattgtct
10801 catgagcgga tacatatttg aatgtatttta gaaaaataaa caaatagggg ttccgcgcac
10861 atttccccga aaagtgccac
```

SEQ ID NO: 48 (cecropin prepro)
AAT TTC TCA AGG ATA TTT

TTC TTC GTG TTC GCT TTG

GTT CTG GCT TTG TCA ACA

GTT TCG GCT GCG CCA GAG

CCG AAA

SEQ ID NO: 49 (cecropin prepro extended)
AAT TTC TCA AGG ATA TTT

TTC TTC GTG TTC GCT TTG

GTT CTG GCT TTG TCA ACA

GTT TCG GCT GCG CCA GAG

CCG AAA TGG AAA GTC TTC

AAG

-continued

SEQ ID NO: 50 (cecropin pro)
GCG CCA GAG CCG AAA

SEQ ID NO: 51 (cecropin pro extended)
GCG CCA GAG CCG AAA TGG AAA GTC TTC AAG

SEQ ID NO: 52 (a Kozak sequence)
ACCATGT

We claim:

1. A method of producing a transgenic chicken or quail comprising, administering to an artery leading to the ovary of a chicken or quail a composition comprising a transposon-based vector, wherein the transposon-based vector comprises a prokaryotic transposase gene operably linked to a first promoter, a modified Kozak sequence positioned 3' to the first promoter so as to encode for at least the first codon of the transposase gene, and one or more genes of interest operably-linked to one or more additional promoters, wherein a plurality of the first twenty codons of the transposase gene are modified from the wild-type sequence by changing the nucleotide at the third base position of the codon to an adenine or thymine without modifying the amino acid encoded by the codon, and wherein the one or more genes of interest and their operably-linked promoters are flanked by transposase insertion sequences recognized by a transposase encoded by the transposase gene, such that the one or more genes of interest and their operably linked promoters and transposase insertion sequences are incorporated into a germ-line cell of the chicken or quail.

2. The method of claim 1, wherein the transposase gene is operably linked to two stop codons.

3. The method of claim 1, wherein the composition is administered to the chicken between approximately 14 and 16 weeks of age.

4. The method of claim 1, wherein the composition is administered to the quail between approximately 5 and 6 weeks of age.

5. The method of claim 1, wherein the transposon-based vector comprises an avian optimized polyA sequence operably linked to the transposase gene.

6. The method of claim 5, wherein the avian optimized polyA sequence comprises between approximately 40 and 100 nucleotides that precede a polyA nucleotide string.

7. The method of claim 1, wherein the transposase is a Tn10 transposase.

8. The method of claim 1, wherein the first promoter is a constitutive promoter.

9. The method of claim 1, wherein the first promoter is an oviduct-specific promoter selected from the group consisting of ovalbumin, ovotransferrin, ovomucoid, ovomucin, g2 ovoglobulin, g3 ovoglobulin, ovoflavoprotein, and ovostatin.

10. The method of claim 1, wherein the first promoter is an ovalbumin promoter having the sequence as set forth in SEQ ID NO: 15 or nucleic acids 4050-4938 of SEQ ID NO: 44.

11. The method of claim 1, wherein the one or more genes of interest are operably-linked to a second promoter.

12. The method of claim 11, wherein the second promoter is an oviduct-specific promoter selected from the group consisting of ovalbumin, ovotransferrin, ovomucoid, ovomucin, g2 ovoglobulin, g3 ovoglobulin, ovoflavoprotein, and ovostatin.

13. The method of claim 11, wherein the second promoter is an ovalbumin promoter having the sequence as set forth in SEQ ID NO: 15 or nucleic acids 4050-4938 of SEQ ID NO: 44.

14. The method of claim 1, wherein the transposon-based vector further comprises an enhancer operably-linked to the one or more genes of interest.

15. The method of claim 14, wherein the enhancer comprises at least a portion of an ovalbumin enhancer.

16. The method of claim 1, wherein the transposon-based vector further comprises an egg directing sequence comprising an ovalbumin signal sequence or vitellogenin signal sequence operably-linked to the one or more genes of interest.

17. The method of claim 16, wherein the egg directing sequence is an ovalbumin signal sequence as set forth in SEQ ID NO:19, SEQ ID NO:20 or SEQ ID NO:21.

* * * * *

```
                            SEQUENCE LISTING

<160> NUMBER OF SEQ ID NOS: 52

<210> SEQ ID NO 1
<211> LENGTH: 6
<212> TYPE: DNA
<213> ORGANISM: Artificial Sequence
<220> FEATURE:
<223> OTHER INFORMATION: Synthetic

<400> SEQUENCE: 1 accatg                                                                       6

<210> SEQ ID NO 2
<211> LENGTH: 7315
<212> TYPE: DNA
<213> ORGANISM: Artificial Sequence
<220> FEATURE:
<223> OTHER INFORMATION: Synthetic

<400> SEQUENCE: 2
ctgacgcgcc ctgtagcggc gcattaagcg cggcgggtgt ggtggttacg cgcagcgtga         60
ccgctacact tgccagcgcc ctagcgcccg ctcctttcgc tttcttccct tcctttctcg        120
ccacgttcgc cggcatcaga ttggctattg gccattgcat acgttgtatc catatcataa        180
tatgtacatt tatattggct catgtccaac attaccgcca tgttgacatt gattattgac        240
tagttattaa tagtaatcaa ttacggggtc attagttcat agcccatata tggagttccg        300
cgttacataa cttacggtaa atggcccgcc tggctgaccg cccaacgacc cccgcccatt        360
gacgtcaata atgacgtatg ttcccatagt aacgccaata gggactttcc attgacgtca        420
atgggtggag tatttacggt aaactgccca cttggcagta catcaagtgt atcatatgcc        480
aagtacgccc cctattgacg tcaatgacgg taaatggccc gcctggcatt atgcccagta        540
catgacctta tgggactttc ctacttggca gtacatctac gtattagtca tcgctattac        600
catggtgatg cggttttggc agtacatcaa tgggcgtgga tagcggtttg actcacgggg        660
atttccaagt ctccacccca ttgacgtcaa tgggagtttg ttttggcacc aaaatcaacg        720
ggactttcca aaatgtcgta acaactccgc cccattgacg caaatgggcg gtaggcgtgt        780
acggtgggag gtctatataa gcagagctcg tttagtgaac cgtcagatcg cctggagacg        840
ccatccacgc tgttttgacc tccatagaag acaccgggac cgatccagcc tccgcggccg        900
ggaacggtgc attggaacgc ggattccccg tgccaagagt gacgtaagta ccgcctatag        960
actctatagg cacaccccTT tggctcttat gcatgctata ctgtttttgg cttggggcct       1020
ataccccccc gcttccttat gctataggtg atggtatagc ttagcctata ggtgtgggtt       1080
attgaccatt attgaccact cccctattgg tgacgatact ttccattact aatccataac       1140
atggctcttt gccacaacta tctctattgg ctatatgcca atactctgtc ttcagagac        1200 tgacacggac tctgtatttt tacaggatgg ggtcccattt attatttaca aattcacata       1260
```

```
tacaacaacg ccgtcccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtcgga ccatgtgcga actcgatatt   1800
ttacacgact ctctttacca attctgcccc gaattacact aaaaacgact caacagctta   1860
acgttggctt gccacgcatt acttgactgt aaaactctca ctcttaccga acttggccgt   1920
aacctgccaa ccaaagcgag aacaaaacat aacatcaaac gaatcgaccg attgttaggt   1980
aatcgtcacc tccacaaaga gcgactcgct gtataccgtt ggcatgctag ctttatctgt   2040
tcgggcaata cgatgcccat tgtacttgtt gactggtctg atattcgtga gcaaaaacga   2100
cttatggtat tgcgagcttc agtcgcacta cacggtcgtt ctgttactct ttatgagaaa   2160
gcgttcccgc tttcagagca atgttcaaag aaagctcatg accaatttct agccgacctt   2220
gcgagcattc taccgagtaa caccacaccg ctcattgtca gtgatgctgg ctttaaagtg   2280
ccatggtata aatccgttga gaagctgggt tggtactggt taagtcgagt aagaggaaaa   2340
gtacaatatg cagacctagg agcggaaaac tggaaaccta tcagcaactt acatgatatg   2400
tcatctagtc actcaaagac tttaggctat aagaggctga ctaaaagcaa tccaatctca   2460
tgccaaattc tattgtataa atctcgctct aaaggccgaa aaaatcagcg ctcgacacgg   2520
actcattgtc accacccgtc acctaaaatc tactcagcgt cggcaaagga gccatgggtt   2580
ctagcaacta acttacctgt tgaaattcga acacccaaac aacttgttaa tatctattcg   2640
aagcgaatgc agattgaaga aaccttccga gacttgaaaa gtcctgccta cggactaggc   2700
ctacgccata gccgaacgag cagctcagag cgttttgata tcatgctgct aatcgccctg   2760
atgcttcaac taacatgttg gcttgcgggc gttcatgctc agaaacaagg ttgggacaag   2820
cacttccagg ctaacacagt cagaaatcga aacgtactct caacagttcg cttaggcatg   2880
gaagttttgc ggcattctgg ctacacaata acaagggaag acttactcgt ggctgcaacc   2940
ctactagctc aaaatttatt cacacatggt tacgctttgg ggaaattatg aggggatcgc   3000
tctagagcga tccgggatct cgggaaaagc gttggtgacc aaaggtgcct tttatcatca   3060
ctttaaaaat aaaaaacaat tactcagtgc ctgttataag cagcaattaa ttatgattga   3120
tgcctacatc acaacaaaaa ctgatttaac aaatggttgg tctgccttag aaagtatatt   3180
tgaacattat cttgattata ttattgataa taataaaaac cttatcccta tccaagaagt   3240
gatgcctatc attggttgga atgaacttga aaaaaattag ccttgaatac attactggta   3300
aggtaaacgc cattgtcagc aaattgatcc aagagaacca acttaaagct ttcctgacgg   3360
aatgttaatt ctcgttgacc ctgagcactg atgaatcccc taatgatttt ggtaaaaatc   3420
attaagttaa ggtggataca catcttgtca tatgatcccg gtaatgtgag ttagctcact   3480
cattaggcac cccaggcttt acactttatg cttccggctc gtatgttgtg tggaattgtg   3540
agcggataac aatttcacac aggaaacagc tatgaccatg attacgccaa gcgcgcaatt   3600
aaccctcact aaagggaaca aaagctggag ctccaccgcg gtggcggccg ctctagaact   3660
```

```
agtggatccc ccgggctgca ggaattcgat atcaagctta tcgataccgc tgacctcgag   3720 gggggggcccg gtacccaatt cgccctatag tgagtcgtat tacgcgcgct cactggccgt   3780
cgttttacaa cgtcgtgact gggaaaaccc tggcgttacc caacttaatc gccttgcagc   3840
acatccccct ttcgccagct ggcgtaatag cgaagaggcc cgcaccgatc gcccttccca   3900
acagttgcgc agcctgaatg gcgaatggaa attgtaagcg ttaatatttt gttaaaattc   3960
gcgttaaatt tttgttaaat cagctcattt tttaaccaat aggccgaaat cggcaaaatc   4020
ccttataaat caaaagaata gaccgagata gggttgagtg ttgttccagt ttggaacaag   4080
agtccactat taaagaacgt ggactccaac gtcaaagggc gaaaaaccgt ctatcagggc   4140
gatggcccac tactccggga tcatatgaca agatgtgtat ccaccttaac ttaatgattt   4200
ttaccaaaat cattagggga ttcatcagtg ctcagggtca acgagaatta acattccgtc   4260
aggaaagctt atgatgatga tgtgcttaaa aacttactca atggctggtt atgcatatcg   4320
caatacatgc gaaaaaccta aaagagcttg ccgataaaaa aggccaattt attgctattt   4380
accgcggctt tttattgagc ttgaaagata aataaaatag ataggtttta tttgaagcta   4440
aatcttcttt atcgtaaaaa atgccctctt gggttatcaa gagggtcatt atatttcgcg   4500
gaataacatc atttggtgac gaaataacta agcacttgtc tcctgtttac tccctgagc   4560 ttgaggggtt aacatgaagg tcatcgatag caggataata atacagtaaa acgctaaacc   4620
aataatccaa atccagccat cccaaattgg tagtgaatga ttataaataa cagcaaacag   4680
taatgggcca ataacaccgg ttgcattggt aaggctcacc aataatccct gtaaagcacc   4740
ttgctgatga ctctttgttt ggatagacat cactccctgt aatgcaggta aagcgatccc   4800
accaccagcc aataaaatta aaacagggaa aactaaccaa ccttcagata taaacgctaa   4860
aaaggcaaat gcactactat ctgcaataaa tccgagcagt actgccgttt tttcgcccat   4920
ttagtggcta ttcttcctgc cacaaaggct tggaatactg agtgtaaaag accaagaccc   4980
gtaatgaaaa gccaaccatc atgctattca tcatcacgat ttctgtaata gcaccacacc   5040
gtgctggatt ggctatcaat gcgctgaaat aataatcaac aaatggcatc gttaaataag   5100
tgatgtatac cgatcagctt ttgttccctt tagtgagggt taattgcgcg cttggcgtaa   5160
tcatggtcat agctgtttcc tgtgtgaaat tgttatccgc tcacaattcc acacaacata   5220
cgagccggaa gcataaagtg taaagcctgg ggtgcctaat gagtgagcta actcacatta   5280
attgcgttgc gctcactgcc cgctttccag tcgggaaacc tgtcgtgcca gctgcattaa   5340
tgaatcggcc aacgcgcggg gagaggcggt ttgcgtattg ggcgctcttc cgcttcctcg   5400
ctcactgact cgctgcgctc ggtcgttcgg ctgcggcgag cggtatcagc tcactcaaag   5460
gcggtaatac ggttatccac agaatcaggg gataacgcag gaaagaacat gtgagcaaaa   5520
ggccagcaaa aggccaggaa ccgtaaaaag gccgcgttgc tggcgttttt ccataggctc   5580
cgcccccctg acgagcatca caaaaatcga cgctcaagtc agaggtggcg aaacccgaca   5640
ggactataaa gataccaggc gtttccccct ggaagctccc tcgtgcgctc tcctgttccg   5700
accctgccgc ttaccggata cctgtccgcc tttctccctt cgggaagcgt ggcgctttct   5760
catagctcac gctgtaggta tctcagttcg gtgtaggtcg ttcgctccaa gctgggctgt   5820
gtgcacgaac cccccgttca gcccgaccgc tgcgccttat ccggtaacta tcgtcttgag   5880
tccaacccgg taagacacga cttatcgcca ctggcagcag ccactggtaa caggattagc   5940
agagcgaggt atgtaggcgg tgctacagag ttcttgaagt ggtggcctaa ctacggctac   6000
actagaagga cagtatttgg tatctgcgct ctgctgaagc cagttacctt cggaaaaaga   6060
```

```
gttggtagct cttgatccgg caaacaaacc accgctggta gcggtggttt ttttgtttgc    6120
aagcagcaga ttacgcgcag aaaaaaagga tctcaagaag atcctttgat cttttctacg    6180
gggtctgacg ctcagtggaa cgaaaactca cgttaaggga ttttggtcat gagattatca    6240
aaaaggatct tcacctagat ccttttaaat taaaaatgaa gttttaaatc aatctaaagt    6300
atatatgagt aaacttggtc tgacagttac caatgcttaa tcagtgaggc acctatctca    6360
gcgatctgtc tatttcgttc atccatagtt gcctgactcc ccgtcgtgta gataactacg    6420
atacgggagg gcttaccatc tggccccagt gctgcaatga taccgcgaga cccacgctca    6480
ccggctccag atttatcagc aataaaccag ccagccggaa gggccgagcg cagaagtggt    6540
cctgcaactt tatccgcctc catccagtct attaattgtt gccgggaagc tagagtaagt    6600
agttcgccag ttaatagttt gcgcaacgtt gttgccattg ctacaggcat cgtggtgtca    6660
cgctcgtcgt ttggtatggc ttcattcagc tccggttccc aacgatcaag gcgagttaca    6720
tgatccccca tgttgtgcaa aaaagcggtt agctccttcg gtcctccgat cgttgtcaga    6780
agtaagttgg ccgcagtgtt atcactcatg gttatggcag cactgcataa ttctcttact    6840
gtcatgccat ccgtaagatg cttttctgtg actggtgagt actcaaccaa gtcattctga    6900
gaatagtgta tgcggcgacc gagttgctct tgcccggcgt caatacggga taataccgcg    6960
ccacatagca gaactttaaa agtgctcatc attggaaaac gttcttcggg gcgaaaactc    7020
tcaaggatct taccgctgtt gagatccagt tcgatgtaac ccactcgtgc acccaactga    7080
tcttcagcat cttttacttt caccagcgtt tctgggtgag caaaaacagg aaggcaaaat    7140
gccgcaaaaa agggaataag ggcgacacgg aaatgttgaa tactcatact cttccttttt    7200
caatattatt gaagcattta tcagggttat tgtctcatga gcggatacat atttgaatgt    7260
atttagaaaa ataaacaaat aggggttccg cgcacatttc cccgaaaagt gccac         7315

<210> SEQ ID NO 3
<211> LENGTH: 7689
<212> TYPE: DNA
<213> ORGANISM: Artificial Sequence
<220> FEATURE:
<223> OTHER INFORMATION: Synthetic

<400> SEQUENCE: 3
ctgacgcgcc ctgtagcggc gcattaagcg cggcgggtgt ggtggttacg cgcagcgtga      60
ccgctacact tgccagcgcc ctagcgcccg ctcctttcgc tttcttccct tcctttctcg     120
ccacgttcgc cggcatcaga ttggctattg gccattgcat acgttgtatc catatcataa     180
tatgtacatt tatattggct catgtccaac attaccgcca tgttgacatt gattattgac     240
tagttattaa tagtaatcaa ttacggggtc attagttcat agcccatata tggagttccg     300
cgttacataa cttacggtaa atggcccgcc tggctgaccg cccaacgacc cccgcccatt     360
gacgtcaata atgacgtatg ttcccatagt aacgccaata gggactttcc attgacgtca     420
atgggtggag tatttacggt aaactgccca cttggcagta catcaagtgt atcatatgcc     480
aagtacgccc cctattgacg tcaatgacgg taaatggccc gcctggcatt atgcccagta     540
catgacctta tgggactttc ctacttggca gtacatctac gtattagtca tcgctattac     600
catggtgatg cggttttggc agtacatcaa tgggcgtgga tagcggtttg actcacgggg     660
atttccaagt ctccacccca ttgacgtcaa tgggagtttg ttttggcacc aaaatcaacg     720
ggactttcca aaatgtcgta acaactccgc cccattgacg caaatgggcg gtaggcgtgt     780
acggtgggag gtctatataa gcagagctcg tttagtgaac cgtcagatcg cctggagacg     840
```

```
ccatccacgc tgttttgacc tccatagaag acaccgggac cgatccagcc tccgcggccg    900
ggaacggtgc attggaacgc ggattccccg tgccaagagt gacgtaagta ccgcctatag    960
actctatagg cacaccccctt tggctcttat gcatgctata ctgttttttgg cttggggcct  1020 atacacccccc gcttccttat gctataggtg atggtatagc ttagcctata ggtgtgggtt  1080
attgaccatt attgaccact cccctattgg tgacgatact ttccattact aatccataac   1140
atggctcttt gccacaacta tctctattgg ctatatgcca atactctgtc cttcagagac   1200
tgacacggac tctgtatttt tacaggatgg ggtcccattt attatttaca aattcacata   1260
tacaacaacg ccgtccccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtcgga ccatgtgtga acttgatatt   1800
ttacatgatt ctcttttacca attctgcccc gaattacact taaaacgact caacagctta   1860
acgttggctt gccacgcatt acttgactgt aaaactctca ctcttaccga acttggccgt   1920
aacctgccaa ccaaagcgag aacaaaacat aacatcaaac gaatcgaccg attgttaggt   1980
aatcgtcacc tccacaaaga gcgactcgct gtataccgtt ggcatgctag ctttatctgt   2040
tcgggaatac gatgcccatt gtacttgttg actggtctga tattcgtgag caaaaacgac   2100
ttatggtatt gcgagcttca gtcgcactac acggtcgttc tgttactctt tatgagaaag   2160
cgttcccgct ttcagagcaa tgttcaaaga aagctcatga ccaatttcta gccgaccttg   2220
cgagcattct accgagtaac accacaccgc tcattgtcag tgatgctggc tttaaagtgc   2280
catggtataa atccgttgag aagctgggtt ggtactggtt aagtcgagta agaggaaaag   2340
tacaatatgc agacctagga gcggaaaact ggaaacctat cagcaactta catgatatgt   2400
catctagtca ctcaaagact ttaggctata agaggctgac taaaagcaat ccaatctcat   2460
gccaaattct attgtataaa tctcgctcta aaggccgaaa aaatcagcgc tcgacacgga   2520
ctcattgtca ccacccgtca cctaaaatct actcagcgtc ggcaaaggag ccatgggttc   2580
tagcaactaa cttacctgtt gaaattcgaa cacccaaaca acttgttaat atctattcga   2640
agcgaatgca gattgaagaa accttccgag acttgaaaag tcctgcctac ggactaggcc   2700
tacgccatag ccgaacgagc agctcagagc gttttgatat catgctgcta atcgccctga   2760
tgcttcaact aacatgttgg cttgcgggcg ttcatgctca gaaacaaggt tgggacaagc   2820
acttccaggc taacacagtc agaaatcgaa acgtactctc aacagttcgc ttaggcatgg   2880
aagttttgcg gcattctggc tacacaataa caagggaaga cttactcgtg gctgcaaccc   2940
tactagctca aaatttattc acacatggtt acgctttggg gaaattatga taatgatcca   3000
gatcacttct ggctaataaa agatcagagc tctagagatc tgtgtgttgg tttttttgtgg  3060 atctgctgtg ccttctagtt gccagccatc tgttgtttgc ccctccccg tgccttcctt    3120 gaccctggaa ggtgccactc ccactgtcct ttcctaataa aatgaggaaa ttgcatcgca   3180
ttgtctgagt aggtgtcatt ctattctggg gggtggggtg gggcagcaca gcaaggggga   3240
```

```
ggattgggaa gacaatagca ggcatgctgg ggatgcggtg ggctctatgg gtacctctct    3300
ctctctctct ctctctctct ctctctctct ctctcggtac ctctctctct ctctctctct    3360
ctctctctct ctctctctct cggtaccagg tgctgaagaa ttgacccggt gaccaaaggt    3420
gccttttatc atcactttaa aaataaaaaa caattactca gtgcctgtta taagcagcaa    3480
ttaattatga ttgatgccta catcacaaca aaaactgatt taacaaatgg ttggtctgcc    3540
ttagaaagta tatttgaaca ttatcttgat tatattattg ataataataa aaaccttatc    3600
cctatccaag aagtgatgcc tatcattggt tggaatgaac ttgaaaaaaa ttagccttga    3660
atacattact ggtaaggtaa acgccattgt cagcaaattg atccaagaga accaacttaa    3720
agctttcctg acggaatgtt aattctcgtt gaccctgagc actgatgaat cccctaatga    3780
ttttggtaaa aatcattaag ttaaggtgga tacacatctt gtcatatgat cccggtaatg    3840
tgagttagct cactcattag gcaccccagg ctttacactt tatgcttccg gctcgtatgt    3900
tgtgtggaat tgtgagcgga taacaatttc acacaggaaa cagctatgac catgattacg    3960
ccaagcgcgc aattaaccct cactaaaggg aacaaaagct ggagctccac cgcggtggcg    4020
gccgctctag aactagtgga tcccccgggc tgcaggaatt cgatatcaag cttatcgata    4080
ccgctgacct cgagggggg cccggtaccc aattcgccct atagtgagtc gtattacgcg    4140
cgctcactgg ccgtcgtttt acaacgtcgt gactgggaaa accctggcgt tacccaactt    4200
aatcgccttg cagcacatcc ccctttcgcc agctggcgta atagcgaaga ggcccgcacc    4260
gatcgccctt cccaacagtt gcgcagcctg aatggcgaat ggaaattgta agcgttaata    4320
ttttgttaaa attcgcgtta aattttttgtt aaatcagctc attttttaac caataggccg    4380
aaatcggcaa aatcccttat aaatcaaaag aatagaccga gatagggttg agtgttgttc    4440
cagtttggaa caagagtcca ctattaaaga acgtggactc caacgtcaaa gggcgaaaaa    4500
ccgtctatca gggcgatggc ccactactcc gggatcatat gacaagatgt gtatccacct    4560
taacttaatg attttttacca aaatcattag gggattcatc agtgctcagg gtcaacgaga    4620
attaacattc cgtcaggaaa gcttatgatg atgatgtgct taaaaactta ctcaatggct    4680
ggttatgcat atcgcaatac atgcgaaaaa cctaaaagag cttgccgata aaaaaggcca    4740
atttattgct atttaccgcg gcttttttatt gagcttgaaa gataaataaa atagataggt    4800
tttatttgaa gctaaatctt ctttatcgta aaaaatgccc tcttgggtta tcaagagggt    4860
cattatattt cgcggaataa catcatttgg tgacgaaata actaagcact tgtctcctgt    4920
ttactcccct gagcttgagg ggttaacatg aaggtcatcg atagcaggat aataatacag    4980
taaaacgcta aaccaataat ccaaatccag ccatcccaaa ttggtagtga atgattataa    5040
ataacagcaa acagtaatgg gccaataaca ccggttgcat tggtaaggct caccaataat    5100
ccctgtaaag caccttgctg atgactcttt gtttggatag acatcactcc ctgtaatgca    5160
ggtaaagcga tcccaccacc agccaataaa attaaaacag ggaaaactaa ccaaccttca    5220
gatataaacg ctaaaaaggc aaatgcacta ctatctgcaa taaatccgag cagtactgcc    5280
gttttttcgc ccatttagtg gctattcttc ctgccacaaa ggcttggaat actgagtgta    5340
aaagaccaag acccgtaatg aaaagccaac catcatgcta ttcatcatca cgatttctgt    5400
aatagcacca caccgtgctg gattggctat caatgcgctg aaataataat caacaaatgg    5460
catcgttaaa taagtgatgt ataccgatca gcttttgttc cctttagtga gggttaattg    5520
cgcgcttggc gtaatcatgg tcatagctgt ttcctgtgtg aaattgttat ccgctcacaa    5580
ttccacacaa catacgagcc ggaagcataa agtgtaaagc ctggggtgcc taatgagtga    5640
```

| gctaactcac attaattgcg ttgcgctcac tgcccgcttt ccagtcggga aacctgtcgt | 5700 |
|---|---|
| gccagctgca ttaatgaatc ggccaacgcg cggggagagg cggtttgcgt attgggcgct | 5760 |
| cttccgcttc ctcgctcact gactcgctgc gctcggtcgt tcggctgcgg cgagcggtat | 5820 |
| cagctcactc aaaggcggta atacggttat ccacagaatc aggggataac gcaggaaaga | 5880 |
| acatgtgagc aaaaggccag caaaaggcca ggaaccgtaa aaaggccgcg ttgctggcgt | 5940 |
| ttttccatag gctccgcccc cctgacgagc atcacaaaaa tcgacgctca agtcagaggt | 6000 |
| ggcgaaaccc gacaggacta taaagatacc aggcgtttcc ccctggaagc tccctcgtgc | 6060 |
| gctctcctgt tccgaccctg ccgcttaccg gatacctgtc cgcctttctc ccttcgggaa | 6120 |
| gcgtggcgct ttctcatagc tcacgctgta ggtatctcag ttcggtgtag gtcgttcgct | 6180 |
| ccaagctggg ctgtgtgcac gaaccccccg ttcagcccga ccgctgcgcc ttatccggta | 6240 |
| actatcgtct tgagtccaac ccggtaagac acgacttatc gccactggca gcagccactg | 6300 |
| gtaacaggat tagcagagcg aggtatgtag gcggtgctac agagttcttg aagtggtggc | 6360 |
| ctaactacgg ctacactaga aggacagtat ttggtatctg cgctctgctg aagccagtta | 6420 |
| ccttcggaaa aagagttggt agctcttgat ccggcaaaca aaccaccgct ggtagcggtg | 6480 |
| gtttttttgt ttgcaagcag cagattacgc gcagaaaaaa aggatctcaa gaagatcctt | 6540 |
| tgatcttttc tacggggtct gacgctcagt ggaacgaaaa ctcacgttaa gggattttgg | 6600 |
| tcatgagatt atcaaaaagg atcttcacct agatcctttt aaattaaaaa tgaagtttta | 6660 |
| aatcaatcta agtatatat gagtaaactt ggtctgacag ttaccaatgc ttaatcagtg | 6720 |
| aggcacctat ctcagcgatc tgtctatttc gttcatccat agttgcctga ctccccgtcg | 6780 |
| tgtagataac tacgatacgg gagggcttac catctggccc cagtgctgca atgataccgc | 6840 |
| gagacccacg ctcaccggct ccagatttat cagcaataaa ccagccagcc ggaagggccg | 6900 |
| agcgcagaag tggtcctgca actttatccg cctccatcca gtctattaat tgttgccggg | 6960 |
| aagctagagt aagtagttcg ccagttaata gtttgcgcaa cgttgttgcc attgctacag | 7020 |
| gcatcgtggt gtcacgctcg tcgtttggta tggcttcatt cagctccggt tcccaacgat | 7080 |
| caaggcgagt tacatgatcc cccatgttgt gcaaaaaagc ggttagctcc ttcggtcctc | 7140 |
| cgatcgttgt cagaagtaag ttggccgcag tgttatcact catggttatg gcagcactgc | 7200 |
| ataattctct tactgtcatg ccatccgtaa gatgcttttc tgtgactggt gagtactcaa | 7260 |
| ccaagtcatt ctgagaatag tgtatgcggc gaccgagttg ctcttgcccg gcgtcaatac | 7320 |
| gggataatac cgcgccacat agcagaactt taaaagtgct catcattgga aaacgttctt | 7380 |
| cggggcgaaa actctcaagg atcttaccgc tgttgagatc cagttcgatg taacccactc | 7440 |
| gtgcacccaa ctgatcttca gcatctttta ctttcaccag cgtttctggg tgagcaaaaa | 7500 |
| caggaaggca aaatgccgca aaaaagggaa taagggcgac acggaaatgt tgaatactca | 7560 |
| tactcttcct ttttcaatat tattgaagca tttatcaggg ttattgtctc atgagcggat | 7620 |
| acatatttga atgtatttag aaaaataaac aaataggggt tccgcgcaca tttccccgaa | 7680 |
| aagtgccac | 7689 |

<210> SEQ ID NO 4
<211> LENGTH: 7
<212> TYPE: DNA
<213> ORGANISM: Artificial Sequence
<220> FEATURE:
<223> OTHER INFORMATION: Synthetic

<400> SEQUENCE: 4

```
accatgg                                                             7

<210> SEQ ID NO 5
<211> LENGTH: 7
<212> TYPE: DNA
<213> ORGANISM: Artificial Sequence
<220> FEATURE:
<223> OTHER INFORMATION: Synthetic

<400> SEQUENCE: 5 aagatgt                                                             7

<210> SEQ ID NO 6
<211> LENGTH: 7
<212> TYPE: DNA
<213> ORGANISM: Artificial Sequence
<220> FEATURE:
<223> OTHER INFORMATION: Synthetic

<400> SEQUENCE: 6 acgatga                                                             7

<210> SEQ ID NO 7
<211> LENGTH: 7
<212> TYPE: DNA
<213> ORGANISM: Artificial Sequence
<220> FEATURE:
<223> OTHER INFORMATION: Synthetic

<400> SEQUENCE: 7 aagatgg                                                             7

<210> SEQ ID NO 8
<211> LENGTH: 7
<212> TYPE: DNA
<213> ORGANISM: Artificial Sequence
<220> FEATURE:
<223> OTHER INFORMATION: Synthetic

<400> SEQUENCE: 8 gacatga                                                             7

<210> SEQ ID NO 9
<211> LENGTH: 7
<212> TYPE: DNA
<213> ORGANISM: Artificial Sequence
<220> FEATURE:
<223> OTHER INFORMATION: Synthetic

<400> SEQUENCE: 9 accatga                                                             7

<210> SEQ ID NO 10

<400> SEQUENCE: 10

000

<210> SEQ ID NO 11
<211> LENGTH: 315
<212> TYPE: DNA
<213> ORGANISM: Gallus sp.

<400> SEQUENCE: 11
tctgccattg ctgcttcctc tgcccttcct cgtcactctg aatgtggctt cttcgctact      60
```

```
gccacagcaa gaaataaaat ctcaacatct aaatgggttt cctgaggttt ttcaagagtc    120
gttaagcaca ttccttcccc agcaccccett gctgcaggcc agtgccaggc accaacttgg    180
ctactgctgc ccatgagaga aatccagttc aatattttcc aaagcaaaat ggattacata    240
tgccctagat cctgattaac aggcgtttgt attatctagt gctttcgctt cacccagatt    300
atcccattgc ctccc                                                     315
```

```
<210> SEQ ID NO 12
<211> LENGTH: 361
<212> TYPE: DNA
<213> ORGANISM: Artificial Sequence
<220> FEATURE:
<223> OTHER INFORMATION: Synthetic

<400> SEQUENCE: 12
ggcgcctgga tccagatcac ttctggctaa taaaagatca gagctctaga gatctgtgtg     60
ttggtttttt gtggatctgc tgtgccttct agttgccagc catctgttgt ttgcccctcc    120
cccgtgcctt ccttgaccct ggaaggtgcc actcccactg tcctttccta ataaaatgag    180
gaaattgcat cgcattgtct gagtaggtgt cattctattc tggggggtgg ggtggggcag    240
cacagcaagg gggaggattg ggaagacaat agcaggcatg ctgggatgc ggtgggctct     300 atgggtacct ctctctctct ctctctctct ctctctctcg gtacctctct               360
c                                                                    361
```

```
<210> SEQ ID NO 13
<211> LENGTH: 350
<212> TYPE: DNA
<213> ORGANISM: Artificial Sequence
<220> FEATURE:
<223> OTHER INFORMATION: Synthetic

<400> SEQUENCE: 13
ggggatcgct ctagagcgat ccgggatctc gggaaaagcg ttggtgacca aggtgccttt     60
ttatcatcac tttaaaaata aaaaacaatt actcagtgcc tgttataagc agcaattaat    120
tatgattgat gcctacatca caacaaaaac tgatttaaca aatggttggt ctgccttaga    180
aagtatattt gaacattatc ttgattatat tattgataat aataaaaacc ttatccctat    240
ccaagaagtg atgcctatca ttggttggaa tgaacttgaa aaaaattagc cttgaataca    300
ttactggtaa ggtaaacgcc attgtcagca aattgatcca agagaaccaa                350
```

```
<210> SEQ ID NO 14
<211> LENGTH: 908
<212> TYPE: DNA
<213> ORGANISM: Artificial Sequence
<220> FEATURE:
<223> OTHER INFORMATION: Synthetic

<400> SEQUENCE: 14
tgaatgtgtt cttgtgttat caatataaat cacagttagt gatgaagttg gctgcaagcc     60
tgcatcagtt cagctacttg gctgcattt gtatttggtt ctgtaggaaa tgcaaaaggt     120
tctaggctga cctgcacttc tatccctctt gccttactgc tgagaatctc tgcaggtttt    180
aattgttcac attttgctcc catttacttt ggaagataaa atatttacag aatgcttatg    240
aaacctttgt tcatttaaaa atattcctgg tcagcgtgac cggagctgaa agaacacatt    300
gatcccgtga tttcaataaa tacatatgtt ccatatattg tttctcagta gcctcttaaa    360
tcatgtgcgt tggtgcacat atgaatacat gaatagcaaa ggtttatctg gattacgctc    420
```

```
tggcctgcag gaatggccat aaaccaaagc tgagggaaga gggagagtat agtcaatgta      480
gattatactg attgctgatt gggttattat cagctagata caacttggg tcaggtgcca       540 ggtcaacata acctgggcaa aaccagtctc atctgtggca ggaccatgta ccagcagcca      600
gccgtgaccc aatctaggaa agcaagtagc acatcaattt taaatttatt gtaaatgccg      660
tagtagaagt gttttactgt gatacattga aacttctggt caatcagaaa aaggtttttt      720
atcagagatg ccaaggtatt atttgatttt ctttattcgc cgtgaagaga atttatgatt      780
gcaaaaagag gagtgtttac ataaactgat aaaaaacttg aggaattcag cagaaaacag      840
ccacgtgttc ctgaacattc ttccataaaa gtctcaccat gcctggcaga gccctattca      900
ccttcgct                                                              908

<210> SEQ ID NO 15
<211> LENGTH: 901
<212> TYPE: DNA
<213> ORGANISM: Gallus

<400> SEQUENCE: 15
gaggtcagaa tggtttcttt actgtttgtc aattctatta tttcaataca gaacaatagc       60
ttctataact gaaatatatt tgctattgta tattatgatt gtccctcgaa ccatgaacac      120
tcctccagct gaatttcaca attcctctgt catctgccag gccattaagt tattcatgga      180
agatctttga ggaacactgc aagttcatat cataaacaca tttgaaattg agtattgttt      240
tgcattgtat ggagctatgt tttgctgtat cctcagaaaa aaagtttgtt ataaagcatt      300
cacacccata aaaagataga tttaaatatt ccagctatag gaaagaaagt gcgtctgctc      360
ttcactctag tctcagttgg ctccttcaca tgcatgcttc tttatttctc ctattttgtc      420
aagaaaataa taggtcacgt cttgttctca cttatgtcct gcctagcatg gctcagatgc      480
acgttgtaga tacaagaagg atcaaatgaa acagacttct ggtctgttac tacaaccata      540
gtaataagca cactaactaa taattgctaa ttatgttttc catctctaag gttcccacat      600
ttttctgttt tcttaaagat cccattatct ggttgtaact gaagctcaat ggaacatgag      660
caatatttcc cagtcttctc tcccatccaa cagtcctgat ggattagcag aacaggcaga      720
aaacacattg ttacccagaa ttaaaaacta atatttgctc tccattcaat ccaaatgga       780 cctattgaaa ctaaaatcta acccaatccc attaaatgat ttctatgcg tcaaaggtca      840 aacttctgaa gggaacctgt gggtgggtca caattcaggc tatatattcc ccagggctca      900
g                                                                     901

<210> SEQ ID NO 16
<211> LENGTH: 680
<212> TYPE: DNA
<213> ORGANISM: Gallus

<400> SEQUENCE: 16
ccgggctgca gaaaaatgcc aggtggacta tgaactcaca tccaaaggag cttgacctga       60
tacctgattt tcttcaaact ggggaaacaa cacaatccca caaacagct cagagagaaa       120 ccatcactga tggctacagc accaaggtat gcaatggcaa tccattcgac attcatctgt      180
gacctgagca aaatgattta tctctccatg aatggttgct tctttccctc atgaaaaggc      240
aatttccaca ctcacaatat gcaacaaaga caaacagaga acaattaatg tgctccttcc      300
taatgtcaaa attgtagtgg caaagaggag aacaaaatct caagttctga gtaggtttta      360
gtgattggat aagaggcttt gacctgtgag ctcacctgga cttcatatcc ttttggataa      420
```

```
aaagtgcttt tataactttc aggtctccga gtctttattc atgagactgt tggtttaggg      480
acagacccac aatgaaatgc ctggcatagg aaagggcagc agagccttag ctgacctttt      540
cttgggacaa gcattgtcaa acaatgtgtg acaaaactat ttgtactgct ttgcacagct      600
gtgctgggca gggcaatcca ttgccaccta tcccaggtaa ccttccaact gcaagaagat      660
tgttgcttac tctctctaga                                                  680

<210> SEQ ID NO 17
<211> LENGTH: 72
<212> TYPE: DNA
<213> ORGANISM: Artificial Sequence
<220> FEATURE:
<223> OTHER INFORMATION: Synthetic

<400> SEQUENCE: 17
gtggatcaac atacagctag aaagctgtat tgcctttagc actcaagctc aaaagacaac       60
tcagagttca cc                                                           72

<210> SEQ ID NO 18
<211> LENGTH: 62
<212> TYPE: DNA
<213> ORGANISM: Artificial Sequence
<220> FEATURE:
<223> OTHER INFORMATION: Synthetic

<400> SEQUENCE: 18
acatacagct agaaagctgt attgccttta gcactcaagc tcaaaagaca actcagagtt       60
ca                                                                      62

<210> SEQ ID NO 19
<211> LENGTH: 1158
<212> TYPE: DNA
<213> ORGANISM: Gallus

<400> SEQUENCE: 19
atgggctcca tcggcgcagc aagcatggaa ttttgttttg atgtattcaa ggagctcaaa       60
gtccaccatg ccaatgagaa catcttctac tgccccattg ccatcatgtc agctctagcc      120
atggtatacc tgggtgcaaa agacagcacc aggacacaga taaataaggt tgttcgcttt      180
gataaacttc caggattcgg agacagtatt gaagctcagt gtggcacatc tgtaaacgtt      240
cactcttcac ttagagacat cctcaaccaa atcaccaaac caatgatgt ttattcgttc      300 agccttgcca gtagacttta tgctgaagag agatacccaa tcctgccaga atacttgcag      360
tgtgtgaagg aactgtatag aggaggcttg gaacctatca actttcaaac agctgcagat      420
caagccagag agctcatcaa ttcctgggta gaaagtcaga caaatggaat tatcagaaat      480
gtccttcagc caagctccgt ggattctcaa actgcaatgg ttctggttaa tgccattgtc      540
ttcaaaggac tgtgggagaa acatttaag gatgaagaca cacaagcaat gcctttcaga      600
gtgactgagc aagaaagcaa acctgtgcag atgatgtacc agattggttt atttagagtg      660
gcatcaatgg cttctgagaa aatgaagatc ctggagcttc catttgccag tgggacaatg      720
agcatgttgg tgctgttgcc tgatgaagtc tcaggccttg agcagcttga gagtataatc      780
aactttgaaa aactgactga atggaccagt tctaatgtta tggaagagag gaagatcaaa      840
gtgtacttac ctcgcatgaa gatggaggaa aaatacaacc tcacatctgt cttaatggct      900
atgggcatta ctgacgtgtt tagctcttca gccaatctgt ctggcatctc ctcagcagag      960
agcctgaaga tatctcaagc tgtccatgca gcacatgcag aaatcaatga agcaggcaga     1020
```

```
gaggtggtag ggtcagcaga ggctggagtg gatgctgcaa gcgtctctga agaatttagg    1080
gctgaccatc cattcctctt ctgtatcaag cacatcgcaa ccaacgccgt tctcttcttt    1140
ggcagatgtg tttcccct                                                  1158

<210> SEQ ID NO 20
<211> LENGTH: 53
<212> TYPE: DNA
<213> ORGANISM: Gallus

<400> SEQUENCE: 20
atgggctcca tcggcgcagc aagcatggaa ttttgttttg atgtattcaa gga           53

<210> SEQ ID NO 21
<211> LENGTH: 103
<212> TYPE: DNA
<213> ORGANISM: Gallus

<400> SEQUENCE: 21
atgggctcca tcggcgcagc aagcatggaa ttttgttttg atgtattcaa ggagctcaaa    60
gtccaccatg ccaatgagaa catcttctac tgccccattg cca                     103

<210> SEQ ID NO 22
<211> LENGTH: 63
<212> TYPE: DNA
<213> ORGANISM: Artificial Sequence
<220> FEATURE:
<223> OTHER INFORMATION: Synthetic

<400> SEQUENCE: 22
atgaggggga tcatactggc attagtgctc acccttgtag gcagccagaa gtttgacatt    60
ggt                                                                  63

<210> SEQ ID NO 23
<211> LENGTH: 260
<212> TYPE: DNA
<213> ORGANISM: Artificial Sequence
<220> FEATURE:
<223> OTHER INFORMATION: Synthetic

<400> SEQUENCE: 23
tttgtgaacc aacacctgtg cggctcacac ctggtggaag ctctctacct agtgtgcggg    60
gaacgaggct tcttctacac acccaagacc cgccgggagg cagaggacct gcaggtgggg   120
caggtggagc tgggcggggg ccctggtgca ggcagcctgc agcccttggc cctggagggg   180
tccctgcaga agcgtggcat tgtggaacaa tgctgtacca gcatctgctc cctctaccag   240
ctggagaact ctgcaactag                                               260

<210> SEQ ID NO 24
<211> LENGTH: 13
<212> TYPE: PRT
<213> ORGANISM: Artificial Sequence
<220> FEATURE:
<223> OTHER INFORMATION: Synthetic

<400> SEQUENCE: 24

Lys Tyr Lys Lys Ala Leu Lys Lys Leu Ala Lys Leu Leu
1               5                   10

<210> SEQ ID NO 25
<211> LENGTH: 39
<212> TYPE: DNA
<213> ORGANISM: Artificial Sequence
```

```
<220> FEATURE:
<223> OTHER INFORMATION: Synthetic

<400> SEQUENCE: 25
aaatacaaaa aagcactgaa aaaactggca aaactgctg                                39

<210> SEQ ID NO 26
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)..(4)
<223> OTHER INFORMATION: Repeating unit from about 3 to about 9

<400> SEQUENCE: 26

Gly Pro Gly Gly
1

<210> SEQ ID NO 27
<211> LENGTH: 12
<212> TYPE: PRT
<213> ORGANISM: Artificial Sequence
<220> FEATURE:
<223> OTHER INFORMATION: Synthetic

<400> SEQUENCE: 27

Gly Pro Gly Gly Gly Pro Gly Gly Gly Pro Gly Gly
1               5                  10

<210> SEQ ID NO 28
<211> LENGTH: 15
<212> TYPE: PRT
<213> ORGANISM: Artificial Sequence
<220> FEATURE:
<223> OTHER INFORMATION: Synthetic

<400> SEQUENCE: 28

Gly Gly Gly Gly Ser Gly Gly Gly Gly Ser Gly Gly Gly Gly Ser
1               5                  10                  15

<210> SEQ ID NO 29
<211> LENGTH: 20
<212> TYPE: PRT
<213> ORGANISM: Artificial Sequence
<220> FEATURE:
<223> OTHER INFORMATION: Synthetic

<400> SEQUENCE: 29

Gly Gly Gly Gly Ser Gly Gly Gly Gly Ser Gly Gly Gly Gly Ser Gly
1               5                  10                  15

Gly Gly Gly Ser
            20

<210> SEQ ID NO 30
<211> LENGTH: 5
<212> TYPE: PRT
<213> ORGANISM: Artificial Sequence
<220> FEATURE:
<223> OTHER INFORMATION: Synthetic

<400> SEQUENCE: 30

Pro Ala Asp Asp Ala
1               5
```

<210> SEQ ID NO 31
<211> LENGTH: 5
<212> TYPE: PRT
<213> ORGANISM: Artificial Sequence
<220> FEATURE:
<223> OTHER INFORMATION: Synthetic

<400> SEQUENCE: 31

Pro Ala Asp Asp Ala
1               5

<210> SEQ ID NO 32
<211> LENGTH: 16
<212> TYPE: PRT
<213> ORGANISM: Artificial Sequence
<220> FEATURE:
<223> OTHER INFORMATION: Synthetic

<400> SEQUENCE: 32

Ala Thr Thr Cys Ile Leu Lys Gly Ser Cys Gly Trp Ile Gly Leu Leu
1               5                   10                  15

<210> SEQ ID NO 33
<211> LENGTH: 30
<212> TYPE: PRT
<213> ORGANISM: Artificial Sequence
<220> FEATURE:
<223> OTHER INFORMATION: Synthetic

<400> SEQUENCE: 33

Pro Ala Asp Asp Ala Pro Ala Asp Asp Ala Thr Thr Cys Ile Leu Lys
1               5                   10                  15

Gly Ser Cys Gly Trp Ile Gly Leu Leu Asp Asp Asp Asp Lys
            20                  25                  30

<210> SEQ ID NO 34
<211> LENGTH: 5
<212> TYPE: PRT
<213> ORGANISM: Artificial Sequence
<220> FEATURE:
<223> OTHER INFORMATION: Synthetic

<400> SEQUENCE: 34

Asp Asp Asp Asp Lys
1               5

<210> SEQ ID NO 35
<211> LENGTH: 50
<212> TYPE: PRT
<213> ORGANISM: Artificial Sequence
<220> FEATURE:
<223> OTHER INFORMATION: Synthetic

<400> SEQUENCE: 35

Pro Ala Asp Asp Ala Pro Ala Asp Asp Ala Pro Ala Asp Asp Ala Pro
1               5                   10                  15

Ala Asp Asp Ala Pro Ala Asp Asp Ala Pro Ala Asp Asp Ala Thr Thr
            20                  25                  30

Cys Ile Leu Lys Gly Ser Cys Gly Trp Ile Gly Leu Leu Asp Asp Asp
        35                  40                  45

Asp Lys
    50

<210> SEQ ID NO 36
<211> LENGTH: 48
<212> TYPE: DNA

-continued

<213> ORGANISM: Artificial Sequence
<220> FEATURE:
<223> OTHER INFORMATION: Synthetic

<400> SEQUENCE: 36
atctcgagac catgtgtgaa cttgatattt tacatgattc tctttacc        48

<210> SEQ ID NO 37
<211> LENGTH: 36
<212> TYPE: DNA
<213> ORGANISM: Artificial Sequence
<220> FEATURE:
<223> OTHER INFORMATION: Synthetic

<400> SEQUENCE: 37
gattgatcat tatcataatt tccccaaagc gtaacc                     36

<210> SEQ ID NO 38
<211> LENGTH: 6
<212> TYPE: DNA
<213> ORGANISM: Artificial Sequence
<220> FEATURE:
<223> OTHER INFORMATION: Synthetic

<400> SEQUENCE: 38 ctcgag                                                       6

<210> SEQ ID NO 39
<211> LENGTH: 6
<212> TYPE: DNA
<213> ORGANISM: Artificial Sequence
<220> FEATURE:
<223> OTHER INFORMATION: Synthetic

<400> SEQUENCE: 39 tgatca                                                       6

<210> SEQ ID NO 40
<211> LENGTH: 22
<212> TYPE: DNA
<213> ORGANISM: Artificial Sequence
<220> FEATURE:
<223> OTHER INFORMATION: Synthetic

<400> SEQUENCE: 40
ttgccggcat cagattggct at                                    22

<210> SEQ ID NO 41
<211> LENGTH: 34
<212> TYPE: DNA
<213> ORGANISM: Artificial Sequence
<220> FEATURE:
<223> OTHER INFORMATION: Synthetic

<400> SEQUENCE: 41
agaggtcacc gggtcaattc ttcagcacct ggta                       34

<210> SEQ ID NO 42
<211> LENGTH: 10512
<212> TYPE: DNA
<213> ORGANISM: Artificial Sequence
<220> FEATURE:
<223> OTHER INFORMATION: Synthetic

<400> SEQUENCE: 42
ctgacgcgcc ctgtagcggc gcattaagcg cggcgggtgt ggtggttacg cgcagcgtga    60

```
ccgctacact tgccagcgcc ctagcgcccg ctcctttcgc tttcttccct tcctttctcg    120
ccacgttcgc cggcatcaga ttggctattg gccattgcat acgttgtatc catatcataa    180
tatgtacatt tatattggct catgtccaac attaccgcca tgttgacatt gattattgac    240
tagttattaa tagtaatcaa ttacggggtc attagttcat agcccatata tggagttccg    300
cgttacataa cttacggtaa atggcccgcc tggctgaccg cccaacgacc cccgcccatt    360
gacgtcaata atgacgtatg ttcccatagt aacgccaata gggactttcc attgacgtca    420
atgggtggag tatttacggt aaactgccca cttggcagta catcaagtgt atcatatgcc    480
aagtacgccc cctattgacg tcaatgacgg taaatggccc gcctggcatt atgcccagta    540
catgacctta tgggactttc ctacttggca gtacatctac gtattagtca tcgctattac    600
catggtgatg cggttttggc agtacatcaa tgggcgtgga tagcggtttg actcacgggg    660
atttccaagt ctccacccca ttgacgtcaa tgggagtttg ttttggcacc aaaatcaacg    720
ggactttcca aaatgtcgta acaactccgc cccattgacg caaatgggcg gtaggcgtgt    780
acggtgggag gtctatataa gcagagctcg tttagtgaac cgtcagatcg cctggagacg    840
ccatccacgc tgttttgacc tccatagaag acaccgggac cgatccagcc tccgcggccg    900
ggaacggtgc attggaacgc ggattccccg tgccaagagt gacgtaagta ccgcctatag    960
actctatagg cacacccctt tggctcttat gcatgctata ctgtttttgg cttggggcct   1020
atacaccccc gcttccttat gctataggtg atggtatagc ttagcctata ggtgtgggtt   1080
attgaccatt attgaccact cccctattgg tgacgatact tccattact aatccataac     1140 atggctcttt gccacaacta tctctattgg ctatatgcca atactctgtc cttcagagac   1200
tgacacggac tctgtatttt tacaggatgg ggtcccattt attatttaca aattcacata   1260
tacaacaacg ccgtcccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtcgga ccatgtgtga acttgatatt   1800
ttacatgatt ctctttacca attctgcccc gaattacact taaaacgact caacagctta   1860
acgttggctt gccacgcatt acttgactgt aaaactctca ctcttaccga acttggccgt   1920
aacctgccaa ccaaagcgag aacaaaacat aacatcaaac gaatcgaccg attgttaggt   1980
aatcgtcacc tccacaaaga gcgactcgct gtataccgtt ggcatgctag ctttatctgt   2040
tcgggaatac gatgcccatt gtacttgttg actggtctga tattcgtgag caaaaacgac   2100
ttatggtatt gcgagcttca gtcgcactac acgtcgttc tgttactctt tatgagaaag    2160
cgttcccgct ttcagagcaa tgttcaaaga aagctcatga ccaatttcta gccgaccttg   2220
cgagcattct accgagtaac accacaccgc tcattgtcag tgatgctggc tttaaagtgc   2280
catggtataa atccgttgag aagctgggtt ggtactggtt aagtcgagta agaggaaaag   2340
tacaatatgc agacctagga gcggaaaact ggaaacctat cagcaactta catgatatgt   2400
catctagtca ctcaaagact ttaggctata agaggctgac taaaagcaat ccaatctcat   2460
```

```
gccaaattct attgtataaa tctcgctcta aaggccgaaa aaatcagcgc tcgacacgga    2520
ctcattgtca ccacccgtca cctaaaatct actcagcgtc ggcaaaggag ccatgggttc    2580
tagcaactaa cttacctgtt gaaattcgaa cacccaaaca acttgttaat atctattcga    2640
agcgaatgca gattgaagaa accttccgag acttgaaaag tcctgcctac ggactaggcc    2700
tacgccatag ccgaacgagc agctcagagc gttttgatat catgctgcta atcgccctga    2760
tgcttcaact aacatgttgg cttgcgggcg ttcatgctca gaaacaaggt tgggacaagc    2820
acttccaggc taacacagtc agaaatcgaa acgtactctc aacagttcgc ttaggcatgg    2880
aagttttgcg gcattctggc tacacaataa caagggaaga cttactcgtg gctgcaaccc    2940
tactagctca aaatttattc acacatggtt acgctttggg gaaattatga taatgatcca    3000
gatcacttct ggctaataaa agatcagagc tctagagatc tgtgtgttgg ttttttgtgg    3060
atctgctgtg ccttctagtt gccagccatc tgttgtttgc ccctcccccg tgccttcctt    3120 gacccctggaa ggtgccactc ccactgtcct ttcctaataa aatgaggaaa ttgcatcgca    3180
ttgtctgagt aggtgtcatt ctattctggg gggtggggtg gggcagcaca gcaaggggga    3240
ggattgggaa gacaatagca ggcatgctgg ggatgcggtg ggctctatgg gtacctctct    3300
ctctctctct ctctctctct ctctctctct ctctcggtac ctctctctct ctctctctct    3360
ctctctctct ctctctctct cggtaccagg tgctgaagaa ttgacccggt gaccaaaggt    3420 gcctttatc atcactttaa aaataaaaaa caattactca gtgcctgtta taagcagcaa    3480
ttaattatga ttgatgccta catcacaaca aaaactgatt taacaaatgg ttggtctgcc    3540
ttagaaagta tatttgaaca ttatcttgat tatattattg ataataataa aaaccttatc    3600
cctatccaag aagtgatgcc tatcattggt tggaatgaac ttgaaaaaaa ttagccttga    3660
atacattact ggtaaggtaa acgccattgt cagcaaattg atccaagaga accaacttaa    3720
agctttcctg acggaatgtt aattctcgtt gaccctgagc actgatgaat cccctaatga    3780
ttttggtaaa aatcattaag ttaaggtgga tacacatctt gtcatatgat cccggtaatg    3840
tgagttagct cactcattag gcaccccagg ctttacactt tatgcttccg gctcgtatgt    3900
tgtgtggaat tgtgagcgga taacaatttc acacaggaaa cagctatgac catgattacg    3960
ccaagcgcgc aattaaccct cactaaaggg aacaaaagct ggagctccac cgcggtggcg    4020
gccgctctag aactagtgga tcccccgggg aggtcagaat ggtttcttta ctgtttgtca    4080
attctattat ttcaatacag aacaatagct tctataactg aaatatattt gctattgtat    4140
attatgattg tccctcgaac catgaacact cctccagctg aatttcacaa ttcctctgtc    4200
atctgccagg ccattaagtt attcatggaa gatctttgag gaacactgca agttcatatc    4260
ataaacacat ttgaaattga gtattgtttt gcattgtatg gagctatgtt ttgctgtatc    4320
ctcagaaaaa aagtttgtta taaagcattc acacccataa aagatagat ttaaatattc    4380 cagctatagg aaagaaagtg cgtctgctct tcactctagt ctcagttggc tccttcacat    4440
gcatgcttct ttatttctcc tatttttgtca agaaaataat aggtcacgtc ttgttctcac    4500
ttatgtcctg cctagcatgg ctcagatgca cgttgtagat acaagaagga tcaaatgaaa    4560
cagacttctg gtctgttact acaaccatag taataagcac actaactaat aattgctaat    4620
tatgttttcc atctctaagg ttcccacatt tttctgtttt cttaaagatc ccattatctg    4680
gttgtaactg aagctcaatg gaacatgagc aatatttccc agtcttctct cccatccaac    4740
agtcctgatg gattagcaga acaggcagaa aacacattgt tacccagaat taaaaactaa    4800
tatttgctct ccattcaatc caaaatggac ctattgaaac taaaatctaa cccaatccca    4860
```

-continued

```
ttaaatgatt tctatggcgt caaaggtcaa acttctgaag ggaacctgtg ggtgggtcac    4920
aattcaggct atatattccc cagggctcag cggatccatg ggctccatcg gcgcagcaag    4980
catggaattt tgttttgatg tattcaagga gctcaaagtc caccatgcca atgagaacat    5040
cttctactgc cccattgcca tcatgtcagc tctagccatg gtatacctgg gtgcaaaaga    5100
cagcaccagg acacagataa ataaggttgt tcgctttgat aaacttccag gattcggaga    5160
cagtattgaa gctcagtgtg gcacatctgt aaacgttcac tcttcactta gagacatcct    5220
caaccaaatc accaaaccaa atgatgttta ttcgttcagc cttgccagta gactttatgc    5280
tgaagagaga tacccaatcc tgccagaata cttgcagtgt gtgaaggaac tgtatagagg    5340
aggcttggaa cctatcaact ttcaaacagc tgcagatcaa gccagagagc tcatcaattc    5400
ctgggtagaa agtcagacaa atggaattat cagaaatgtc cttcagccaa gctccgtgga    5460
ttctcaaact gcaatggttc tggttaatgc cattgtcttc aaaggactgt gggagaaaac    5520
atttaaggat gaagacacac aagcaatgcc tttcagagtg actgagcaag aaagcaaacc    5580
tgtgcagatg atgtaccaga ttggtttatt tagagtggca tcaatggctt ctgagaaaat    5640
gaagatcctg gagcttccat tgccagtgg gacaatgagc atgttggtgc tgttgcctga    5700
tgaagtctca ggccttgagc agcttgagag tataatcaac tttgaaaaac tgactgaatg    5760
gaccagttct aatgttatgg aagagaggaa gatcaaagtg tacttacctc gcatgaagat    5820
ggaggaaaaa tacaacctca catctgtctt aatggctatg gcattactg acgtgtttag    5880 ctcttcagcc aatctgtctg gcatctcctc agcagagagc ctgaagatat ctcaagctgt    5940
ccatgcagca catgcagaaa tcaatgaagc aggcagagag gtggtagggt cagcagaggc    6000
tggagtggat gctgcaagcg tctctgaaga atttagggct gaccatccat tcctcttctg    6060
tatcaagcac atcgcaacca acgccgttct cttctttggc agatgtgttt ccccctccgcg    6120 gccagcagat gacgcaccag cagatgacgc accagcagat gacgcaccag cagatgacgc    6180
accagcagat gacgcaccag cagatgacgc aacaacatgt atcctgaaag gctcttgtgg    6240
ctggatcggc ctgctggatg acgatgacaa atttgtgaac caacacctgt gcggctcaca    6300
cctggtggaa gctctctacc tagtgtgcgg ggaacgagcc ttcttctaca cacccaagac    6360
ccgccgggag gcagaggacc tgcaggtggg gcaggtggag ctgggcgggg ccctggtgc    6420 aggcagcctg cagcccttgg ccctggaggg gtccctgcag aagcgtggca ttgtggaaca    6480
atgctgtacc agcatctgct ccctctacca gctggagaac tactgcaact agggcgcctg    6540
gatccagatc acttctggct aataaaagat cagagctcta gagatctgtg tgttggtttt    6600
ttgtggatct gctgtgcctt ctagttgcca gccatctgtt gtttgcccct cccccgtgcc    6660
ttccttgacc ctggaaggtg ccactcccac tgtcctttcc taataaaatg aggaaattgc    6720
atcgcattgt ctgagtaggt gtcattctat tctgggggggt ggggtggggc agcacagcaa    6780
gggggaggat tgggaagaca atagcaggca tgctggggat gcggtgggct ctatgggtac    6840
ctctctctct ctctctctct ctctctctct ctctctctct cggtacctct ctcgaggggg    6900
ggcccggtac ccaattcgcc ctatagtgag tcgtattacg cgcgctcact ggccgtcgtt    6960
ttacaacgtc gtgactggga aaaccctggc gttacccaac ttaatcgcct tgcagcacat    7020
ccccctttcg ccagctggcg taatagcgaa gaggcccgca ccgatcgccc ttcccaacag    7080
ttgcgcagcc tgaatggcga atggaaattg taagcgttaa tattttgtta aaattcgcgt    7140 taaattttttg ttaaatcagc tcatttttta accaataggc cgaaatcggc aaaatccctt    7200
ataaatcaaa agaatagacc gagatagggt tgagtgttgt tccagtttgg aacaagagtc    7260
```

```
cactattaaa gaacgtggac tccaacgtca aagggcgaaa aaccgtctat cagggcgatg   7320
gcccactact ccgggatcat atgacaagat gtgtatccac cttaacttaa tgattttac    7380 caaaatcatt aggggattca tcagtgctca gggtcaacga gaattaacat tccgtcagga   7440
aagcttatga tgatgatgtg cttaaaaact tactcaatgg ctggttatgc atatcgcaat   7500
acatgcgaaa aacctaaaag agcttgccga taaaaaggc caatttattg ctatttaccg    7560
cggcttttta ttgagcttga aagataaata aaatagatag gtttatttg aagctaaatc     7620 ttctttatcg taaaaaatgc cctcttgggt tatcaagagg gtcattatat ttcgcggaat   7680
aacatcattt ggtgacgaaa taactaagca cttgtctcct gtttactccc ctgagcttga   7740
ggggttaaca tgaaggtcat cgatagcagg ataataatac agtaaaacgc taaaccaata   7800
atccaaatcc agccatccca aattggtagt gaatgattat aaataacagc aaacagtaat   7860 ggccaataa  caccggttgc attggtaagg ctcaccaata atccctgtaa agcaccttgc   7920
tgatgactct ttgtttggat agacatcact ccctgtaatg caggtaaagc gatcccacca   7980
ccagccaata aaattaaaac agggaaaact aaccaaccct cagatataaa cgctaaaaag   8040
gcaaatgcac tactatctgc aataaatccg agcagtactg ccgttttttc gccccattta   8100
gtggctattc ttcctgccac aaaggcttgg aatactgagt gtaaaagacc aagacccgct   8160
aatgaaaagc caaccatcat gctattccat ccaaaacgat tttcggtaaa tagcacccac   8220
accgttgcgg gaatttggcc tatcaattgc gctgaaaaat aaataatcaa caaaatggca   8280
tcgttttaaa taaagtgatg tataccgaat tcagcttttg ttccctttag tgagggttaa   8340
ttgcgcgctt ggcgtaatca tggtcatagc tgtttcctgt gtgaaattgt tatccgctca   8400
caattccaca caacatacga gccggaagca taaagtgtaa agcctggggt gcctaatgag   8460
tgagctaact cacattaatt gcgttgcgct cactgcccgc tttccagtcg ggaaacctgt   8520
cgtgccagct gcattaatga atcggccaac gcgcggggag aggcggtttg cgtattgggc   8580
gctcttccgc ttcctcgctc actgactcgc tgcgctcggt cgttcggctg cggcgagcgg   8640
tatcagctca ctcaaaggcg gtaatacggt tatccacaga atcaggggat aacgcaggaa   8700
agaacatgtg agcaaaaggc cagcaaaagg ccaggaaccg taaaaaggcc gcgttgctgg   8760
cgttttccca taggctccgc cccctgacg  agcatcacaa aaatcgacgc tcaagtcaga   8820
ggtggcgaaa cccgacagga ctataaagat accaggcgtt tccccctgga agctccctcg   8880
tgcgctctcc tgttccgacc ctgccgctta ccggatacct gtccgccttt ctcccttcgg   8940
gaagcgtggc gctttctcat agctcacgct gtaggtatct cagttcggtg taggtcgttc   9000
gctccaagct gggctgtgtg cacgaacccc ccgttcagcc cgaccgctgc gccttatccg    9060
gtaactatcg tcttgagtcc aacccggtaa gacacgactt atcgccactg gcagcagcca   9120
ctggtaacag gattagcaga gcgaggtatg taggcggtgc tacagagttc ttgaagtggt   9180
ggcctaacta cggctacact agaaggacag tatttggtat ctgcgctctg ctgaagccag   9240
ttaccttcgg aaaaagagtt ggtagctctt gatccggcaa acaaaccacc gctggtagcg   9300
gtggtttttt tgtttgcaag cagcagatta cgcgcagaaa aaaaggatct caagaagatc   9360
ctttgatctt ttctacgggg tctgacgctc agtggaacga aaactcacgt taagggattt   9420
tggtcatgag attatcaaaa aggatcttca cctagatcct ttaaattaa  aaatgaagtt   9480 ttaaatcaat ctaaagtata tatgagtaaa cttggtctga cagttaccaa tgcttaatca   9540
gtgaggcacc tatctcagcg atctgtctat ttcgttcatc catagttgcc tgactccccg   9600
tcgtgtagat aactacgata cgggagggct taccatctgg ccccagtgct gcaatgatac   9660
```

| | |
|---|---|
| cgcgagaccc acgctcaccg gctccagatt tatcagcaat aaaccagcca gccggaaggg | 9720 |
| ccgagcgcag aagtggtcct gcaactttat ccgcctccat ccagtctatt aattgttgcc | 9780 |
| gggaagctag agtaagtagt tcgccagtta atagtttgcg caacgttgtt gccattgcta | 9840 |
| caggcatcgt ggtgtcacgc tcgtcgtttg gtatggcttc attcagctcc ggttcccaac | 9900 |
| gatcaaggcg agttacatga tcccccatgt tgtgcaaaaa agcggttagc tccttcggtc | 9960 |
| ctccgatcgt tgtcagaagt aagttggccg cagtgttatc actcatggtt atggcagcac | 10020 |
| tgcataattc tcttactgtc atgccatccg taagatgctt ttctgtgact ggtgagtact | 10080 |
| caaccaagtc attctgagaa tagtgtatgc ggcgaccgag ttgctcttgc ccggcgtcaa | 10140 |
| tacgggataa taccgcgcca catagcagaa ctttaaaagt gctcatcatt ggaaaacgtt | 10200 |
| cttcggggcg aaaactctca aggatcttac cgctgttgag atccagttcg atgtaaccca | 10260 |
| ctcgtgcacc caactgatct tcagcatctt ttactttcac cagcgtttct gggtgagcaa | 10320 |
| aaacaggaag gcaaaatgcc gcaaaaaagg aataagggc gacacggaaa tgttgaatac | 10380 |
| tcatactctt cctttttcaa tattattgaa gcatttatca gggttattgt ctcatgagcg | 10440 |
| gatacatatt tgaatgtatt tagaaaaata aacaaatagg ggttccgcgc acatttcccc | 10500 |
| gaaaagtgcc ac | 10512 |

<210> SEQ ID NO 43
<211> LENGTH: 11255
<212> TYPE: DNA
<213> ORGANISM: Artificial Sequence
<220> FEATURE:
<223> OTHER INFORMATION: Synthetic

<400> SEQUENCE: 43

| | |
|---|---|
| ctgacgcgcc ctgtagcggc gcattaagcg cggcggtgt ggtggttacg cgcagcgtga | 60 |
| ccgctacact tgccagcgcc ctagcgcccg ctcctttcgc tttcttccct tcctttctcg | 120 |
| ccacgttcgc cggcatcaga ttggctattg gccattgcat acgttgtatc catatcataa | 180 |
| tatgtacatt tatattggct catgtccaac attaccgcca tgttgacatt gattattgac | 240 |
| tagttattaa tagtaatcaa ttacggggtc attagttcat agcccatata tggagttccg | 300 |
| cgttacataa cttacggtaa atggcccgcc tggctgaccg cccaacgacc cccgcccatt | 360 |
| gacgtcaata atgacgtatg ttcccatagt aacgccaata gggactttcc attgacgtca | 420 |
| atgggtggag tatttacggt aaactgccca cttggcagta catcaagtgt atcatatgcc | 480 |
| aagtacgccc cctattgacg tcaatgacgg taaatggccc gcctggcatt atgcccagta | 540 |
| catgacctta tgggactttc ctacttggca gtacatctac gtattagtca tcgctattac | 600 |
| catggtgatg cggttttggc agtacatcaa tgggcgtgga tagcggtttg actcacgggg | 660 |
| atttccaagt ctccacccca ttgacgtcaa tgggagtttg ttttggcacc aaaatcaacg | 720 |
| ggactttcca aaatgtcgta caactccgc cccattgacg caaatgggcg gtaggcgtgt | 780 |
| acggtgggag gtctatataa gcagagctcg tttagtgaac cgtcagatcg cctggagacg | 840 |
| ccatccacgc tgttttgacc tccatagaag acaccgggac cgatccagcc tccgcggccg | 900 |
| ggaacggtgc attggaacgc ggattccccg tgccaagagt gacgtaagta ccgcctatag | 960 |
| actctatagg cacaccccett tggctcttat gcatgctata ctgttttgg cttgggcct | 1020 |
| atacaccccc gcttccttat gctataggtg atggtatagc ttagcctata ggtgtgggtt | 1080 |
| attgaccatt attgaccact cccctattgg tgacgatact ttccattact aatccataac | 1140 |
| atggctcttt gccacaacta tctctattgg ctatatgcca atactctgtc cttcagagac | 1200 |

```
tgacacggac tctgtatttt tacaggatgg ggtcccattt attatttaca aattcacata   1260
tacaacaacg ccgtcccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtcgga ccatgtgtga acttgatatt   1800
ttacatgatt ctctttacca attctgcccc gaattacact taaaacgact caacagctta   1860
acgttggctt gccacgcatt acttgactgt aaaactctca ctcttaccga acttggccgt   1920
aacctgccaa ccaaagcgag aacaaaacat aacatcaaac gaatcgaccg attgttaggt   1980
aatcgtcacc tccacaaaga gcgactcgct gtataccgtt ggcatgctag ctttatctgt   2040
tcgggcaata cgatgcccat tgtacttgtt gactggtctg atattcgtga gcaaaaacga   2100
cttatggtat tgcgagcttc agtcgcacta cacggtcgtt ctgttactct ttatgagaaa   2160
gcgttcccgc tttcagagca atgttcaaag aaagctcatg accaatttct agccgacctt   2220
gcgagcattc taccgagtaa caccacaccg ctcattgtca gtgatgctgg ctttaaagtg   2280
ccatggtata aatccgttga gaagctgggt tggtactggt taagtcgagt aagaggaaaa   2340
gtacaatatg cagacctagg agcggaaaac tggaaaccta tcagcaactt acatgatatg   2400
tcatctagtc actcaaagac tttaggctat aagaggctga ctaaaagcaa tccaatctca   2460
tgccaaattc tattgtataa atctcgctct aaaggccgaa aaaatcagcg ctcgacacgg   2520
actcattgtc accacccgtc acctaaaatc tactcagcgt cggcaaagga gccatgggtt   2580
ctagcaacta acttacctgt tgaaattcga acacccaaac aacttgttaa tatctattcg   2640
aagcgaatgc agattgaaga aaccttccga gacttgaaaa gtcctgccta cggactaggc   2700
ctacgccata gccgaacgag cagctcagag cgttttgata tcatgctgct aatcgccctg   2760
atgcttcaac taacatgttg gcttgcgggc gttcatgctc agaaacaagg ttgggacaag   2820
cacttccagg ctaacacagt cagaaatcga aacgtactct caacagttcg cttaggcatg   2880
gaagttttgc ggcattctgg ctacacaata acaaggggaag acttactcgt ggctgcaacc   2940
ctactagctc aaaatttatt cacacatggt tacgctttgg ggaaattatg ataatgatcc   3000
agatcacttc tggctaataa aagatcagag ctctagagat ctgtgtgttg gttttttgtg   3060
gatctgctgt gccttctagt tgccagccat ctgttgtttg ccctccccc gtgccttcct   3120 tgaccctgga aggtgccact cccactgtcc tttcctaata aaatgaggaa attgcatcgc   3180
attgtctgag taggtgtcat tctattctgg ggggtggggt ggggcagcac agcaaggggg   3240
aggattggga agacaatagc aggcatgctg gggatgcggt gggctctatg ggtacctctc   3300
tctctctctc tctctctctc tctctctctc tctctcggta cctctctctc tctctctctc   3360
tctctctctc tctctctctc tcggtaccag gtgctgaaga attgacccgg tgaccaaagg   3420 tgcctttat catcacttta aaataaaaa acaattactc agtgcctgtt ataagcagca   3480
attaattatg attgatgcct acatcacaac aaaaactgat ttaacaaatg gttggtctgc   3540
cttagaaagt atatttgaac attatcttga ttatattatt gataataata aaaaccttat   3600
```

```
ccctatccaa gaagtgatgc ctatcattgg ttggaatgaa cttgaaaaaa attagccttg    3660
aatacattac tggtaaggta aacgccattg tcagcaaatt gatccaagag aaccaactta    3720
aagctttcct gacggaatgt taattctcgt tgaccctgag cactgatgaa tccctaatg     3780
attttggtaa aaatcattaa gttaaggtgg atacacatct tgtcatatga tcccggtaat    3840
gtgagttagc tcactcatta ggcaccccag gctttacact ttatgcttcc ggctcgtatg    3900
ttgtgtggaa ttgtgagcgg ataacaattt cacacaggaa acagctatga ccatgattac    3960
gccaagcgcg caattaaccc tcactaaagg gaacaaaagc tggagctcca ccgcggtggc    4020
ggccgctcta gaactagtgg atccccggg catcagattg gctattggcc attgcatacg     4080
ttgtatccat atcataatat gtacatttat attggctcat gtccaacatt accgccatgt    4140
tgacattgat tattgactag ttattaatag taatcaatta cggggtcatt agttcatagc    4200
ccatatatgg agttccgcgt tacataactt acggtaaatg gcccgcctgg ctgaccgccc    4260
aacgaccccc gcccattgac gtcaataatg acgtatgttc ccatagtaac gccaataggg    4320
actttccatt gacgtcaatg ggtggagtat ttacggtaaa ctgcccactt ggcagtacat    4380
caagtgtatc atatgccaag tacgccccct attgacgtca atgacggtaa atggcccgcc    4440
tggcattatg cccagtacat gaccttatgg gactttccta cttggcagta catctacgta    4500
ttagtcatcg ctattaccat ggtgatgcgg ttttggcagt acatcaatgg gcgtggatag    4560
cggtttgact cacggggatt tccaagtctc cacccccattg acgtcaatgg gagtttgttt    4620
tggcaccaaa atcaacggga ctttccaaaa tgtcgtaaca actccgcccc attgacgcaa    4680
atgggcggta ggcgtgtacg gtgggaggtc tatataagca gagctcgttt agtgaaccgt    4740
cagatcgcct ggagacgcca tccacgctgt tttgacctcc atagaagaca ccgggaccga    4800
tccagcctcc gcggccggga acggtgcatt ggaacgcgga ttccccgtgc caagagtgac    4860
gtaagtaccg cctatagact ctataggcac accccttttgg ctcttatgca tgctatactg    4920
tttttggctt ggggcctata caccccgct tccttatgct ataggtgatg gtatagctta     4980
gcctataggt gtgggttatt gaccattatt gaccactccc ctattggtga cgatactttc    5040
cattactaat ccataacatg gctctttgcc acaactatct ctattggcta tatgccaata    5100
ctctgtcctt cagagactga cacggactct gtattttac aggatgggt cccatttatt      5160
atttacaaat tcacatatac aacaacgccg tccccgtgc ccgcagtttt tattaaacat     5220
agcgtgggat ctccacgcga atctcgggta cgtgttccgg acatgggctc ttctccggta    5280
gcggcggagc ttccacatcc gagccctggt cccatgcctc cagcggctca tggtcgctcg    5340
gcagctcctt gctcctaaca gtggaggcca gacttaggca cagcacaatg cccaccacca    5400
ccagtgtgcc gcacaaggcc gtggcggtag ggtatgtgtc tgaaaatgag cgtggagatt    5460
gggctcgcac ggctgacgca gatggaagac ttaaggcagc ggcagaagaa gatgcaggca    5520
gctgagttgt tgtattctga taagagtcag aggtaactcc cgttgcggtg ctgttaacgg    5580
tggagggcag tgtagtctga gcagtactcg ttgctgccgc gcgcgccacc agacataata    5640
gctgacagac taacagactg ttcctttcca tgggtctttt ctgcagtcac cgtcggatca    5700
atgggctcca tcggtgcagc aagcatggaa ttttgttttg atgtattcaa ggagctcaaa    5760
gtccaccatg ccaatgagaa catcttctac tgccccattg ccatcatgtc agctctagcc    5820
atggtatacc tgggtgcaaa agacagcacc aggacacaaa taataaggt tgttcgcttt      5880
gataaacttc caggattcgg agacagtatt gaagctcagt gtggcacatc tgtaaacgtt    5940
cactcttcac ttagagacat cctcaaccaa atcaccaaac caaatgatgt ttattcgttc    6000
```

```
agccttgcca gtagacttta tgctgaagag agatacccaa tcctgccaga atacttgcag   6060
tgtgtgaagg aactgtatag aggaggcttg gaacctatca actttcaaac agctgcagat   6120
caagccagag agctcatcaa ttcctgggta gaaagtcaga caaatggaat tatcagaaat   6180
gtccttcagc caagctccgt ggattctcaa actgcaatgg ttctggttaa tgccattgtc   6240
ttcaaaggac tgtgggagaa agcatttaag gatgaagaca cacaagcaat gcctttcaga   6300
gtgactgagc aagaaagcaa acctgtgcag atgatgtacc agattggttt atttagagtg   6360
gcatcaatgg cttctgagaa aatgaagatc ctggagcttc catttgccag tgggacaatg   6420
agcatgttgg tgctgttgcc tgatgaagtc tcaggccttg agcagcttga gagtataatc   6480
aactttgaaa aactgactga atggaccagt tctaatgtta tggaagagag aagatcaaag   6540
tgtacttacc tcgcatgaag atggaggaaa aatacaacct cacatctgtc ttaatggcta   6600
tgggcattac tgacgtgttt agctcttcag ccaatctgtc tggcatctcc tcagcagaga   6660
gcctgaagat atctcaagct gtccatgcag cacatgcaga aatcaatgaa gcaggcagag   6720
aggtggtagg gtcagcagag gctggagtgg atgctgcaag cgtctctgaa gaatttaggg   6780
ctgaccatcc attcctcttc tgtatcaagc acatcgcaac caacgccgtt ctcttctttt   6840
ggcagatgtg tttcccgcgg ccagcagatg acgcaccagc agatgacgca ccagcagatg   6900
acgcaccagc agatgacgca ccagcagatg acgcaacaac atgtatcctg aaaggctctt   6960
gtggctggat cggcctgctg gatgacgatg acaaatttgt gaaccaacac ctgtgcggct   7020
cacacctggt ggaagctctc tacctagtgt gcggggaacg aggcttcttc tacacaccca   7080
agacccgccg ggaggcagag gacctgcagg tgggcaggt ggagctgggc ggggccctg   7140 gtgcaggcag cctgcagccc ttggccctgg aggggtccct gcagaagcgt ggcattgtgg   7200
aacaatgctg taccagcatc tgctccctct accagctgga gaactactgc aactagggcg   7260
cctaaagggc gaattatcgc ggccgctcta gaccaggcgc ctggatccag atcacttctg   7320
gctaataaaa gatcagagct ctagagatct gtgtgttggt tttttgtgga tctgctgtgc   7380
cttctagttg ccagccatct gttgtttgcc cctcccccgt gccttccttg accctggaag   7440
gtgccactcc cactgtcctt tcctaataaa atgaggaaat tgcatcgcat tgtctgagta   7500
ggtgtcattc tattctgggg gtggggtgg ggcagcacag caaggggag gattgggaag   7560 acaatagcag gcatgctggg gatgcggtgg gctctatggg tacctctctc tctctctctc   7620
tctctctcac tctctctctc tctcggtacc tctcctcgag ggggggcccg gtacccaatt   7680
cgccctatag tgagtcgtat tacgcgcgct cactggccgt cgttttacaa cgtcgtgact   7740
gggaaaaccc tggcgttacc caacttaatc gccttgcagc acatccccct ttcgccagct   7800
ggcgtaatag cgaagaggcc cgcaccgatc gcccttccca acagttgcgc agcctgaatg   7860
gcgaatggaa attgtaagcg ttaatatttt gttaaaattc gcgttaaatt tttgttaaat   7920
cagctcattt tttaaccaat aggccgaaat cggcaaaatc ccttataaat caaaagaata   7980
gaccgagata gggttgagtg ttgttccagt ttggaacaag agtccactat taaagaacgt   8040
ggactccaac gtcaaaggc gaaaaaccgt ctatcagggc gatggcccac tactccggga   8100
tcatatgaca agatgtgtat ccaccttaac ttaatgattt ttaccaaaat cattagggga   8160
ttcatcagtg ctcagggtca acgagaatta acattccgtc aggaaagctt atgatgatga   8220
tgtgcttaaa aacttactca atggctggtt atgcatatcg caatacatgc gaaaaaccta   8280
aaagagcttg ccgataaaaa aggccaattt attgctattt accgcggctt tttattgagc   8340
ttgaaagata aataaaatag ataggtttta tttgaagcta aatcttcttt atcgtaaaaa   8400
```

```
atgccctctt gggttatcaa gagggtcatt atatttcgcg gaataacatc atttggtgac   8460
gaaataacta agcacttgtc tcctgtttac tcccctgagc ttgaggggtt aacatgaagg   8520
tcatcgatag caggataata atacagtaaa acgctaaacc aataatccaa atccagccat   8580
cccaaattgg tagtgaatga ttataaataa cagcaaacag taatgggcca ataacaccgg   8640
ttgcattggt aaggctcacc aataatccct gtaaagcacc ttgctgatga ctctttgttt   8700
ggatagacat cactccctgt aatgcaggta aagcgatccc accaccagcc aataaaatta   8760
aaacagggaa aactaaccaa ccttcagata taaacgctaa aaaggcaaat gcactactat   8820
ctgcaataaa tccgagcagt actgccgttt tttcgcccat ttagtggcta ttcttcctgc   8880
cacaaaggct tggaatactg agtgtaaaag accaagaccc gtaatgaaaa gccaaccatc   8940
atgctattca tcatcacgat ttctgtaata gcaccacacc gtgctggatt ggctatcaat   9000
gcgctgaaat aataatcaac aaatggcatc gttaaataag tgatgtatac cgatcagctt   9060
ttgttccctt tagtgagggt taattgcgcg cttggcgtaa tcatggtcat agctgtttcc   9120
tgtgtgaaat tgttatccgc tcacaattcc acacaacata cgagccggaa gcataaagtg   9180
taaagcctgg ggtgcctaat gagtgagcta actcacatta attgcgttgc gctcactgcc   9240
cgctttccag tcgggaaacc tgtcgtgcca gctgcattaa tgaatcggcc aacgcgcggg   9300
gagaggcggt ttgcgtattg ggcgctcttc cgcttcctcg ctcactgact cgctgcgctc   9360
ggtcgttcgg ctgcggcgag cggtatcagc tcactcaaag gcggtaatac ggttatccac   9420
agaatcaggg gataacgcag gaaagaacat gtgagcaaaa ggccagcaaa aggccaggaa   9480
ccgtaaaaag gccgcgttgc tggcgttttt ccataggctc cgcccccctg acgagcatca   9540
caaaatcga cgctcaagtc agaggtggcg aaacccgaca ggactataaa gataccaggc   9600
gtttccccct ggaagctccc tcgtgcgctc tcctgttccg accctgccgc ttaccggata   9660
cctgtccgcc tttctccctt cgggaagcgt ggcgctttct catagctcac gctgtaggta   9720
tctcagttcg gtgtaggtcg ttcgctccaa gctgggctgt gtgcacgaac ccccgttca   9780
gcccgaccgc tgcgccttat ccggtaacta tcgtcttgag tccaacccgg taagacacga   9840
cttatcgcca ctggcagcag ccactggtaa caggattagc agagcgaggt atgtaggcgg   9900
tgctacagag ttcttgaagt ggtggcctaa ctacggctac actagaagga cagtatttgg   9960
tatctgcgct ctgctgaagc cagttacctt cggaaaaaga gttggtagct cttgatccgg  10020
caaacaaacc accgctggta gcggtggttt ttttgtttgc aagcagcaga ttacgcgcag  10080
aaaaaaagga tctcaagaag atcctttgat cttttctacg gggtctgacg ctcagtggaa  10140
cgaaaactca cgttaaggga ttttggtcat gagattatca aaaaggatct tcacctagat  10200
ccttttaaat taaaaatgaa gttttaaatc aatctaaagt atatatgagt aaacttggtc  10260
tgacagttac caatgcttaa tcagtgaggc acctatctca gcgatctgtc tatttcgttc  10320
atccatagtt gcctgactcc ccgtcgtgta gataactacg atacgggagg gcttaccatc  10380
tggccccagt gctgcaatga taccgcgaga cccacgctca ccggctccag atttatcagc  10440
aataaaccag ccagccggaa gggccgagcg cagaagtggt cctgcaactt tatccgcctc  10500
catccagtct attaattgtt gccgggaagc tagagtaagt agttcgccag ttaatagttt  10560
gcgcaacgtt gttgccattg ctacaggcat cgtggtgtca cgctcgtcgt ttggtatggc  10620
ttcattcagc tccggttccc aacgatcaag gcgagttaca tgatccccca tgttgtgcaa  10680
aaaagcggtt agctccttcg gtcctccgat cgttgtcaga agtaagttgg ccgcagtgtt  10740
atcactcatg gttatggcag cactgcataa ttctcttact gtcatgccat ccgtaagatg  10800
```

| | |
|---|---|
| cttttctgtg actggtgagt actcaaccaa gtcattctga aatagtgta tgcggcgacc | 10860 |
| gagttgctct tgcccggcgt caatacggga taataccgcg ccacatagca gaactttaaa | 10920 |
| agtgctcatc attggaaaac gttcttcggg gcgaaaactc tcaaggatct taccgctgtt | 10980 |
| gagatccagt tcgatgtaac ccactcgtgc acccaactga tcttcagcat ctttacttt | 11040 |
| caccagcgtt tctgggtgag caaaaacagg aaggcaaaat gccgcaaaaa agggaataag | 11100 |
| ggcgacacgg aaatgttgaa tactcatact cttccttttt caatattatt gaagcattta | 11160 |
| tcagggttat tgtctcatga gcggatacat atttgaatgt atttagaaaa ataaacaaat | 11220 |
| aggggttccg cgcacatttc cccgaaaagt gccac | 11255 |

<210> SEQ ID NO 44
<211> LENGTH: 10487
<212> TYPE: DNA
<213> ORGANISM: Artificial Sequence
<220> FEATURE:
<223> OTHER INFORMATION: Synthetic

<400> SEQUENCE: 44

| | |
|---|---|
| ctgacgcgcc ctgtagcggc gcattaagcg cggcgggtgt ggtggttacg cgcagcgtga | 60 |
| ccgctacact tgccagcgcc ctagcgcccg ctcctttcgc tttcttccct tcctttctcg | 120 |
| ccacgttcgc cggcatcaga ttggctattg gccattgcat acgttgtatc catatcataa | 180 |
| tatgtacatt tatattggct catgtccaac attaccgcca tgttgacatt gattattgac | 240 |
| tagttattaa tagtaatcaa ttacggggtc attagttcat agcccatata tggagttccg | 300 |
| cgttacataa cttacggtaa atggcccgcc tggctgaccg cccaacgacc cccgcccatt | 360 |
| gacgtcaata atgacgtatg ttcccatagt aacgccaata gggactttcc attgacgtca | 420 |
| atgggtggag tatttacggt aaactgccca cttggcagta catcaagtgt atcatatgcc | 480 |
| aagtacgccc cctattgacg tcaatgacgg taaatggccc gcctggcatt atgcccagta | 540 |
| catgacctta tgggactttc ctacttggca gtacatctac gtattagtca tcgctattac | 600 |
| catggtgatg cggttttggc agtacatcaa tgggcgtgga tagcggtttg actcacgggg | 660 |
| atttccaagt ctccacccca ttgacgtcaa tgggagtttg ttttggcacc aaaatcaacg | 720 |
| ggactttcca aaatgtcgta acaactccgc cccattgacg caaatgggcg gtaggcgtgt | 780 |
| acggtgggag gtctatataa gcagagctcg tttagtgaac cgtcagatcg cctggagacg | 840 |
| ccatccacgc tgttttgacc tccatagaag acaccgggac cgatccagcc tccgcggccg | 900 |
| ggaacggtgc attggaacgc ggattccccg tgccaagagt gacgtaagta ccgcctatag | 960 |
| actctatagg cacaccccct tggctcttat gcatgctata ctgtttttgg cttggggcct | 1020 |
| atacaccccc gcttccttat gctataggtg atggtatagc ttagcctata ggtgtgggtt | 1080 |
| attgaccatt attgaccact cccctattgg tgacgatact ttccattact aatccataac | 1140 |
| atggctcttt gccacaacta tctctattgg ctatatgcca atactctgtc cttcagagac | 1200 |
| tgacacggac tctgtatttt tacaggatgg ggtcccattt attatttaca aattcacata | 1260 |
| tacaacaacg ccgtccccccg tgcccgcagt ttttattaaa catagcgtgg gatctccacg | 1320 |
| cgaatctcgg gtacgtgttc cggacatggg ctcttctccg gtagcggcgg agcttccaca | 1380 |
| tccgagccct ggtccatgc ctccagcggc tcatggtcgc tcggcagctc cttgctccta | 1440 |
| acagtggagg ccagacttag gcacagcaca atgcccacca ccaccagtgt gccgcacaag | 1500 |
| gccgtggcgg tagggtatgt gtctgaaaat gagcgtggag attgggctcg cacggctgac | 1560 |
| gcagatggaa gacttaaggc agcggcagaa gaagatgcag gcagctgagt tgttgtattc | 1620 |

```
tgataagagt cagaggtaac tcccgttgcg gtgctgttaa cggtggaggg cagtgtagtc    1680
tgagcagtac tcgttgctgc cgcgcgcgcc accagacata atagctgaca gactaacaga    1740 ctgttcctttt ccatgggtct tttctgcagt caccgtcgga ccatgtgtga acttgatatt   1800
ttacatgatt ctctttacca attctgcccc gaattacact aaaacgact caacagctta    1860 acgttggctt gccacgcatt acttgactgt aaaactctca ctcttaccga acttggccgt    1920
aacctgccaa ccaaagcgag aacaaaacat aacatcaaac gaatcgaccg attgttaggt    1980
aatcgtcacc tccacaaaga gcgactcgct gtataccgtt ggcatgctag ctttatctgt    2040
tcgggaatac gatgcccatt gtacttgttg actggtctga tattcgtgag caaaaacgac    2100
ttatggtatt gcgagcttca gtcgcactac acggtcgttc tgttactctt tatgagaaag    2160
cgttcccgct ttcagagcaa tgttcaaaga aagctcatga ccaatttcta gccgaccttg    2220
cgagcattct accgagtaac accacaccgc tcattgtcag tgatgctggc tttaaagtgc    2280
catggtataa atccgttgag aagctgggtt ggtactggtt aagtcgagta agaggaaaag    2340
tacaatatgc agacctagga gcggaaaact ggaaacctat cagcaactta catgatatgt    2400
catctagtca ctcaaagact ttaggctata agaggctgac taaaagcaat ccaatctcat    2460
gccaaattct attgtataaa tctcgctcta aaggccgaaa aaatcagcgc tcgacacgga    2520
ctcattgtca ccaccgtca cctaaaatct actcagcgtc ggcaaaggag ccatgggttc    2580
tagcaactaa cttacctgtt gaaattcgaa cacccaaaca acttgttaat atctattcga    2640
agcgaatgca gattgaagaa accttccgag acttgaaaag tcctgcctac ggactaggcc    2700
tacgccatag ccgaacgagc agctcagagc gttttgatat catgctgcta atcgccctga    2760
tgcttcaact aacatgttgg cttgcgggcg ttcatgctca gaaacaaggt tgggacaagc    2820
acttccaggc taacacagtc agaaatcgaa acgtactctc aacagttcgc ttaggcatgg    2880
aagttttgcg gcattctggc tacacaataa caagggaaga cttactcgtg gctgcaaccc    2940
tactagctca aaatttattc acacatggtt acgctttggg gaaattatga taatgatcca    3000
gatcacttct ggctaataaa agatcagagc tctagagatc tgtgtgttgg ttttttgtgg    3060
atctgctgtg ccttctagtt gccagccatc tgttgtttgc ccctcccccg tgccttcctt    3120
gaccctggaa ggtgccactc ccactgtcct ttcctaataa aatgaggaaa ttgcatcgca    3180
ttgtctgagt aggtgtcatt ctattctggg ggtgggggtg gggcagcaca gcaaggggga    3240
ggattgggaa gacaatagca ggcatgctgg ggatgcggtg ggctctatgg gtacctctct    3300
ctctctctct ctctctctct ctctcggtac ctctctctct ctctctctct              3360
ctctctctct ctctctctct cggtaccagg tgctgaagaa ttgacccggt gaccaaaggt    3420
gccttttatc atcactttaa aaataaaaaa caattactca gtgcctgtta taagcagcaa    3480
ttaattatga ttgatgccta catcacaaca aaaactgatt taacaaatgg ttggtctgcc    3540
ttagaaagta tatttgaaca ttatcttgat tatattattg ataataataa aaaccttatc    3600
cctatccaag aagtgatgcc tatcattggt tggaatgaac ttgaaaaaaa ttagccttga    3660
atacattact ggtaaggtaa acgccattgt cagcaaattg atccaagaga accaacttaa    3720
agctttcctg acggaatgtt aattctcgtt gaccctgagc actgatgaat cccctaatga    3780
ttttggtaaa aatcattaag ttaaggtgga tacacatctt gtcatatgat cccggtaatg    3840
tgagttagct cactcattag gcaccccagg ctttacactt tatgcttccg gctcgtatgt    3900
tgtgtggaat tgtgagcgga taacaatttc acacaggaaa cagctatgac catgattacg    3960
ccaagcgcgc aattaaccct cactaaaggg aacaaaagct ggagctccac cgcggtggcg    4020
```

```
gccgctctag aactagtgga tccccgggg aggtcagaat ggtttcttta ctgtttgtca    4080
attctattat ttcaatacag aacaaaagct tctataactg aaatatattt gctattgtat    4140
attatgattg tccctcgaac catgaacact cctccagctg aatttcacaa ttcctctgtc    4200
atctgccagg ctggaagatc atggaagatc tctgaggaac attgcaagtt cataccataa    4260
actcatttgg aattgagtat tattttgctt tgaatggagc tatgttttgc agttccctca    4320
gaagaaaagc ttgttataaa gcgtctacac ccatcaaaag atatatttaa atattccaac    4380
tacagaaaga ttttgtctgc tcttcactct gatctcagtt ggtttcttca cgtacatgct    4440
tctttatttg cctattttgt caagaaaata ataggtcaag tcctgttctc acttatctcc    4500
tgcctagcat ggcttagatg cacgttgtac attcaagaag gatcaaatga aacagacttc    4560
tggtctgtta caacaaccat agtaataaac agactaacta ataattgcta attatgtttt    4620
ccatctctaa ggttcccaca tttttctgtt ttaagatccc attatctggt tgtaactgaa    4680
gctcaatgga acatgaacag tatttctcag tcttttctcc agcaatcctg acggattaga    4740
agaactggca gaaaacactt tgttacccag aattaaaaac taatatttgc tctcccttca    4800
atccaaaatg gacctattga aactaaaatc tgacccaatc ccattaaatt atttctatgg    4860
cgtcaaaggt caaacttttg aagggaacct gtgggtgggt cccaattcag gctatatatt    4920
ccccagggct cagccagtgg atccatgggc tccatcggtg cagcaagcat ggaattttgt    4980
tttgatgtat tcaaggagct caaagtccac catgccaatg acaacatgct ctactccccc    5040
tttgccatct tgtcaactct ggccatggtc ttcctaggtg caaaagacag caccaggacc    5100
cagataaata aggttgttca ctttgataaa cttccaggat tcggagacag tattgaagct    5160
cagtgtggca catctgtaaa tgttcactct tcacttagag acatactcaa ccaaatcacc    5220
aaacaaaatg atgcttattc gttcagcctt gccagtagac tttatgctca agagacatac    5280
acagtcgtgc cggaatactt gcaatgtgtg aaggaactgt atagaggagg cttagaatcc    5340
gtcaactttc aaacagctgc agatcaagcc agaggcctca tcaatgcctg ggtagaaagt    5400
cagacaaacg gaattatcag aaacatcctt cagccaagct ccgtggattc tcaaactgca    5460
atggtcctgg ttaatgccat tgccttcaag ggactgtggg agaaagcatt taaggctgaa    5520
gacacgcaaa caatacccttt cagagtgact gagcaagaaa gcaaacctgt gcagatgatg    5580
taccagattg gttcatttaa agtggcatca atggcttctg agaaaatgaa gatcctggag    5640
cttccatttg ccagtggaac aatgagcatg ttggtgctgt tgcctgatga tgtctcaggc    5700
cttgagcagc ttgagagtat aatcagcttt gaaaaactga ctgaatggac cagttctagt    5760
attatggaag agaggaaggt caaagtgtac ttaccctcgca tgaagatgga ggagaaatac    5820
aacctcacat ctctcttaat ggctatggga attactgacc tgttcagctc ttcagccaat    5880
ctgtctggca tctcctcagt agggagcctg aagatatctc aagctgtcca tgcagcacat    5940
gcagaaatca atgaagcggg cagagatgtg gtaggctcag cagaggctgg agtggatgct    6000
actgaagaat ttagggctga ccatccattc ctcttctgtg tcaagcacat cgaaaccaac    6060
gccattctcc tctttggcag atgtgttcct ccgcggccag cagatgacgc accagcagat    6120
gacgcaccag cagatgacgc accagcagat gacgcaccag cagatgacgc accagcagat    6180
gacgcaacaa catgtatcct gaaaggctct tgtggctgga tcggcctgct ggatgacgat    6240
gacaaatttg tgaaccaaca cctgtgcggc tcacacctgg tggaagctct ctacctagtg    6300
tgcggggaac gaggcttctt ctacacaccc aagacccgcc gggaggcaga ggacctgcag    6360
gtggggcagg tggagctggg cggggggccct ggtgcaggca gcctgcagcc cttggccctg    6420
```

```
gaggggtccc tgcagaagcg tggcattgtg aacaatgct gtaccagcat ctgctccctc   6480
taccagctgg agaactactg caactagggc gcctggatcc agatcacttc tggctaataa   6540
aagatcagag ctctagagat ctgtgtgttg gttttttgtg gatctgctgt gccttctagt   6600
tgccagccat ctgttgtttg ccctccccc gtgccttcct tgaccctgga aggtgccact   6660
cccactgtcc tttcctaata aaatgaggaa attgcatcgc attgtctgag taggtgtcat   6720
tctattctgg ggggtggggt ggggcagcac agcaagggg aggattggga agacaatagc   6780
aggcatgctg gggatgcggt gggctctatg ggtacctctc tctctctctc tctctctctc   6840
tctctctctc tctctcggta cctctctcga ggggggcccc ggtacccaat tcgccctata   6900
gtgagtcgta ttacgcgcgc tcactggccg tcgttttaca acgtcgtgac tgggaaaacc   6960
ctggcgttac ccaacttaat cgccttgcag cacatcccc tttcgccagc tggcgtaata   7020
gcgaagaggc ccgcaccgat cgcccttccc aacagttgcg cagcctgaat ggcgaatgga   7080
aattgtaagc gttaatattt tgttaaaatt cgcgttaaat ttttgttaaa tcagctcatt   7140
ttttaaccaa taggccgaaa tcggcaaaat cccttataaa tcaaaagaat agaccgagat   7200
agggttgagt gttgttccag tttggaacaa gagtccacta ttaaagaacg tggactccaa   7260
cgtcaaaggg cgaaaaaccg tctatcaggg cgatggccca ctactccggg atcatatgac   7320
aagatgtgta tccaccttaa cttaatgatt tttaccaaaa tcattagggg attcatcagt   7380
gctcagggtc aacgagaatt aacattccgt caggaaagct tatgatgatg atgtgcttaa   7440
aaacttactc aatggctggt tatgcatatc gcaatacatg cgaaaaacct aaaagagctt   7500
gccgataaaa aaggccaatt tattgctatt taccgcggct ttttattgag cttgaaagat   7560
aaataaaata gataggtttt atttgaagct aaatcttctt tatcgtaaaa atgccctct   7620 tgggttatca agagggtcat tatatttcgc ggaataacat catttggtga cgaaataact   7680
aagcacttgt ctcctgttta ctcccctgag cttgaggggt taacatgaag gtcatcgata   7740
gcaggataat aatacagtaa aacgctaaac caataatcca aatccagcca tcccaaattg   7800
gtagtgaatg attataaata acagcaaaca gtaatgggcc aataacaccg gttgcattgg   7860
taaggctcac caataatccc tgtaaagcac cttgctgatg actctttgtt tggatagaca   7920
tcactccctg taatgcaggt aaagcgatcc caccaccagc caataaaatt aaaacaggga   7980
aaactaacca acctcagat ataaacgcta aaaggcaaa tgcactacta ctgcaataa   8040 atccgagcag tactgccgtt ttttcgcccc atttagtggc tattcttcct gccacaaagg   8100
cttggaatac tgagtgtaaa agaccaagac ccgctaatga aaagccaacc atcatgctat   8160
tccatccaaa acgattttcg gtaaatagca cccacaccgt tgcgggaatt tggcctatca   8220
attgcgctga aaataaata atcaacaaaa tggcatcgtt ttaaataaag tgatgtatac   8280
cgaattcagc ttttgttccc tttagtgagg gttaattgcg cgcttggcgt aatcatggtc   8340
atagctgttt cctgtgtgaa attgttatcc gctcacaatt ccacacaaca tacgagccgg   8400
aagcataaag tgtaaagcct ggggtgccta atgagtgagc taactcacat taattgcgtt   8460
gcgctcactg cccgctttcc agtcgggaaa cctgtcgtgc cagctgcatt aatgaatcgg   8520
ccaacgcgcg gggagaggcg gtttgcgtat tgggcgctct tccgcttcct cgctcactga   8580
ctcgctgcgc tcggtcgttc ggctgcggcg agcggtatca gctcactcaa aggcggtaat   8640
acggttatcc acagaatcag gggataacgc aggaaagaac atgtgagcaa aaggccagca   8700
aaaggccagg aaccgtaaaa aggccgcgtt gctggcgttt ttccataggc tccgccccc   8760 tgacgagcat cacaaaaatc gacgctcaag tcagaggtgg cgaaacccga caggactata   8820
```

```
aagataccag gcgtttcccc ctggaagctc cctcgtgcgc tctcctgttc cgaccctgcc    8880
gcttaccgga tacctgtccg cctttctccc ttcgggaagc gtggcgcttt ctcatagctc    8940
acgctgtagg tatctcagtt cggtgtaggt cgttcgctcc aagctgggct gtgtgcacga    9000 acccccgtt cagcccgacc gctgcgcctt atccggtaac tatcgtcttg agtccaaccc    9060
ggtaagacac gacttatcgc cactggcagc agccactggt aacaggatta gcagagcgag    9120
gtatgtaggc ggtgctacag agttcttgaa gtggtggcct aactacggct acactagaag    9180
gacagtattt ggtatctgcg ctctgctgaa gccagttacc ttcggaaaaa gagttggtag    9240
ctcttgatcc ggcaaacaaa ccaccgctgg tagcggtggt ttttttgttt gcaagcagca    9300
gattacgcgc agaaaaaaag gatctcaaga agatcctttg atcttttcta cggggtctga    9360
cgctcagtgg aacgaaaact cacgttaagg gattttggtc atgagattat caaaaaggat    9420
cttcacctag atccttttaa attaaaaatg aagttttaaa tcaatctaaa gtatatatga    9480
gtaaacttgg tctgacagtt accaatgctt aatcagtgag gcacctatct cagcgatctg    9540
tctatttcgt tcatccatag ttgcctgact ccccgtcgtg tagataacta cgatacggga    9600
gggcttacca tctggcccca gtgctgcaat gataccgcga gacccacgct caccggctcc    9660
agatttatca gcaataaacc agccagccgg aagggccgag cgcagaagtg gtcctgcaac    9720
tttatccgcc tccatccagt ctattaattg ttgccgggaa gctagagtaa gtagttcgcc    9780
agttaatagt ttgcgcaacg ttgttgccat tgctacaggc atcgtggtgt cacgctcgtc    9840
gtttggtatg gcttcattca gctccggttc ccaacgatca aggcgagtta catgatcccc    9900
catgttgtgc aaaaaagcgg ttagctcctt cggtcctccg atcgttgtca gaagtaagtt    9960
ggccgcagtg ttatcactca tggttatggc agcactgcat aattctctta ctgtcatgcc   10020
atccgtaaga tgcttttctg tgactggtga gtactcaacc aagtcattct gagaatagtg   10080
tatgcggcga ccgagttgct cttgcccggc gtcaatacgg gataataccg cgccacatag   10140
cagaacttta aaagtgctca tcattggaaa acgttcttcg gggcgaaaac tctcaaggat   10200
cttaccgctg ttgagatcca gttcgatgta acccactcgt gcacccaact gatcttcagc   10260
atcttttact ttcaccagcg tttctgggtg agcaaaaaca ggaaggcaaa atgccgcaaa   10320
aaagggaata agggcgacac ggaaatgttg aatactcata ctcttccttt ttcaatatta   10380
ttgaagcatt tatcagggtt attgtctcat gagcggatac atatttgaat gtatttagaa   10440
aaataaacaa ataggggttc cgcgcacatt tccccgaaaa gtgccac              10487
```

<210> SEQ ID NO 45
<211> LENGTH: 10297
<212> TYPE: DNA
<213> ORGANISM: Artificial Sequence
<220> FEATURE:
<223> OTHER INFORMATION: Synthetic

<400> SEQUENCE: 45

```
ctgacgcgcc ctgtagcggc gcattaagcg cggcgggtgt ggtggttacg cgcagcgtga      60
ccgctacact tgccagcgcc ctagcgcccg ctcctttcgc tttcttccct tcctttctcg     120
ccacgttcgc cggcatcaga ttggctattg gccattgcat acgttgtatc catatcataa     180
tatgtacatt tatattggct catgtccaac attaccgcca tgttgacatt gattattgac     240
tagttattaa tagtaatcaa ttacggggtc attagttcat agcccatata tggagttccg     300
cgttacataa cttacggtaa atggcccgcc tggctgaccg cccaacgacc cccgcccatt     360
gacgtcaata atgacgtatg ttcccatagt aacgccaata gggactttcc attgacgtca     420
```

```
atgggtggag tatttacggt aaactgccca cttggcagta catcaagtgt atcatatgcc    480
aagtacgccc cctattgacg tcaatgacgg taaatggccc gcctggcatt atgcccagta    540
catgacctta tgggactttc ctacttggca gtacatctac gtattagtca tcgctattac    600
catggtgatg cggttttggc agtacatcaa tgggcgtgga tagcggtttg actcacgggg    660
atttccaagt ctccaccca ttgacgtcaa tgggagtttg ttttggcacc aaaatcaacg     720
ggactttcca aaatgtcgta acaactccgc cccattgacg caaatgggcg gtaggcgtgt    780
acggtgggag gtctatataa gcagagctcg tttagtgaac cgtcagatcg cctggagacg    840
ccatccacgc tgttttgacc tccatagaag acaccgggac cgatccagcc tccgcggccg    900
ggaacggtgc attggaacgc ggattccccg tgccaagagt gacgtaagta ccgcctatag    960
actctatagg cacaccctt tggctcttat gcatgctata ctgttttgg cttggggcct      1020
atacaccccc gcttccttat gctataggtg atggtatagc ttagcctata ggtgtgggtt    1080
attgaccatt attgaccact cccctattgg tgacgatact ttccattact aatccataac    1140
atggctcttt gccacaacta tctctattgg ctatatgcca atactctgtc cttcagagac    1200
tgacacggac tctgtatttt tacaggatgg ggtcccattt attatttaca aattcacata    1260
tacaacaacg ccgtcccccg tgcccgcagt ttttattaaa catagcgtgg gatctccacg    1320
cgaatctcgg gtacgtgttc cggacatggg ctcttctccg gtagcggcgg agcttccaca    1380
tccgagccct ggtcccatgc ctccagcggc tcatggtcgc tcggcagctc cttgctccta    1440
acagtggagg ccagacttag gcacagcaca atgcccacca ccaccagtgt gccgcacaag    1500
gccgtggcgg tagggtatgt gtctgaaaat gagcgtggag attgggctcg cacggctgac    1560
gcagatggaa gacttaaggc agcggcagaa gaagatgcag gcagctgagt tgttgtattc    1620
tgataagagt cagaggtaac tcccgttgcg gtgctgttaa cggtggaggg cagtgtagtc    1680
tgagcagtac tcgttgctgc cgcgcgcgcc accagacata atagctgaca gactaacaga    1740
ctgttccttt ccatgggtct tttctgcagt caccgtcgga ccatgtgtga acttgatatt    1800
ttacatgatt ctctttacca attctgcccc gaattacact taaaacgact caacagctta    1860
acgttggctt gccacgcatt acttgactgt aaaactctca ctcttaccga acttggccgt    1920
aacctgccaa ccaaagcgag aacaaaaacat aacatcaaac gaatcgaccg attgttaggt   1980
aatcgtcacc tccacaaaga gcgactcgct gtataccgtt ggcatgctag ctttatctgt    2040
tcgggaatac gatgcccatt gtacttgttg actggtctga tattcgtgag caaaaacgac    2100
ttatggtatt gcgagcttca gtcgcactac acggtcgttc tgttactctt tatgagaaag    2160
cgttcccgct ttcagagcaa tgttcaaaga aagctcatga ccaatttcta gccgaccttg    2220
cgagcattct accgagtaac accacaccgc tcattgtcag tgatgctggc tttaaagtgc    2280
catggtataa atccgttgag aagctgggtt ggtactggtt aagtcgagta agaggaaaag    2340
tacaatatgc agacctagga gcggaaaact ggaaacctat cagcaactta catgatatgt    2400
catctagtca ctcaaagact ttaggctata agaggctgac taaaagcaat ccaatctcat    2460
gccaaattct attgtataaa tctcgctcta aaggccgaaa aaatcagcgc tcgacacgga    2520
ctcattgtca ccaccgtca cctaaaatct actcagcgtc ggcaaggag ccatgggttc      2580
tagcaactaa cttacctgtt gaaattcgaa cacccaaaca acttgttaat atctattcga    2640
agcgaatgca gattgaagaa accttccgag acttgaaaag tcctgcctac ggactaggcc    2700
tacgccatag ccgaacgagc agctcagagc gttttgatat catgctgcta atcgccctga    2760
tgcttcaact aacatgttgg cttgcgggcg ttcatgctca gaaacaaggt tgggacaagc    2820
```

```
acttccaggc taacacagtc agaaatcgaa acgtactctc aacagttcgc ttaggcatgg    2880
aagttttgcg gcattctggc tacacaataa caagggaaga cttactcgtg gctgcaaccc    2940
tactagctca aaatttattc acacatggtt acgctttggg gaaattatga taatgatcca    3000
gatcacttct ggctaataaa agatcagagc tctagagatc tgtgtgttgg ttttttgtgg    3060
atctgctgtg ccttctagtt gccagccatc tgttgtttgc ccctcccccg tgccttcctt    3120
gaccctggaa ggtgccactc ccactgtcct ttcctaataa aatgaggaaa ttgcatcgca    3180
ttgtctgagt aggtgtcatt ctattctggg gggtggggtg gggcagcaca gcaaggggga    3240
ggattgggaa gacaatagca ggcatgctgg ggatgcggtg ggctctatgg gtacctctct    3300
ctctctctct ctctctctct ctctctctct ctctcggtac ctctctctct ctctctctct    3360
ctctctctct ctctctctct cggtaccagg tgctgaagaa ttgacccggt gaccaaaggt    3420 gcctttatc atcactttaa aaataaaaaa caattactca gtgcctgtta taagcagcaa    3480
ttaattatga ttgatgccta catcacaaca aaaactgatt taacaaatgg ttggtctgcc    3540
ttagaaagta tatttgaaca ttatcttgat tatattattg ataataataa aaaccttatc    3600
cctatccaag aagtgatgcc tatcattggt tggaatgaac ttgaaaaaaa ttagccttga    3660
atacattact ggtaaggtaa acgccattgt cagcaaattg atccaagaga accaacttaa    3720
agctttcctg acggaatgtt aattctcgtt gaccctgagc actgatgaat cccctaatga    3780
ttttggtaaa aatcattaag ttaaggtgga tacacatctt gtcatatgat cccggtaatg    3840
tgagttagct cactcattag gcaccccagg ctttacactt tatgcttccg gctcgtatgt    3900
tgtgtggaat tgtgagcgga taacaatttc acacaggaaa cagctatgac catgattacg    3960
ccaagcgcgc aattaaccct cactaaaggg aacaaaagct ggagctccac cgcggtggcg    4020
gccgctctag aactagtgga tccccgggg aggtcagaat ggtttcttta ctgtttgtca    4080
attctattat ttcaatacag aacaatagct tctataactg aaatatattt gctattgtat    4140
attatgattg tccctcgaac catgaacact cctccagctg aatttcacaa ttcctctgtc    4200
atctgccagg ccattaagtt attcatggaa gatctttgag gaacactgca agttcatatc    4260
ataaacacat ttgaaattga gtattgtttt gcattgtatg gagctatgtt ttgctgtatc    4320
ctcagaaaaa aagtttgtta taaagcattc acacccataa aaagatagat ttaaatattc    4380
cagctatagg aaagaaagtg cgtctgctct tcactctagt ctcagttggc tccttcacat    4440
gcatgcttct ttatttctcc tattttgtca agaaaataat aggtcacgtc ttgttctcac    4500
ttatgtcctg cctagcatgg ctcagatgca cgttgtagat acaagaagga tcaaatgaaa    4560
cagacttctg gtctgttact acaaccatag taataagcac actaactaat aattgctaat    4620
tatgttttcc atctctaagg ttcccacatt tttctgtttt cttaaagatc ccattatctg    4680
gttgtaactg aagctcaatg gaacatgagc aatatttccc agtcttctct cccatccaac    4740
agtcctgatg gattagcaga acaggcagaa aacacattgt tacccagaat taaaaactaa    4800
tatttgctct ccattcaatc caaaatggac ctattgaaac taaaatctaa cccaatccca    4860
ttaaatgatt tctatggcgt caaaggtcaa acttctgaag ggaacctgtg ggtgggtcac    4920
aattcaggct atatattccc cagggctcag cggatccatg ggctccatcg gcgcagcaag    4980
catggaattt tgttttgatg tattcaagga gctcaaagtc caccatgcca atgagaacat    5040
cttctactgc cccattgcca tcatgtcagc tctagccatg gtatacctgg gtgcaaaaga    5100
cagcaccagg acagataaa ataaggttgt tcgctttgat aaacttccag gattcggaga    5160
cagtattgaa gctcagtgtg gcacatctgt aaacgttcac tcttcactta gagacatcct    5220
```

```
caaccaaatc accaaaccaa atgatgttta ttcgttcagc cttgccagta gactttatgc    5280
tgaagagaga tacccaatcc tgccagaata cttgcagtgt gtgaaggaac tgtatagagg    5340
aggcttggaa cctatcaact ttcaaacagc tgcagatcaa gccagagagc tcatcaattc    5400
ctgggtagaa agtcagacaa atggaattat cagaaatgtc cttcagccaa gctccgtgga    5460
ttctcaaact gcaatggttc tggttaatgc cattgtcttc aaaggactgt gggagaaaac    5520
atttaaggat gaagacacac aagcaatgcc tttcagagtg actgagcaag aaagcaaacc    5580
tgtgcagatg atgtaccaga ttggtttatt tagagtggca tcaatggctt ctgagaaaat    5640
gaagatcctg gagcttccat tgccagtgg gacaatgagc atgttggtgc tgttgcctga    5700
tgaagtctca ggccttgagc agcttgagag tataatcaac tttgaaaaac tgactgaatg    5760
gaccagttct aatgttatgg aagagaggaa gatcaaagtg tacttacctc gcatgaagat    5820
ggaggaaaaa tacaacctca catctgtctt aatggctatg ggcattactg acgtgtttag    5880
ctcttcagcc aatctgtctg gcatctcctc agcagagagc tgaagatat ctcaagctgt     5940 ccatgcagca catgcagaaa tcaatgaagc aggcagagag gtggtagggt cagcagaggc    6000
tggagtggat gctgcaagcg tctctgaaga atttagggct gaccatccat tcctcttctg    6060
tatcaagcac atcgcaacca acgccgttct ctctttggc agatgtgttt cccctccgcg     6120
gccagcagat gacgcaccag cagatgacgc accagcagat gacgcaccag cagatgacgc    6180
accagcagat gacgcaccag cagatgacgc aacaacatgt atcctgaaag gctcttgtgg    6240
ctggatcggc ctgctggatg acgatgacaa aaaatacaaa aaagcactga aaaactggc     6300 aaaactgctg taatgagggc gcctggatcc agatcacttc tggctaataa agatcagag     6360 ctctagagat ctgtgtgttg gtttttttgtg gatctgctgt gccttctagt tgccagccat    6420
ctgttgtttg cccctccccc gtgccttcct gaccctggaa aggtgccact cccactgtcc    6480
tttcctaata aaatgaggaa attgcatcgc attgtctgag taggtgtcat tctattctgg    6540
ggggtggggt ggggcagcac agcaaggggg aggattggga agacaatagc aggcatgctg    6600
gggatgcggt gggctctatg ggtacctctc tctctctctc tctctctctc tctctctctc    6660
tctctcggta cctctctcga gggggggccc ggtacccaat tcgccctata gtgagtcgta    6720
ttacgcgcgc tcactggccg tcgttttaca acgtcgtgac tgggaaaacc ctggcgttac    6780
ccaacttaat cgccttgcag cacatccccc tttcgccagc tggcgtaata gcgaagaggc    6840
ccgcaccgat cgcccttccc aacagttgcg cagcctgaat ggcgaatgga aattgtaagc    6900
gttaatattt tgttaaaatt cgcgttaaat ttttgttaaa tcagctcatt ttttaaccaa    6960
taggccgaaa tcggcaaaat cccttataaa tcaaaagaat agaccgagat agggttgagt    7020
gttgttccag tttggaacaa gagtccacta ttaaagaacg tggactccaa cgtcaaaggg    7080
cgaaaaaccg tctatcaggg cgatggccca ctactccggg atcatatgac aagatgtgta    7140
tccaccttaa cttaatgatt tttaccaaaa tcattagggg attcatcagt gctcagggtc    7200
aacgagaatt aacattccgt caggaaagct tatgatgatg atgtgcttaa aaacttactc    7260
aatggctggt tatgcatatc gcaatacatg cgaaaaacct aaaagagctt gccgataaaa    7320
aaggccaatt tattgctatt taccgcggct ttttattgag cttgaaagat aaataaaata    7380
gataggtttt atttgaagct aaatcttctt tatcgtaaaa aatgccctct tgggttatca    7440
agagggtcat tatatttcgc ggaataacat catttggtga cgaaataact aagcacttgt    7500 ctcctgtttta ctcccctgag cttgaggggt taacatgaag gtcatcgata gcaggataat    7560
aatacagtaa aacgctaaac caataatcca aatccagcca tcccaaattg gtagtgaatg    7620
```

```
attataaata acagcaaaca gtaatgggcc aataacaccg gttgcattgg taaggctcac    7680
caataatccc tgtaaagcac cttgctgatg actctttgtt tggatagaca tcactccctg    7740
taatgcaggt aaagcgatcc caccaccagc caataaaatt aaaacaggga aaactaacca    7800
accttcagat ataaacgcta aaaaggcaaa tgcactacta tctgcaataa atccgagcag    7860
tactgccgtt ttttcgcccc atttagtggc tattcttcct gccacaaagg cttggaatac    7920
tgagtgtaaa agaccaagac ccgctaatga aaagccaacc atcatgctat tccatccaaa    7980
acgattttcg gtaaatagca cccacaccgt tgcgggaatt tggcctatca attgcgctga    8040
aaaataaata atcaacaaaa tggcatcgtt ttaaataaag tgatgtatac cgaattcagc    8100
ttttgttccc tttagtgagg gttaattgcg cgcttggcgt aatcatggtc atagctgttt    8160
cctgtgtgaa attgttatcc gctcacaatt ccacacaaca tacgagccgg aagcataaag    8220
tgtaaagcct ggggtgccta atgagtgagc taactcacat taattgcgtt gcgctcactg    8280
cccgctttcc agtcgggaaa cctgtcgtgc cagctgcatt aatgaatcgg ccaacgcgcg    8340
gggagaggcg gtttgcgtat tgggcgctct tccgcttcct cgctcactga ctcgctgcgc    8400
tcggtcgttc ggctgcggcg agcggtatca gctcactcaa aggcggtaat acggttatcc    8460
acagaatcag gggataacgc aggaaagaac atgtgagcaa aaggccagca aaaggccagg    8520
aaccgtaaaa aggccgcgtt gctggcgttt ttccataggc tccgcccccc tgacgagcat    8580
cacaaaaatc gacgctcaag tcagaggtgg cgaaacccga caggactata agataccag    8640 gcgtttcccc ctggaagctc cctcgtgcgc tctcctgttc cgaccctgcc gcttaccgga    8700
tacctgtccg cctttctccc ttcgggaagc gtggcgcttt ctcatagctc acgctgtagg    8760
tatctcagtt cggtgtaggt cgttcgctcc aagctgggct gtgtgcacga accccccgtt    8820
cagcccgacc gctgcgcctt atccggtaac tatcgtcttg agtccaaccc ggtaagacac    8880
gacttatcgc cactggcagc agccactggt aacaggatta gcagagcgag gtatgtaggc    8940
ggtgctacag agttcttgaa gtggtggcct aactacggct acactagaag gacagtattt    9000
ggtatctgcg ctctgctgaa gccagttacc ttcggaaaaa gagttggtag ctcttgatcc    9060
ggcaaacaaa ccaccgctgg tagcggtggt ttttttgttt gcaagcagca gattacgcgc    9120
agaaaaaaag gatctcaaga agatcctttg atcttttcta cggggtctga cgctcagtgg    9180
aacgaaaact cacgttaagg gattttggtc atgagattat caaaaaggat cttcacctag    9240 atcctttta attaaaaatg aagttttaaa tcaatctaaa gtatatatga gtaaacttgg    9300
tctgacagtt accaatgctt aatcagtgag gcacctatct cagcgatctg tctatttcgt    9360
tcatccatag ttgcctgact ccccgtcgtg tagataacta cgatacggga gggcttacca    9420
tctggcccca gtgctgcaat gataccgcga gacccacgct caccggctcc agatttatca    9480
gcaataaacc agccagccgg aagggccgag cgcagaagtg gtcctgcaac tttatccgcc    9540
tccatccagt ctattaattg ttgccgggaa gctagagtaa gtagttcgcc agttaatagt    9600
ttgcgcaacg ttgttgccat tgctacaggc atcgtggtgt cacgctcgtc gtttggtatg    9660
gcttcattca gctccggttc ccaacgatca aggcgagtta catgatcccc catgttgtgc    9720
aaaaaagcgg ttagctcctt cggtcctccg atcgttgtca gaagtaagtt ggccgcagtg    9780
ttatcactca tggttatggc agcactgcat aattctctta ctgtcatgcc atccgtaaga    9840
tgcttttctg tgactggtga gtactcaacc aagtcattct gagaatagtg tatgcggcga    9900
ccgagttgct cttgcccggc gtcaatacgg gataataccg cgccacatag cagaacttta    9960
aaagtgctca tcattggaaa acgttcttcg gggcgaaaac tctcaaggat cttaccgctg   10020
```

-continued

| | |
|---|---|
| ttgagatcca gttcgatgta acccactcgt gcacccaact gatcttcagc atcttttact | 10080 |
| ttcaccagcg tttctggtgt agcaaaaaca ggaaggcaaa atgccgcaaa aaagggaata | 10140 |
| agggcgacac ggaaatgttg aatactcata ctcttccttt ttcaatatta ttgaagcatt | 10200 |
| tatcagggtt attgtctcat gagcggatac atatttgaat gtatttagaa aaataaacaa | 10260 |
| atagggggttc cgcgcacatt tccccgaaaa gtgccac | 10297 |

<210> SEQ ID NO 46
<211> LENGTH: 10272
<212> TYPE: DNA
<213> ORGANISM: Artificial Sequence
<220> FEATURE:
<223> OTHER INFORMATION: Synthetic

<400> SEQUENCE: 46

| | |
|---|---|
| ctgacgcgcc ctgtagcggc gcattaagcg cggcgggtgt ggtggttacg cgcagcgtga | 60 |
| ccgctacact tgccagcgcc ctagcgcccg ctcctttcgc tttcttccct tcctttctcg | 120 |
| ccacgttcgc cggcatcaga ttggctattg gccattgcat acgttgtatc catatcataa | 180 |
| tatgtacatt tatattggct catgtccaac attaccgcca tgttgacatt gattattgac | 240 |
| tagttattaa tagtaatcaa ttacggggtc attagttcat agcccatata tggagttccg | 300 |
| cgttacataa cttacggtaa atggcccgcc tggctgaccg cccaacgacc cccgcccatt | 360 |
| gacgtcaata atgacgtatg ttcccatagt aacgccaata gggactttcc attgacgtca | 420 |
| atgggtggag tatttacggt aaactgccca cttggcagta catcaagtgt atcatatgcc | 480 |
| aagtacgccc cctattgacg tcaatgacgg taaatggccc gcctggcatt atgcccagta | 540 |
| catgacctta tgggactttc ctacttggca gtacatctac gtattagtca tcgctattac | 600 |
| catggtgatg cggttttggc agtacatcaa tgggcgtgga tagcggtttg actcacgggg | 660 |
| atttccaagt ctccacccca ttgacgtcaa tgggagtttg ttttggcacc aaaatcaacg | 720 |
| ggactttcca aaatgtcgta acaactccgc cccattgacg caaatgggcg gtaggcgtgt | 780 |
| acggtgggag gtctatataa gcagagctcg tttagtgaac cgtcagatcg cctggagacg | 840 |
| ccatccacgc tgttttgacc tccatagaag acaccggac cgatccagcc tccgcggccg | 900 |
| ggaacggtgc attggaacgc ggattccccg tgccaagagt gacgtaagta ccgcctatag | 960 |
| actctatagg cacaccccct tggctcttat gcatgctata ctgtttttgg cttggggcct | 1020 |
| atacaccccc gcttccttat gctataggtg atggtatagc ttagcctata ggtgtgggtt | 1080 |
| attgaccatt attgaccact cccctattgg tgacgtatac ttccattact aatccataac | 1140 |
| atggctcttt gccacaacta tctctattgg ctatatgcca atactctgtc cttcagagac | 1200 |
| tgacacggac tctgtatttt tacaggatgg ggtcccattt attatttaca aattcacata | 1260 |
| tacaacaacg ccgtcccccg tgcccgcagt ttttattaaa catagcgtgg gatctccacg | 1320 |
| cgaatctcgg gtacgtgttc cggacatggg ctcttctccg gtagcggcgg agcttccaca | 1380 |
| tccgagccct ggtcccatgc ctccagcggc tcatggtcgc tcggcagctc cttgctccta | 1440 |
| acagtggagg ccagacttag gcacagcaca atgcccacca ccaccagtgt gccgcacaag | 1500 |
| gccgtggcgg tagggtatgt gtctgaaaat gagcgtggag attgggctcg cacggctgac | 1560 |
| gcagatggaa gacttaaggc agcggcagaa gaagatgcag gcagctgagt tgttgtattc | 1620 |
| tgataagagt cagaggtaac tcccgttgcg gtgctgttaa cggtggaggg cagtgtagtc | 1680 |
| tgagcagtac tcgttgctgc cgcgcgcgcc accagacata atagctgaca gactaacaga | 1740 |
| ctgttccttt ccatgggtct tttctgcagt caccgtcgga ccatgtgtga acttgatatt | 1800 |

```
ttacatgatt ctctttacca attctgcccc gaattacact taaaacgact caacagctta    1860
acgttggctt gccacgcatt acttgactgt aaaactctca ctcttaccga acttggccgt    1920
aacctgccaa ccaaagcgag aacaaaacat aacatcaaac gaatcgaccg attgttaggt    1980
aatcgtcacc tccacaaaga gcgactcgct gtataccgtt ggcatgctag ctttatctgt    2040
tcgggaatac gatgcccatt gtacttgttg actggtctga tattcgtgag caaaaacgac    2100
ttatggtatt gcgagcttca gtcgcactac acgtcgttc tgttactctt tatgagaaag     2160
cgttcccgct ttcagagcaa tgttcaaaga aagctcatga ccaatttcta gccgaccttg    2220
cgagcattct accgagtaac accacaccgc tcattgtcag tgatgctggc tttaaagtgc    2280
catggtataa atccgttgag aagctgggtt ggtactggtt aagtcgagta agaggaaaag    2340
tacaatatgc agacctagga gcggaaaact ggaaacctat cagcaactta catgatatgt    2400
catctagtca ctcaaagact ttaggctata agaggctgac taaaagcaat ccaatctcat    2460
gccaaattct attgtataaa tctcgctcta aaggccgaaa aaatcagcgc tcgacacgga    2520
ctcattgtca ccacccgtca cctaaaatct actcagcgtc ggcaaaggag ccatgggttc    2580
tagcaactaa cttacctgtt gaaattcgaa cacccaaaca acttgttaat atctattcga    2640
agcgaatgca gattgaagaa accttccgag acttgaaaag tcctgcctac ggactaggcc    2700
tacgccatag ccgaacgagc agctcagagc gttttgatat catgctgcta atcgccctga    2760
tgcttcaact aacatgttgg cttgcgggcg ttcatgctca gaaacaaggt tgggacaagc    2820
acttccaggc taacacagtc agaaatcgaa acgtactctc aacagttcgc ttaggcatgg    2880
aagttttgcg gcattctggc tacacaataa caagggaaga cttactcgtg gctgcaaccc    2940
tactagctca aaatttattc acacatggtt acgctttggg gaaattatga taatgatcca    3000
gatcacttct ggctaataaa agatcagagc tctagagatc tgtgtgttgg ttttttgtgg    3060
atctgctgtg ccttctagtt gccagccatc tgttgtttgc ccctcccccg tgccttcctt    3120
gaccctggaa ggtgccactc ccactgtcct ttcctaataa aatgaggaaa ttgcatcgca    3180
ttgtctgagt aggtgtcatt ctattctggg gggtggggtg gggcagcaca gcaaggggga    3240
ggattgggaa gacaatagca ggcatgctgg ggatgcggtg gctctatgg gtacctctct     3300 ctctctctct ctctctctct ctctctctct ctctcggtac ctctctctct ctctctctct    3360
ctctctctct ctctctctct cggtaccagg tgctgaagaa ttgacccggt gaccaaaggt    3420
gccttttatc atcactttaa aaataaaaaa caattactca gtgcctgtta taagcagcaa    3480
ttaattatga ttgatgccta catcacaaca aaaactgatt taacaaatgg ttggtctgcc    3540
ttagaaagta tatttgaaca ttatcttgat tatattattg ataataataa aaaccttatc    3600
cctatccaag aagtgatgcc tatcattggt tggaatgaac ttgaaaaaaa ttagccttga    3660
atacattact ggtaaggtaa acgccattgt cagcaaattg atccaagaga accaacttaa    3720
agctttcctg acggaatgtt aattctcgtt gaccctgagc actgatgaat cccctaatga    3780
ttttggtaaa aatcattaag ttaaggtgga tacacatctt gtcatatgat cccggtaatg    3840
tgagttagct cactcattag gcaccccagg ctttacactt tatgcttccg gctcgtatgt    3900
tgtgtggaat tgtgagcgga taacaatttc acacaggaaa cagctatgac catgattacg    3960
ccaagcgcgc aattaaccct cactaaaggg aacaaaagct ggagctccac cgcggtggcg    4020
gccgctctag aactagtgga tcccccgggg aggtcagaat ggtttcttta ctgtttgtca    4080
attctattat ttcaatacag aacaaaagct tctataactg aaatatattt gctattgtat    4140
attatgattg tccctcgaac catgaacact cctccagctg aatttcacaa ttcctctgtc    4200
```

```
atctgccagg ctggaagatc atggaagatc tctgaggaac attgcaagtt cataccataa      4260
actcatttgg aattgagtat tattttgctt tgaatggagc tatgttttgc agttccctca      4320
gaagaaaagc ttgttataaa gcgtctacac ccatcaaaag atatatttaa atattccaac      4380
tacagaaaga ttttgtctgc tcttcactct gatctcagtt ggtttcttca cgtacatgct      4440
tctttatttg cctattttgt caagaaaata ataggtcaag tcctgttctc acttatctcc      4500
tgcctagcat ggcttagatg cacgttgtac attcaagaag gatcaaatga aacagacttc      4560
tggtctgtta caacaaccat agtaataaac agactaacta ataattgcta attatgtttt      4620
ccatctctaa ggttcccaca tttttctgtt ttaagatccc attatctggt tgtaactgaa      4680
gctcaatgga acatgaacag tatttctcag tcttttctcc agcaatcctg acggattaga      4740
agaactggca gaaaacactt tgttacccag aattaaaaac taatatttgc tctcccttca      4800
atccaaaatg gacctattga aactaaaatc tgacccaatc ccattaaatt atttctatgg      4860
cgtcaaaggt caaacttttg aagggaacct gtgggtgggt cccaattcag gctatatatt      4920
ccccagggct cagccagtgg atccatgggc tccatcggtg cagcaagcat ggaattttgt      4980
tttgatgtat tcaaggagct caaagtccac catgccaatg acaacatgct ctactccccc      5040
tttgccatct tgtcaactct ggccatggtc ttcctaggtg caaaagacag caccaggacc      5100
cagataaata aggttgttca ctttgataaa cttccaggat tcggagacag tattgaagct      5160
cagtgtggca catctgtaaa tgttcactct tcacttagag acatactcaa ccaaatcacc      5220
aaacaaaatg atgcttattc gttcagcctt gccagtagac tttatgctca agagacatac      5280
acagtcgtgc cggaatactt gcaatgtgtg aaggaactgt atagaggagg cttagaatcc      5340
gtcaactttc aaacagctgc agatcaagcc agaggcctca tcaatgcctg ggtagaaagt      5400
cagacaaacg gaattatcag aaacatcctt cagccaagct ccgtggattc tcaaactgca      5460
atggtcctgg ttaatgccat tgccttcaag ggactgtggg agaaagcatt taaggctgaa      5520
gacacgcaaa caataccttt cagagtgact gagcaagaaa gcaaacctgt gcagatgatg      5580
taccagattg gttcatttaa agtggcatca atggcttctg agaaaatgaa gatcctggag      5640
cttccatttg ccagtggaac aatgagcatg ttggtgctgt tgcctgatga tgtctcaggc      5700
cttgagcagc ttgagagtat aatcagctt gaaaaactga ctgaatggac cagttctagt      5760
attatgaag agaggaaggt caaagtgtac ttacctcgca tgaagatgga ggagaaatac      5820
aacctcacat ctctcttaat ggctatggga attactgacc tgttcagctc ttcagccaat      5880
ctgtctggca tctcctcagt agggagcctg aagatatctc aagctgtcca tgcagcacat      5940
gcagaaatca tgaagcgggc cagagatgtg gtaggctcag cagaggctgg agtggatgct      6000
actgaagaat ttagggctga ccatccattc ctcttctgtg tcaagcacat cgaaccaac      6060
gccattctcc tctttggcag atgtgtttct ccgcggccag cagatgacgc accagcagat      6120
gacgcaccag cagatgacgc accagcagat gacgcaccag cagatgacgc accagcagat      6180
gacgcaacaa catgtatcct gaaaggctct tgtggctgga tcggcctgct ggatgacgat      6240
gacaaaaaat acaaaaaagc actgaaaaaa ctggcaaaac tgctgtaatg agggcgcctg      6300
gatccagatc acttctggct aataaaagat cagagctcta gagatctgtg tgttggtttt      6360
ttgtggatct gctgtgcctt ctagttgcca gccatctgtt gtttgcccct cccccgtgcc      6420
ttccttgacc ctggaaggtg ccactcccac tgtccttcc taataaaatg aggaaattgc      6480
atcgcattgt ctgagtaggt gtcattctat tctgggggg ggggtggggc agcacagcaa      6540
gggggaggat tgggaagaca atagcaggca tgctggggat gcggtgggct ctatgggtac      6600
```

```
ctctctctct ctctctctct ctctctctct ctctctctct cggtacctct ctcgaggggg    6660
ggcccggtac ccaattcgcc ctatagtgag tcgtattacg cgcgctcact ggccgtcgtt    6720
ttacaacgtc gtgactggga aaccctggcg ttacccaac ttaatcgcct tgcagcacat     6780
ccccctttcg ccagctggcg taatagcgaa gaggcccgca ccgatcgccc ttcccaacag    6840
ttgcgcagcc tgaatggcga atggaaattg taagcgttaa tattttgtta aaattcgcgt    6900 taaattttg ttaaatcagc tcatttttta accaataggc cgaaatcggc aaaatccctt    6960
ataaatcaaa agaatagacc gagatagggt tgagtgttgt tccagtttgg aacaagagtc    7020
cactattaaa gaacgtggac tccaacgtca agggcgaaa aaccgtctat cagggcgatg     7080
gcccactact ccgggatcat atgacaagat gtgtatccac cttaacttaa tgatttttac    7140
caaaatcatt aggggattca tcagtgctca gggtcaacga gaattaacat tccgtcagga    7200
aagcttatga tgatgatgtg cttaaaaact tactcaatgg ctggttatgc atatcgcaat    7260
acatgcgaaa aacctaaaag agcttgccga taaaaaggc caatttattg ctatttaccg     7320 cggctttta ttgagcttga aagataaata aaatagatag gttttatttg aagctaaatc     7380
ttctttatcg taaaaatgc cctcttgggt tatcaagagg gtcattatat ttcgcggaat     7440
aacatcattt ggtgacgaaa taactaagca cttgtctcct gtttactccc ctgagcttga    7500
ggggttaaca tgaaggtcat cgatagcagg ataataatac agtaaaacgc taaaccaata    7560
atccaaatcc agccatccca aattggtagt gaatgattat aaataacagc aaacagtaat    7620 gggcaataa caccggttgc attggtaagg ctcaccaata atccctgtaa agcaccttgc     7680
tgatgactct ttgtttggat agacatcact ccctgtaatg caggtaaagc gatcccacca    7740
ccagccaata aaattaaaac agggaaaact aaccaacctt cagatataaa cgctaaaaag    7800
gcaaatgcac tactatctgc aataaatccg agcagtactg ccgttttttc gccccattta    7860
gtggctattc ttcctgccac aaaggcttgg aatactgagt gtaaagacc aagacccgct     7920 aatgaaaagc caaccatcat gctattccat ccaaaacgat tttcggtaaa tagcacccac    7980
accgttgcgg gaatttggcc tatcaattgc gctgaaaaat aaataatcaa caaaatggca    8040
tcgttttaaa taaagtgatg tataccgaat tcagcttttg ttcccttag tgagggttaa     8100 ttgcgcgctt ggcgtaatca tggtcatagc tgtttcctgt gtgaaattgt tatccgctca    8160
caattccaca acatacga gccggaagca taaagtgtaa agcctggggt gcctaatgag      8220
tgagctaact cacattaatt gcgttgcgct cactgcccgc tttccagtcg ggaaacctgt    8280
cgtgccagct gcattaatga atcggccaac gcgcggggag aggcggtttg cgtattgggc    8340
gctcttccgc ttcctcgctc actgactcgc tgcgctcggt cgttcggctg cggcgagcgg    8400
tatcagctca ctcaaaggcg gtaatacggt tatccacaga atcaggggat aacgcaggaa    8460
agaacatgtg agcaaaaggc cagcaaaagg ccaggaaccg taaaaaggcc gcgttgctgg    8520
cgttttccca taggctccgc ccccctgacg agcatcacaa aaatcgacgc tcaagtcaga    8580
ggtggcgaaa cccgacagga ctataaagat accaggcgtt tcccctgga agctccctcg     8640 tgcgctctcc tgttccgacc ctgccgctta ccggatacct gtccgccttt ctcccttcgg    8700
gaagcgtggc gctttctcat agctcacgct gtaggtatct cagttcggtg taggtcgttc    8760
gctccaagct gggctgtgtg cacgaacccc ccgttcagcc cgaccgctgc gccttatccg    8820
gtaactatcg tcttgagtcc aacccggtaa gacacgactt atcgccactg gcagcagcca    8880
ctggtaacag gattagcaga gcgaggtatg taggcggtgc tacagagttc ttgaagtggt    8940
ggcctaacta cggctacact agaaggacag tatttggtat ctgcgctctg ctgaagccag    9000
```

```
ttaccttcgg aaaaagagtt ggtagctctt gatccggcaa acaaaccacc gctggtagcg    9060
gtggtttttt tgtttgcaag cagcagatta cgcgcagaaa aaaaggatct caagaagatc    9120
ctttgatctt ttctacgggg tctgacgctc agtggaacga aaactcacgt taagggattt    9180
tggtcatgag attatcaaaa aggatcttca cctagatcct tttaaattaa aaatgaagtt    9240
ttaaatcaat ctaaagtata tatgagtaaa cttggtctga cagttaccaa tgcttaatca    9300
gtgaggcacc tatctcagcg atctgtctat ttcgttcatc catagttgcc tgactccccg    9360
tcgtgtagat aactacgata cgggagggct taccatctgg ccccagtgct gcaatgatac    9420
cgcgagaccc acgctcaccg gctccagatt tatcagcaat aaaccagcca gccggaaggg    9480
ccgagcgcag aagtggtcct gcaactttat ccgcctccat ccagtctatt aattgttgcc    9540
gggaagctag agtaagtagt tcgccagtta atagtttgcg caacgttgtt gccattgcta    9600
caggcatcgt ggtgtcacgc tcgtcgtttg gtatggcttc attcagctcc ggttcccaac    9660
gatcaaggcg agttacatga tcccccatgt tgtgcaaaaa agcggttagc tccttcggtc    9720
ctccgatcgt tgtcagaagt aagttggccg cagtgttatc actcatggtt atggcagcac    9780
tgcataattc tcttactgtc atgccatccg taagatgctt ttctgtgact ggtgagtact    9840
caaccaagtc attctgagaa tagtgtatgc ggcgaccgag ttgctcttgc ccggcgtcaa    9900
tacgggataa taccgcgcca catagcagaa ctttaaaagt gctcatcatt ggaaaacgtt    9960
cttcggggcg aaaactctca aggatcttac cgctgttgag atccagttcg atgtaaccca   10020
ctcgtgcacc caactgatct tcagcatctt ttactttcac cagcgtttct gggtgagcaa   10080
aaacaggaag gcaaaatgcc gcaaaaaagg gaataagggc gacacggaaa tgttgaatac   10140
tcatactctt cctttttcaa tattattgaa gcatttatca gggttattgt ctcatgagcg   10200
gatacatatt tgaatgtatt tagaaaaata acaaataggg gttccgcgc acatttcccc   10260
gaaaagtgcc ac                                                       10272
```

<210> SEQ ID NO 47
<211> LENGTH: 10880
<212> TYPE: DNA
<213> ORGANISM: Artificial Sequence
<220> FEATURE:
<223> OTHER INFORMATION: Synthetic

<400> SEQUENCE: 47

```
ctgacgcgcc ctgtagcggc gcattaagcg cggcgggtgt ggtggttacg cgcagcgtga     60
ccgctacact tgccagcgcc ctagcgcccg ctcctttcgc tttcttccct tcctttctcg    120
ccacgttcgc cggcatcaga ttggctattg gccattgcat acgttgtatc catatcataa    180
tatgtacatt tatattggct catgtccaac attaccgcca tgttgacatt gattattgac    240
tagttattaa tagtaatcaa ttacggggtc attagttcat agcccatata tggagttccg    300
cgttacataa cttacggtaa atggcccgcc tggctgaccg cccaacgacc cccgcccatt    360
gacgtcaata atgacgtatg ttcccatagt aacgccaata gggactttcc attgacgtca    420
atgggtggag tatttacggt aaactgccca cttggcagta catcaagtgt atcatatgcc    480
aagtacgccc cctattgacg tcaatgacgg taaatggccc gcctggcatt atgcccagta    540
catgacctta tgggactttc ctacttggca gtacatctac gtattagtca tcgctattac    600
catggtgatg cggttttggc agtacatcaa tgggcgtgga tagcggtttg actcacgggg    660
atttccaagt ctccacccca ttgacgtcaa tgggagtttg ttttggcacc aaaatcaacg    720
ggactttcca aaatgtcgta acaactccgc cccattgacg caaatgggcg gtaggcgtgt    780
```

```
acggtgggag gtctatataa gcagagctcg tttagtgaac cgtcagatcg cctggagacg    840
ccatccacgc tgttttgacc tccatagaag acaccgggac cgatccagcc tccgcggccg    900
ggaacggtgc attggaacgc ggattccccg tgccaagagt gacgtaagta ccgcctatag    960
actctatagg cacacccctt tggctcttat gcatgctata ctgtttttgg cttggggcct   1020
atacaccccc gcttccttat gctataggtg atggtatagc ttagcctata ggtgtgggtt   1080
attgaccatt attgaccact cccctattgg tgacgatact ttccattact aatccataac   1140
atggctcttt gccacaacta tctctattgg ctatatgcca atactctgtc cttcagagac   1200
tgacacggac tctgtatttt tacaggatgg ggtcccattt attatttaca aattcacata   1260
tacaacaacg ccgtcccccg tgcccgcagt ttttattaaa catgcgtgg gatctccacg    1320 cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtcgga ccatgtgcga actcgatatt   1800
ttacacgact ctctttacca attctgcccc gaattacact taaaacgact caacagctta   1860
acgttggctt gccacgcatt acttgactgt aaaactctca ctcttaccga acttggccgt   1920
aacctgccaa ccaaagcgag aacaaaacat aacatcaaac gaatcgaccg attgttaggt   1980
aatcgtcacc tccacaaaga gcgactcgct gtataccgtt ggcatgctag ctttatctgt   2040
tcgggcaata cgatgcccat tgtacttgtt gactggtctg atattcgtga gcaaaaacga   2100
cttatggtat tgcgagcttc agtcgcacta cacggtcgtt ctgttactct ttatgagaaa   2160
gcgttcccgc tttcagagca atgttcaaag aaagctcatg accaatttct agccgacctt   2220
gcgagcattc taccgagtaa caccacaccg ctcattgtca gtgatgctgg ctttaaagtg   2280
ccatggtata aatccgttga gaagctgggt tggtactggt taagtcgagt aagaggaaaa   2340
gtacaatatg cagacctagg agcggaaaac tggaaaccta tcagcaactt acatgatatg   2400
tcatctagtc actcaaagac tttaggctat aagaggctga ctaaaagcaa tccaatctca   2460
tgccaaattc tattgtataa atctcgctct aaaggccgaa aaaatcagcg ctcgacacgg   2520
actcattgtc accacccgtc acctaaaatc tactcagcgt cggcaaagga gccatgggtt   2580
ctagcaacta acttacctgt tgaaattcga cacccaaac aacttgttaa tatctattcg    2640
aagcgaatgc agattgaaga aaccttccga gacttgaaaa gtcctgccta cggactaggc   2700
ctacgccata gccgaacgag cagctcagag cgttttgata tcatgctgct aatcgccctg   2760
atgcttcaac taacatgttg gcttgcgggc gttcatgctc agaaacaagg ttgggacaag   2820
cacttccagg ctaacacagt cagaaatcga acgtactct caacagttcg cttaggcatg    2880
gaagttttgc ggcattctgg ctacacaata acaagggaag acttactcgt ggctgcaacc   2940
ctactagctc aaaatttatt cacacatggt tacgctttgg ggaaattatg aggggatcgc   3000
tctagagcga tccgggatct cgggaaaagc gttggtgacc aaaggtgcct tttatcatca   3060
ctttaaaaat aaaaaacaat tactcagtgc ctgttataag cagcaattaa ttatgattga   3120
tgcctacatc acaacaaaaa ctgatttaac aaatggttgg tctgccttag aaagtatatt   3180
```

```
tgaacattat cttgattata ttattgataa taataaaaac cttatcccta tccaagaagt    3240
gatgcctatc attggttgga atgaacttga aaaaaattag ccttgaatac attactggta    3300
aggtaaacgc cattgtcagc aaattgatcc aagagaacca acttaaagct ttcctgacgg    3360
aatgttaatt ctcgttgacc ctgagcactg atgaatcccc taatgatttt ggtaaaaatc    3420
attaagttaa ggtggataca catcttgtca tatgatcccg gtaatgtgag ttagctcact    3480
cattaggcac cccaggcttt acactttatg cttccggctc gtatgttgtg tggaattgtg    3540
agcggataac aatttcacac aggaaacagc tatgaccatg attacgccaa gcgcgcaatt    3600
aaccctcact aaagggaaca aaagctggag ctccaccgcg gtggcggccg ctctagaact    3660
agtggatccc ccgggcatca gattggctat tggccattgc atacgttgta tccatatcat    3720
aatatgtaca tttatattgg ctcatgtcca acattaccgc catgttgaca ttgattattg    3780
actagttatt aatagtaatc aattacgggg tcattagttc atagcccata tatggagttc    3840
cgcgttacat aacttacggt aaatggcccg cctggctgac cgcccaacga ccccgccca    3900 ttgacgtcaa taatgacgta tgttcccata gtaacgccaa tagggacttt ccattgacgt    3960
caatgggtgg agtatttacg gtaaactgcc cacttggcag tacatcaagt gtatcatatg    4020
ccaagtacgc cccctattga cgtcaatgac ggtaaatggc ccgcctggca ttatgcccag    4080
tacatgacct tatgggactt tcctacttgg cagtacatct acgtattagt catcgctatt    4140
accatggtga tgcggttttg gcagtacatc aatgggcgtg atagcggttt tgactcacgg    4200
ggatttccaa gtctccaccc cattgacgtc aatgggagtt tgttttggca ccaaaatcaa    4260
cgggactttc caaaatgtcg taacaactcc gccccattga cgcaaatggg cggtaggcgt    4320
gtacggtggg aggtctatat aagcagagct cgtttagtga accgtcagat cgcctggaga    4380
cgccatccac gctgttttga cctccataga agacaccggg accgatccag cctccgcggc    4440
cgggaacggt gcattggaac gcggattccc cgtgccaaga gtgacgtaag taccgcctat    4500
agactctata ggcacacccc tttggctctt atgcatgcta tactgttttt ggcttggggc    4560
ctatacaccc ccgcttcctt atgctatagg tgatggtata gcttagccta taggtgtggg    4620
ttattgacca ttattgacca ctcccctatt ggtgacgata ctttccatta ctaatccata    4680
acatggctct tgccacaac tatctctatt ggctatatgc caatactctg tccttcagag    4740
actgacacgg actctgtatt tttacaggat ggggtcccat ttattattta caaattcaca    4800
tatacaacaa cgccgtcccc cgtgcccgca gttttttatta aacatagcgt gggatctcca    4860
cgcgaatctc gggtacgtgt tccgacatg gctcttctc cggtagcggc ggagcttcca    4920
catccgagcc ctggtcccat gcctccagcg gctcatggtc gctcggcagc tccttgctcc    4980
taacagtgga ggccagactt aggcacagca caatgcccac caccaccagt gtgccgcaca    5040
aggccgtggc ggtagggtat gtgtctgaaa atgagcgtgg agattgggct cgcacggctg    5100
acgcagatgg aagacttaag gcagcggcag aagaagatgc aggcagctga gttgttgtat    5160
tctgataaga gtcagaggta actcccgttg cggtgctgtt aacggtggag ggcagtgtag    5220
tctgagcagt actcgttgct gccgcgcgcg ccaccagaca taatagctga cagactaaca    5280
gactgttcct ttccatgggt ctttttctgca gtcaccgtcg gatcaatggg ctccatcggt    5340
gcagcaagca tggaattttg ttttgatgta ttcaaggagc tcaaagtcca ccatgccaat    5400
gagaacatct tctactgccc cattgccatc atgtcagctc tagccatggt atacctgggt    5460
gcaaaagaca gcaccaggac acaaataaat aaggttgttc gctttgataa acttccagga    5520
ttcggagaca gtattgaagc tcagtgtggc acatctgtaa acgttcactc ttcacttaga    5580
```

```
gacatcctca accaaatcac caaaccaaat gatgtttatt cgttcagcct tgccagtaga   5640
ctttatgctg aagagagata cccaatcctg ccagaatact tgcagtgtgt gaaggaactg   5700
tatagaggag gcttggaacc tatcaacttt caaacagctg cagatcaagc cagagagctc   5760
atcaattcct gggtagaaag tcagacaaat ggaattatca gaaatgtcct tcagccaagc   5820
tccgtggatt ctcaaactgc aatggttctg gttaatgcca ttgtcttcaa aggactgtgg   5880
gagaaagcat ttaaggatga agacacacaa gcaatgcctt tcagagtgac tgagcaagaa   5940
agcaaacctg tgcagatgat gtaccagatt ggtttattta gagtggcatc aatggcttct   6000
gagaaaatga agatcctgga gcttccattt gccagtggga caatgagcat gttggtgctg   6060
ttgcctgatg aagtctcagg ccttgagcag cttgagagta taatcaactt tgaaaaactg   6120
actgaatgga ccagttctaa tgttatggaa gagagaagat caaagtgtac ttacctcgca   6180
tgaagatgga ggaaaaatac aacctcacat ctgtcttaat ggctatgggc attactgacg   6240
tgtttagctc ttcagccaat ctgtctggca tctcctcagc agagagcctg aagatatctc   6300
aagctgtcca tgcagcacat gcagaaatca atgaagcagg cagagaggtg gtagggtcag   6360
cagaggctgg agtggatgct gcaagcgtct ctgaagaatt tagggctgac catccattcc   6420
tcttctgtat caagcacatc gcaaccaacg ccgttctctt cttttggcag atgtgtttcc   6480
cgcggccagc agatgacgca ccagcagatg acgcaccagc agatgacgca ccagcagatg   6540
acgcaccagc agatgacgca acaacatgta tcctgaaagg ctcttgtggc tggatcggcc   6600
tgctggatga cgatgacaaa tttgtgaacc aacacctgtg cggctcacac ctggtggaag   6660
ctctctacct agtgtgcggg gaacgaggct tcttctacac acccaagacc cgccgggagg   6720
cagaggacct gcaggtgggg caggtggagc tgggcggggg ccctggtgca ggcagcctgc   6780
agcccttggc cctggagggg tccctgcaga agcgtggcat tgtggaacaa tgctgtacca   6840
gcatctgctc cctctaccag ctggagaact actgcaacta gggcgcctaa agggcgaatt   6900
atcgcggccg ctctagacca ggcgcctgga tccagatcac ttctggctaa taaaagatca   6960
gagctctaga gatctgtgtg ttggtttttt gtggatctgc tgtgccttct agttgccagc   7020
catctgttgt ttgcccctcc cccgtgcctt ccttgaccct ggaaggtgcc actcccactg   7080
tcctttccta taaaatgag gaaattgcat cgcattgtct gagtaggtgt cattctattc   7140
tggggggtgg ggtggggcag cacagcaagg gggaggattg ggaagacaat agcaggcatg   7200
ctggggatgc ggtgggctct atgggtacct ctctctctct ctctctctct ctcactctct   7260
ctctctctcg gtacctctcc tcgagggggg gcccggtacc caattcgccc tatagtgagt   7320
cgtattacgc gcgctcactg gccgtcgttt tacaacgtcg tgactgggaa accctggcg   7380
ttacccaact taatcgcctt gcagcacatc cccctttcgc cagctggcgt aatagcgaag   7440
aggcccgcac cgatcgccct tcccaacagt tgcgcagcct gaatggcgaa tggaaattgt   7500
aagcgttaat attttgttaa aattcgcgtt aaatttttgt taaatcagct cattttttaa   7560
ccaataggcc gaaatcggca aaatccctta taatcaaaa gaatagaccg agatagggtt   7620
gagtgttgtt ccagtttgga acaagagtcc actattaaag aacgtggact ccaacgtcaa   7680
agggcgaaaa accgtctatc agggcgatgg cccactactc cgggatcata tgacaagatg   7740
tgtatccacc ttaacttaat gattttacc aaaatcatta ggggattcat cagtgctcag   7800
ggtcaacgag aattaacatt ccgtcaggaa agcttatgat gatgatgtgc ttaaaaactt   7860
actcaatggc tggttatgca tatcgcaata catgcgaaaa acctaaaaga gcttgccgat   7920
aaaaaaggcc aatttattgc tatttaccgc ggcttttat tgagcttgaa agataaataa   7980
```

```
aatagatagg ttttatttga agctaaatct tctttatcgt aaaaaatgcc ctcttgggtt    8040
atcaagaggg tcattatatt tcgcggaata acatcatttg gtgacgaaat aactaagcac    8100
ttgtctcctg tttactcccc tgagcttgag gggttaacat gaaggtcatc gatagcagga    8160
taataataca gtaaaacgct aaaccaataa tccaaatcca gccatcccaa attggtagtg    8220
aatgattata aataacagca aacagtaatg ggccaataac accggttgca ttggtaaggc    8280
tcaccaataa tccctgtaaa gcaccttgct gatgactctt tgtttggata gacatcactc    8340
cctgtaatgc aggtaaagcg atcccaccac cagccaataa aattaaaaca gggaaaacta    8400
accaaccttc agatataaac gctaaaaagg caaatgcact actatctgca ataaatccga    8460
gcagtactgc cgttttttcg cccatttagt ggctattctt cctgccacaa aggcttggaa    8520
tactgagtgt aaaagaccaa gacccgtaat gaaaagccaa ccatcatgct attcatcatc    8580
acgatttctg taatagcacc acaccgtgct ggattggcta tcaatgcgct gaaataataa    8640
tcaacaaatg gcatcgttaa ataagtgatg tataccgatc agcttttgtt ccctttagtg    8700
agggttaatt gcgcgcttgg cgtaatcatg gtcatagctg tttcctgtgt gaaattgtta    8760
tccgctcaca attccacaca acatacgagc cggaagcata aagtgtaaag cctggggtgc    8820
ctaatgagtg agctaactca cattaattgc gttgcgctca ctgcccgctt tccagtcggg    8880
aaacctgtcg tgccagctgc attaatgaat cggccaacgc gcggggagag gcggtttgcg    8940
tattgggcgc tcttccgctt cctcgctcac tgactcgctg cgctcggtcg ttcggctgcg    9000
gcgagcggta tcagctcact caaaggcggt aatacggtta ccacagaat cagggataa     9060 cgcaggaaag aacatgtgag caaaaggcca gcaaaaggcc aggaaccgta aaaaggccgc    9120
gttgctggcg ttttttccata ggctccgccc ccctgacgag catcacaaaa atcgacgctc    9180
aagtcagagg tggcgaaacc cgacaggact ataaagatac caggcgtttc cccctggaag    9240
ctccctcgtg cgctctcctg ttccgaccct gccgcttacc ggatacctgt ccgcctttct    9300
cccttcggga agcgtggcgc tttctcatag ctcacgctgt aggtatctca gttcggtgta    9360
ggtcgttcgc tccaagctgg gctgtgtgca cgaaccccc gttcagcccg accgctgcgc     9420
cttatccggt aactatcgtc ttgagtccaa cccggtaaga cacgacttat cgccactggc    9480
agcagccact ggtaacagga ttagcagagc gaggtatgta ggcggtgcta cagagttctt    9540
gaagtggtgg cctaactacg gctacactag aaggacagta tttggtatct gcgctctgct    9600
gaagccagtt accttcggaa aaagagttgg tagctcttga tccggcaaac aaaccaccgc    9660
tggtagcggt ggttttttg tttgcaagca gcagattacg cgcagaaaaa aaggatctca    9720
agaagatcct ttgatctttt ctacggggtc tgacgctcag tggaacgaaa actcacgtta    9780
agggattttg gtcatgagat tatcaaaaag gatcttcacc tagatccttt taaattaaaa    9840
atgaagtttt aaatcaatct aaagtatata tgagtaaact tggtctgaca gttaccaatg    9900
cttaatcagt gaggcaccta tctcagcgat ctgtctattt cgttcatcca tagttgcctg    9960
actccccgtc gtgtagataa ctacgatacg ggagggctta ccatctggcc ccagtgctgc   10020
aatgataccg cgagacccac gctcaccggc tccagattta tcagcaataa accagccagc   10080
cggaagggcc gagcgcagaa gtggtcctgc aactttatcc gcctccatcc agtctattaa   10140
ttgttgccgg gaagctagag taagtagttc gccagttaat agtttgcgca acgttgttgc   10200
cattgctaca ggcatcgtgg tgtcacgctc gtcgtttggt atggcttcat tcagctccgg   10260
ttcccaacga tcaaggcgag ttacatgatc ccccatgttg tgcaaaaaag cggttagctc   10320
cttcggtcct ccgatcgttg tcagaagtaa gttggccgca gtgttatcac tcatggttat   10380
```

```
ggcagcactg cataattctc ttactgtcat gccatccgta agatgctttt ctgtgactgg      10440
tgagtactca accaagtcat tctgagaata gtgtatgcgg cgaccgagtt gctcttgccc      10500
ggcgtcaata cgggataata ccgcgccaca tagcagaact ttaaaagtgc tcatcattgg      10560
aaaacgttct cgggcgaa aactctcaag gatcttaccg ctgttgagat ccagttcgat        10620
gtaacccact cgtgcaccca actgatcttc agcatctttt actttcacca gcgtttctgg     10680
gtgagcaaaa acaggaaggc aaaatgccgc aaaaaggga ataagggcga cacggaaatg       10740
ttgaatactc atactcttcc ttttcaata ttattgaagc atttatcagg gttattgtct       10800
catgagcgga tacatatttg aatgtattta gaaaataaa caaatagggg ttccgcgcac       10860
atttccccga aaagtgccac                                                  10880

<210> SEQ ID NO 48
<211> LENGTH: 78
<212> TYPE: DNA
<213> ORGANISM: Artificial Sequence
<220> FEATURE:
<223> OTHER INFORMATION: Synthetic

<400> SEQUENCE: 48
aatttctcaa ggatattttt cttcgtgttc gctttggttc tggctttgtc aacagtttcg     60
gctgcgccag agccgaaa                                                    78

<210> SEQ ID NO 49
<211> LENGTH: 93
<212> TYPE: DNA
<213> ORGANISM: Artificial Sequence
<220> FEATURE:
<223> OTHER INFORMATION: Synthetic

<400> SEQUENCE: 49
aatttctcaa ggatattttt cttcgtgttc gctttggttc tggctttgtc aacagtttcg     60
gctgcgccag agccgaaatg gaaagtcttc aag                                   93

<210> SEQ ID NO 50
<211> LENGTH: 15
<212> TYPE: DNA
<213> ORGANISM: Artificial Sequence
<220> FEATURE:
<223> OTHER INFORMATION: Synthetic

<400> SEQUENCE: 50
gcgccagagc cgaaa                                                       15

<210> SEQ ID NO 51
<211> LENGTH: 30
<212> TYPE: DNA
<213> ORGANISM: Artificial Sequence
<220> FEATURE:
<223> OTHER INFORMATION: Synthetic

<400> SEQUENCE: 51
gcgccagagc cgaaatggaa agtcttcaag                                       30

<210> SEQ ID NO 52
<211> LENGTH: 7
<212> TYPE: DNA
<213> ORGANISM: Artificial Sequence
```

```
<220> FEATURE:
<223> OTHER INFORMATION: Synthetic

<400> SEQUENCE: 52 accatgt                                                                        7
```